(12) United States Patent
Poland et al.

(10) Patent No.: US 12,653,880 B2
(45) Date of Patent: Jun. 16, 2026

(54) SARS-COV-2 POLYPEPTIDES

(71) Applicant: MAYO FOUNDATION FOR MEDICAL EDUCATION AND RESEARCH, Rochester, MN (US)

(72) Inventors: Gregory A. Poland, Marco Island, FL (US); Inna G. Ovsyannikova, Rochester, MN (US); Richard B. Kennedy, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 1005 days.

(21) Appl. No.: 17/748,715

(22) Filed: May 19, 2022

(65) Prior Publication Data

US 2022/0370601 A1 Nov. 24, 2022

Related U.S. Application Data

(60) Provisional application No. 63/341,771, filed on May 13, 2022, provisional application No. 63/190,964, filed on May 20, 2021.

(51) Int. Cl.
| | |
|---|---|
| *A61K 39/215* | (2006.01) |
| *A61K 39/39* | (2006.01) |
| *A61P 31/14* | (2006.01) |
| *A61K 39/00* | (2006.01) |

(52) U.S. Cl.
CPC ............ *A61K 39/215* (2013.01); *A61K 39/39* (2013.01); *A61P 31/14* (2018.01); *A61K 2039/55561* (2013.01); *A61K 2039/575* (2013.01)

(58) Field of Classification Search
CPC .. A61K 2039/5258; A61K 2039/55561; A61K 2039/55566; A61K 2039/575; A61K 39/12; A61K 39/215; A61K 39/39; A61P 31/14; C07K 14/005; C12N 2770/20034; C12N 2770/20071; C12N 2770/20022
See application file for complete search history.

(56) References Cited

U.S. PATENT DOCUMENTS

| | | | |
|---|---|---|---|
| 10,954,289 B1 | 3/2021 | Babb et al. | |
| 11,191,827 B1 | 12/2021 | Saadi | |
| 11,510,977 B2 * | 11/2022 | Ying | A61K 39/12 |

FOREIGN PATENT DOCUMENTS

| | | |
|---|---|---|
| WO | 2013/003579 A1 | 1/2013 |
| WO | 2015/130488 A2 | 9/2015 |
| WO | 2015/175361 A1 | 11/2015 |
| WO | 2018/127689 A1 | 7/2018 |
| WO | 2019/058133 A2 | 3/2019 |
| WO | 2019/135086 A1 | 7/2019 |
| WO | 2019/186199 A1 | 10/2019 |
| WO | 2019/186200 A1 | 10/2019 |
| WO | 2019/220150 A1 | 11/2019 |
| WO | 2021/214297 A1 | 10/2021 |
| WO | 2021/245140 A2 | 12/2021 |
| WO | 2022/023727 A1 | 2/2022 |
| WO | 2022/175330 A1 | 8/2022 |
| WO | 2022/253917 A1 | 12/2022 |

OTHER PUBLICATIONS

Albagi et al., "A multiple peptides vaccine against COVID-19 designed from the nucleocapsid phosphoprotein (N) and Spike Glycoprotein (S) via the immunoinformatics approach," *Informatics in Medicine Unlocked*, 21:100476, 13 pp. (2020), Elsevier Ltd. (publisher), Amsterdam, Netherlands.
Belyakov et al., "Mucosal immunization with HIV-1 peptide vaccine induces mucosal and systemic cytotoxic T lymphocytes and protective immunity in mice against intrarectal recombinant HIV-vaccinia challenge," *Proc. Natl. Acad. Sci. USA*, 95(4):1709-1714 (1998), Penske Media Corporation (publisher), New York, NY.
Crooke et al., "Immunoinformatic identification of B cell and T cell epitopes in the SARS-CoV-2 proteome," *Sci. Rep.*, 10(1):14179 (2020).
Fougeroux et al., "Capsid-like particles decorated with the SARS-CoV-2 receptor-binding domain elicit strong virus neutralization activity," *Nature Communications*, 12:324, 1-11 (2021) (obtained online).
Grifoni et al., "A Sequence Homology and Bioinformatic Approach Can Predict Candidate Targets for Immune Responses to SARS-CoV-2," *Cell Host Microbe*, 27(4):671-680 (2020).
Herrera, "Immunoinformatics approach in designing SARS-CoV-2 vaccine from experimentally determined SARS-CoV T-cell epitopes," *Journal of Applied Pharmaceutical Science*, 11(03):029-036 (2021) (available online).
International Search Report dated Aug. 18, 2022, from International Application PCT/US2022/030068.
Jackson et al., "A totally synthetic vaccine of generic structure that targets Toll-like receptor 2 on dendritic cells and promotes antibody or cytotoxic T cell responses," *Proc. Natl. Acad. Sci. USA*, 101(43):15440-15445 (2004), Penske Media Corporation (publisher), New York, NY.
Nelde et al., "SARS-CoV-2-derived peptides define heterologous and COVID-19-induced T cell recognition," *Nature Immunology*, 22:74-85 (2021) (obtained online).
Rammensee et al., "A new synthetic toll-like receptor 1/2 ligand is an efficient adjuvant for peptide vaccination in a human volunteer," *Journal for ImmunoTherapy of Cancer*, 7:307, 18 pp. (2019) (obtained online).
Rammensee et al., "Designing a SARS-CoV-2 T-Cell-Inducing Vaccine for High-Risk Patient Groups," *Vaccines*, 9(5):428, 14 pp. (2021), MDPI (publisher), Basel, Switzerland.

(Continued)

*Primary Examiner* — Bao Q Li
(74) *Attorney, Agent, or Firm* — Arnold & Porter Kaye Scholer LLP

(57) ABSTRACT

This document provides methods and materials related to selected severe acute respiratory distress coronavirus 2 (SARS-CoV-2) polypeptides. For example, this document provides vaccine compositions that contain one or more selected SARS-CoV-2 polypeptides provided herein and that have the ability to induce or increase immune responses against coronaviruses such as SARS-CoV-2 within a mammal (e.g., a human).

20 Claims, 80 Drawing Sheets

Specification includes a Sequence Listing.

(56)          References Cited

OTHER PUBLICATIONS

Ruckwardt et al., "Safety, tolerability, and immunogenicity of the respiratory syncytial virus prefusion F subunit vaccine DS-Cav1: a phase 1, randomised, open-label, dose-escalation clinical trial," *Lancet Respir. Med.*, 9(10):1111-1120 (2021), Elsevier (publisher), Amsterdam, Netherlands.

Srivastava et al., "Structural basis to design multi-epitope vaccines against Novel Coronavirus 19 (COVID19)infection, the ongoing pandemic emergency: an in silico approach," *bioRxiv*, 73 pp. available at https://doi.org/10.1101/2020.04.01.019299 (posted Apr. 16, 2020).

Wadhwa et al., "Harmonization and standardization of immunogenicity assessment of biotherapeutic products," *Bioanalysis*, 11(17):1593-1604 (2019), Newlands Press Ltd. (publisher), London, England.

Ferretti et al., "Unbiased Screens Show CD8(+) T Cells of COVID-19 Patients Recognize Shared Epitopes in SARS-CoV-2 that Largely Reside outside the Spike Protein," *Immunity*, 53(5):1095-1107 (Nov. 2020) (epub Oct. 20, 2020).

Grifoni et al., "SARS-CoV-2 human T cell epitopes: Adaptive immune response against COVID-19," *Cell Host Microbe*, 29(7):1076-1092 (18 pp.) (Jul. 2021) (epub May 21, 2021).

Heitmann et al., "A COVID-19 peptide vaccine for the induction of SARS-CoV-2 T cell immunity," *Nature*, 601(7894):617-622 (22 pp.) (Jan. 2022) (epub Nov. 23, 2021).

Khairkhah et al., "Immunological investigation of a multiepitope peptide vaccine candidate based on main proteins of SARS-CoV-2 pathogen," *PLoS One*, 17(6):e0268251, 23 pp. (Jun. 2022) (epub Jun. 9, 2022).

Meyers et al., "Highly conserved, non-human-like, and cross-reactive SARS-CoV-2 T cell epitopes for COVID-19 vaccine design and validation," *NPJ Vaccines*, 6(1):71, pp. 1-14 (May 2021) (epub May 13, 2021).

Nagler et al., "Identification of presented SARS-CoV-2 HLA class I and HLA class II peptides using HLA peptidomics," *Cell Rep.*, 35(13):109305, pp. 1-12 and e1-e7 (20 pp. ) (Jun. 2021) (epub Jun. 8, 2021).

Pan et al., "Mass spectrometric identification of immunogenic SARS-CoV-2 epitopes and cognate TCRs," *Proc. Nat'l Acad. Sci. USA*, 118(46):e2111815118, 12 pp. (Nov. 2021).

Pardieck et al. "A third vaccination with a single T cell epitope confers protection in a murine model of SARS-CoV-2 infection," *Nat. Commun.*, 13(1):3966, pp. 1-11 (Jul. 2022) (epub Jul. 9, 2022).

Tada et al., "Single-epitope T cell-based vaccine protects against SARS-CoV-2 infection in a preclinical animal model," *JCI Insight*, 8(7):e167306, pp. 1-18 (Apr. 2023) (epub Apr. 11, 2023).

Weingarten-Gabbay et al., "Profiling SARS-CoV-2 HLA-I peptidome reveals T cell epitopes from out-of-frame ORFs," *Cell*, 184(15):3962-3980, e17 (38 pp.) (Jul. 2021) (epub Jun. 3, 2021).

Birtles et al., "Identifying Distinct Structural Features of the SARS-CoV-2 Spike Protein Fusion Domain Essential for Membrane Interaction," *Biochemistry*, 60(40):2978-2986 (Sep. 2021).

Examination Report dated Oct. 6, 2025, in European Patent Application No. 22 735 677.1, 7 pages.

Stoddard et al., "Epitope profiling reveals binding signatures of SARS-CoV-2 immune response in natural infection and cross-reactivity with endemic human CoVs," *Cell Reports*, 35(8):109164 pp. 1-12 (May 2021).

\* cited by examiner

N7 + CA/IFA + CpG

N7 + CFA/IFA + CpG

N15 + CFA/IFA +CpG

N15 + CFA/IFA +CpG

```
                        SEQUENCE LISTING

<160> NUMBER OF SEQ ID NOS: 87

<210> SEQ ID NO 1
<211> LENGTH: 22
<212> TYPE: PRT
<213> ORGANISM: Artificial Sequence
<220> FEATURE:
<223> OTHER INFORMATION: Nucleocapsid (N-1)

<400> SEQUENCE: 1

Leu Gly Thr Gly Pro Glu Ala Gly Leu Pro Tyr Gly Ala Asn Lys Asp
1               5                   10                  15

Gly Ile Ile Trp Val Ala
            20

<210> SEQ ID NO 2
<211> LENGTH: 23
<212> TYPE: PRT
<213> ORGANISM: Artificial Sequence
<220> FEATURE:
<223> OTHER INFORMATION: Nucleocapsid (N-2)

<400> SEQUENCE: 2

Asp Gln Glu Leu Ile Arg Gln Gly Thr Asp Tyr Lys His Trp Pro Gln
1               5                   10                  15

Ile Ala Gln Phe Ala Pro Ser
            20

<210> SEQ ID NO 3
<211> LENGTH: 15
<212> TYPE: PRT
<213> ORGANISM: Artificial Sequence
<220> FEATURE:
<223> OTHER INFORMATION: Nucleocapsid (N-3)

<400> SEQUENCE: 3

Ser Arg Ile Gly Met Glu Val Thr Pro Ser Gly Thr Trp Leu Thr
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Nucleocapsid (N-4)

<400> SEQUENCE: 4

Val Thr Pro Ser Gly Thr Trp Leu Thr Tyr Thr Gly Ala Ile Lys
1               5                   10                  15

<210> SEQ ID NO 5
<211> LENGTH: 10
<212> TYPE: PRT
<213> ORGANISM: Artificial Sequence
<220> FEATURE:
<223> OTHER INFORMATION: Nucleocapsid (N-5)

<400> SEQUENCE: 5

Met Glu Val Thr Pro Ser Gly Thr Trp Leu
1               5                   10
```

```
<210> SEQ ID NO 6
<211> LENGTH: 24
<212> TYPE: PRT
<213> ORGANISM: Artificial Sequence
<220> FEATURE:
<223> OTHER INFORMATION: Nucleocapsid (N-6)

<400> SEQUENCE: 6

Val Thr Pro Ser Gly Thr Trp Leu Thr Tyr Thr Gly Ala Ile Lys Leu
1               5                   10                  15

Asp Asp Lys Asp Pro Asn Phe Lys
            20

<210> SEQ ID NO 7
<211> LENGTH: 14
<212> TYPE: PRT
<213> ORGANISM: Artificial Sequence
<220> FEATURE:
<223> OTHER INFORMATION: ORF9B

<400> SEQUENCE: 7

Pro Lys Ile Ser Glu Met His Pro Ala Leu Arg Leu Val Asp
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Nucleocapsid (N-7)

<400> SEQUENCE: 8

Asp Gln Val Ile Leu Leu Asn Lys His Ile Asp Ala Tyr Lys
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Membrane (M-1)

<400> SEQUENCE: 9

Arg Thr Leu Ser Tyr Tyr Lys Leu Gly Ala Ser Gln Arg Val Ala
1               5                   10                  15

<210> SEQ ID NO 10
<211> LENGTH: 9
<212> TYPE: PRT
<213> ORGANISM: Artificial Sequence
<220> FEATURE:
<223> OTHER INFORMATION: Membrane (M-2)

<400> SEQUENCE: 10

Thr Leu Ala Cys Phe Val Leu Ala Ala
1               5

<210> SEQ ID NO 11
<211> LENGTH: 9
<212> TYPE: PRT
<213> ORGANISM: Artificial Sequence
<220> FEATURE:
<223> OTHER INFORMATION: Membrane (M-3)

<400> SEQUENCE: 11
```

```
Trp Leu Leu Trp Pro Val Thr Leu Ala
1               5

<210> SEQ ID NO 12
<211> LENGTH: 15
<212> TYPE: PRT
<213> ORGANISM: Artificial Sequence
<220> FEATURE:
<223> OTHER INFORMATION: Spike (S-1)

<400> SEQUENCE: 12

Cys Thr Phe Glu Tyr Val Ser Gln Pro Phe Leu Met Asp Leu Glu
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Spike (S-2)

<400> SEQUENCE: 13

Asn Leu Leu Leu Gln Tyr Gly Ser Phe Cys Thr Gln Leu Asn Arg
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Spike (S-3)

<400> SEQUENCE: 14

Thr Asp Glu Met Ile Ala Gln Tyr Thr Ser Ala Leu Leu Ala Gly
1               5                   10                  15

<210> SEQ ID NO 15
<211> LENGTH: 18
<212> TYPE: PRT
<213> ORGANISM: Artificial Sequence
<220> FEATURE:
<223> OTHER INFORMATION: Nucleocapsid (N-8)

<400> SEQUENCE: 15

Leu Ser Pro Arg Trp Tyr Phe Tyr Tyr Leu Gly Thr Gly Pro Glu Ala
1               5                   10                  15

Gly Leu

<210> SEQ ID NO 16
<211> LENGTH: 18
<212> TYPE: PRT
<213> ORGANISM: Artificial Sequence
<220> FEATURE:
<223> OTHER INFORMATION: Membrane (M-4)

<400> SEQUENCE: 16

Gly Ala Val Ile Leu Arg Gly His Leu Arg Ile Ala Gly His His Leu
1               5                   10                  15

Gly Arg

<210> SEQ ID NO 17
<211> LENGTH: 17
<212> TYPE: PRT
<213> ORGANISM: Artificial Sequence
<220> FEATURE:
<223> OTHER INFORMATION: Membrane (M-5)
```

<400> SEQUENCE: 17

Thr Ser Arg Thr Leu Ser Tyr Tyr Lys Leu Gly Ala Ser Gln Arg Val
1               5                   10                  15

Ala

<210> SEQ ID NO 18
<211> LENGTH: 20
<212> TYPE: PRT
<213> ORGANISM: Artificial Sequence
<220> FEATURE:
<223> OTHER INFORMATION: ORF3 (ORF-3a)

<400> SEQUENCE: 18

Tyr Phe Thr Ser Asp Tyr Tyr Gln Leu Tyr Ser Thr Gln Leu Ser Thr
1               5                   10                  15

Asp Thr Gly Val
            20

<210> SEQ ID NO 19
<211> LENGTH: 10
<212> TYPE: PRT
<213> ORGANISM: Artificial Sequence
<220> FEATURE:
<223> OTHER INFORMATION: Spike (S-4)

<400> SEQUENCE: 19

Phe Ile Glu Asp Leu Leu Phe Asn Lys Val
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Nucleocapsid (N-18)

<400> SEQUENCE: 20

Trp Leu Thr Tyr Thr Gly Ala Ile Lys Leu
1               5                   10

<210> SEQ ID NO 21
<211> LENGTH: 8
<212> TYPE: PRT
<213> ORGANISM: Artificial Sequence
<220> FEATURE:
<223> OTHER INFORMATION: ORF9B (ORF9b.1*7)

<400> SEQUENCE: 21

Leu Val Asp Pro Gln Ile Gln Leu
1               5

<210> SEQ ID NO 22
<211> LENGTH: 11
<212> TYPE: PRT
<213> ORGANISM: Artificial Sequence
<220> FEATURE:
<223> OTHER INFORMATION: ORF9B (ORF9b.1*8)

<400> SEQUENCE: 22

Lys Leu Ala Thr Thr Glu Glu Leu Pro Asp Glu
1               5                   10

<210> SEQ ID NO 23
<211> LENGTH: 8

<212> TYPE: PRT
<213> ORGANISM: Artificial Sequence
<220> FEATURE:
<223> OTHER INFORMATION: ORF9B (ORF9b.1*9)

<400> SEQUENCE: 23

Thr Glu Glu Leu Pro Asp Glu Phe
1               5

<210> SEQ ID NO 24
<211> LENGTH: 19
<212> TYPE: PRT
<213> ORGANISM: Artificial Sequence
<220> FEATURE:
<223> OTHER INFORMATION: ORF9B (ORF9b.1*10)

<400> SEQUENCE: 24

Asn Ala Val Gly Arg Asp Gln Asn Asn Val Gly Pro Lys Val Tyr Pro
1               5                   10                  15

Ile Ile Leu

<210> SEQ ID NO 25
<211> LENGTH: 15
<212> TYPE: PRT
<213> ORGANISM: Artificial Sequence
<220> FEATURE:
<223> OTHER INFORMATION: Spike (S-9)

<400> SEQUENCE: 25

Phe Asn Cys Tyr Phe Pro Leu Gln Ser Tyr Gly Phe Gln Pro Thr
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Spike (S-10)

<400> SEQUENCE: 26

Leu Thr Asp Glu Met Ile Ala Gln Tyr Thr Ser Ala Leu Leu Ala
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Spike (S-11)

<400> SEQUENCE: 27

Arg Phe Ala Ser Val Tyr Ala Trp Asn Arg Lys Arg Ile Ser Asn
1               5                   10                  15

<210> SEQ ID NO 28
<211> LENGTH: 9
<212> TYPE: PRT
<213> ORGANISM: Artificial Sequence
<220> FEATURE:
<223> OTHER INFORMATION: Spike (S-12)

<400> SEQUENCE: 28

Val Val Phe Leu His Val Thr Tyr Val
1               5

<210> SEQ ID NO 29

```
<211> LENGTH: 15
<212> TYPE: PRT
<213> ORGANISM: Artificial Sequence
<220> FEATURE:
<223> OTHER INFORMATION: Membrane (M-8)

<400> SEQUENCE: 29

Glu Ile Thr Val Ala Thr Ser Arg Thr Leu Ser Tyr Tyr Lys Leu
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Membrane (M-9)

<400> SEQUENCE: 30

Tyr Arg Ile Asn Trp Ile Thr Gly Gly Ile Ala Ile Ala Met Ala
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Membrane (M-10)

<400> SEQUENCE: 31

Ser Tyr Phe Ile Ala Ser Phe Arg Leu Phe Ala Arg Thr Arg Ser
1               5                   10                  15

<210> SEQ ID NO 32
<211> LENGTH: 9
<212> TYPE: PRT
<213> ORGANISM: Artificial Sequence
<220> FEATURE:
<223> OTHER INFORMATION: Membrane (M-11)

<400> SEQUENCE: 32

Ser Met Trp Ser Phe Asn Pro Glu Thr
1               5

<210> SEQ ID NO 33
<211> LENGTH: 10
<212> TYPE: PRT
<213> ORGANISM: Artificial Sequence
<220> FEATURE:
<223> OTHER INFORMATION: Membrane (M-12)

<400> SEQUENCE: 33

Leu Leu Trp Pro Val Thr Leu Ala Cys Phe
1               5                   10

<210> SEQ ID NO 34
<211> LENGTH: 15
<212> TYPE: PRT
<213> ORGANISM: Artificial Sequence
<220> FEATURE:
<223> OTHER INFORMATION: Membrane (M-13)

<400> SEQUENCE: 34

Glu Ser Glu Leu Val Ile Gly Ala Val Ile Leu Arg Gly His Leu
1               5                   10                  15

<210> SEQ ID NO 35
<211> LENGTH: 14
```

```
<212> TYPE: PRT
<213> ORGANISM: Artificial Sequence
<220> FEATURE:
<223> OTHER INFORMATION: Nucleocapsid (N-11)

<400> SEQUENCE: 35

Thr Gly Pro Glu Ala Gly Leu Pro Tyr Gly Ala Asn Lys Asp
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Nucleocapsid (N-12)

<400> SEQUENCE: 36

Pro Asn Phe Lys Asp Gln Val Ile Leu Leu
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Nucleocapsid (N-13)

<400> SEQUENCE: 37

Leu Leu Asn Lys His Ile Asp Ala Tyr
1               5

<210> SEQ ID NO 38
<211> LENGTH: 17
<212> TYPE: PRT
<213> ORGANISM: Artificial Sequence
<220> FEATURE:
<223> OTHER INFORMATION: ORF9B (ORF9B.1*11)

<400> SEQUENCE: 38

Pro Gln Ile Gln Leu Ala Val Thr Arg Met Glu Asn Ala Val Gly Arg
1               5                   10                  15

Asp

<210> SEQ ID NO 39
<211> LENGTH: 25
<212> TYPE: PRT
<213> ORGANISM: Artificial Sequence
<220> FEATURE:
<223> OTHER INFORMATION: Nucleocapsid (N-15)

<400> SEQUENCE: 39

Ile Arg Gln Gly Thr Asp Tyr Lys His Trp Pro Gln Ile Ala Gln Phe
1               5                   10                  15

Ala Pro Ser Ala Ser Ala Phe Phe Gly
            20                  25

<210> SEQ ID NO 40
<211> LENGTH: 10
<212> TYPE: PRT
<213> ORGANISM: Artificial Sequence
<220> FEATURE:
<223> OTHER INFORMATION: Nucleocapsid (N-16)

<400> SEQUENCE: 40

Val Thr Pro Ser Gly Thr Trp Leu Thr Tyr
1               5                   10
```

-continued

```
<210> SEQ ID NO 41
<211> LENGTH: 15
<212> TYPE: PRT
<213> ORGANISM: Artificial Sequence
<220> FEATURE:
<223> OTHER INFORMATION: Membrane (M-14)

<400> SEQUENCE: 41

Ser Gln Arg Val Ala Gly Asp Ser Gly Phe Ala Ala Tyr Ser Arg
1               5                   10                  15

<210> SEQ ID NO 42
<211> LENGTH: 9
<212> TYPE: PRT
<213> ORGANISM: Artificial Sequence
<220> FEATURE:
<223> OTHER INFORMATION: Spike (S-13)

<400> SEQUENCE: 42

Val Leu Asn Asp Ile Leu Ser Arg Leu
1               5

<210> SEQ ID NO 43
<211> LENGTH: 15
<212> TYPE: PRT
<213> ORGANISM: Artificial Sequence
<220> FEATURE:
<223> OTHER INFORMATION: Spike (S-14)

<400> SEQUENCE: 43

Pro Phe Phe Ser Asn Val Thr Trp Phe His Ala Ile His Val Ser
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Spike (S-15)

<400> SEQUENCE: 44

Ser Asn Val Thr Trp Phe His Ala Ile His Val Ser Gly Thr Asn
1               5                   10                  15

<210> SEQ ID NO 45
<211> LENGTH: 10
<212> TYPE: PRT
<213> ORGANISM: Artificial Sequence
<220> FEATURE:
<223> OTHER INFORMATION: Spike (S-16)

<400> SEQUENCE: 45

Lys Leu Asn Asp Leu Cys Phe Thr Asn Val
1               5                   10

<210> SEQ ID NO 46
<211> LENGTH: 9
<212> TYPE: PRT
<213> ORGANISM: Artificial Sequence
<220> FEATURE:
<223> OTHER INFORMATION: Spike (S-17)

<400> SEQUENCE: 46

Phe Ile Ala Gly Leu Ile Ala Ile Val
1               5
```

<210> SEQ ID NO 47
<211> LENGTH: 15
<212> TYPE: PRT
<213> ORGANISM: Artificial Sequence
<220> FEATURE:
<223> OTHER INFORMATION: ORF7

<400> SEQUENCE: 47

Val Lys His Val Tyr Gln Leu Arg Ala Arg Ser Val Ser Pro Lys
1               5                   10                  15

<210> SEQ ID NO 48
<211> LENGTH: 9
<212> TYPE: PRT
<213> ORGANISM: Artificial Sequence
<220> FEATURE:
<223> OTHER INFORMATION: Spike (S-18)

<400> SEQUENCE: 48

Tyr Ser Ser Ala Asn Asn Cys Thr Phe
1               5

<210> SEQ ID NO 49
<211> LENGTH: 15
<212> TYPE: PRT
<213> ORGANISM: Artificial Sequence
<220> FEATURE:
<223> OTHER INFORMATION: Spike (S-19)

<400> SEQUENCE: 49

Asn Cys Thr Phe Glu Tyr Val Ser Gln Pro Phe Leu Met Asp Leu
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Spike (S-20)

<400> SEQUENCE: 50

Asn Ile Thr Arg Phe Gln Thr Leu Leu Ala Leu His Arg Ser Tyr
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Spike (S-21)

<400> SEQUENCE: 51

Ala Ser Val Tyr Ala Trp Asn Arg Lys Arg Ile Ser Asn Cys Val Ala
1               5                   10                  15

<210> SEQ ID NO 52
<211> LENGTH: 13
<212> TYPE: PRT
<213> ORGANISM: Artificial Sequence
<220> FEATURE:
<223> OTHER INFORMATION: Spike (S-22)

<400> SEQUENCE: 52

Gln Thr Gln Thr Asn Ser Pro Arg Arg Ala Arg Ser Val
1               5                   10

-continued

```
<210> SEQ ID NO 53
<211> LENGTH: 15
<212> TYPE: PRT
<213> ORGANISM: Artificial Sequence
<220> FEATURE:
<223> OTHER INFORMATION: Spike (S-23)

<400> SEQUENCE: 53

Arg Ser Phe Ile Glu Asp Leu Leu Phe Asn Lys Val Thr Leu Ala
1               5                   10                  15

<210> SEQ ID NO 54
<211> LENGTH: 10
<212> TYPE: PRT
<213> ORGANISM: Artificial Sequence
<220> FEATURE:
<223> OTHER INFORMATION: Polypeptide Sequence

<400> SEQUENCE: 54

Leu Ile Glu Asp Leu Leu Phe Asn Lys Val
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Polypeptide Sequence

<400> SEQUENCE: 55

Phe Val Glu Asp Leu Leu Phe Asn Lys Val
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Polypeptide Sequence

<400> SEQUENCE: 56

Phe Ile Glu Asp Ile Leu Phe Asn Lys Val
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Polypeptide Sequence

<400> SEQUENCE: 57

Phe Ile Glu Asp Leu Leu Phe Asp Lys Val
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Polypeptide Sequence

<400> SEQUENCE: 58

Phe Ile Glu Asp Leu Leu Phe Asp Arg Met
1               5                   10

<210> SEQ ID NO 59
```

```
<211> LENGTH: 14
<212> TYPE: PRT
<213> ORGANISM: Artificial Sequence
<220> FEATURE:
<223> OTHER INFORMATION: Polypeptide Sequence

<400> SEQUENCE: 59

Ser Lys Arg Ser Phe Ile Glu Asp Leu Leu Phe Asn Lys Val
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Polypeptide Sequence

<400> SEQUENCE: 60

Phe Ile Glu Asp Leu Leu Phe Asn Lys Val Thr Leu Ala
1               5                   10

<210> SEQ ID NO 61
<211> LENGTH: 22
<212> TYPE: PRT
<213> ORGANISM: Artificial Sequence
<220> FEATURE:
<223> OTHER INFORMATION: Polypeptide Sequence

<400> SEQUENCE: 61

Leu Leu Thr Asp Glu Met Ile Ala Gln Tyr Thr Ser Ala Leu Leu Ala
1               5                   10                  15

Gly Thr Ile Thr Ser Gly
            20

<210> SEQ ID NO 62
<211> LENGTH: 15
<212> TYPE: PRT
<213> ORGANISM: Artificial Sequence
<220> FEATURE:
<223> OTHER INFORMATION: Polypeptide Sequence

<400> SEQUENCE: 62

Thr Asp Gly Met Thr Ala Gln Tyr Ala Ser Ala Leu Leu Ala Gly
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Polypeptide Sequence

<400> SEQUENCE: 63

Thr Asp Glu Met Ile Ala Gln Tyr Thr Ala Ala Leu Leu Ala Gly
1               5                   10                  15

<210> SEQ ID NO 64
<211> LENGTH: 20
<212> TYPE: PRT
<213> ORGANISM: Artificial Sequence
<220> FEATURE:
<223> OTHER INFORMATION: Polypeptide Sequence

<400> SEQUENCE: 64

Leu Pro Pro Leu Leu Thr Tyr Glu Met Ile Ala Gln Tyr Thr Ser Ala
1               5                   10                  15
```

Leu Leu Ser Gly
        20

<210> SEQ ID NO 65
<211> LENGTH: 28
<212> TYPE: PRT
<213> ORGANISM: Artificial Sequence
<220> FEATURE:
<223> OTHER INFORMATION: Polypeptide Sequence

<400> SEQUENCE: 65

Gln Gly Asn Phe Gly Asp Gln Glu Leu Ile Arg Gln Gly Thr Asp Tyr
1               5                   10                  15

Lys His Trp Pro Gln Ile Ala Gln Phe Ala Pro Ser
        20                  25

<210> SEQ ID NO 66
<211> LENGTH: 23
<212> TYPE: PRT
<213> ORGANISM: Artificial Sequence
<220> FEATURE:
<223> OTHER INFORMATION: Polypeptide Sequence

<400> SEQUENCE: 66

Asp Gln Glu Leu Asn Arg Gln Gly Ile Asn Tyr Lys His Trp Pro Gln
1               5                   10                  15

Ile Ala Gln Phe Ala Pro Ser
        20

<210> SEQ ID NO 67
<211> LENGTH: 20
<212> TYPE: PRT
<213> ORGANISM: Artificial Sequence
<220> FEATURE:
<223> OTHER INFORMATION: Polypeptide Sequence

<400> SEQUENCE: 67

Lys Asp Gln Val Phe Leu Leu Asn Lys His Val Asp Ala Tyr Lys Thr
1               5                   10                  15

Phe Pro Pro Thr
        20

<210> SEQ ID NO 68
<211> LENGTH: 40
<212> TYPE: PRT
<213> ORGANISM: Artificial Sequence
<220> FEATURE:
<223> OTHER INFORMATION: S-1 Long

<400> SEQUENCE: 68

Glu Ser Glu Phe Arg Val Tyr Ser Ser Ala Asn Asn Cys Thr Phe Glu
1               5                   10                  15

Tyr Val Ser Gln Pro Phe Leu Met Asp Leu Glu Gly Lys Gln Gly Asn
        20                  25                  30

Phe Lys Asn Leu Arg Glu Phe Val
        35                  40

<210> SEQ ID NO 69
<211> LENGTH: 40
<212> TYPE: PRT
<213> ORGANISM: Artificial Sequence
<220> FEATURE:
<223> OTHER INFORMATION: S-2 Long

<400> SEQUENCE: 69

Thr Met Tyr Ile Cys Gly Asp Ser Thr Glu Cys Ser Asn Leu Leu Leu
1               5                   10                  15

Gln Tyr Gly Ser Phe Cys Thr Gln Leu Asn Arg Ala Leu Thr Gly Ile
            20                  25                  30

Ala Val Glu Gln Asp Lys Asn Thr
        35                  40

<210> SEQ ID NO 70
<211> LENGTH: 40
<212> TYPE: PRT
<213> ORGANISM: Artificial Sequence
<220> FEATURE:
<223> OTHER INFORMATION: S-9 Long

<400> SEQUENCE: 70

Gln Ala Gly Ser Thr Pro Cys Asn Gly Val Glu Gly Phe Asn Cys Tyr
1               5                   10                  15

Phe Pro Leu Gln Ser Tyr Gly Phe Gln Pro Thr Asn Gly Val Gly Tyr
            20                  25                  30

Gln Pro Tyr Arg Val Val Val Leu
        35                  40

<210> SEQ ID NO 71
<211> LENGTH: 40
<212> TYPE: PRT
<213> ORGANISM: Artificial Sequence
<220> FEATURE:
<223> OTHER INFORMATION: S-14 Long

<400> SEQUENCE: 71

Ser Ser Val Leu His Ser Thr Gln Asp Leu Phe Leu Pro Phe Phe Ser
1               5                   10                  15

Asn Val Thr Trp Phe His Ala Ile His Val Ser Gly Thr Asn Gly Thr
            20                  25                  30

Lys Arg Phe Asp Asn Pro Val Leu
        35                  40

<210> SEQ ID NO 72
<211> LENGTH: 40
<212> TYPE: PRT
<213> ORGANISM: Artificial Sequence
<220> FEATURE:
<223> OTHER INFORMATION: S-15 Long

<400> SEQUENCE: 72

Val Leu His Ser Thr Gln Asp Leu Phe Leu Pro Phe Phe Ser Asn Val
1               5                   10                  15

Thr Trp Phe His Ala Ile His Val Ser Gly Thr Asn Gly Thr Lys Arg
            20                  25                  30

Phe Asp Asn Pro Val Leu Pro Phe
        35                  40

<210> SEQ ID NO 73
<211> LENGTH: 40
<212> TYPE: PRT
<213> ORGANISM: Artificial Sequence
<220> FEATURE:
<223> OTHER INFORMATION: S-21 Long

<400> SEQUENCE: 73

Ser Gln Ile Leu Pro Asp Pro Ser Lys Pro Ser Lys Arg Ser Phe Ile
1               5                   10                  15

Glu Asp Leu Leu Phe Asn Lys Val Thr Leu Ala Asp Ala Gly Phe Ile
            20                  25                  30

Lys Gln Tyr Gly Asp Cys Leu Gly
        35                  40

<210> SEQ ID NO 74
<211> LENGTH: 40
<212> TYPE: PRT
<213> ORGANISM: Artificial Sequence
<220> FEATURE:
<223> OTHER INFORMATION: ORF9b-1*11 Long

<400> SEQUENCE: 74

Ile Ser Glu Met His Pro Ala Leu Arg Leu Val Asp Pro Gln Ile Gln
1               5                   10                  15

Leu Ala Val Thr Arg Met Glu Asn Ala Val Gly Arg Asp Gln Asn Asn
            20                  25                  30

Val Gly Pro Lys Val Tyr Pro Ile
        35                  40

<210> SEQ ID NO 75
<211> LENGTH: 40
<212> TYPE: PRT
<213> ORGANISM: Artificial Sequence
<220> FEATURE:
<223> OTHER INFORMATION: N-8 Long

<400> SEQUENCE: 75

Lys Met Lys Asp Leu Ser Pro Arg Trp Tyr Phe Tyr Tyr Leu Gly Thr
1               5                   10                  15

Gly Pro Glu Ala Gly Leu Pro Tyr Gly Ala Asn Lys Asp Gly Ile Ile
            20                  25                  30

Trp Val Ala Thr Glu Gly Ala Leu
        35                  40

<210> SEQ ID NO 76
<211> LENGTH: 40
<212> TYPE: PRT
<213> ORGANISM: Artificial Sequence
<220> FEATURE:
<223> OTHER INFORMATION: N-15 Long

<400> SEQUENCE: 76

Asn Phe Gly Asp Gln Glu Leu Ile Arg Gln Gly Thr Asp Tyr Lys His
1               5                   10                  15

Trp Pro Gln Ile Ala Gln Phe Ala Pro Ser Ala Ser Ala Phe Phe Gly
            20                  25                  30

Met Ser Arg Ile Gly Met Glu Val
        35                  40

<210> SEQ ID NO 77
<211> LENGTH: 40
<212> TYPE: PRT
<213> ORGANISM: Artificial Sequence
<220> FEATURE:
<223> OTHER INFORMATION: M-13 Long

<400> SEQUENCE: 77

Pro Leu His Gly Thr Ile Leu Thr Arg Pro Leu Leu Glu Ser Glu Leu
1               5                   10                  15

Val Ile Gly Ala Val Ile Leu Arg Gly His Leu Arg Ile Ala Gly His
            20                  25                  30

-continued

```
His Leu Gly Arg Cys Asp Ile Lys
        35                  40

<210> SEQ ID NO 78
<211> LENGTH: 40
<212> TYPE: PRT
<213> ORGANISM: Artificial Sequence
<220> FEATURE:
<223> OTHER INFORMATION: ORF3a Long

<400> SEQUENCE: 78

Gly Val Lys Asp Cys Val Val Leu His Ser Tyr Phe Thr Ser Asp Tyr
1               5                   10                  15

Tyr Gln Leu Tyr Ser Thr Gln Leu Ser Thr Asp Thr Gly Val Glu His
            20                  25                  30

Val Thr Phe Phe Ile Tyr Asn Lys
        35                  40

<210> SEQ ID NO 79
<211> LENGTH: 40
<212> TYPE: PRT
<213> ORGANISM: Artificial Sequence
<220> FEATURE:
<223> OTHER INFORMATION: M-2 Long

<400> SEQUENCE: 79

Leu Tyr Ile Ile Lys Leu Ile Phe Leu Trp Leu Leu Trp Pro Val Thr
1               5                   10                  15

Leu Ala Cys Phe Val Leu Ala Ala Val Tyr Arg Ile Asn Trp Ile Thr
            20                  25                  30

Gly Gly Ile Ala Ile Ala Met Ala
        35                  40

<210> SEQ ID NO 80
<211> LENGTH: 40
<212> TYPE: PRT
<213> ORGANISM: Artificial Sequence
<220> FEATURE:
<223> OTHER INFORMATION: M-8 Long

<400> SEQUENCE: 80

His Leu Gly Arg Cys Asp Ile Lys Asp Leu Pro Lys Glu Ile Thr Val
1               5                   10                  15

Ala Thr Ser Arg Thr Leu Ser Tyr Tyr Lys Leu Gly Ala Ser Gln Arg
            20                  25                  30

Val Ala Gly Asp Ser Gly Phe Ala
        35                  40

<210> SEQ ID NO 81
<211> LENGTH: 40
<212> TYPE: PRT
<213> ORGANISM: Artificial Sequence
<220> FEATURE:
<223> OTHER INFORMATION: M-10 Long

<400> SEQUENCE: 81

Ile Ala Met Ala Cys Leu Val Gly Leu Met Trp Leu Ser Tyr Phe Ile
1               5                   10                  15

Ala Ser Phe Arg Leu Phe Ala Arg Thr Arg Ser Met Trp Ser Phe Asn
            20                  25                  30

Pro Glu Thr Asn Ile Leu Leu Asn
        35                  40
```

<210> SEQ ID NO 82
<211> LENGTH: 40
<212> TYPE: PRT
<213> ORGANISM: Artificial Sequence
<220> FEATURE:
<223> OTHER INFORMATION: N-6 Long

<400> SEQUENCE: 82

Gly Met Ser Arg Ile Gly Met Glu Val Thr Pro Ser Gly Thr Trp Leu
1               5                   10                  15

Thr Tyr Thr Gly Ala Ile Lys Leu Asp Asp Lys Asp Pro Asn Phe Lys
            20                  25                  30

Asp Gln Val Ile Leu Leu Asn Lys
        35                  40

<210> SEQ ID NO 83
<211> LENGTH: 40
<212> TYPE: PRT
<213> ORGANISM: Artificial Sequence
<220> FEATURE:
<223> OTHER INFORMATION: N-13 Long

<400> SEQUENCE: 83

Ile Lys Leu Asp Asp Lys Asp Pro Asn Phe Lys Asp Gln Val Ile Leu
1               5                   10                  15

Leu Asn Lys His Ile Asp Ala Tyr Lys Thr Phe Pro Pro Thr Glu Pro
            20                  25                  30

Lys Lys Asp Lys Lys Lys Lys Ala
        35                  40

<210> SEQ ID NO 84
<211> LENGTH: 44
<212> TYPE: PRT
<213> ORGANISM: Artificial Sequence
<220> FEATURE:
<223> OTHER INFORMATION: N-overlap Long

<400> SEQUENCE: 84

Ser Arg Ile Gly Met Glu Val Thr Pro Ser Gly Thr Trp Leu Thr Tyr
1               5                   10                  15

Thr Gly Ala Ile Lys Leu Asp Asp Lys Asp Pro Asn Phe Lys Asp Gln
            20                  25                  30

Val Ile Leu Leu Asn Lys His Ile Asp Ala Tyr Lys
        35                  40

<210> SEQ ID NO 85
<211> LENGTH: 40
<212> TYPE: PRT
<213> ORGANISM: Artificial Sequence
<220> FEATURE:
<223> OTHER INFORMATION: ORF9b-1*8 Long

<400> SEQUENCE: 85

Arg Lys Thr Leu Asn Ser Leu Glu Asp Lys Ala Phe Gln Leu Thr Pro
1               5                   10                  15

Ile Ala Val Gln Met Thr Lys Leu Ala Thr Thr Glu Glu Leu Pro Asp
            20                  25                  30

Glu Phe Val Val Val Thr Val Lys
        35                  40

<210> SEQ ID NO 86

-continued

```
<211> LENGTH: 40
<212> TYPE: PRT
<213> ORGANISM: Artificial Sequence
<220> FEATURE:
<223> OTHER INFORMATION: S-22 Long

<400> SEQUENCE: 86

Cys Asp Ile Pro Ile Gly Ala Gly Ile Cys Ala Ser Tyr Gln Thr Gln
1               5                   10                  15

Thr Asn Ser Pro Arg Arg Ala Arg Ser Val Ala Ser Gln Ser Ile Ile
            20                  25                  30

Ala Tyr Thr Met Ser Leu Gly Ala
        35                  40

<210> SEQ ID NO 87
<211> LENGTH: 42
<212> TYPE: PRT
<213> ORGANISM: Artificial Sequence
<220> FEATURE:
<223> OTHER INFORMATION: S-F Long

<400> SEQUENCE: 87

Ser Phe Ile Glu Asp Leu Leu Phe Asn Lys Val Thr Leu Ala Asp Ala
1               5                   10                  15

Gly Phe Ile Lys Gln Tyr Gly Asp Cys Leu Gly Asp Ile Ala Ala Arg
            20                  25                  30

Asp Leu Ile Cys Ala Gln Lys Phe Asn Gly
        35                  40
```

SARS-COV-2 POLYPEPTIDES

CROSS-REFERENCE TO RELATED APPLICATIONS

This application claims the benefit of priority of U.S. Provisional Application No. 63/190,964 filed May 20, 2021, and U.S. Provisional Application No. 63/341,771 filed May 13, 2022, each of which is herein incorporated by reference in its entirety.

INCORPORATION OF SEQUENCE LISTING

This application contains a sequence listing, submitted herewith electronically, containing the file named "P35125US02_SEQ.txt" which is 25,052 bytes in size (measured in MS-Windows®) which was created on May 19, 2022, and which is herein incorporated by reference in its entirety.

TECHNICAL FIELD

This document provides methods and materials related to selected severe acute respiratory distress coronavirus 2 (SARS-CoV-2) polypeptides. For example, this document provides vaccine compositions that contain one or more selected SARS-CoV-2 polypeptides provided herein and that have the ability to induce or increase immune responses against coronaviruses such as SARS-CoV-2 within a mammal (e.g., a human).

BACKGROUND INFORMATION

An infectious COVID-19 disease caused by a coronavirus known as SARS-CoV-2 was first reported to the World Health Organization (WHO) Country Office in China on Dec. 31, 2019. As of Apr. 12, 2021, approximately 135,646, 617 confirmed cases of COVID-19, including 2,930,732 deaths, have been reported to the WHO (covid19.who.int/). As of May 13, 2022, approximately 517,648,631 confirmed cases of COVID-19, including 6,261,708 deaths, have been reported to the WHO.

The novel coronavirus outbreak that began in China in 2019 has rapidly become a world-wide pandemic that has caused hundreds of millions of cases, millions of deaths, and societal disruption rivaling that of the World Wars of the last century. While the disease (COVID-19) caused by this new coronavirus (SARS-CoV-2) is self-limiting in most (~70%) of patients, there is a significant increase in risk of severe pneumonia, acute respiratory distress syndrome, other significant complications, and death; particularly in individuals who are older and those who have underlying health problems including such conditions as: diabetes, heart or lung disease, cancer, or any condition that weakens the immune system. In addition, it is increasingly apparent that younger healthy individuals can also develop significant disease— indeed 40% of the first 2,500 COVID-19 patients hospitalized in the United States were between the ages of 20-54. Thus, there is a critical and urgent need for safe and effective vaccines.

Peptide vaccines circumvent multiple issues inherent with live virus and inactivated vaccines—peptide vaccines are inexpensive, can be rapidly produced, require no cold chain, have extended (if not indefinite) stability, require no special training for use, and do not have contraindications prohibiting their use. Peptide vaccines can be safely administered to the young, the elderly, those with comorbidities, and the immunocompromised.

SUMMARY

This document provides methods and materials related to selected SARS-CoV-2 polypeptides. For example, this document provides the isolated polypeptides set forth in Table 1, Table 2, and Table 3. In some cases, a selected SARS-CoV-2 polypeptide provided herein can be a substantially pure polypeptide that comprises, consists essentially of, or consists of the amino acid sequence set forth in any one of SEQ ID NOs:1-87. This document also provides methods for increasing an immune response against a coronavirus infection (e.g., a SARS-CoV-2 infection such as COVID-19) within a mammal (e.g., a human). For example, compositions (e.g., vaccine compositions) that contain one or more selected SARS-CoV-2 polypeptides provided herein can be administered to a mammal (e.g., human) to induce or increase an immune response against a coronavirus infection (e.g., a SARS-CoV-2 infection such as COVID-19) within the mammal. For example, compositions (e.g., vaccine compositions) that contain one or more selected SARS-CoV-2 polypeptides provided herein can be administered to a mammal (e.g., human) having or at risk of developing a coronavirus infection (e.g., a SARS-CoV-2 infection such as COVID-19) to treat the mammal.

As described herein, selected SARS-CoV-2 polypeptides can induce broad recall immune responses against SARS-CoV-2. In an aspect, the present disclosure provides selected SARS-CoV-2 polypeptides that can induce broad recall immune responses against SARS-CoV-2 polypeptides. In an aspect, the present disclosure provides selected SARS-CoV-2 polypeptides that can induce broad recall immune responses against SARS-CoV-2 polypeptides from PBMCs of convalescent COVID-19 individuals. Having the ability to induce broad recall immune responses using selected SARS-CoV-2 polypeptides can enable the development of peptide-based vaccines that are inexpensive, can be rapidly produced, require little or no cold chain, have extended stability, and are not associated with contraindications.

In general, one aspect of this disclosure provides substantially pure polypeptides consisting essentially of or consisting of the amino acid sequence set forth in any one of SEQ ID NOs:1-87.

In another aspect, this disclosure provides compositions comprising a substantially pure polypeptide consisting essentially of or consisting of the amino acid sequence set forth in any one of SEQ ID NOs:1-87. The composition can include a polypeptide consisting of the amino acid sequence set forth in SEQ ID NO:1, a polypeptide consisting of the amino acid sequence set forth in SEQ ID NO:5, a polypeptide consisting of the amino acid sequence set forth in SEQ ID NO:13, a polypeptide consisting of the amino acid sequence set forth in SEQ ID NO:15, a polypeptide consisting of the amino acid sequence set forth in SEQ ID NO:37, and a polypeptide consisting of the amino acid sequence set forth in SEQ ID NO:40. The composition can include a polypeptide consisting of the amino acid sequence set forth in SEQ ID NO:1, a polypeptide consisting of the amino acid sequence set forth in SEQ ID NO:9, a polypeptide consisting of the amino acid sequence set forth in SEQ ID NO:12, a polypeptide consisting of the amino acid sequence set forth in SEQ ID NO:18, a polypeptide consisting of the amino acid sequence set forth in SEQ ID NO:21, and a polypeptide consisting of the amino acid sequence set forth in SEQ ID NO:46. The composition can include a polypeptide consisting of the amino acid sequence set forth in SEQ ID NO:12, a polypeptide consisting of the amino acid sequence set forth in SEQ ID NO:14, a polypeptide consisting of the amino acid sequence set forth in SEQ ID NO:25, a polypeptide consisting of the amino acid sequence set forth in SEQ ID NO:27, a polypeptide consisting of the amino acid sequence set forth in SEQ ID NO:44, and a polypeptide consisting of the amino acid sequence set forth in SEQ ID NO:45. The composition can include a polypeptide consisting of the amino acid sequence set forth in SEQ ID NO:3, a polypeptide consisting of the amino acid sequence set forth in SEQ ID NO:16, a polypeptide consisting of the amino acid sequence set forth in SEQ ID NO:19, a polypeptide consisting of the amino acid sequence set forth in SEQ ID NO:28, a polypeptide consisting of the amino acid sequence set forth in SEQ ID NO:31, and a polypeptide consisting of the amino acid sequence set forth in SEQ ID NO:37. The composition can include a polypeptide consisting of the amino acid sequence set forth in SEQ ID NO:2, a polypeptide consisting of the amino acid sequence set forth in SEQ ID NO:9, a polypeptide consisting of the amino acid sequence set forth in SEQ ID NO:17, a polypeptide consisting of the amino acid sequence set forth in SEQ ID NO:24, a polypeptide consisting of the amino acid sequence set forth in SEQ ID NO:27, a polypeptide consisting of the amino acid sequence set forth in SEQ ID NO:39, and a polypeptide consisting of the amino acid sequence set forth in SEQ ID NO:43. The composition can include a polypeptide consisting of the amino acid sequence set forth in SEQ ID NO:1, a polypeptide consisting of the amino acid sequence set forth in SEQ ID NO:2, a polypeptide consisting of the amino acid sequence set forth in SEQ ID NO:8, a polypeptide consisting of the amino acid sequence set forth in SEQ ID NO:10, a polypeptide consisting of the amino acid sequence set forth in SEQ ID NO:11, a polypeptide consisting of the amino acid sequence set forth in SEQ ID NO:14, a polypeptide consisting of the amino acid sequence set forth in SEQ ID NO:18, and a polypeptide consisting of the amino acid sequence set forth in SEQ ID NO:19. The composition can include a polypeptide consisting of the amino acid sequence set forth in SEQ ID NO:12, a polypeptide consisting of the amino acid sequence set forth in SEQ ID NO:13, a polypeptide consisting of the amino acid sequence set forth in SEQ ID NO:25, a polypeptide consisting of the amino acid sequence set forth in SEQ ID NO:43, a polypeptide consisting of the amino acid sequence set forth in SEQ ID NO:53, a polypeptide consisting of the amino acid sequence set forth in SEQ ID NO:38, a polypeptide consisting of the amino acid sequence set forth in SEQ ID NO:15, a polypeptide consisting of the amino acid sequence set forth in SEQ ID NO:39, a polypeptide consisting of the amino acid sequence set forth in SEQ ID NO:34, and a polypeptide consisting of the amino acid sequence set forth in SEQ ID NO:18. The composition can include a polypeptide consisting of the amino acid sequence set forth in SEQ ID NO:68, a polypeptide consisting of the amino acid sequence set forth in SEQ ID NO:69, a polypeptide consisting of the amino acid sequence set forth in SEQ ID NO:70, a polypeptide consisting of the amino acid sequence set forth in SEQ ID NO:71, a polypeptide consisting of the amino acid sequence set forth in SEQ ID NO:72, a polypeptide consisting of the amino acid sequence set forth in SEQ ID NO:73, a polypeptide consisting of the amino acid sequence set forth in SEQ ID NO:74, a polypeptide consisting of the amino acid sequence set forth in SEQ ID NO:75, a polypeptide consisting of the amino acid sequence set forth in SEQ ID NO:76, a polypeptide consisting of the amino acid sequence set forth in SEQ ID NO:77, and a polypeptide consisting of the amino acid sequence set forth in SEQ ID NO:78. The composition can include a polypeptide consisting of the amino acid sequence set forth in SEQ ID NO:68, a polypeptide consisting of the amino acid sequence set forth in SEQ ID NO:69, a polypeptide consisting of the amino acid sequence set forth in SEQ ID NO:70, a polypeptide consisting of the amino acid sequence set forth in SEQ ID NO:71, a polypeptide consisting of the amino acid sequence set forth in SEQ ID NO:73, a polypeptide consisting of the amino acid sequence set forth in SEQ ID NO:74, a polypeptide consisting of the amino acid sequence set forth in SEQ ID NO:75, a polypeptide consisting of the amino acid sequence set forth in SEQ ID NO:76, a polypeptide consisting of the amino acid sequence set forth in SEQ ID NO:77, and a polypeptide consisting of the amino acid sequence set forth in SEQ ID NO:78. The composition can include one or more of an adjuvant or an immunostimulatory molecule. The adjuvant or immunostimulatory molecule can be a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles, or GLA. In an aspect, one or more adjuvants or immunostimulatory molecules is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA. In an aspect, one or more adjuvants or immunostimulatory molecules is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, retinoic acid-inducible gene I (RIG-I), lipid nanoparticles (e.g., LION), and GLA. In an aspect, the polypeptides disclosed herein are linked to poly(lactic-co-glycolic acid) (PLGA) nanoparticles. In an aspect, the polypeptides are attached to one or more virus-like particles (VLP). In an aspect, the VLPs are made from viruses selected from the group consisting of Parvoviridae, Retroviridae, Flaviviridae, Paramyxoviridae and bacteriophages. In an aspect, the VLPs are made from Q-beta bacteriophage In another aspect, this disclosure provides compositions including at least two polypeptides, where each of the at least two polypeptides is a polypeptide consisting essentially of or consisting of the amino acid sequence set forth in any one of SEQ ID NOs:1-87. The composition can include a polypeptide consisting of the amino acid sequence set forth in SEQ ID NO:1, a polypeptide consisting of the amino acid sequence set forth in SEQ ID NO:5, a polypeptide consisting of the amino acid sequence set forth in SEQ ID NO:13, a polypeptide consisting of the amino acid sequence set forth in SEQ ID NO:15, a polypeptide consisting of the amino acid sequence set forth in SEQ ID NO:37, and a polypeptide consisting of the amino acid sequence set forth in SEQ ID NO:40. The composition can include a polypeptide consisting of the amino acid sequence set forth in SEQ ID NO:1, a polypeptide consisting of the amino acid sequence set forth in SEQ ID NO:9, a polypeptide consisting of the amino acid sequence set forth in SEQ ID NO:12, a polypeptide consisting of the amino acid sequence set forth in SEQ ID NO:18, a polypeptide consisting of the amino acid sequence set forth in SEQ ID NO:21, and a polypeptide consisting of the amino acid sequence set forth in SEQ ID NO:46. The composition can include a polypeptide consisting of the amino acid sequence set forth in SEQ ID NO:12, a polypeptide consisting of the amino acid sequence set forth in SEQ ID NO:14, a polypeptide consisting of the amino acid sequence set forth in SEQ ID NO:25, a polypeptide consisting of the amino acid sequence set forth in SEQ ID NO:27, a polypeptide consisting of the amino acid sequence set forth in SEQ ID NO:44, and a polypeptide consisting of the amino acid sequence set forth in SEQ ID NO:45. The composition can include a polypeptide consisting of the amino acid sequence set forth in SEQ ID NO:3, a polypeptide consisting of the amino acid sequence set forth in SEQ ID NO:16, a polypeptide consisting of the amino acid sequence set forth in SEQ ID NO:19, a polypeptide consisting of the amino acid sequence set forth in SEQ ID NO:28, a polypeptide consisting of the amino acid sequence set forth in SEQ ID NO:31, and a polypeptide consisting of the amino acid sequence set forth in SEQ ID NO:37. The composition can include a polypeptide consisting of the amino acid sequence set forth in SEQ ID NO:2, a polypeptide consisting of the amino acid sequence set forth in SEQ ID NO:9, a polypeptide consisting of the amino acid sequence set forth in SEQ ID NO:17, a polypeptide consisting of the amino acid sequence set forth in SEQ ID NO:24, a polypeptide consisting of the amino acid sequence set forth in SEQ ID NO:27, a polypeptide consisting of the amino acid sequence set forth in SEQ ID NO:39, and a polypeptide consisting of the amino acid sequence set forth in SEQ ID NO:43. The composition can include a polypeptide consisting of the amino acid sequence set forth in SEQ ID NO:1, a polypeptide consisting of the amino acid sequence set forth in SEQ ID NO:2, a polypeptide consisting of the amino acid sequence set forth in SEQ ID NO:8, a polypeptide consisting of the amino acid sequence set forth in SEQ ID NO:10, a polypeptide consisting of the amino acid sequence set forth in SEQ ID NO:11, a polypeptide consisting of the amino acid sequence set forth in SEQ ID NO:14, a polypeptide consisting of the amino acid sequence set forth in SEQ ID NO:18, and a polypeptide consisting of the amino acid sequence set forth in SEQ ID NO:19. The composition can include a polypeptide consisting of the amino acid sequence set forth in SEQ ID NO:12, a polypeptide consisting of the amino acid sequence set forth in SEQ ID NO:13, a polypeptide consisting of the amino acid sequence set forth in SEQ ID NO:25, a polypeptide consisting of the amino acid sequence set forth in SEQ ID NO:43, a polypeptide consisting of the amino acid sequence set forth in SEQ ID NO:53, a polypeptide consisting of the amino acid sequence set forth in SEQ ID NO:38, a polypeptide consisting of the amino acid sequence set forth in SEQ ID NO:15, a polypeptide consisting of the amino acid sequence set forth in SEQ ID NO:39, a polypeptide consisting of the amino acid sequence set forth in SEQ ID NO:34, and a polypeptide consisting of the amino acid sequence set forth in SEQ ID NO:18. The composition can include a polypeptide consisting of the amino acid sequence set forth in SEQ ID NO:68, a polypeptide consisting of the amino acid sequence set forth in SEQ ID NO:69, a polypeptide consisting of the amino acid sequence set forth in SEQ ID NO:70, a polypeptide consisting of the amino acid sequence set forth in SEQ ID NO:71, a polypeptide consisting of the amino acid sequence set forth in SEQ ID NO:72, a polypeptide consisting of the amino acid sequence set forth in SEQ ID NO:73, a polypeptide consisting of the amino acid sequence set forth in SEQ ID NO:74, a polypeptide consisting of the amino acid sequence set forth in SEQ ID NO:75, a polypeptide consisting of the amino acid sequence set forth in SEQ ID NO:76, a polypeptide consisting of the amino acid sequence set forth in SEQ ID NO:77, and a polypeptide consisting of the amino acid sequence set forth in SEQ ID NO:78. The composition can include a polypeptide consisting of the amino acid sequence set forth in SEQ ID NO:68, a polypeptide consisting of the amino acid sequence set forth in SEQ ID NO:69, a polypeptide consisting of the amino acid sequence set forth in SEQ ID NO:70, a polypeptide consisting of the amino acid sequence set forth in SEQ ID NO:71, a polypeptide consisting of the amino acid sequence set forth in SEQ ID NO:73, a polypeptide consisting of the amino acid sequence set forth in SEQ ID NO:74, a polypeptide consisting of the amino acid sequence set forth in SEQ ID NO:75, a polypeptide consisting of the amino acid sequence set forth in SEQ ID NO:76, a polypeptide consisting of the amino acid sequence set forth in SEQ ID NO:77, and a polypeptide consisting of the amino acid sequence set forth in SEQ ID NO:78. The composition can include an adjuvant or an immunostimulatory molecule. The composition can include one or more of an adjuvant or an immunostimulatory molecule. The adjuvant or immunostimulatory molecule can be a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles, or GLA. In an aspect, one or more adjuvants or immunostimulatory molecules is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA. In an aspect, one or more adjuvants or immunostimulatory molecules is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, retinoic acid-inducible gene I (RIG-I), lipid nanoparticles (e.g., LION), and GLA. In an aspect, the polypeptides disclosed herein are linked to poly(lactic-co-glycolic acid) (PLGA) nanoparticles. In an aspect, the polypeptides are attached to one or more virus-like particles (VLP). In an aspect, the polypeptides are attached to one or more virus-like particles (VLP). IN an aspect, the VLPs are made from viruses selected from the group consisting of Parvoviridae, Retroviridae, Flaviviridae, Paramyxoviridae and bacteriophages. In an aspect, the VLPs are made from Q-beta bacteriophage.

In another aspect, this disclosure provides a composition comprising nucleic acids encoding a polypeptide consisting essentially of or consisting of the amino acid sequence set forth in any one of SEQ ID NOs:1-87. The composition can include a polypeptide consisting of the amino acid sequence set forth in SEQ ID NO:1, a polypeptide consisting of the amino acid sequence set forth in SEQ ID NO:5, a polypeptide consisting of the amino acid sequence set forth in SEQ ID NO:13, a polypeptide consisting of the amino acid sequence set forth in SEQ ID NO:15, a polypeptide consisting of the amino acid sequence set forth in SEQ ID NO:37, and a polypeptide consisting of the amino acid sequence set forth in SEQ ID NO:40. The composition can include a polypeptide consisting of the amino acid sequence set forth in SEQ ID NO:1, a polypeptide consisting of the amino acid sequence set forth in SEQ ID NO:9, a polypeptide consisting of the amino acid sequence set forth in SEQ ID NO:12, a polypeptide consisting of the amino acid sequence set forth in SEQ ID NO:18, a polypeptide consisting of the amino acid sequence set forth in SEQ ID NO:21, and a polypeptide consisting of the amino acid sequence set forth in SEQ ID NO:46. The composition can include a polypeptide consisting of the amino acid sequence set forth in SEQ ID NO:12, a polypeptide consisting of the amino acid sequence set forth in SEQ ID NO:14, a polypeptide consisting of the amino acid sequence set forth in SEQ ID NO:25, a polypeptide consisting of the amino acid sequence set forth in SEQ ID NO:27, a polypeptide consisting of the amino acid sequence set forth in SEQ ID NO:44, and a polypeptide consisting of the amino acid sequence set forth in SEQ ID NO:45. The composition can include a polypeptide consisting of the amino acid sequence set forth in SEQ ID NO:3, a polypeptide consisting of the amino acid sequence set forth in SEQ ID NO:16, a polypeptide consisting of the amino acid sequence set forth in SEQ ID NO:19, a polypeptide consisting of the amino acid sequence set forth in SEQ ID NO:28, a polypeptide consisting of the amino acid sequence set forth in SEQ ID NO:31, and a polypeptide consisting of the amino acid sequence set forth in SEQ ID NO:37. The composition can include a polypeptide consisting of the amino acid sequence set forth in SEQ ID NO:2, a polypeptide consisting of the amino acid sequence set forth in SEQ ID NO:9, a polypeptide consisting of the amino acid sequence set forth in SEQ ID NO:17, a polypeptide consisting of the amino acid sequence set forth in SEQ ID NO:24, a polypeptide consisting of the amino acid sequence set forth in SEQ ID NO:27, a polypeptide consisting of the amino acid sequence set forth in SEQ ID NO:39, and a polypeptide consisting of the amino acid sequence set forth in SEQ ID NO:43. The composition can include a polypeptide consisting of the amino acid sequence set forth in SEQ ID NO:1, a polypeptide consisting of the amino acid sequence set forth in SEQ ID NO:2, a polypeptide consisting of the amino acid sequence set forth in SEQ ID NO:8, a polypeptide consisting of the amino acid sequence set forth in SEQ ID NO:10, a polypeptide consisting of the amino acid sequence set forth in SEQ ID NO:11, a polypeptide consisting of the amino acid sequence set forth in SEQ ID NO:14, a polypeptide consisting of the amino acid sequence set forth in SEQ ID NO:18, and a polypeptide consisting of the amino acid sequence set forth in SEQ ID NO:19. The composition can include a polypeptide consisting of the amino acid sequence set forth in SEQ ID NO:12, a polypeptide consisting of the amino acid sequence set forth in SEQ ID NO:13, a polypeptide consisting of the amino acid sequence set forth in SEQ ID NO:25, a polypeptide consisting of the amino acid sequence set forth in SEQ ID NO:43, a polypeptide consisting of the amino acid sequence set forth in SEQ ID NO:53, a polypeptide consisting of the amino acid sequence set forth in SEQ ID NO:38, a polypeptide consisting of the amino acid sequence set forth in SEQ ID NO:15, a polypeptide consisting of the amino acid sequence set forth in SEQ ID NO:39, a polypeptide consisting of the amino acid sequence set forth in SEQ ID NO:34, and a polypeptide consisting of the amino acid sequence set forth in SEQ ID NO:18. The composition can include a polypeptide consisting of the amino acid sequence set forth in SEQ ID NO:68, a polypeptide consisting of the amino acid sequence set forth in SEQ ID NO:69, a polypeptide consisting of the amino acid sequence set forth in SEQ ID NO:70, a polypeptide consisting of the amino acid sequence set forth in SEQ ID NO:71, a polypeptide consisting of the amino acid sequence set forth in SEQ ID NO:72, a polypeptide consisting of the amino acid sequence set forth in SEQ ID NO:73, a polypeptide consisting of the amino acid sequence set forth in SEQ ID NO:74, a polypeptide consisting of the amino acid sequence set forth in SEQ ID NO:75, a polypeptide consisting of the amino acid sequence set forth in SEQ ID NO:76, a polypeptide consisting of the amino acid sequence set forth in SEQ ID NO:77, and a polypeptide consisting of the amino acid sequence set forth in SEQ ID NO:78. The composition can include a polypeptide consisting of the amino acid sequence set forth in SEQ ID NO:68, a polypeptide consisting of the amino acid sequence set forth in SEQ ID NO:69, a polypeptide consisting of the amino acid sequence set forth in SEQ ID NO:70, a polypeptide consisting of the amino acid sequence set forth in SEQ ID NO:71, a polypeptide consisting of the amino acid sequence set forth in SEQ ID NO:73, a polypeptide consisting of the amino acid sequence set forth in SEQ ID NO:74, a polypeptide consisting of the amino acid sequence set forth in SEQ ID NO:75, a polypeptide consisting of the amino acid sequence set forth in SEQ ID NO:76, a polypeptide consisting of the amino acid sequence set forth in SEQ ID NO:77, and a polypeptide consisting of the amino acid sequence set forth in SEQ ID NO:78. The composition can include an adjuvant or an immunostimulatory molecule. The composition can include one or more of an adjuvant or an immunostimulatory molecule. The adjuvant or immunostimulatory molecule can be a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AIT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles, or GLA. In an aspect, one or more adjuvants or immunostimulatory molecules is selected from the group consisting of a water in oil emulsion (e.g., Montanide 720, Montanide 51), a CpG oligonucleotide motif, toll-like receptor 4 (TLR4) agonists (e.g., MiT4, EmT4, AIT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA. In an aspect, one or more adjuvants or immunostimulatory molecules is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, retinoic acid-inducible gene I (RIG-I), lipid nanoparticles (e.g., LION), and GLA. In an aspect, the polypeptides disclosed herein are linked to poly(lactic-co-glycolic acid) (PLGA) nanoparticles. In an aspect, the polypeptides are attached to one or more virus-like particles (VLP). In an aspect, the polypeptides are attached to one or more virus-like particles (VLP). In an aspect, the VLPs are made from viruses selected from the group consisting of Parvoviridae, Retroviridae, Flaviviridae, Paramyxoviridae and bacteriophages. In an aspect, the VLPs are made from Q-beta bacteriophage. The nucleic acid can be in the form of a non-viral vector. The non-viral vector can be an expression plasmid. The nucleic acid can be in the form of a viral vector. The viral vector can be a vector based on an adenoviruses, a vector based on an adeno-associated virus (AAV), a vector based on an retrovirus, a vector based on an lentivirus, a vector based on a measles virus, a vector based on a vesicular stomatitis virus, and a vector based on vaccinia virus.

In another aspect, this disclosure provides nucleic acid encoding at least two polypeptides, where each of the at least two polypeptides is a polypeptide consisting essentially of or consisting of the amino acid sequence set forth in any one of SEQ ID NOs:1-87. The composition can include a polypeptide consisting of the amino acid sequence set forth in SEQ ID NO:1, a polypeptide consisting of the amino acid sequence set forth in SEQ ID NO:5, a polypeptide consisting of the amino acid sequence set forth in SEQ ID NO:13, a polypeptide consisting of the amino acid sequence set forth in SEQ ID NO:15, a polypeptide consisting of the amino acid sequence set forth in SEQ ID NO:37, and a polypeptide consisting of the amino acid sequence set forth in SEQ ID NO:40. The composition can include a polypeptide consisting of the amino acid sequence set forth in SEQ ID NO:1, a polypeptide consisting of the amino acid sequence set forth in SEQ ID NO:9, a polypeptide consisting of the amino acid sequence set forth in SEQ ID NO:12, a polypeptide consisting of the amino acid sequence set forth in SEQ ID NO:18, a polypeptide consisting of the amino acid sequence set forth in SEQ ID NO:21, and a polypeptide consisting of the amino acid sequence set forth in SEQ ID NO:46. The composition can include a polypeptide consisting of the amino acid sequence set forth in SEQ ID NO:12, a polypeptide consisting of the amino acid sequence set forth in SEQ ID NO:14, a polypeptide consisting of the amino acid sequence set forth in SEQ ID NO:25, a polypeptide consisting of the amino acid sequence set forth in SEQ ID NO:27, a polypeptide consisting of the amino acid sequence set forth in SEQ ID NO:44, and a polypeptide consisting of the amino acid sequence set forth in SEQ ID NO:45. The composition can include a polypeptide consisting of the amino acid sequence set forth in SEQ ID NO:3, a polypeptide consisting of the amino acid sequence set forth in SEQ ID NO:16, a polypeptide consisting of the amino acid sequence set forth in SEQ ID NO:19, a polypeptide consisting of the amino acid sequence set forth in SEQ ID NO:28, a polypeptide consisting of the amino acid sequence set forth in SEQ ID NO:31, and a polypeptide consisting of the amino acid sequence set forth in SEQ ID NO:37. The composition can include a polypeptide consisting of the amino acid sequence set forth in SEQ ID NO:2, a polypeptide consisting of the amino acid sequence set forth in SEQ ID NO:9, a polypeptide consisting of the amino acid sequence set forth in SEQ ID NO:17, a polypeptide consisting of the amino acid sequence set forth in SEQ ID NO:24, a polypeptide consisting of the amino acid sequence set forth in SEQ ID NO:27, a polypeptide consisting of the amino acid sequence set forth in SEQ ID NO:39, and a polypeptide consisting of the amino acid sequence set forth in SEQ ID NO:43. The composition can include a polypeptide consisting of the amino acid sequence set forth in SEQ ID NO:1, a polypeptide consisting of the amino acid sequence set forth in SEQ ID NO:2, a polypeptide consisting of the amino acid sequence set forth in SEQ ID NO:8, a polypeptide consisting of the amino acid sequence set forth in SEQ ID NO:10, a polypeptide consisting of the amino acid sequence set forth in SEQ ID NO:11, a polypeptide consisting of the amino acid sequence set forth in SEQ ID NO:14, a polypeptide consisting of the amino acid sequence set forth in SEQ ID NO:18, and a polypeptide consisting of the amino acid sequence set forth in SEQ ID NO:19. The composition can include a polypeptide consisting of the amino acid sequence set forth in SEQ ID NO:12, a polypeptide consisting of the amino acid sequence set forth in SEQ ID NO:13, a polypeptide consisting of the amino acid sequence set forth in SEQ ID NO:25, a polypeptide consisting of the amino acid sequence set forth in SEQ ID NO:43, a polypeptide consisting of the amino acid sequence set forth in SEQ ID NO:53, a polypeptide consisting of the amino acid sequence set forth in SEQ ID NO:38, a polypeptide consisting of the amino acid sequence set forth in SEQ ID NO:15, a polypeptide consisting of the amino acid sequence set forth in SEQ ID NO:39, a polypeptide consisting of the amino acid sequence set forth in SEQ ID NO:34, and a polypeptide consisting of the amino acid sequence set forth in SEQ ID NO:18. The composition can include a polypeptide consisting of the amino acid sequence set forth in SEQ ID NO:68, a polypeptide consisting of the amino acid sequence set forth in SEQ ID NO:69, a polypeptide consisting of the amino acid sequence set forth in SEQ ID NO:70, a polypeptide consisting of the amino acid sequence set forth in SEQ ID NO:71, a polypeptide consisting of the amino acid sequence set forth in SEQ ID NO:72, a polypeptide consisting of the amino acid sequence set forth in SEQ ID NO:73, a polypeptide consisting of the amino acid sequence set forth in SEQ ID NO:74, a polypeptide consisting of the amino acid sequence set forth in SEQ ID NO:75, a polypeptide consisting of the amino acid sequence set forth in SEQ ID NO:76, a polypeptide consisting of the amino acid sequence set forth in SEQ ID NO:77, and a polypeptide consisting of the amino acid sequence set forth in SEQ ID NO:78. The composition can include a polypeptide consisting of the amino acid sequence set forth in SEQ ID NO:68, a polypeptide consisting of the amino acid sequence set forth in SEQ ID NO:69, a polypeptide consisting of the amino acid sequence set forth in SEQ ID NO:70, a polypeptide consisting of the amino acid sequence set forth in SEQ ID NO:71, a polypeptide consisting of the amino acid sequence set forth in SEQ ID NO:73, a polypeptide consisting of the amino acid sequence set forth in SEQ ID NO:74, a polypeptide consisting of the amino acid sequence set forth in SEQ ID NO:75, a polypeptide consisting of the amino acid sequence set forth in SEQ ID NO:76, a polypeptide consisting of the amino acid sequence set forth in SEQ ID NO:77, and a polypeptide consisting of the amino acid sequence set forth in SEQ ID NO:78. The composition can include an adjuvant or an immunostimulatory molecule. The composition can include one or more of an adjuvant or an immunostimulatory molecule. In an aspect, one or more adjuvants or immunostimulatory molecules can be a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles, and GLA. In an aspect, one or more adjuvants or immunostimulatory molecules is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA. In an aspect, one or more adjuvants or immunostimulatory molecules is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, retinoic acid-inducible gene I (RIG-I), lipid nanoparticles (e.g., LION), and GLA. In an aspect, the polypeptides disclosed herein are linked to poly(lactic-co-glycolic acid) (PLGA) nanoparticles. In an aspect, the polypeptides are attached to one or more virus-like particles (VLP). The nucleic acid can be in the form of a non-viral vector. The non-viral vector can be an expression plasmid. The nucleic acid can be in the form of a viral vector. The viral vector can be a vector based on an adenoviruses, a vector based on an adeno-associated virus (AAV), a vector based on an retrovirus, a vector based on an lentivirus, a vector based on a measles virus, a vector based on a vesicular stomatitis virus, and a vector based on vaccinia virus.

In another aspect, this disclosure provides methods for increasing an immune response against a coronavirus in a mammal. The methods can comprise, or consist essentially of, administering to a mammal a composition including a polypeptide consisting essentially of or consisting of the amino acid sequence set forth in any one of SEQ ID NOs:1-87 or nucleic acid encoding the polypeptide. The mammal can be a human. The coronavirus can be a SARS-CoV-2. The composition can include an adjuvant or an immunostimulatory molecule. The composition can include one or more of an adjuvant or an immunostimulatory molecule. In an aspect, one or more adjuvants or immunostimulatory molecules is selected from a group consisting of a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles, and GLA. In an aspect, adjuvant or immunostimulatory molecule is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA. In an aspect, one or more adjuvants or immunostimulatory molecules is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, retinoic acid-inducible gene I (RIG-I), lipid nanoparticles (e.g., LION), and GLA. In an aspect, the polypeptides disclosed herein are linked to poly(lactic-co-glycolic acid) (PLGA) nanoparticles. In an aspect, the polypeptides are attached to one or more virus-like particles (VLP). In an aspect, at least two doses of the composition are administered. In an aspect, two doses of the composition are administered. In an aspect, the polypeptide is presented on one or more virus-like particles (VLP). In an aspect, the VLPs are made from viruses selected from the group consisting of Parvoviridae, Retroviridae, Flaviviridae, Paramyxoviridae and bacteriophages. In an aspect, the VLPs are made from Q-beta bacteriophage.

In another aspect, this disclosure provides methods for treating a mammal at risk of developing a coronavirus infection. The methods can include, or consist essentially of, administering to a mammal at risk of developing a coronavirus infection a composition including a polypeptide consisting essentially of or consisting of the amino acid sequence set forth in any one of SEQ ID NOs:1-87 or nucleic acid encoding the polypeptide. The mammal can be a human. The coronavirus infection can be COVID-19. The composition can include an adjuvant or an immunostimulatory molecule. The composition can include one or more of an adjuvant or an immunostimulatory molecule. In an aspect, one or more adjuvants or immunostimulatory molecules can be a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles, and GLA. In an aspect, adjuvant or immunostimulatory molecule is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA. In an aspect, one or more adjuvants or immunostimulatory molecules is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, retinoic acid-inducible gene I (RIG-I), lipid nanoparticles (e.g., LION), and GLA. In an aspect, the polypeptides disclosed herein are linked to poly(lactic-co-glycolic acid) (PLGA) nanoparticles. In an aspect, the polypeptides are attached to one or more virus-like particles (VLP). In an aspect, at least two doses of the composition are administered. In an aspect, two doses of the composition are administered. In an aspect, the polypeptide is presented on one or more virus-like particles (VLP). In an aspect, the VLPs are made from viruses selected from the group consisting of Parvoviridae, Retroviridae, Flaviviridae, Paramyxoviridae and bacteriophages. In an aspect, the VLPs are made from Q-beta bacteriophage.

In another aspect, this document features methods for treating a mammal having a coronavirus infection. The methods can include, or consist essentially of, administering to a mammal having a coronavirus infection a composition including a polypeptide consisting essentially of or consisting of the amino acid sequence set forth in any one of SEQ ID NOs:1-87 or nucleic acid encoding the polypeptide. The mammal can be a human. The coronavirus infection can be COVID-19. The composition can include an adjuvant or an immunostimulatory molecule. The composition can include one or more of an adjuvant or an immunostimulatory molecule. In an aspect, one or more adjuvants or immunostimulatory molecules can be a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles, and GLA. In an aspect, one or more adjuvants or immunostimulatory molecules is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA. In an aspect, one or more adjuvants or immunostimulatory molecules is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, retinoic acid-inducible gene I (RIG-I), lipid nanoparticles (e.g., LION), and GLA. In an aspect, the polypeptides disclosed herein are linked to poly(lactic-co-glycolic acid) (PLGA) nanoparticles. In an aspect, the polypeptides are attached to one or more virus-like particles (VLP). In an aspect, at least two doses of the composition are administered. In an aspect, two doses of the composition are administered. In an aspect, the polypeptide is presented on one or more virus-like particles (VLP). In an aspect, the VLPs are made from viruses selected from the group consisting of Parvoviridae, Retroviridae, Flaviviridae, Paramyxoviridae and bacteriophages. In an aspect, the VLPs are made from Q-beta bacteriophage.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

Aspects of the disclosure are herein described, by way of example only, with reference to the accompanying drawings. With specific reference now to the drawings in detail, it is stressed that the particulars shown are by way of example and are for purposes of illustrative discussion of aspects of the disclosure. In this regard, the description and the drawings, considered alone and together, make apparent to those skilled in the art how aspects of the disclosure may be practiced.

Figure 22A:
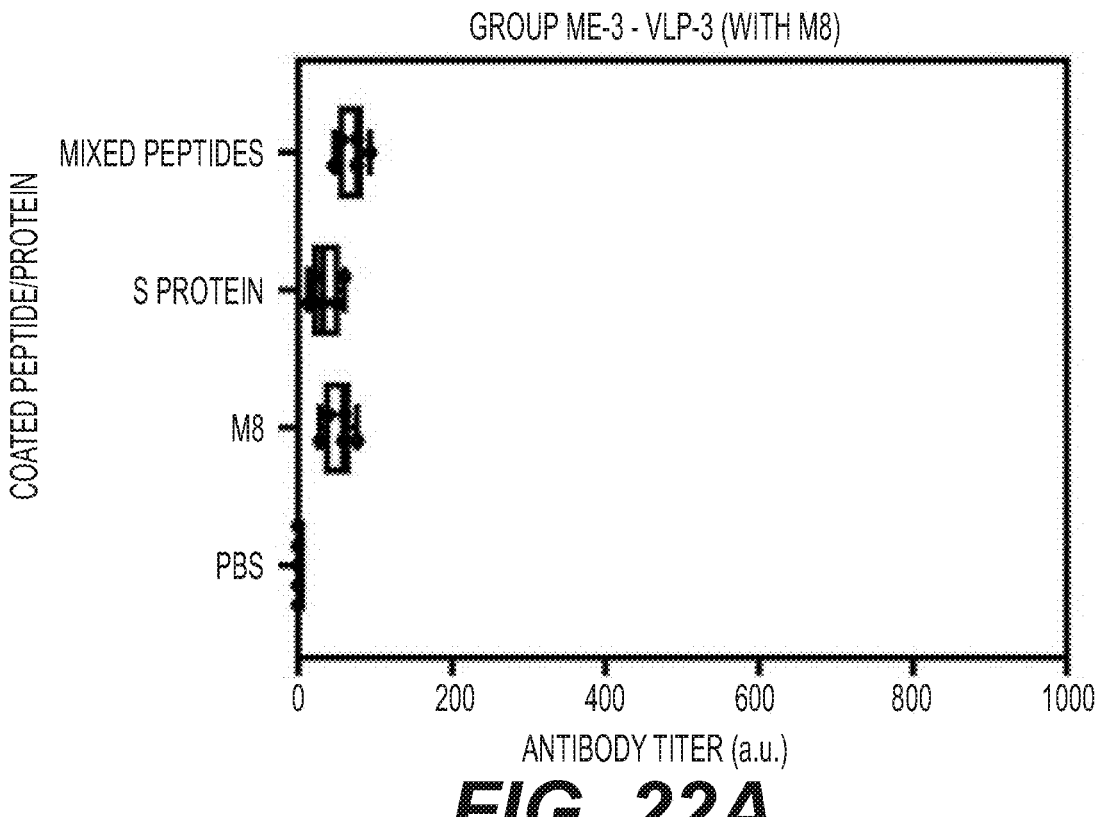
FIG. 22A: Immune responses in mice induced by different long peptides presented on virus-like particles (VLPs), as measured by IgG ELISA.
Figure 22B:
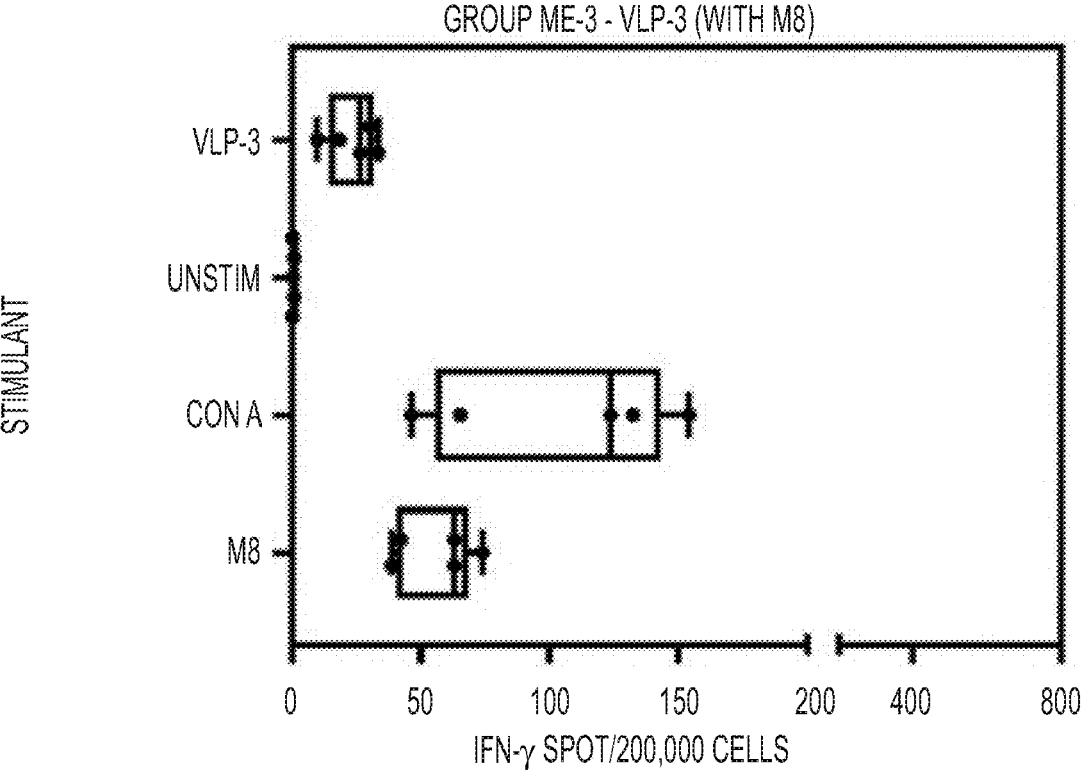
FIG. 22B: Immune responses in mice induced by different long peptides presented on virus-like particles (VLPs), as measured by IFN-γ ELISPOT.
Figure 22C:
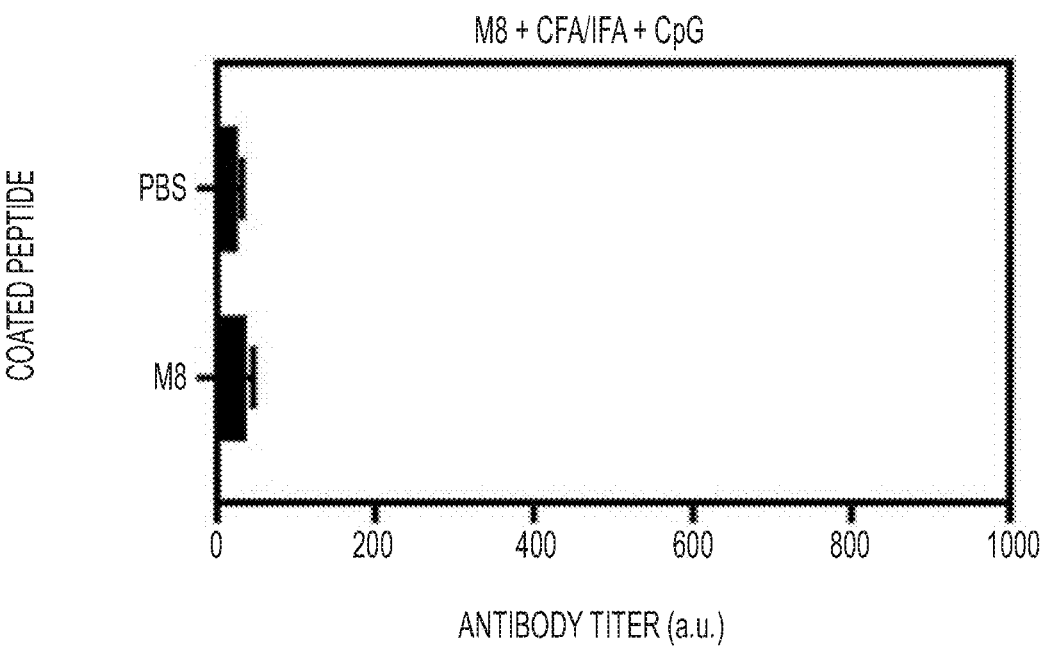

FIG. 22C: Immune responses in mice induced by different long peptides presented on virus-like particles (VLPs), as measured by IgG ELISA.

Figure 22D:
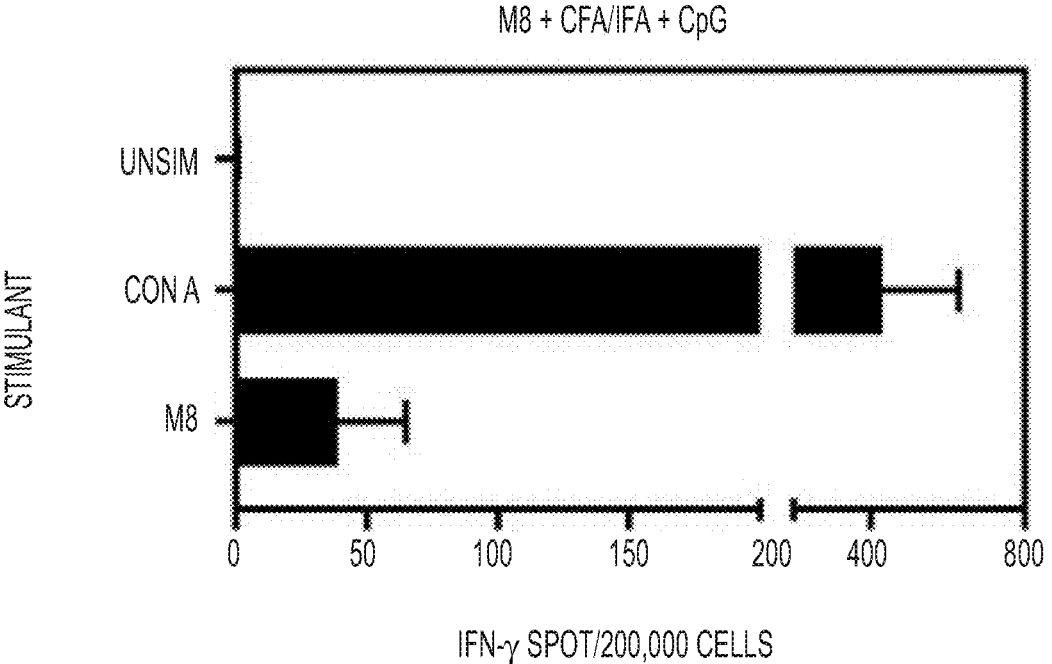

FIG. 22D: Immune responses in mice induced by different long peptides presented on virus-like particles (VLPs), as measured by IFN-γ ELISPOT.

Figure 23A:
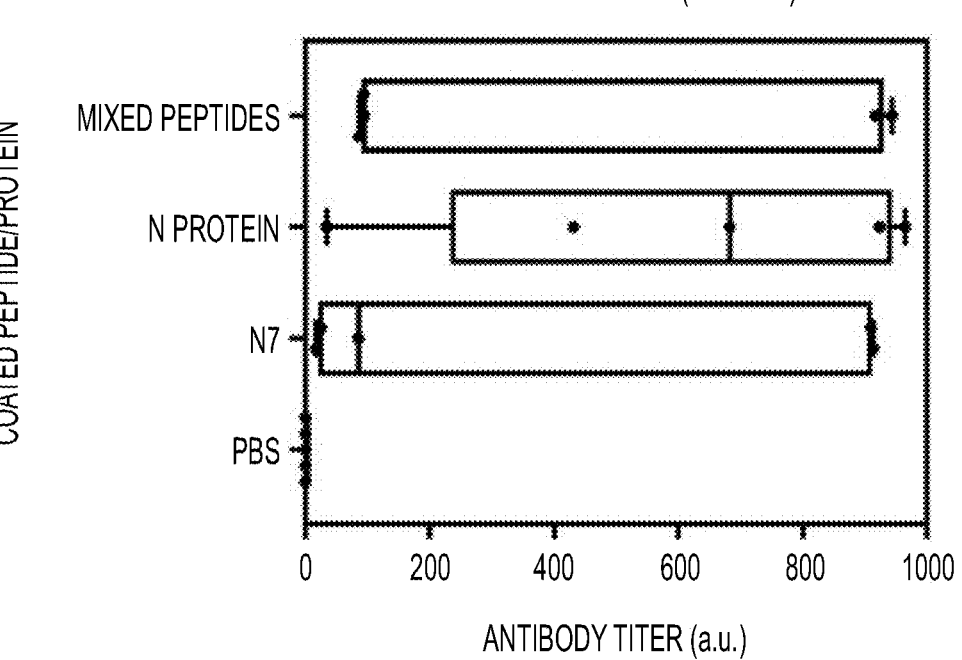

FIG. 23A: Immune responses in mice induced by different long peptides presented on virus-like particles (VLPs), as measured by IgG ELISA.

Figure 23B:
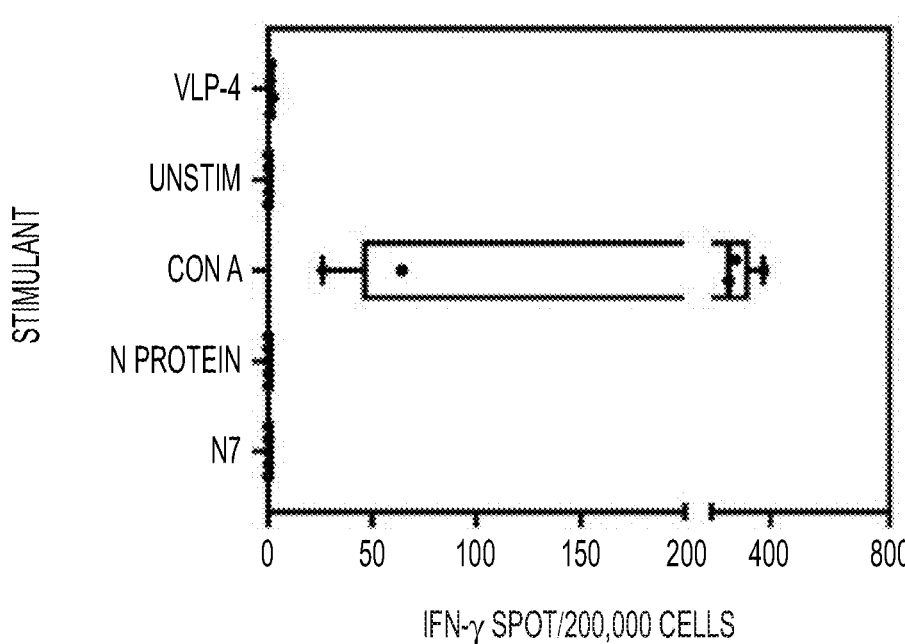

FIG. 23B: Immune responses in mice induced by different long peptides presented on virus-like particles (VLPs), as measured by IFN-γ ELISPOT.

Figure 23C:
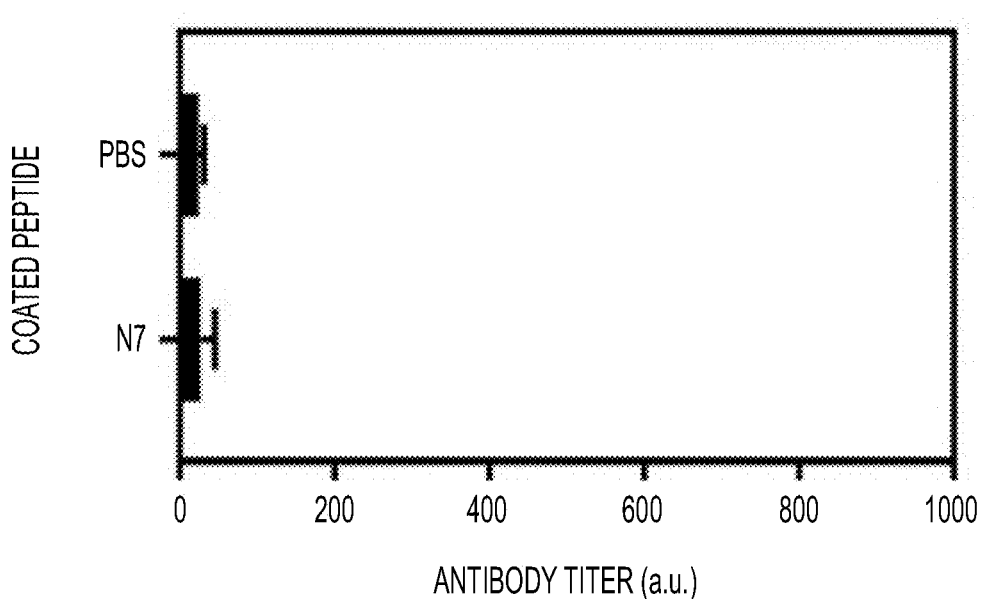

FIG. 23C: Immune responses in mice induced by different long peptides presented on virus-like particles (VLPs), as measured by IgG ELISA.

Figure 23D:
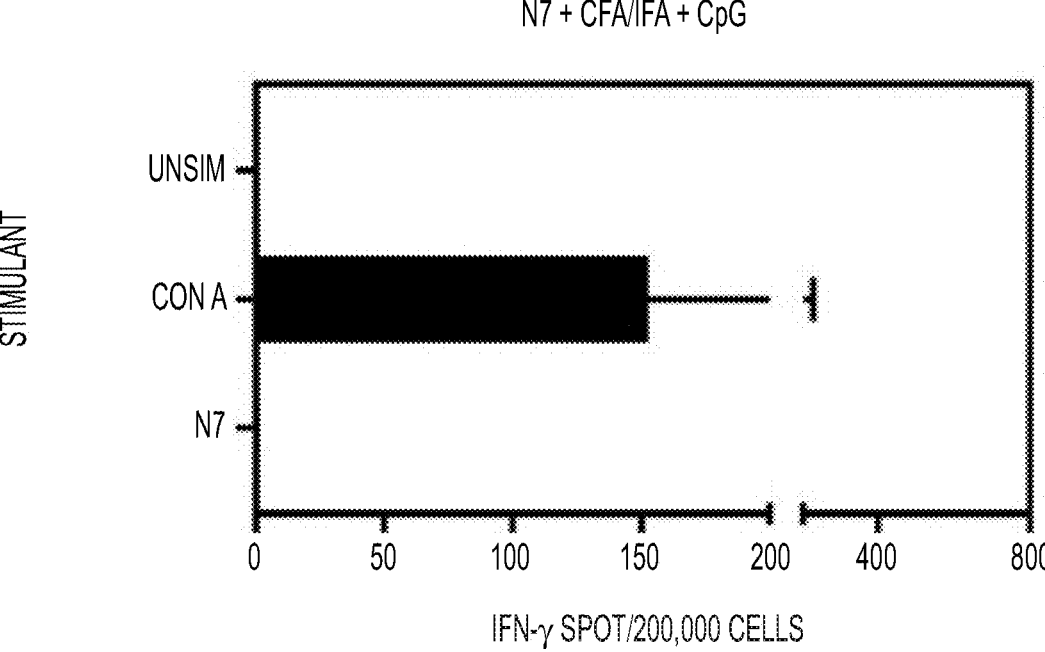

FIG. 23D: Immune responses in mice induced by different long peptides presented on virus-like particles (VLPs), as measured by IFN-γ ELISPOT.

Figure 24A:
Figure 24A:
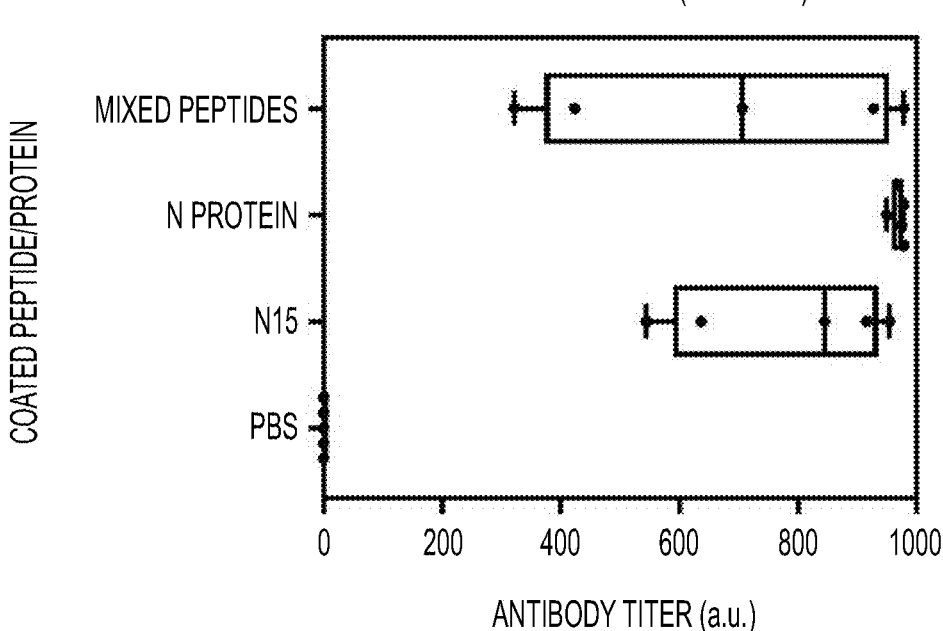

FIG. 24A: Immune responses in mice induced by different long peptides presented on virus-like particles (VLPs), as measured by IgG ELISA.

Figure 24B:
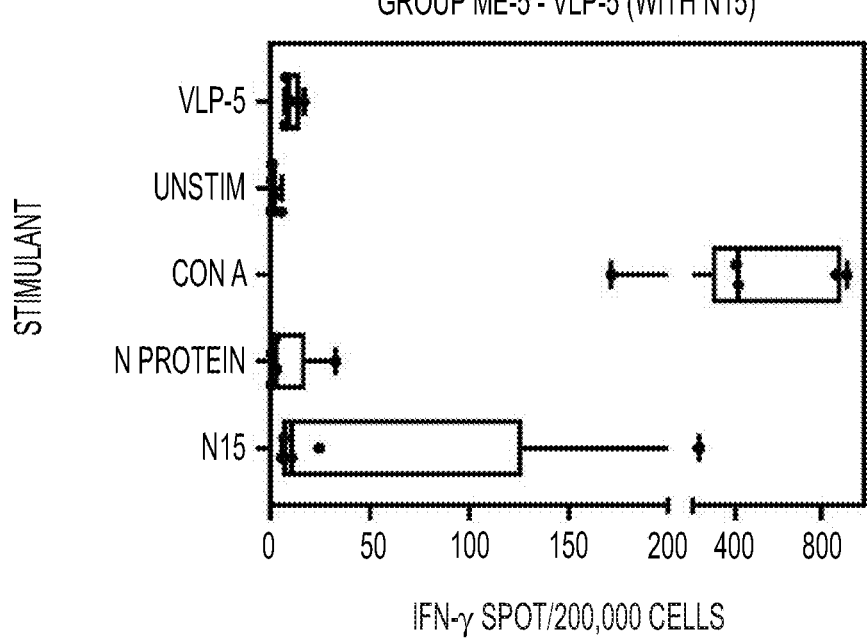

FIG. 24B: Immune responses in mice induced by different long peptides presented on virus-like particles (VLPs), as measured by IFN-γ ELISPOT.

Figure 24C:
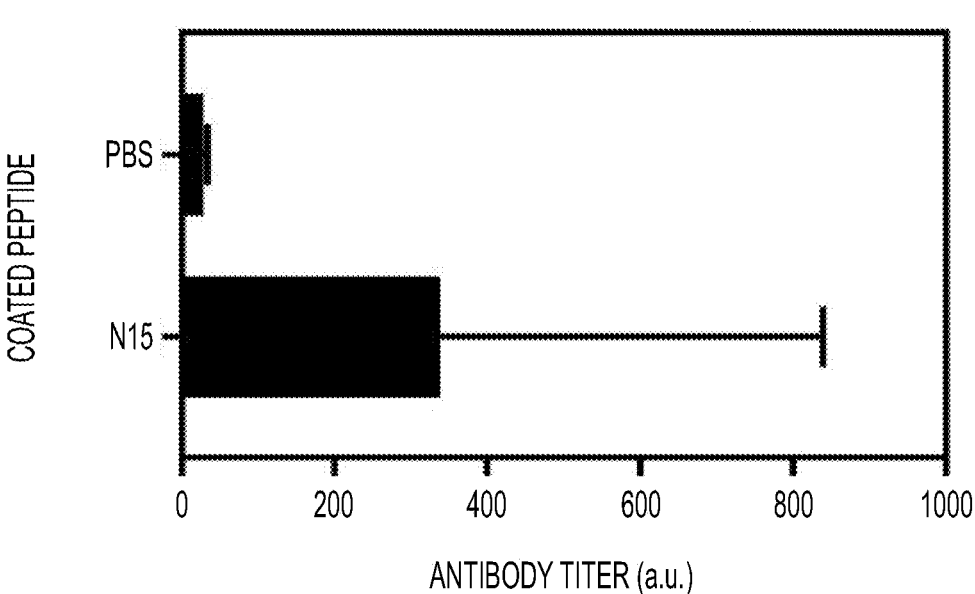

FIG. 24C: Immune responses in mice induced by different long peptides presented on virus-like particles (VLPs), as measured by IgG ELISA.

Figure 24D:
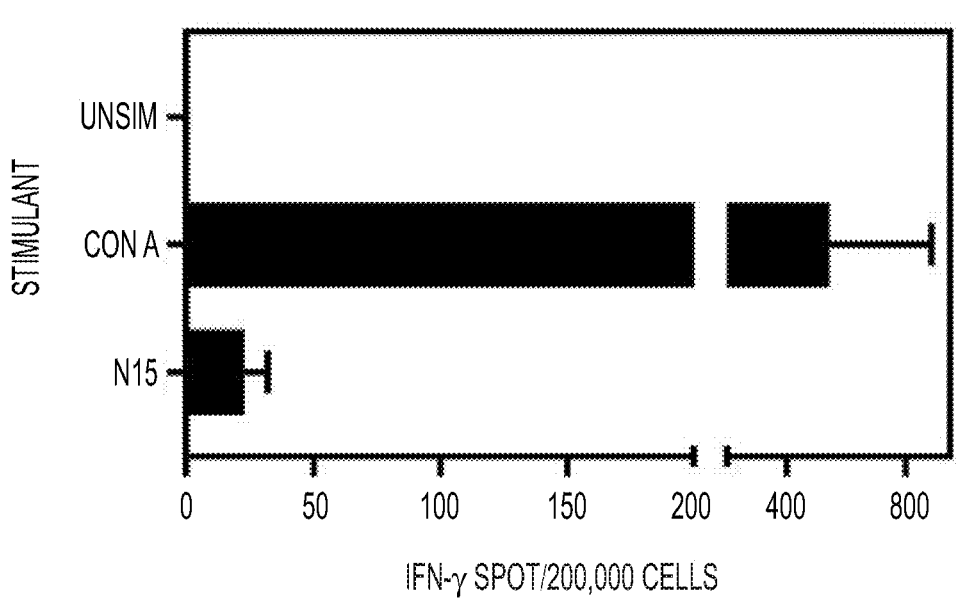

FIG. 24D: Immune responses in mice induced by different long peptides presented on virus-like particles (VLPs), as measured by IFN-γ ELISPOT.

Figure 25A:
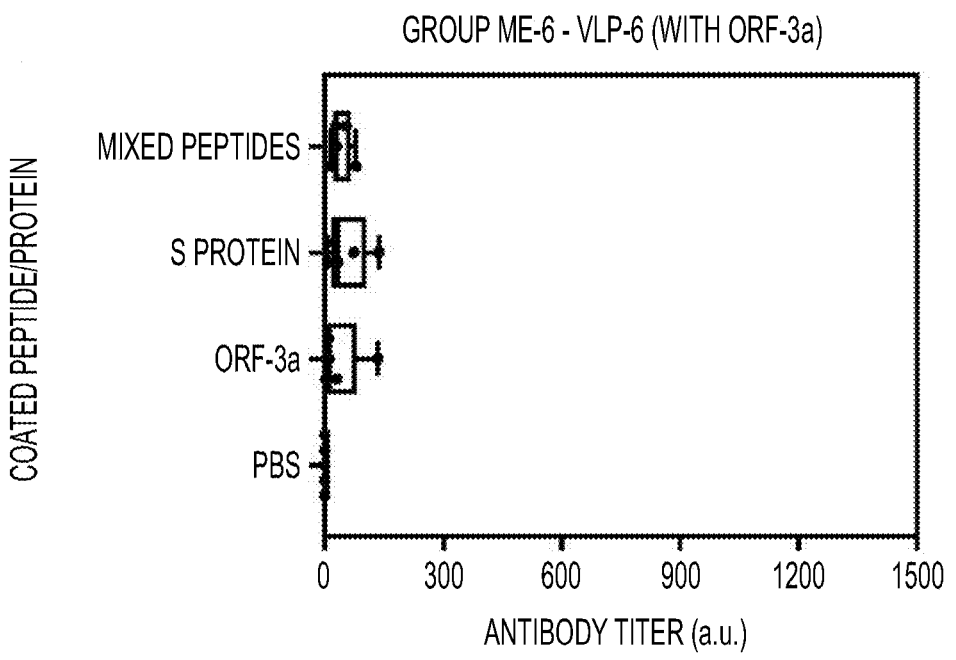

FIG. 25A: Immune responses in mice induced by different long peptides presented on virus-like particles (VLPs), as measured by IgG ELISA.

Figure 25B:
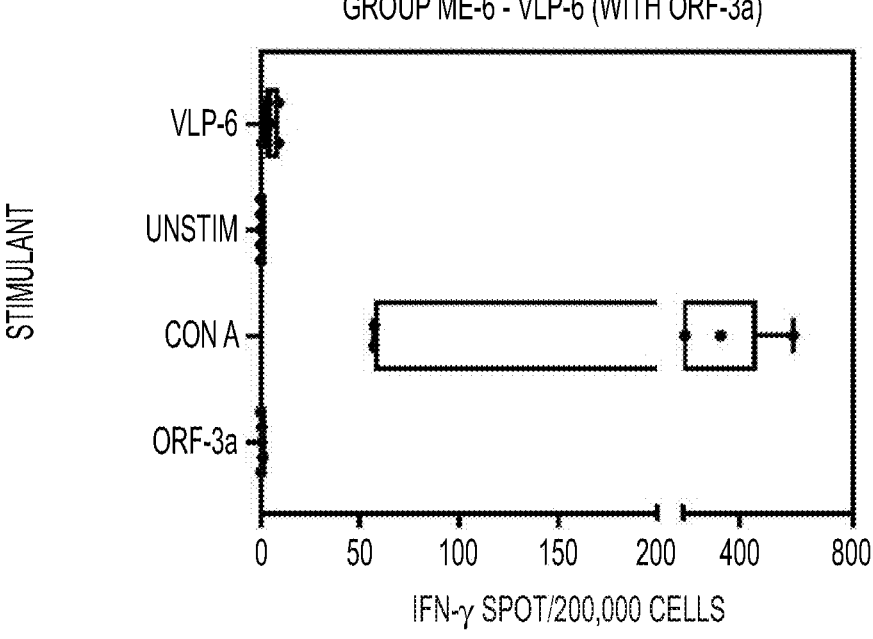

FIG. 25B: Immune responses in mice induced by different long peptides presented on virus-like particles (VLPs), as measured by IFN-γ ELISPOT.

Figure 25C:
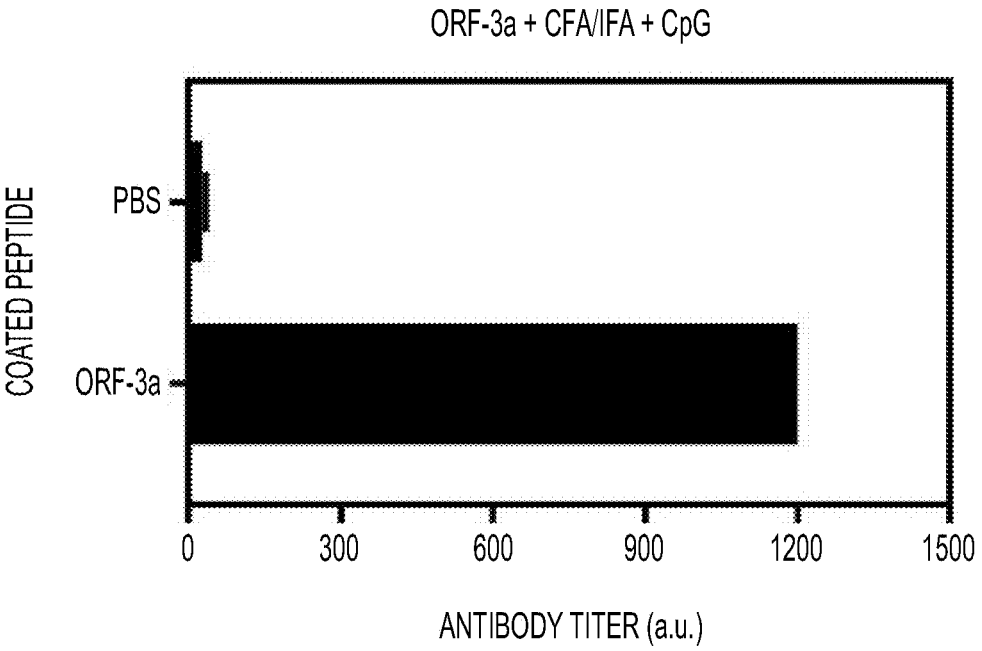

FIG. 25C: Immune responses in mice induced by different long peptides presented on virus-like particles (VLPs), as measured by IgG ELISA.

Figure 25D:
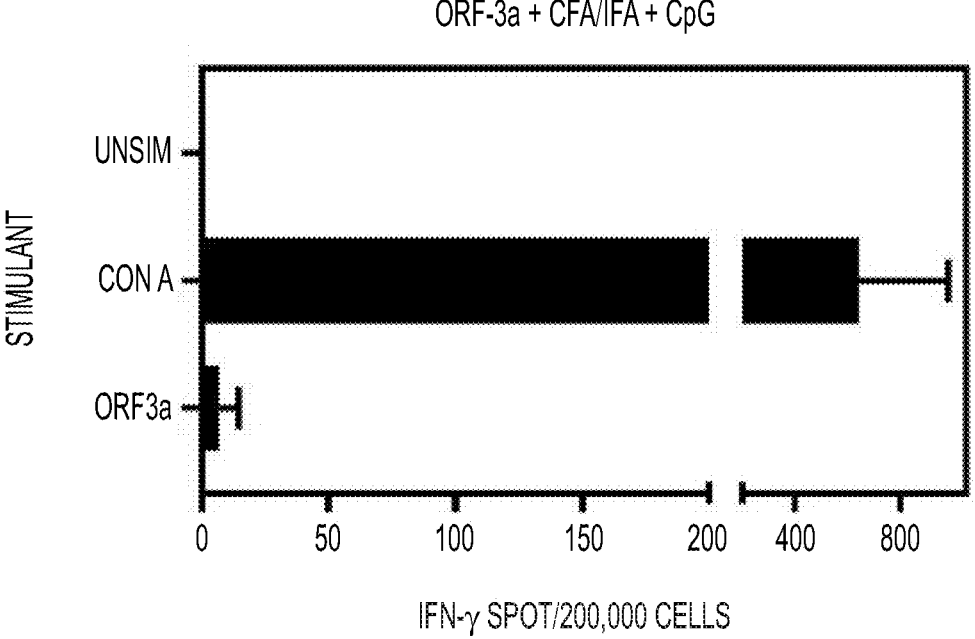

FIG. 25D: Immune responses in mice induced by different long peptides presented on virus-like particles (VLPs), as measured by IFN-γ ELISPOT.

Figure 26B:
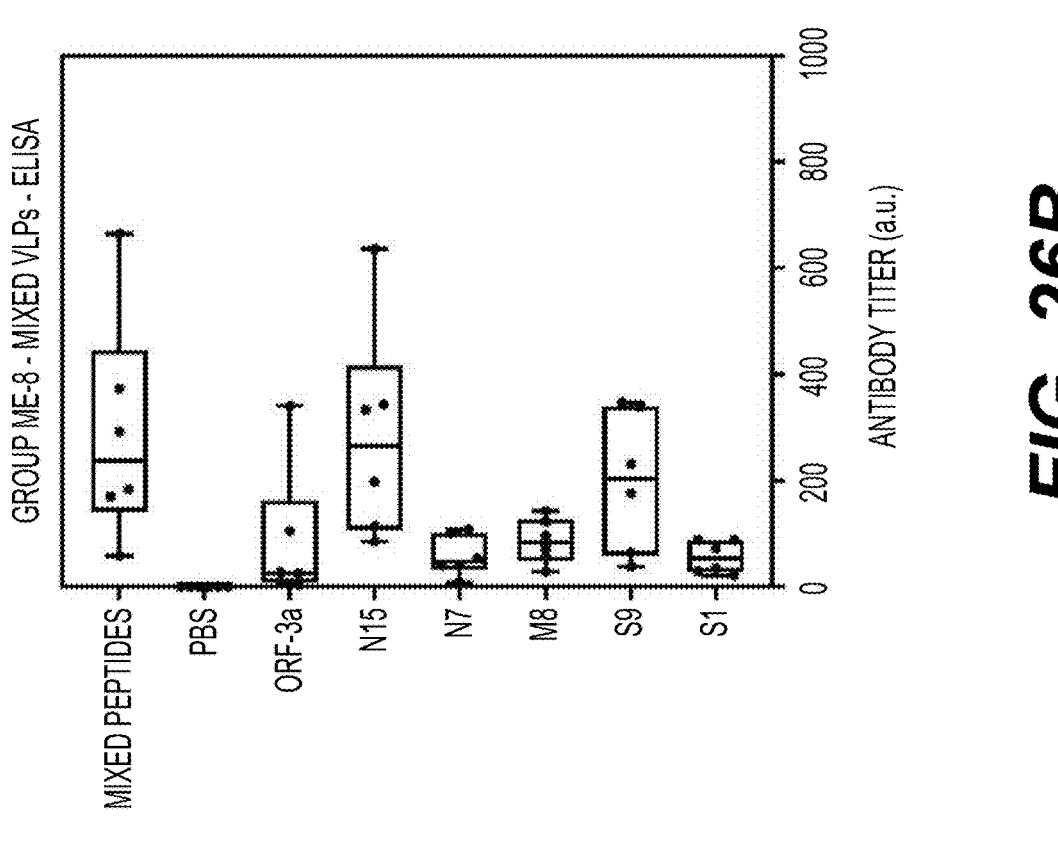
Figure 26A:
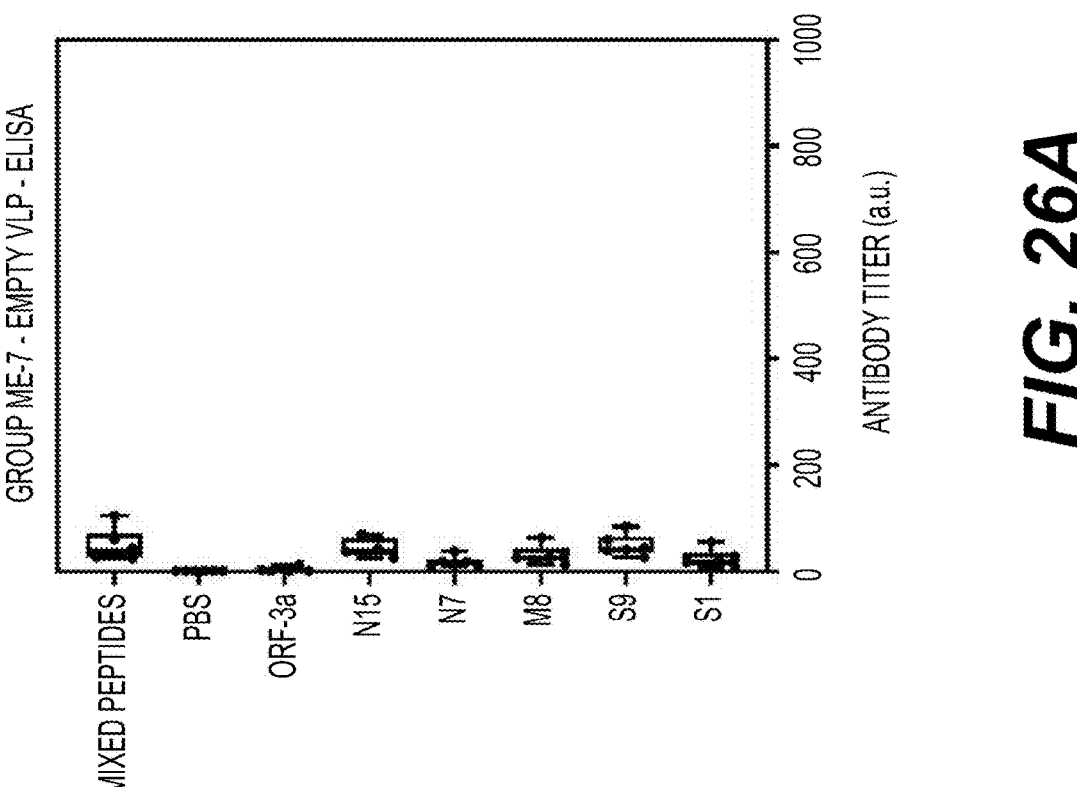

FIG. 26A: Immune responses in mice induced by different long peptides presented on virus-like particles (VLPs), as measured by IgG ELISA.

FIG. 26B: Immune responses in mice induced by different long peptides presented on virus-like particles (VLPs), as measured by IgG ELISA.

Figure 26D:
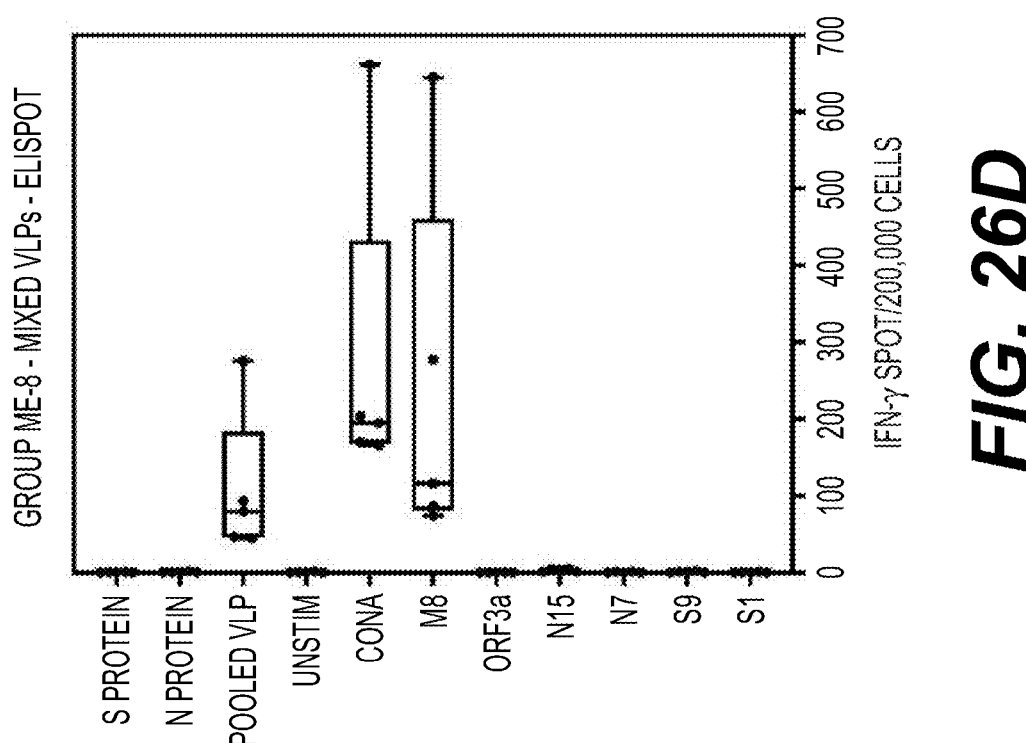
Figure 26C:
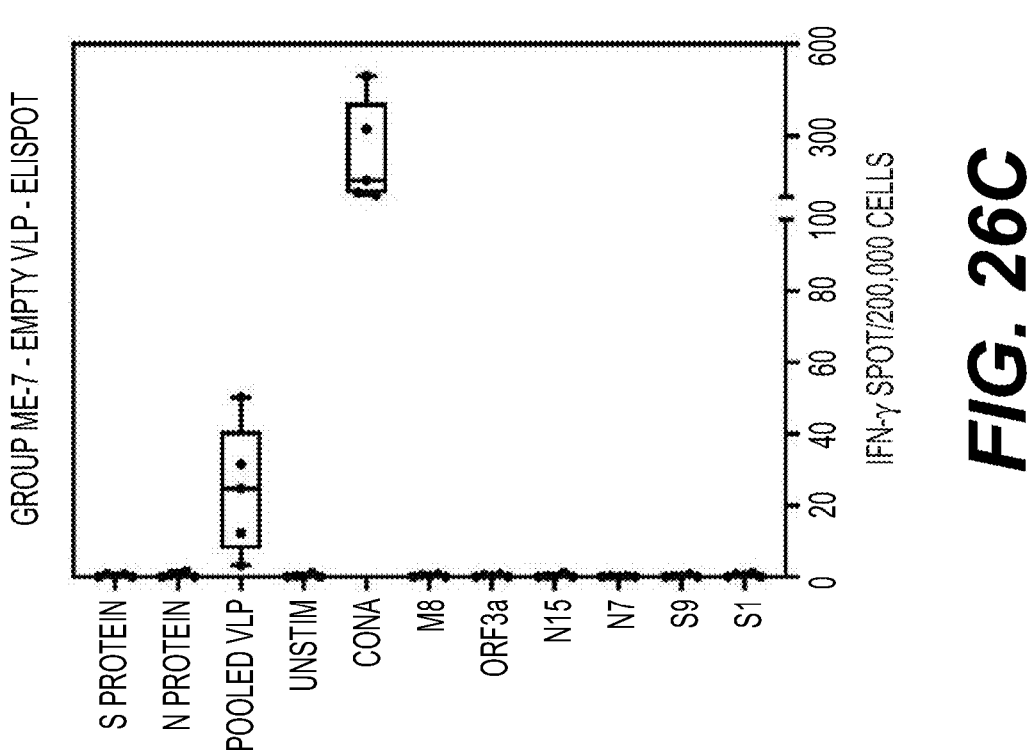

FIG. 26C: Immune responses in mice induced by different long peptides presented on virus-like particles (VLPs), as measured by IFN-γ ELISPOT.

FIG. 26D: Immune responses in mice induced by different long peptides presented on virus-like particles (VLPs), as measured by IFN-γ ELISPOT.

Figure 27B:
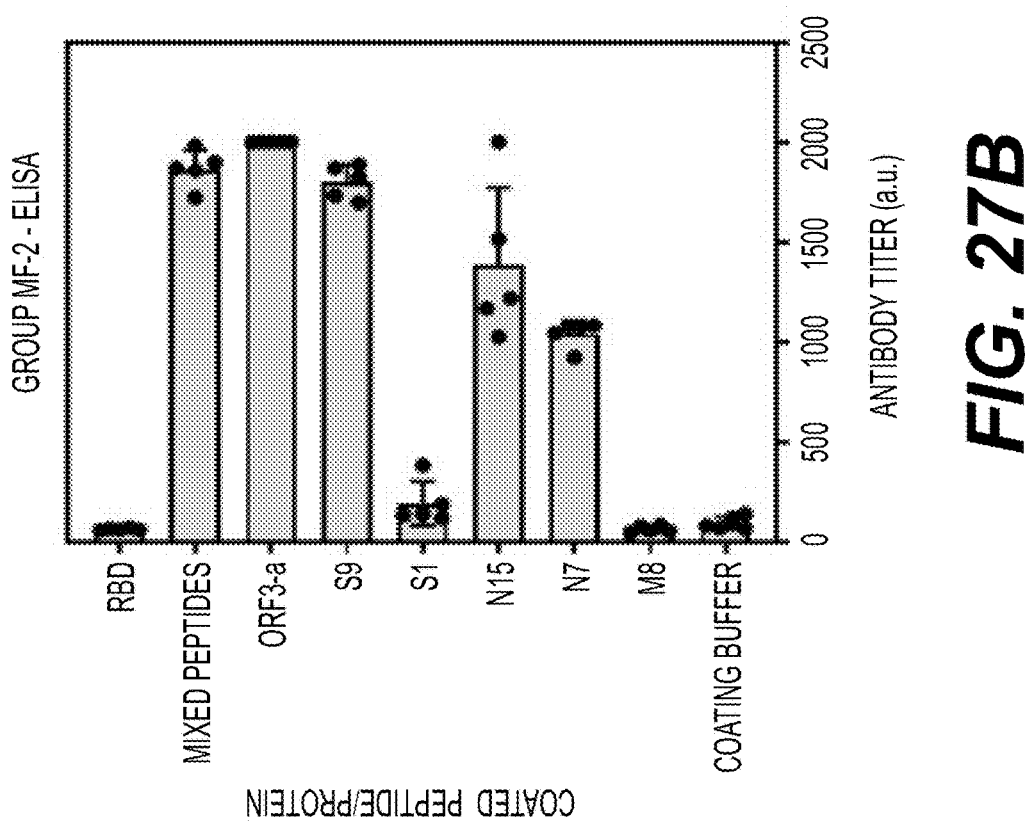
Figure 27A:
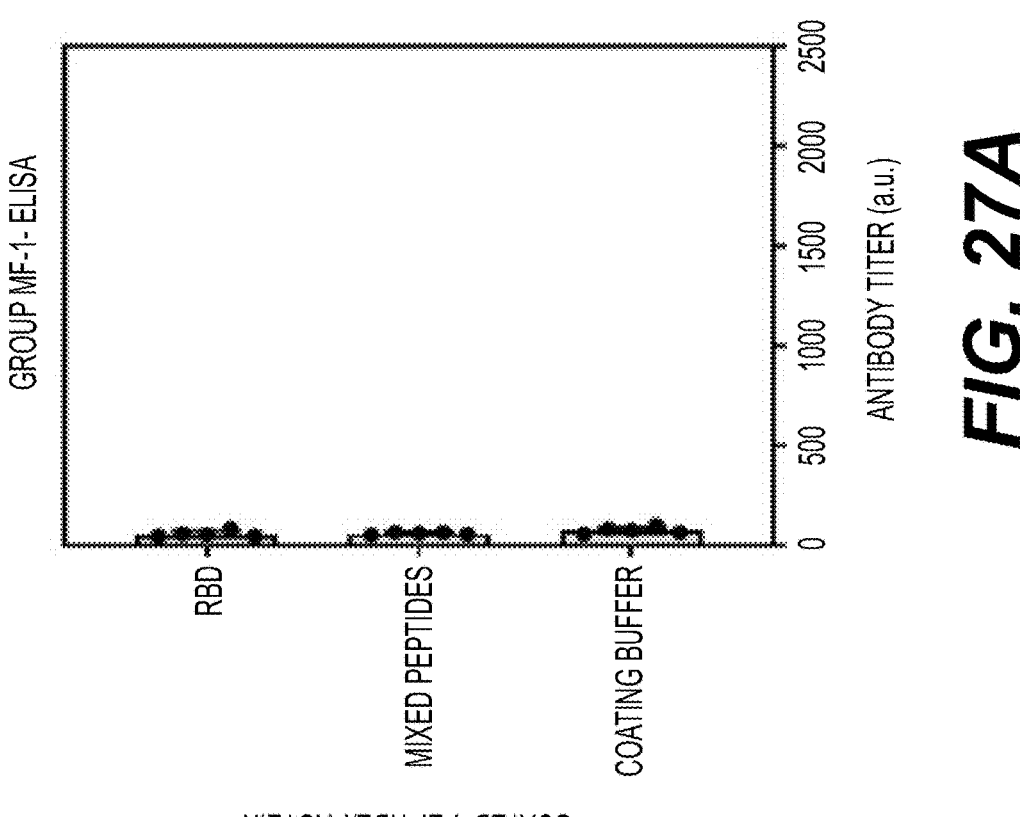

FIG. 27A: Immune responses in mice induced by different peptides with and without the RBD protein, as measured by IgG ELISA.

FIG. 27B: Immune responses in mice induced by different peptides with and without the RBD protein, as measured by IgG ELISA.

Figure 27D:
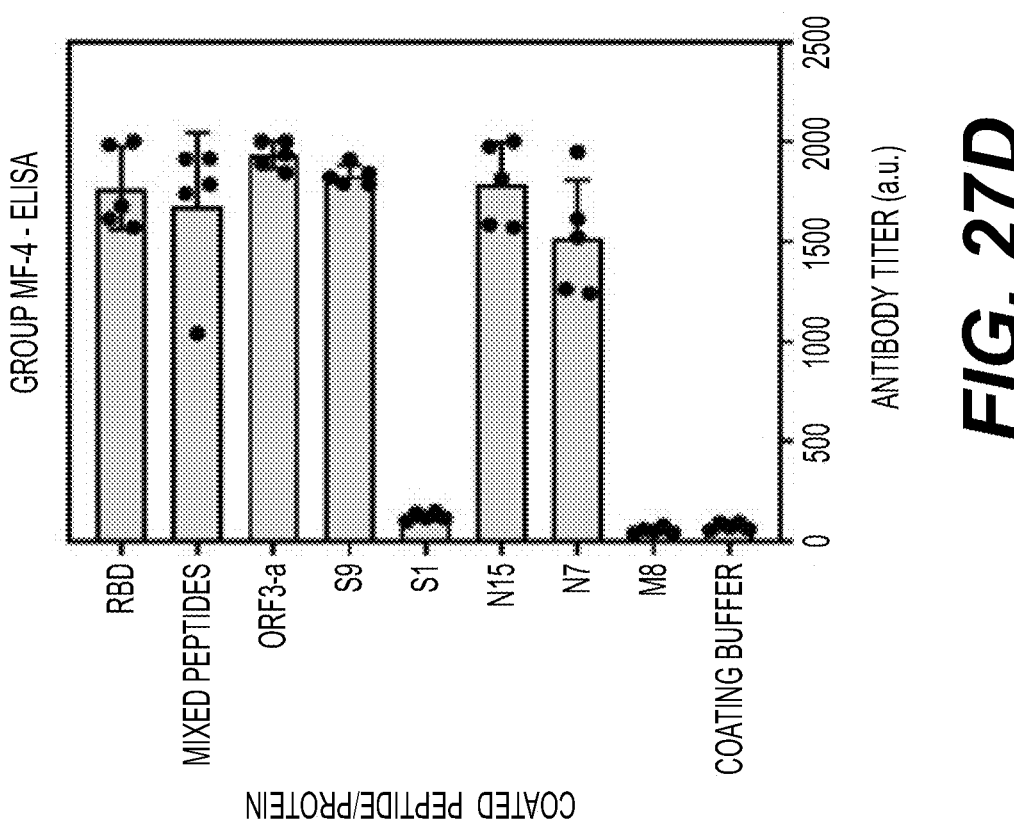
Figure 27C:
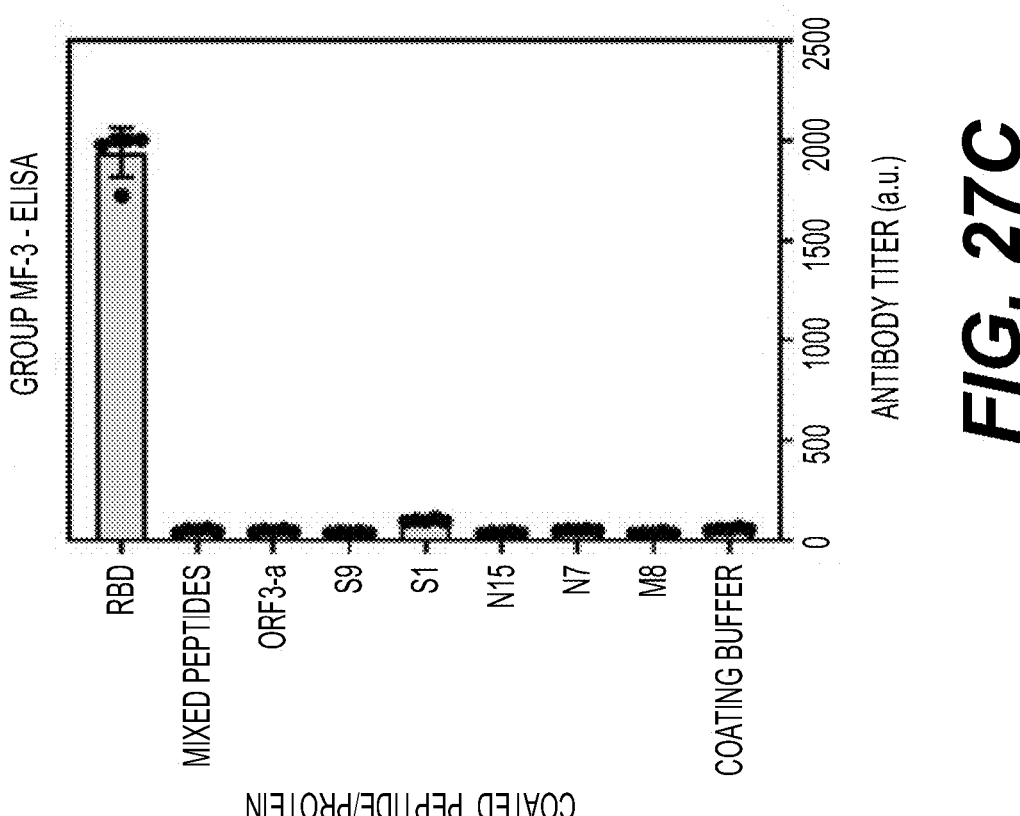

FIG. 27C: Immune responses in mice induced by different peptides with and without the RBD protein, as measured by IgG ELISA.

FIG. 27D: Immune responses in mice induced by different peptides with and without the RBD protein, as measured by IgG ELISA.

Figures 27E, 27F:
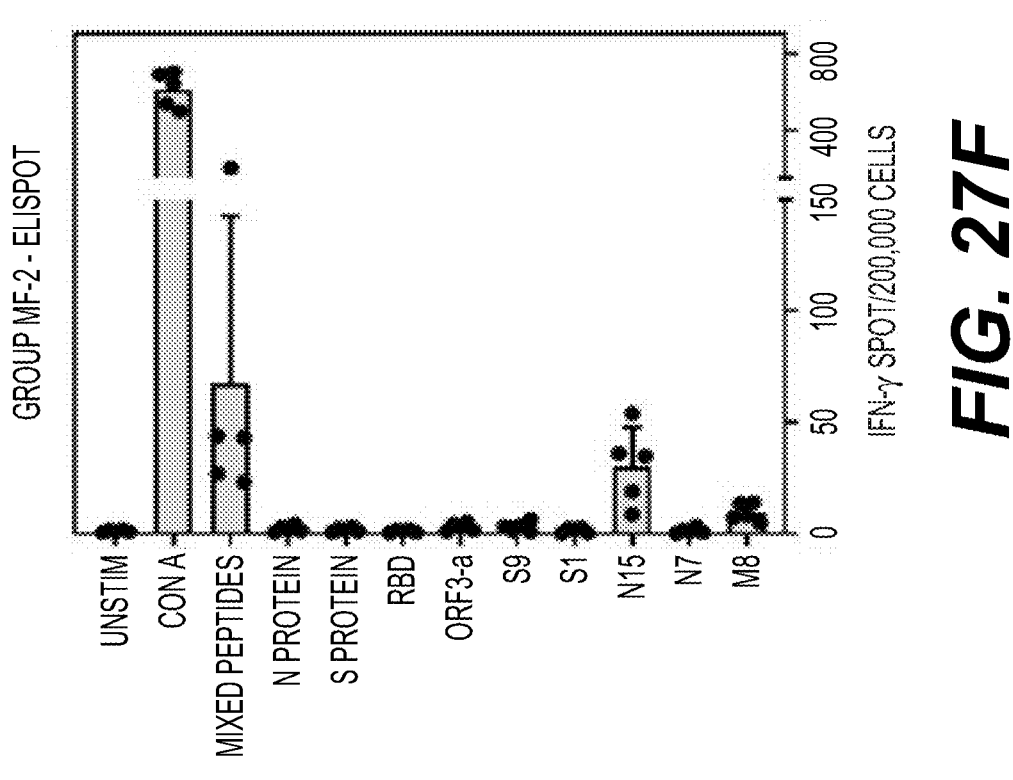

FIG. 27E: Immune responses in mice induced by different peptides with and without the RBD protein, as measured by IFN-γ ELISPOT.

FIG. 27F: Immune responses in mice induced by different peptides with and without the RBD protein, as measured by IFN-γ ELISPOT.

Figure 27H:
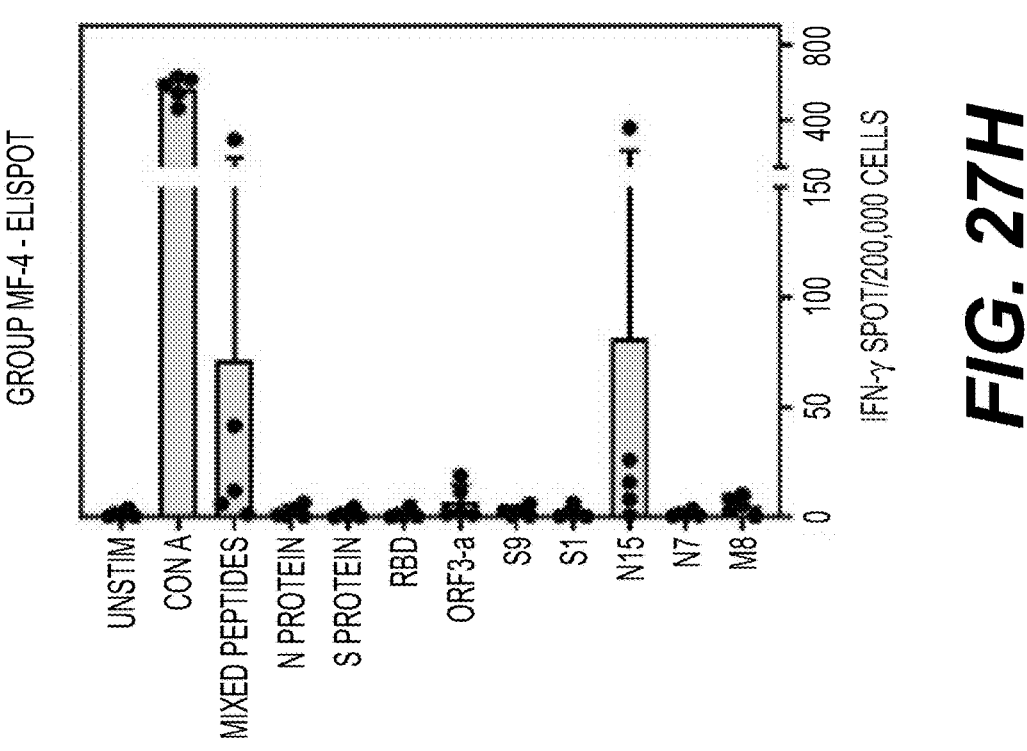
Figure 27G:
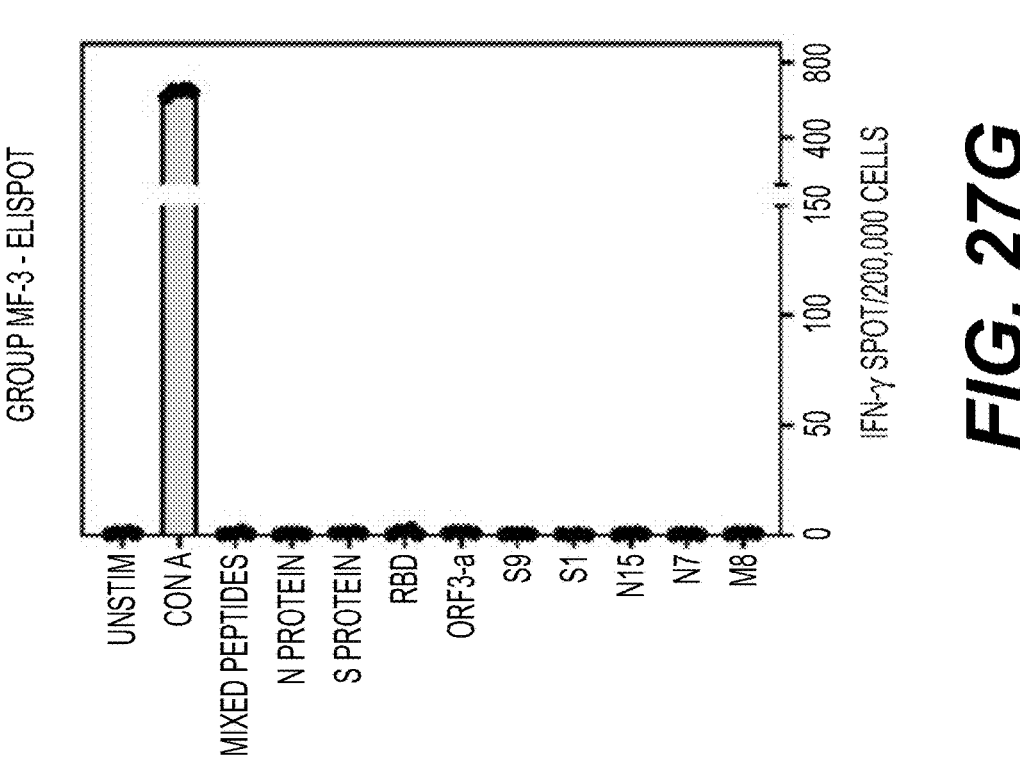

FIG. 27G: Immune responses in mice induced by different peptides with and without the RBD protein, as measured by IFN-γ ELISPOT.

FIG. 27H: Immune responses in mice induced by different peptides with and without the RBD protein, as measured by IFN-γ ELISPOT.

Figure 28B:
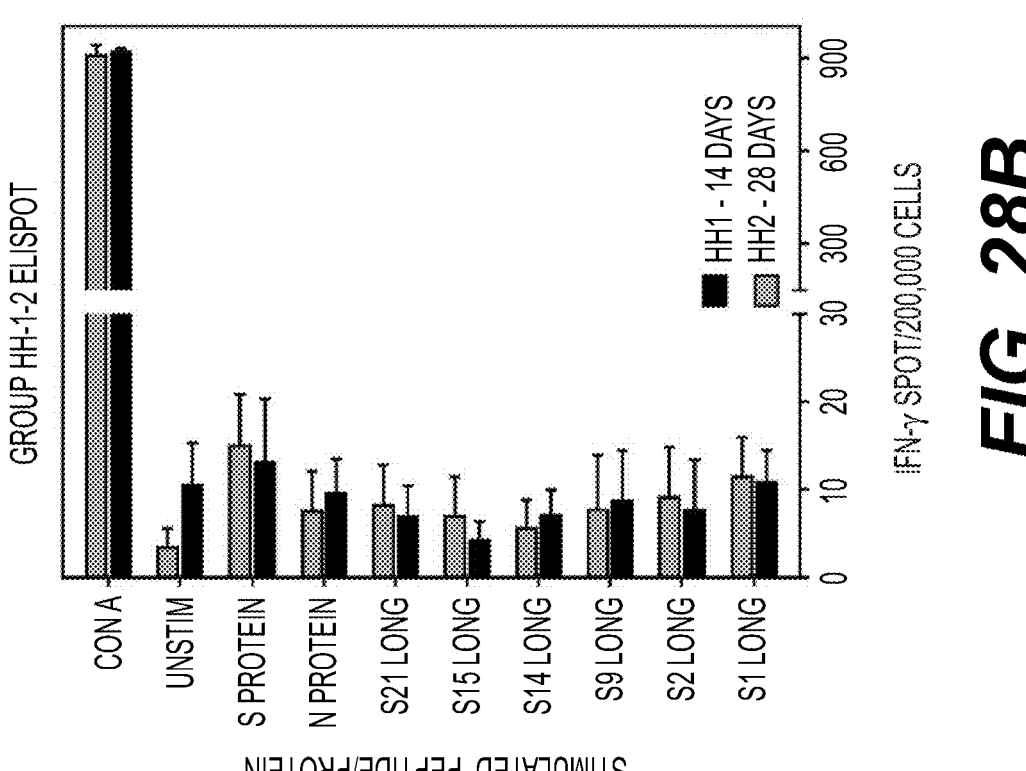
Figure 28A:
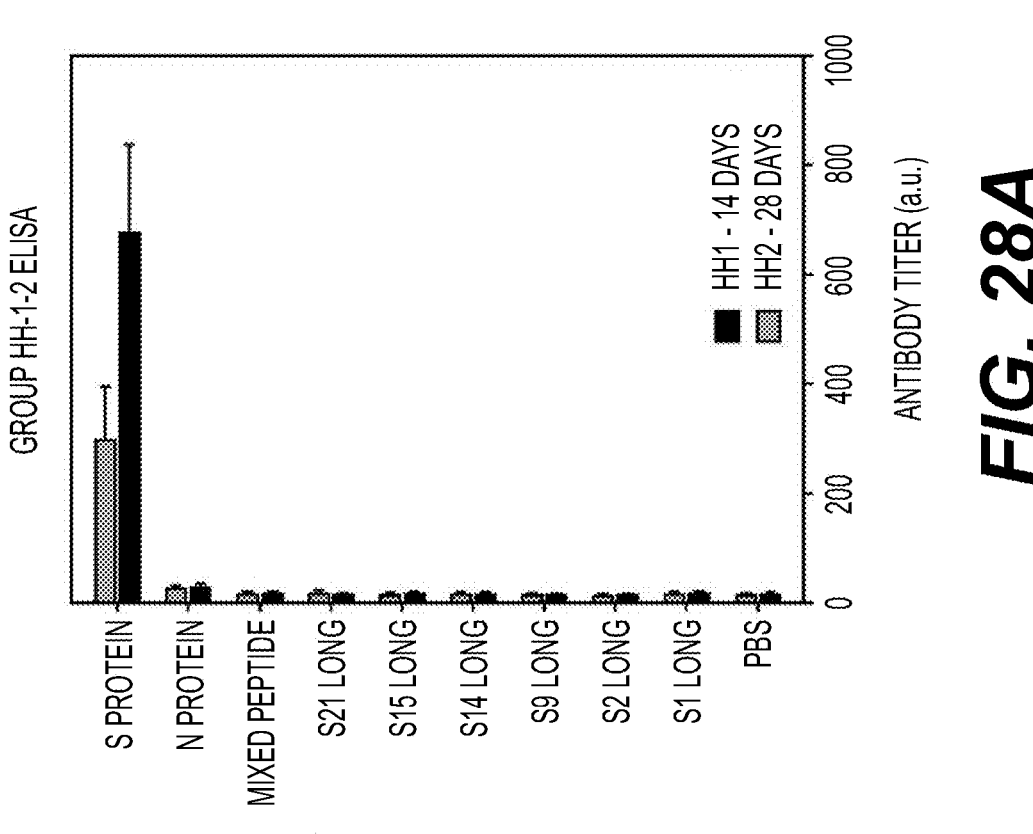

FIG. 28A: Peptide-specific antibody titers as measured by ELISA induced by Pfizer mRNA vaccine in hamsters.

FIG. 28B: Peptide-specific T cell responses as measured by ELISPOT induced by Pfizer mRNA vaccine in hamsters.

Figures 28C, 28D:
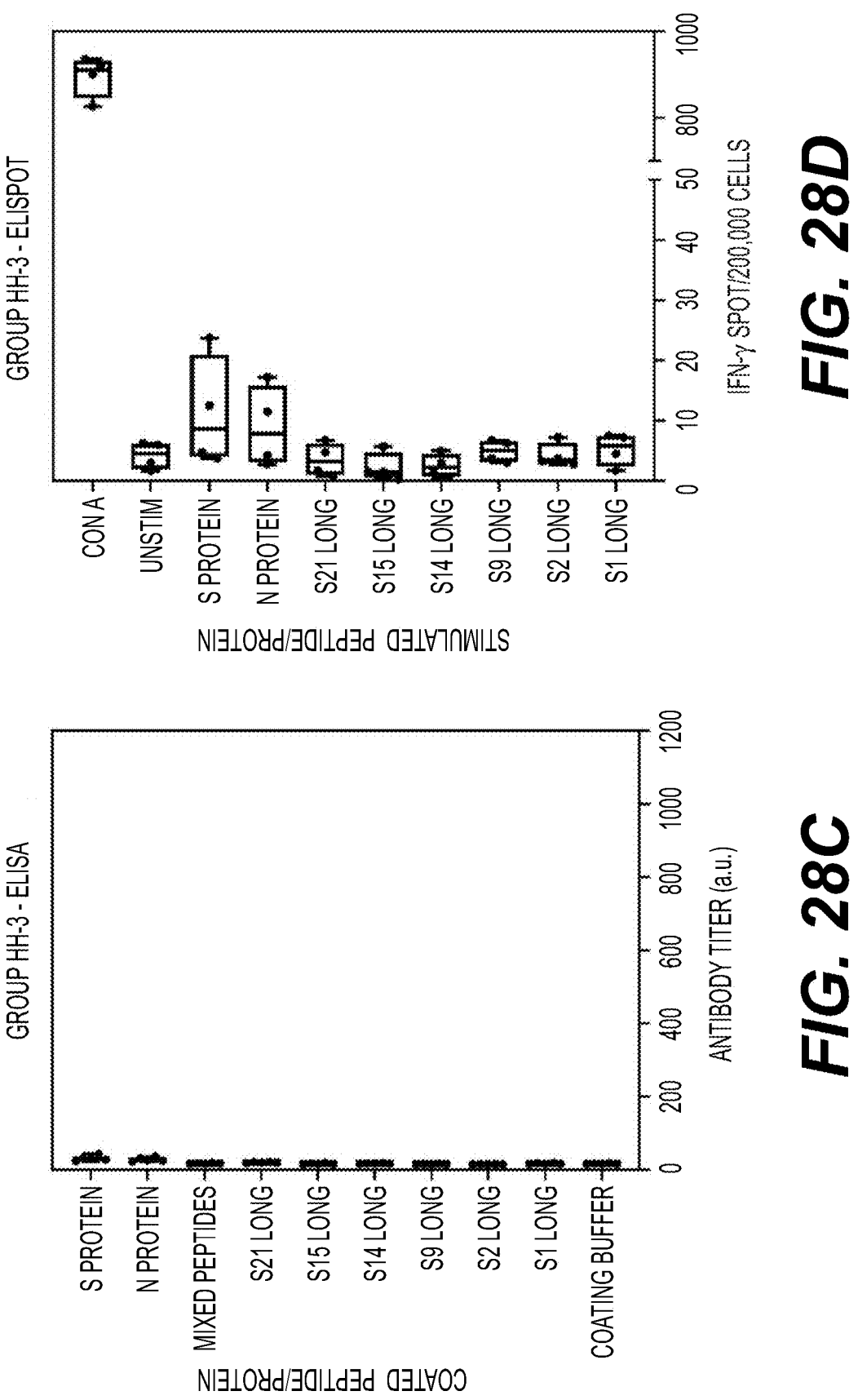

FIG. 28C: Peptide-specific antibody titers as measured by ELISA induced by Pfizer mRNA vaccine in hamsters.

FIG. 28D: Peptide-specific T cell responses as measured by ELISPOT induced by Pfizer mRNA vaccine in hamsters.

Figures 29A, 29B:
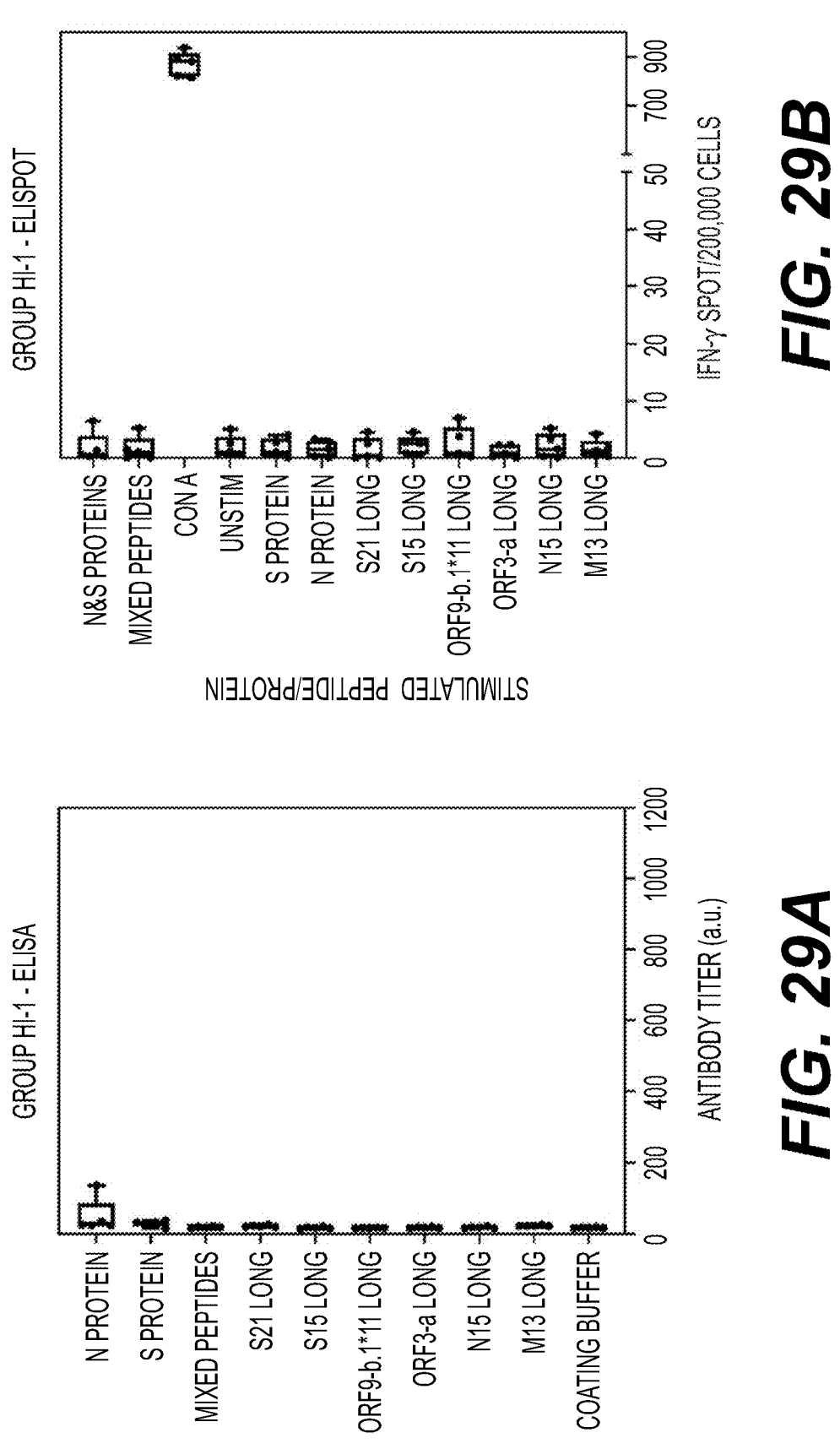

FIG. 29A: Peptide-specific antibody titers as measured by ELISA induced by Pfizer mRNA vaccine in mice.

FIG. 29B: Peptide-specific T cell responses as measured by ELISPOT induced by Pfizer mRNA vaccine in mice.

Figure 29D:
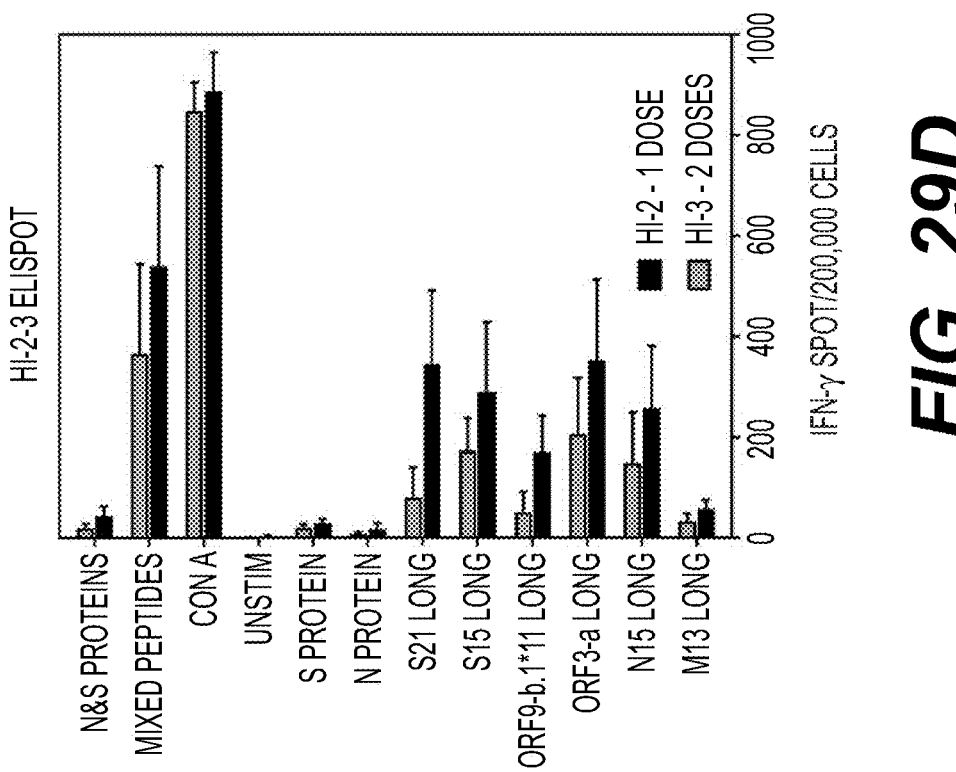
Figure 29C:
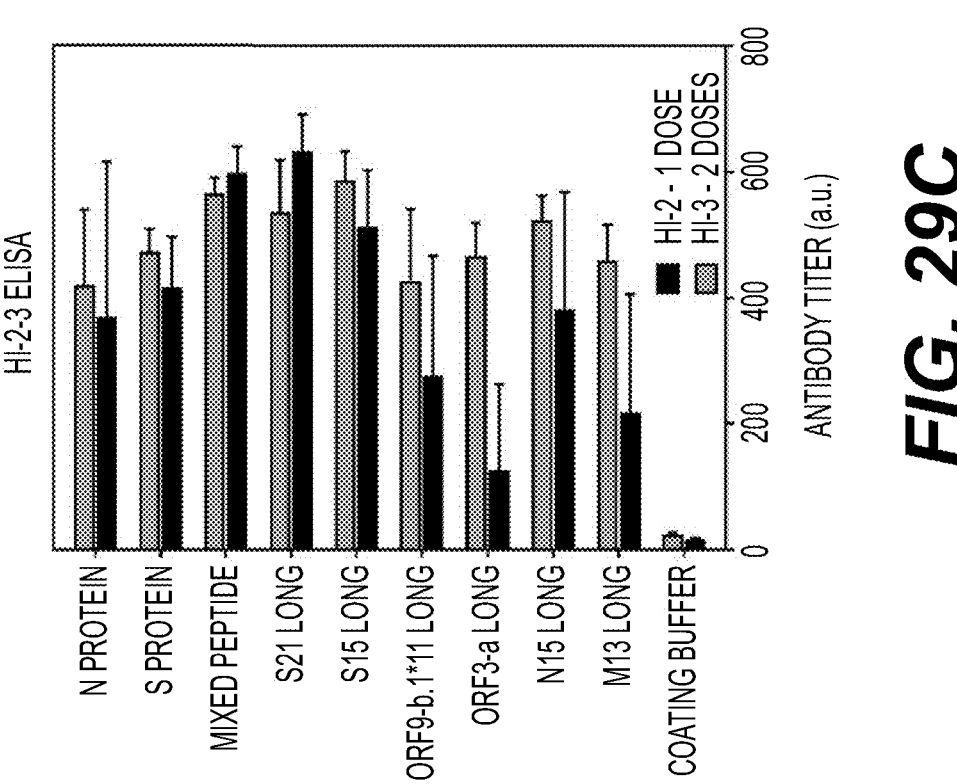

FIG. 29C: Peptide-specific antibody titers as measured by ELISA induced by Pfizer mRNA vaccine in mice.

FIG. 29D: Peptide-specific T cell responses as measured by ELISPOT induced by Pfizer mRNA vaccine in mice.

Figure 30B:
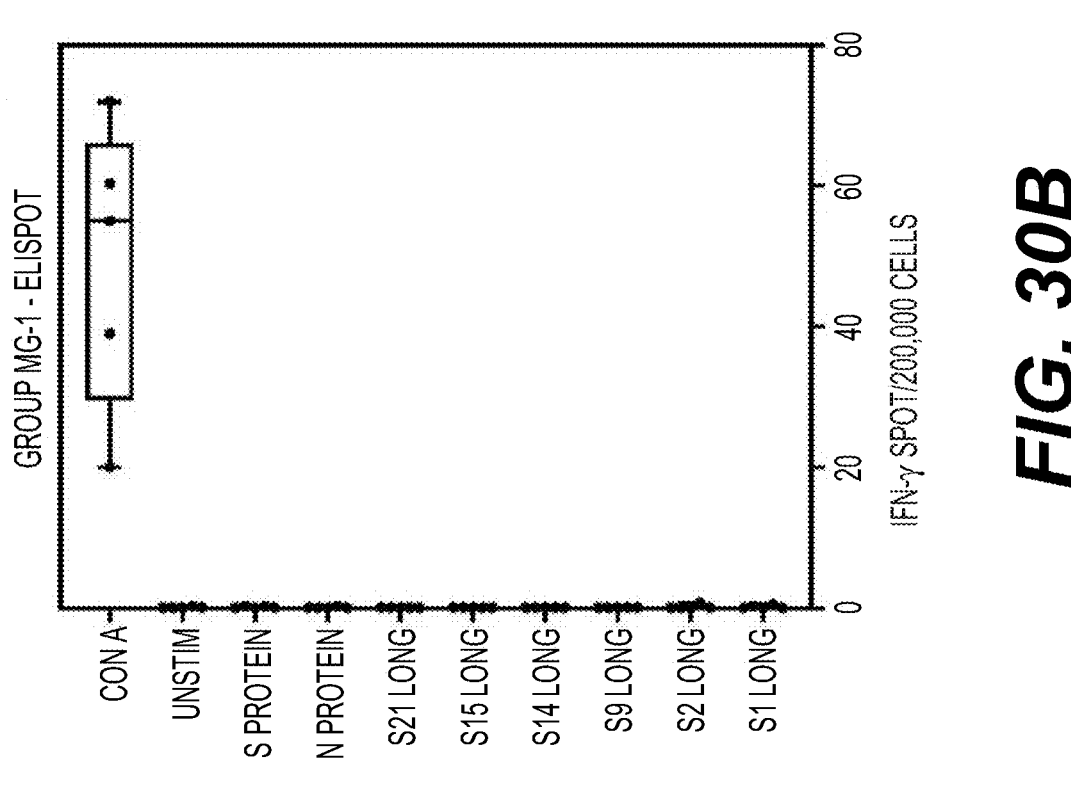
Figure 30A:
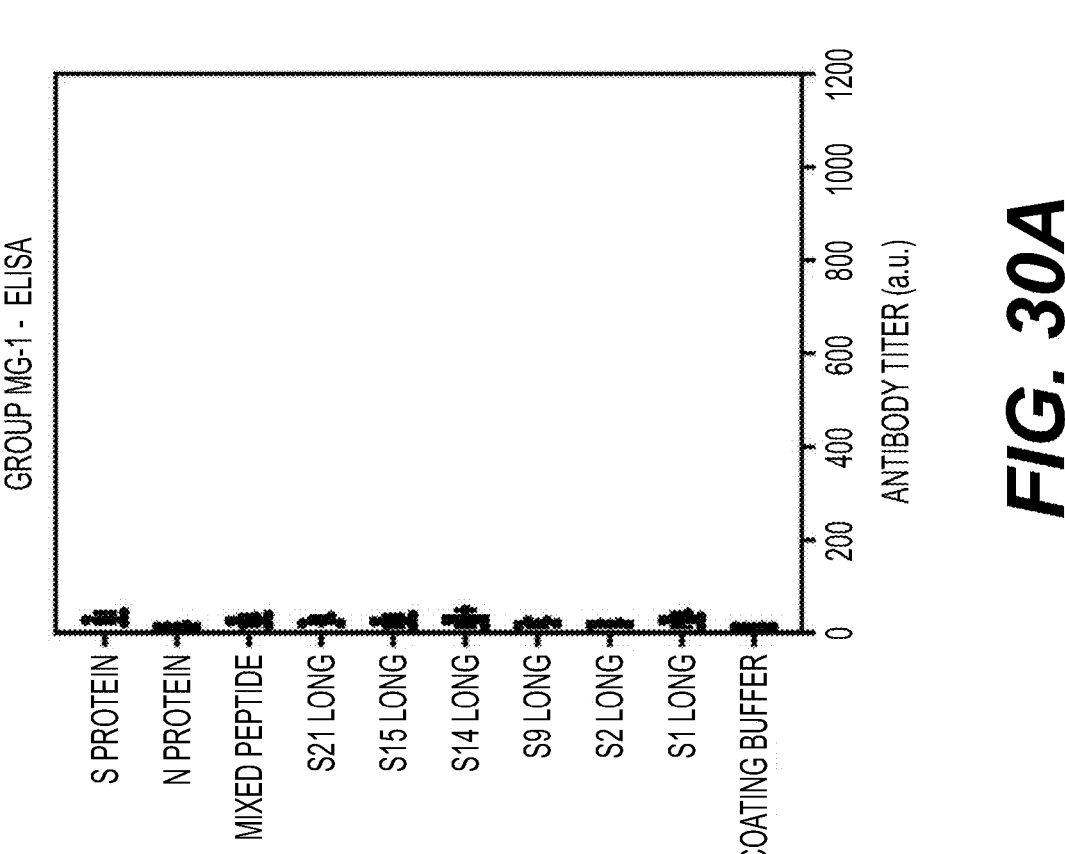

FIG. 30A: Peptide-specific antibody titers as measured by ELISA induced by 6 selected long peptides in hamsters.

FIG. 30B: Peptide-specific T cell responses as measured by ELISPOT induced by 6 selected long peptides in hamsters.

Figures 30C, 30D:
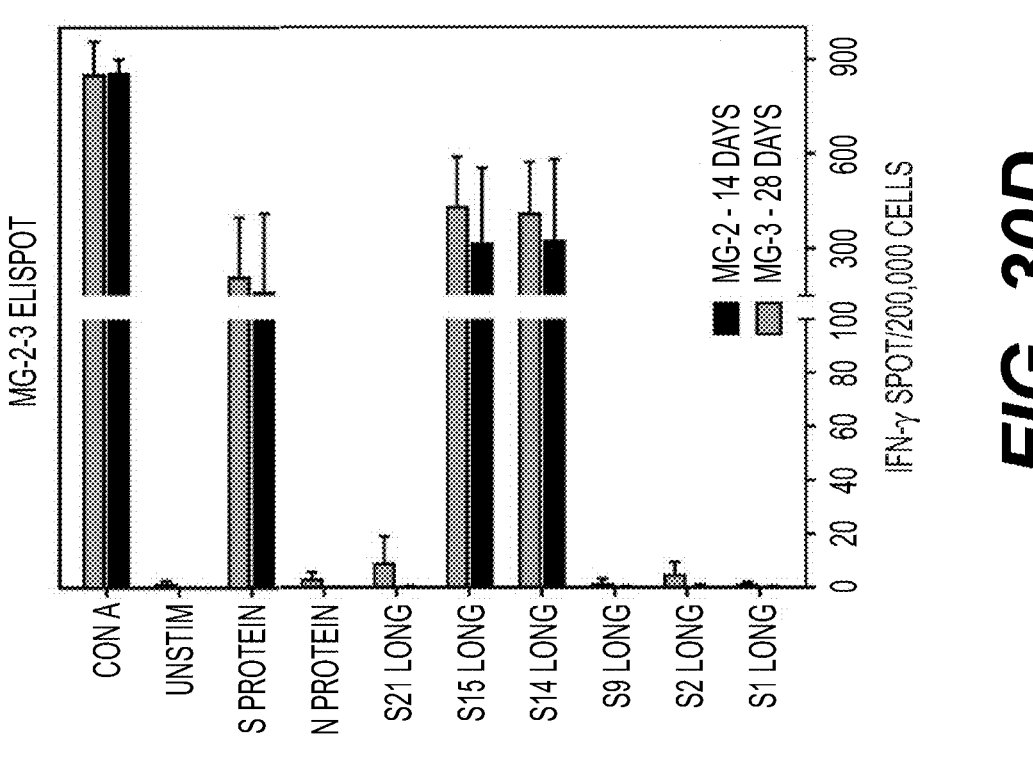

FIG. 30C: Peptide-specific antibody titers as measured by ELISA induced by 6 selected long peptides in hamsters.

FIG. 30D: Peptide-specific T cell responses as measured by ELISPOT induced by 6 selected long peptides in hamsters.

DETAILED DESCRIPTION

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular embodiments of the disclosure, and not to exhaustively specify all permutations, combinations, and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular aspects or embodiments only and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

The methods disclosed herein include and comprise one or more steps or actions for achieving the described method. The method steps and/or actions may be interchanged with one another without departing from the scope of the present disclosure. In other words, unless a specific order of steps or actions is required for proper operation of the embodiment, the order and/or use of specific steps and/or actions may be modified without departing from the scope of the present disclosure.

As used in the description of the disclosure and the appended claims, the singular forms "a," "an," and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a length, a frequency, or a duration and the like, is meant to encompass variations of $\pm20\%$, $\pm10\%$, $\pm5\%$, $\pm1\%$, $\pm0.5\%$, or even $\pm0.1\%$ of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, the term "exemplary" is used to mean serving as an example, instance, or illustration. Any aspect or aspect described as "exemplary" is not necessarily to be construed as preferred or advantageous over other aspects or aspects, nor is it meant to preclude equivalent structures and techniques known to those of ordinary skill in the art. Rather, use of the word exemplary is intended to present concepts in a concrete fashion, and the disclosed subject matter is not limited by such examples.

This document provides methods and materials related to selected SARS-CoV-2 polypeptides. For example, this document provides the isolated polypeptides set forth in Table 1, Table 2, and Table 3. In some cases, a selected SARS-CoV-2 polypeptide provided herein can be a substantially pure polypeptide that comprises, consists essentially of, or consists of the amino acid sequence set forth in any one of SEQ ID NOs:1-87. The term "substantially pure" as used herein with reference to a polypeptide means the polypeptide is substantially free of other polypeptides, lipids, carbohydrates, and nucleic acid with which it is naturally associated. Thus, a substantially pure polypeptide is any polypeptide that is removed from its natural environment and is at least 60 percent pure. A substantially pure polypeptide can be at least about 65, 70, 75, 80, 85, 90, 95, or 99 percent pure. Typically, a substantially pure polypeptide will yield a single major band on a non-reducing polyacrylamide gel. In some cases, a substantially pure polypeptide provided herein can be a polypeptide that is synthesized to have a purity of at least about 60, 65, 70, 75, 80, 85, 90, 95, or 99 percent.

In some cases, a SARS-CoV-2 polypeptide provided herein can have HLA class I binding properties.

In some cases, a SARS-CoV-2 polypeptide provided herein can have HLA class II binding properties.

A SARS-CoV-2 polypeptide provided herein can be any appropriate length (e.g., can include any number of amino acids). For example, a SARS-CoV-2 polypeptide provided herein can be from about 7 amino acids in length to about 100 amino acids (e.g., from about 7 to about 80 amino acids, from about 7 to about 60 amino acids, from about 7 to about 50 amino acids, from about 7 to about 40 amino acids, from about 7 to about 30 amino acids, from about 7 to about 20 amino acids, from about 7 to about 15 amino acids, from about 10 to about 100 amino acids, from about 20 to about 100 amino acids, from about 30 to about 100 amino acids, from about 40 to about 100 amino acids, from about 50 to about 100 amino acids, from about 60 to about 100 amino acids, from about 70 to about 100 amino acids, from about 80 to about 100 amino acids, from about 10 to about 80 amino acids, from about 20 to about 70 amino acids, from about 30 to about 60 amino acids, from about 40 to about 50 amino acids, from about 10 to about 20 amino acids, from about 20 to about 30 amino acids, or from about 30 to about 40 amino acids) in length. In some cases, a SARS-CoV-2 provided herein can be from about 8 to about 12 amino acid sequences in length. For example, a SARS-CoV-2 polypeptide provided herein and having HLA class I binding properties can be from about 8 to about 12 amino acid sequences in length. In some cases, a SARS-CoV-2 polypeptide provided herein can be from about 13 to about 25 amino acid sequences in length. For example, a SARS-CoV-2 polypeptide provided herein and having HLA class II binding properties can be from about 13 to about 25 amino acid sequences in length.

In an aspect, a SARS-CoV-2 polypeptide provided herein can be from about 35 to about 45 amino acid sequences in length. In an aspect, a SARS-CoV-2 polypeptide provided herein can be from about 38 to about 42 amino acid sequences in length. In an aspect, a SARS-CoV-2 polypeptide provided herein can be from about 39 to about 41 amino acid sequences in length. In an aspect, a SARS-CoV-2 polypeptide provided herein can be about 40 amino acid sequences in length.

As used herein, the term "long peptide" refers to a peptide longer than 30 amino acids, but shorter than 50 amino acids. Without being bound by theory, long peptides allow for better display of 3-dimensional structures, and can include multiple smaller epitopes (both B cell and T cell epitopes) within the longer peptide sequence. In an aspect, a long peptide provided herein can be from about 35 to about 45 amino acid sequences in length. In an aspect, a long peptide provided herein can be from about 38 to about 42 amino acid sequences in length. In an aspect, a long peptide provided herein can be from about 39 to about 41 amino acid sequences in length. In an aspect, a long peptide provided herein can be about 40 amino acid sequences in length.

A SARS-CoV-2 polypeptide provided herein can be derived from any SARS-CoV-2 polypeptide. Without being bound by theory, polypeptide vaccines derived from spike (S) protein only, may allow for the development of further viral mutants that can escape, in part or in whole, antibody-mediated immunity. In some cases, a SARS-CoV-2 polypeptide provided herein can be derived from a structural SARS-CoV-2 polypeptide (e.g., a SARS-CoV-2 spike (S)-protein such as a receptor-binding domain (RBD) of a SARS-CoV-2 S-protein, a SARS-CoV-2 nucleocapsid (N)-protein, and a SARS-CoV-2 membrane (M)-protein). In some cases, a SARS-CoV-2 polypeptide provided herein can be derived from a non-structural SARS-CoV-2 polypeptide (e.g., a polypeptide encoded by ORF lab, a polypeptide encoded by ORF3a, and a polypeptide encoded by ORF9b).

In some cases, a SARS-CoV-2 polypeptide provided herein can comprise, consist essentially of, or consist of the amino acid sequence set forth in Table 1.

TABLE 1

| Exemplary SARS-CoV-2 polypeptides. | | | |
|---|---|---|---|
| SEQ ID NO | Sequence | Name | Protein |
| 32 | SMWSFNPET | M-11 | Membrane |
| 34 | ESELVIGAVILRGHL | M-13 | Membrane |
| 16 | GAVILRGHLRIAGHHLGR | M-4 | Membrane |
| 29 | EITVATSRTLSYYKL | M-8 | Membrane |
| 17 | TSRTLSYYKLGASQRVA | M-5 | Membrane |
| 9 | RTLSYYKLGASQRVA | M-1 | Membrane |
| 41 | SQRVAGDSGFAAYSR | M-14 | Membrane |
| 11 | WLLWPVTLA | M-3 | Membrane |
| 33 | LLWPVTLACF | M-12 | Membrane |
| 10 | TLACFVLAA | M-2 | Membrane |
| 30 | YRINWITGGIAIAMA | M-9 | Membrane |
| 31 | SYFIASFRLFARTRS | M-10 | Membrane |
| 15 | LSPRWYFYYLGTGPEAGL | N-8 | Nucleocapsid |
| 1 | LGTGPEAGLPYGANKDGIIWVA | N-1 | Nucleocapsid |
| 35 | TGPEAGLPYGANKD | N-11 | Nucleocapsid |
| 2 | DQELIRQGTDYKHWPQIAQFAPS | N-2 | Nucleocapsid |
| 39 | IRQGTDYKHWPQIAQFAPSASAFFG | N-15 | Nucleocapsid |
| 3 | SRIGMEVTPSGTWLT | N-3 | Nucleocapsid |
| 5 | MEVTPSGTWL | N-5 | Nucleocapsid |
| 40 | VTPSGTWLTY | N-16 | Nucleocapsid |
| 4 | VTPSGTWLTYTGAIK | N-4 | Nucleocapsid |
| 6 | VTPSGTWLTYTGAIKLDDKDPNFK | N-6 | Nucleocapsid |
| 20 | WLTYTGAIKL | N-18 | Nucleocapsid |
| 36 | PNFKDQVILL | N-12 | Nucleocapsid |
| 8 | DQVILLNKHIDAYK | N-7 | Nucleocapsid |
| 37 | LLNKHIDAY | N-13 | Nucleocapsid |
| 38 | PQIQLAVTRMENAVGRD | ORF9B.1*11 | ORF9B |
| 18 | YFTSDYYQLYSTQLSTDTGV | ORF-3a | ORF3 |
| 47 | VKHVYQLRARSVSPK | ORF7 | ORF7 |
| 7 | PKISEMHPALRLVD | ORF9b | ORF9B |

TABLE 1-continued

| Exemplary SARS-CoV-2 polypeptides. | | | |
| --- | --- | --- | --- |
| SEQ ID NO | Sequence | Name | Protein |
| 21 | LVDPQIQL | ORF9b.1*7 | ORF9B |
| 22 | KLATTEELPDE | ORF9b.1*8 | ORF9B |
| 23 | TEELPDEF | ORF9b.1*9 | ORF9B |
| 24 | NAVGRDQNNVGPKVYPIIL | ORF9b.1*10 | ORF9B |
| 28 | VVFLHVTYV | S-12 | Spike |
| 46 | FIAGLIAIV | S-17 | Spike |
| 48 | YSSANNCTF | S-18 | Spike |
| 49 | NCTFEYVSQPFLMDL | S-19 | Spike |
| 12 | CTFEYVSQPFLMDLE | S-1 | Spike |
| 50 | NITRFQTLLALHRSY | S-20 | Spike |
| 27 | RFASVYAWNRKRISN | S-11 | Spike |
| 51 | ASVYAWNRKRISNCVA | S-21 | Spike |
| 45 | KLNDLCFTNV | S-16 | Spike |
| 25 | FNCYFPLQSYGFQPT | S-9 | Spike |
| 43 | PFFSNVTWFHAIHVS | S-14 | Spike |
| 44 | SNVTWFHAIHVSGTN | S-15 | Spike |
| 52 | QTQTNSPRRARSV | S-22 | Spike |
| 13 | NLLLQYGSFCTQLNR | S-2 | Spike |
| 53 | RSFIEDLLFNKVTLA | S-23 | Spike |
| 19 | FIEDLLFNKV | S-4 | Spike |
| 26 | LTDEMIAQYTSALLA | S-10 | Spike |
| 14 | TDEMIAQYTSALLAG | S-3 | Spike |
| 42 | VLNDILSRL | S-13 | Spike |

In some cases, a SARS-CoV-2 polypeptide provided herein that consists essentially of the amino acid sequence set forth in any one of SEQ ID NOs:1-87 is a polypeptide that has zero, one, two, or three amino acid substitutions within the articulated sequence of the sequence identifier (e.g., SEQ ID NO:1), has zero, one, two, three, four, or five amino acid residues preceding the articulated sequence of the sequence identifier (e.g., SEQ ID NO:1), and/or has zero, one, two, three, four, or five amino acid residues following the articulated sequence of the sequence identifier (e.g., SEQ ID NO:1), provided that the SARS-CoV-2 polypeptide has the ability to induce or increase immune responses against a coronavirus such as SARS-CoV-2 within a mammal (e.g., a human). Examples of SARS-CoV-2 polypeptides that consist essentially of the amino acid sequence set forth in any one of SEQ ID NOs:1-53 are set forth in Table 2.

TABLE 2

| Exemplary SARS-CoV-2 polypeptides. | |
| --- | --- |
| Polypeptide Sequence | SEQ ID NO: |
| LIEDLLFNKV | 54 |
| FVEDLLFNKV | 55 |
| FIEDILFNKV | 56 |
| FIEDLLFDKV | 57 |
| FIEDLLFDRM | 58 |
| SKRSFIEDLLFNKV | 59 |
| FIEDLLFNKVTLA | 60 |

TABLE 2-continued

Exemplary SARS-CoV-2 polypeptides.

| Polypeptide Sequence | SEQ ID NO: |
|---|---|
| LLTDEMIAQYTSALLAGTITSG | 61 |
| TDGMTAQYASALLAG | 62 |
| TDEMIAQYTAALLAG | 63 |
| LPPLLTYEMIAQYTSALLSG | 64 |
| QGNFGDQELIRQGTDYKHWPQIAQFAPS | 65 |
| DQELNRQGINYKHWPQIAQFAPS | 66 |
| KDQVFLLNKHVDAYKTFPPT | 67 |

In an aspect, a SARS-CoV-2 polypeptide provided herein comprises the amino acid sequence set forth in any one of SEQ ID NOs:1-87 and 0, 1, 2, 3, 4, 5, 6, 7, 8, 9, 10, 11, 12, 13, 14, 15, 16, 17, 18, 19, 20, 21, 22, 23, 24, or 25 amino acid residues preceding the sequence (e.g., SEQ ID NO: 1), wherein the preceding sequence is from a naturally-found SARS-CoV-2 peptide sequence, provided that the SARS-CoV-2 polypeptide has the ability to induce or increase immune responses against a coronavirus such as SARS-CoV-2 within a mammal (e.g., a human). In an aspect, a SARS-CoV-2 polypeptide provided herein comprises the amino acid sequence set forth in any one of SEQ ID NOs:1-87 and 0, 1, 2, 3, 4, 5, 6, 7, 8, 9, 10, 11, 12, 13, 14, 15, 16, 17, 18, 19, 20, 21, 22, 23, 24, or 25 amino acid residues following the sequence (e.g., SEQ ID NO: 1), wherein the succeeding sequence is from a naturally-found SARS-CoV-2 peptide sequence, provided that the SARS-CoV-2 polypeptide has the ability to induce or increase immune responses against a coronavirus such as SARS-CoV-2 within a mammal (e.g., a human). In an aspect, a SARS-CoV-2 polypeptide provided herein comprises the amino acid sequence set forth in any one of SEQ ID NOs:1-87 is flanked on both ends by 0, 1, 2, 3, 4, 5, 6, 7, 8, 9, 10, 11, 12, 13, 14, 15, 16, 17, 18, 19, 20, 21, 22, 23, 24, or 25 amino acid residues from a naturally-found SARS-CoV-2 peptide sequence, wherein the preceding and succeeding amino acid sequences may be of different lengths, provided that the SARS-CoV-2 polypeptide has the ability to induce or increase immune responses against a coronavirus such as SARS-CoV-2 within a mammal (e.g., a human).

Class I and class II molecules are important for T cell-mediated adaptive immunity. Without being bound by theory, HLA Class I molecules recognize antigenic peptides of approximately 8-10 amino acids in length, while HLA Class II molecules recognize antigenic peptides of approximately 12-24 amino acids in length. The peptides of the present disclosure are based, in part, on the surprising result that longer peptides of about 40 amino acids are equally or more immunogenic than shorter peptides up to 28 amino acids in length.

In some cases, a SARS-CoV-2 polypeptide provided herein comprises, consists essentially of, or consists of the amino acid sequence set forth in Table 3. Sequences listed in bold correspond to the short peptide or peptides contained within the longer sequence.

TABLE 3

Exemplary SARS-CoV-2 polypeptides.

| Peptide Name | Sequence | SEQ ID NO: |
|---|---|---|
| S-1 Long | ESEFRVYSSANNCTFEYVSQPFLMDLEGKQGNFKNLREFV | 68 |
| S-2 Long | TMYICGDSTECSNLLLQYGSFCTQLNRALTGIAVEQDKNT | 69 |
| S-9 Long | QAGSTPCNGVEGFNCYFPLQSYGFQPTNGVGYQPYRVVVL | 70 |
| S-14 Long | SSVLHSTQDLFLPFFSNVTWFHAIHVSGTNGTKRFDNPVL | 71 |
| S-15 Long | VLHSTQDLFLPFFSNVTWFHAIHVSGTNGTKRFDNPVLPF | 72 |
| S-21 Long | SQILPDPSKPSKRSFIEDLLFNKVTLADAGFIKQYGDCLG | 73 |
| ORF9b-1*11 Long | ISEMHPALRLVDPQIQLAVTRMENAVGRDQNNVGPKVYPI | 74 |
| N-8 Long | KMKDLSPRWYFYYLGTGPEAGLPYGANKDGIIWVATEGAL | 75 |
| N-15 Long | NFGDQELIRQGTDYKHWPQIAQFAPSASAFFGMSRIGMEV | 76 |
| M-13 Long | PLHGTILTRPLLESELVIGAVILRGHLRIAGHHLGRCDIK | 77 |
| ORF3a Long | GVKDCVVLHSYFTSDYYQLYSTQLSTDTGVEHVTFFIYNK | 78 |
| M-2 Long | LYIIKLIFLWLLWPVTLACFVLAAVYRINWITGGIAIAMA | 79 |
| M-8 Long | HLGRCDIKDLPKEITVATSRTLSYYKLGASQRVAGDSGFA | 80 |
| M-10 Long | IAMACLVGLMWLSYFIASFRLFARTRSMWSFNPETNILLN | 81 |
| N-6 Long | GMSRIGMEVTPSGTWLTYTGAIKLDDKDPNFKDQVILLNK | 82 |
| N-13 Long | IKLDDKDPNFKDQVILLNKHIDAYKTFPPTEPKKDKKKKA | 83 |

TABLE 3-continued

| Exemplary SARS-CoV-2 polypeptides. | | |
|---|---|---|
| Peptide Name | Sequence | SEQ ID NO: |
| N-overlap Long | SRIGMEVTPSGTWLTYTGAIKLDDKDPNFKDQVILLNKHIDAYK | 84 |
| ORF9b-1*8 Long | RKTLNSLEDKAFQLTPIAVQMTKLATTEELPDEFVVVTVK | 85 |
| S-22 Long | CDIPIGAGICASYQTQTNSPRRARSVASQSIIAYTMSLGA | 86 |
| S-F Long | SFIEDLLFNKVTLADAGFIKQYGDCLGDIAARDLICAQKFNG | 87 |

A SARS-CoV-2 polypeptide provided herein (e.g., a substantially pure polypeptide that comprises, consists essentially of, or consists of the amino acid sequence set forth in any one of SEQ ID NOs:1-87) can have the ability to induce or increase an immune response against a coronavirus such as SARS-CoV-2 within a mammal (e.g., a human). For example, after administering a SARS-CoV-2 polypeptide provided herein (e.g., a substantially pure polypeptide that comprises, consists essentially of, or consists of the amino acid sequence set forth in any one of SEQ ID NOs:1-87) or nucleic acid encoding a SARS-CoV-2 polypeptide provided herein (e.g., nucleic acid encoding a polypeptide that comprises, consists essentially of, or consists of the amino acid sequence set forth in any one of SEQ ID NOs:1-87) to a mammal (e.g., a human), that mammal can induce or increase an immune response (e.g., an antibody response and/or a T cell response) against a coronavirus such as SARS-CoV-2. Any appropriate method can be used to identify the presence of an immune response against a coronavirus such as SARS-CoV-2.

Any appropriate method can be used to obtain a SARS-CoV-2 polypeptide provided herein (e.g., a substantially pure polypeptide that comprises, consists essentially of, or consists of the amino acid sequence set forth in any one of SEQ ID NOs:1-87). For example, a SARS-CoV-2 polypeptide provided herein (e.g., a substantially pure polypeptide that comprises, consists essentially of, or consists of the amino acid sequence set forth in any one of SEQ ID NOs:1-87) can be obtained by isolating the SARS-CoV-2 polypeptide of interest from cells expressing the SARS-CoV-2 polypeptide (e.g., cells engineered to express the SARS-CoV-2 polypeptide of interest from exogenous nucleic acid encoding that SARS-CoV-2 polypeptide or cells infected with a virus (e.g., SARS-CoV-2) that express the SARS-CoV-2 polypeptide of interest from that virus) or by synthesizing the SARS-CoV-2 polypeptide of interest using appropriate polypeptide synthesizing techniques (e.g., solution phases synthesis (SPS), solid phase peptide synthesis (SPPS), and expressed protein ligation (EPL)).

In some cases, one or more SARS-CoV-2 polypeptides provided herein (e.g., one or more polypeptides that comprises, consists essentially of, or consists of the amino acid sequence set forth in any one of SEQ ID NOs:1-87) can be presented on a particle. For example, one or more SARS-CoV-2 polypeptides provided herein (e.g., one or more polypeptides that comprises, consists essentially of, or consists of the amino acid sequence set forth in any one of SEQ ID NOs:1-87) can be presented on a nanoparticle.

In an aspect, one or more SARS-CoV-2 polypeptides provided herein (e.g., one or more polypeptides that comprises, consists essentially of, or consists of the amino acid sequence set forth in any one of SEQ ID NOs:1-87) are presented on a virus-like particle (VLP). Without being bound by theory, VLPs are nanostructures that closely resemble viruses, with diverse applications in immunization, therapeutics, and diagnostics. VLPs possess self-adjuvanting properties and allow for highly repetitive presentation of over 170 epitopes on its surface. In addition to enhanced antigen presentation, packaging peptides with VLPs may reduce the amount of peptide needed per dose to about 5%-10% of the dose of unpackaged peptides. VLPs are also easier to administer via various routes of administration than emulsions. In an aspect, one or more SARS-CoV-2 polypeptides provided herein (e.g., one or more polypeptides that comprises, consists essentially of, or consists of the amino acid sequence set forth in any one of SEQ ID NOs:1-87) are presented on a virus-like particle (VLP) made from viruses including, but not limited to, Parvoviridae (e.g. adeno-associated virus), Retroviridae (e.g. HIV), Flaviviridae (e.g. Hepatitis C virus), Paramyxoviridae (e.g. Nipah) and bacteriophages (e.g. Qβ, AP205). In an aspect, one or more SARS-CoV-2 polypeptides provided herein (e.g., one or more polypeptides that comprises, consists essentially of, or consists of the amino acid sequence set forth in any one of SEQ ID NOs:1-87) are presented on a virus-like particle (VLP) made from bacteriophage Qβ. In an aspect, one or more SARS-CoV-2 polypeptides provided herein (e.g., one or more polypeptides that comprises, consists essentially of, or consists of the amino acid sequence set forth in any one of SEQ ID NOs:1-87) are presented on a poly(lactic-co-glycolic acid) (PLGA) nanoparticle. In an aspect, the VLP-peptide or PLGA-peptide is formulated with one or more adjuvants and one or more immunostimulatory agents. Examples of adjuvants and one or more immunostimulatory molecules that can be formulated with the VLP-peptide or PLGA-peptide include, without limitation, CpG oligonucleotide motifs, aluminum (e.g., aluminum salts such as aluminum sulfate, aluminum hydroxide, aluminum phosphate, aluminum potassium sulfate, and microfluidized aluminum salts), monophosphoryl lipid A, aluminumphosphylate, MF59, MF59-like, AS03, AS04, AS03-like, AS04-like, AS01B-like, GM-CSF, and GLA. In an aspect, one or more adjuvants or immunostimulatory molecules can be a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AIT4, LiT4), aluminum sulfate, aluminum hydroxide, aluminum phosphate, aluminum potassium sulfate, monophosphoryl lipid A, aluminum-phosphylate, MF59, AS03, AS04, AS03-like, AS04-like, AS01B-like, GM-CSF, Addavax, AddaS03, retinoic acid-inducible gene I (RIG-I), lipid nanoparticles, and GLA. In an aspect, one or more adjuvants or immunostimulatory molecules is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA. In an aspect, one or more adjuvants or immunostimulatory molecules is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, retinoic acid-inducible gene I (RIG-I), lipid nanoparticles (e.g., LION), and GLA. In an aspect, the polypeptides disclosed herein are linked to poly(lactic-co-glycolic acid) (PLGA) nanoparticles. In an aspect, the polypeptides are attached to one or more virus-like particles (VLP). In an aspect, the VLP-peptide is formulated with Alum and CpG. In an aspect, the VLP-peptide is formulated with Montanide 51 and CpG or GLA.

This document also provides nucleic acid encoding one or more SARS-CoV-2 polypeptides provided herein (e.g., one or more polypeptides that comprises, consists essentially of, or consists of the amino acid sequence set forth in any one of SEQ ID NOs:1-87). For example, this document provides vectors (e.g., plasmids and viral vectors) that include nucleic acid encoding one or more SARS-CoV-2 polypeptides provided herein (e.g., one or more polypeptides that comprises, consists essentially of, or consists of the amino acid sequence set forth in any one of SEQ ID NOs:1-87) in a manner such that the SARS-CoV-2 polypeptide can be expressed within a cell.

When a vector including nucleic acid encoding one or more SARS-CoV-2 polypeptides provided herein (e.g., one or more polypeptides that comprises, consists essentially of, or consists of the amino acid sequence set forth in any one of SEQ ID NOs:1-87) is a non-viral vector, any appropriate non-viral vector can be used. In some cases, a non-viral vector can be an expression plasmid (e.g., a cDNA expression vector).

When a vector including nucleic acid encoding one or more SARS-CoV-2 polypeptides provided herein (e.g., one or more polypeptides that comprises, consists essentially of, or consists of the amino acid sequence set forth in any one of SEQ ID NOs:1-87) is a viral vector, any appropriate viral vector can be used. A viral vector can be derived from a positive-strand virus or a negative-strand virus. A viral vector can be derived from a virus having a single-stranded genome or a virus having a double stranded genome. A viral vector can be derived from a virus with a DNA genome or a RNA genome. In some cases, a viral vector can be a chimeric viral vector. In some cases, a viral vector can infect dividing cells. In some cases, a viral vector can infect non-dividing cells. Examples of virus-based vectors that can including nucleic acid encoding a SARS-CoV-2 polypeptide provided herein (e.g., a polypeptide that comprises, consists essentially of, or consists of the amino acid sequence set forth in any one of SEQ ID NOs:1-87) include, without limitation, virus-based vectors based on adenoviruses, adeno-associated viruses (AAVs), retroviruses, lentiviruses, measles viruses, vesicular stomatitis viruses, and vaccinia viruses.

In addition to nucleic acid encoding one or more SARS-CoV-2 polypeptides provided herein (e.g., one or more polypeptides that comprises, consists essentially of, or consists of the amino acid sequence set forth in any one of SEQ ID NOs:1-87), a vector (e.g., a plasmid or a viral vector) can contain one or more regulatory elements operably linked to the nucleic acid encoding one or more SARS-CoV-2 polypeptides provided herein. Such regulatory elements can include promoter sequences, enhancer sequences, response elements, signal peptides, internal ribosome entry sequences, polyadenylation signals, terminators, and inducible elements that modulate expression (e.g., transcription or translation) of a nucleic acid. The choice of regulatory element(s) that can be included in a vector depends on several factors, including, without limitation, inducibility, targeting, and the level of expression desired. For example, a promoter can be included in a vector to facilitate transcription of a nucleic acid encoding one or more SARS-CoV-2 polypeptides provided herein (e.g., a polypeptide that comprises, consists essentially of, or consists of the amino acid sequence set forth in any one of SEQ ID NOs:1-87). A promoter can be a naturally occurring promoter or a recombinant promoter. A promoter can be constitutive or inducible (e.g., in the presence of tetracycline), and can affect the expression of a nucleic acid encoding a polypeptide in a general or cell/tissue-specific manner. Examples of promoters that can be used to drive expression of one or more SARS-CoV-2 polypeptides provided herein (e.g., a polypeptide that comprises, consists essentially of, or consists of the amino acid sequence set forth in any one of SEQ ID NOs:1-87) in cells include, without limitation, CMV promoters, EF1a promoters, SV40 promoters, PGK1 promoters, Ubc promoters, TRE promoters, and CAG promoters. As used herein, "operably linked" refers to positioning of a regulatory element in a vector relative to a nucleic acid encoding a polypeptide in such a way as to permit or facilitate expression of the encoded polypeptide. For example, a vector can contain a promoter and nucleic acid encoding one or more SARS-CoV-2 polypeptides provided herein. In this case, the promoter is operably linked to a nucleic acid encoding one or more SARS-CoV-2 polypeptides provided herein such that it drives expression of the SARS-CoV-2 polypeptide(s) in cells.

This document also provides compositions that include one or more (e.g., one, two, three, four, five, six, seven, eight, nine, ten, 11, 12, 13, 14, 15, 16, 17, 18, 19, 20, or more) of the SARS-CoV-2 polypeptides provided herein and/or nucleic acid encoding one or more (e.g., one, two, three, four, five, six, seven, eight, nine, ten, 11, 12, 13, 14, 15, 16, 17, 18, 19, 20, or more) of the SARS-CoV-2 polypeptides provided herein. For example, a composition provided herein can include one or more of the SARS-CoV-2 polypeptides set forth in Table 1 (or nucleic acid encoding those SARS-CoV-2 polypeptides). For example, a composition provided herein can include one or more of the SARS-CoV-2 polypeptides set forth in Table 2 (or nucleic acid encoding those SARS-CoV-2 polypeptides). For example, a composition provided herein can include one or more of the SARS-CoV-2 polypeptides set forth in Table 3 (or nucleic acid encoding those SARS-CoV-2 polypeptides).

In some cases, a composition provided herein can include at least two (e.g., two, three, four, five, six, seven, eight, nine, ten, 11, 12, 13, 14, 15, 16, 17, 18, 19, 20, or more) of the SARS-CoV-2 polypeptides provided herein and/or nucleic acid encoding at least two (e.g., two, three, four, five, six, seven, eight, nine, ten, 11, 12, 13, 14, 15, 16, 17, 18, 19, 20, or more) of the SARS-CoV-2 polypeptides provided herein. For example, a composition provided herein can include at least two of the SARS-CoV-2 polypeptides set forth in Table 1 (or nucleic acid encoding those SARS-CoV-2 polypeptides). For example, a composition provided herein can include at least two of the SARS-CoV-2 polypeptides set forth in Table 2 (or nucleic acid encoding those SARS-CoV-2 polypeptides). For example, a composition provided herein can include at least two of the SARS-CoV-2 polypeptides set forth in Table 3 (or nucleic acid encoding those SARS-CoV-2 polypeptides). In an aspect, a composition provided herein can include at least two of the SARS-CoV-2 polypeptides set forth in Tables 1, 2, and 3. Examples of other specific combinations of polypeptides that can be used to make a composition provided herein include, without limitation, those set forth in Table 4.

pounds. A term "pharmaceutical excipient" includes materials such as carriers, pH-adjusting and buffering agents, tonicity adjusting agents, wetting agents, colorants, and preservatives.

In some cases, a composition provided herein (e.g., a composition that includes one or more of the SARS-CoV-2 polypeptides provided herein and/or nucleic acid encoding one or more of the SARS-CoV-2 polypeptides provided herein) can be a vaccine composition. For example, a composition containing one or more polypeptides set forth in SEQ ID NOs:1-87 can be formulated into a polypeptide-based vaccine for use in a mammal (e.g., a human). Any appropriate method can be used to formulate a polypeptide-based vaccine such as those described elsewhere (Belyakov et al., *Proc. Natl. Acad. Sci. U.S.A.,* 95:1709-1714 (1998); Jackson et al., *Proc. Natl. Acad. Sci. U.S.A.,* 101:15440-15445 (2004); Ruckwardt et al., Lancet Respir Med., S2213-2600(21)00098-9 (2021)). In some cases, a vaccine compo-

TABLE 4

| Exemplary combinations of polypeptides (or nucleic acid encoding those polypeptides). | |
| --- | --- |
| Composition Number | Combination of polypeptides (or nucleic acid encoding those polypeptides) |
| 1 | SEQ ID NO: 1 + SEQ ID NO: 5 + SEQ ID NO: 15 + SEQ ID NO: 37 + SEQ ID NO: 40 + SEQID NO: 13 |
| 2 | SEQ ID NO: 1 + SEQ ID NO: 9 + SEQ ID NO: 12 + SEQ ID NO: 18 + SEQ ID NO: 21 + SEQ ID NO: 46 |
| 3 | SEQ ID NO: 12 + SEQ ID NO: 14 + SEQ ID NO: 25 + SEQ ID NO: 27 + SEQ ID NO: 44 + SEQ ID NO: 45 |
| 4 | SEQ ID NO: 3 + SEQ ID NO: 37 + SEQ ID NO: 19 + SEQ ID NO: 28 + SEQ ID NO: 16 + SEQID NO: 31 |
| 5 | SEQ ID NO: 9 + SEQ ID NO: 17 + SEQ ID NO: 2 + SEQ ID NO: 39 + SEQ ID NO: 24 + SEQ ID NO: 27 + SEQ ID NO: 43 |
| 6 | SEQ ID NO: 1 + SEQ ID NO: 2 + SEQ ID NO: 8 + SEQ ID NO: 10 + SEQ ID NO: 11 + SEQ ID NO: 14 + SEQ ID NO: 18 + SEQ ID NO: 19 |
| 7 | SEQ ID NO: 12 + SEQ ID NO: 13 + SEQ ID NO: 25 + SEQ ID NO: 43 + SEQ ID NO: 53 + SEQ ID NO: 38 + SEQ ID NO: 15 + SEQ ID NO: 39 + SEQ ID NO: 34 + SEQ ID NO: 18 |
| 8 | SEQ ID NO: 68 + SEQ ID NO: 69 + SEQ ID NO: 70 + SEQ ID NO: 71 + SEQ ID NO: 72 + SEQ ID NO: 73 + SEQ ID NO: 74 + SEQ ID NO: 75 + SEQ ID NO: 76 + SEQ ID NO: 77 + SEQ ID NO: 78 |
| 9 | SEQ ID NO: 68 + SEQ ID NO: 69 + SEQ ID NO: 70 + SEQ ID NO: 71 + SEQ ID NO: 73 + SEQ ID NO: 74 + SEQ ID NO: 75 + SEQ ID NO: 76 + SEQ ID NO: 77 + SEQ ID NO: 78 |
| 10 | SEQ ID NO: 68 + SEQ ID NO: 69 + SEQ ID NO: 70 + SEQ ID NO: 71 + SEQ ID NO: 73 + SEQ ID NO: 74 + SEQ ID NO: 75 + SEQ ID NO: 76 + SEQ ID NO: 77 + SEQ ID NO: 78 + SEQ ID NO: 79 + SEQ ID NO: 80 + SEQ ID NO: 81 + SEQ ID NO: 82 + SEQ ID NO: 83 + SEQ ID NO: 84 + SEQ ID NO: 85 + SEQ ID NO: 86 + SEQ ID NO: 87 |

Any appropriate method can be used to formulate a composition provided herein (e.g., a composition that includes one or more of the SARS-CoV-2 polypeptides provided herein and/or nucleic acid encoding one or more of the SARS-CoV-2 polypeptides provided). For example, the one or more SARS-CoV-2 polypeptides provided herein (and/or nucleic acid encoding such one or more SARS-CoV-2 polypeptides) can be combined with a pharmaceutically acceptable carrier and/or a pharmaceutical excipient. The term "pharmaceutically acceptable" refers to generally non-toxic, inert, and/or physiologically compatible comsition provided herein can include one or more SARS-CoV-2 polypeptides provided herein (e.g., one or more SARS-CoV-2 polypeptides that comprise, consist essentially of, or consist of the amino acid sequence set forth in any of SEQ ID NOs:1-87) and/or nucleic acid encoding one or more of the SARS-CoV-2 polypeptides provided herein (e.g., nucleic acid encoding one or more SARS-CoV-2 polypeptides that comprise, consist essentially of, or consist of the amino acid sequence set forth in any of SEQ ID NOs:1-87) in combination with one or more adjuvants and/or one or more immunostimulatory molecules. Examples of adjuvants and one or more immunostimulatory molecules that can be included within a vaccine composition provided herein include, without limitation, CpG oligonucleotide motifs, aluminum (e.g., aluminum salts such as aluminum sulfate, aluminum hydroxide, aluminum phosphate, aluminum potassium sulfate, and microfluidized aluminum salts), monophosphoryl lipid A, aluminumphosphylate, MF59, MF59-like, AS03, AS04, AS03-like, AS04-like, AS01B-like, GM-CSF, and GLA. In an aspect, one or more adjuvants or immunostimulatory molecules can be formulated with the vaccine compositions provided herein include, but are not limited to, a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA. A person of ordinary skill in the art will be able to identify a suitable adjuvant or immunostimulatory molecule from the adjuvants or immunostimulatory molecules known in the art. In an aspect, one or more adjuvants or immunostimulatory molecules is selected from the group consisting of a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA. In an aspect, one or more adjuvants or immunostimulatory molecules is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA. In an aspect, one or more adjuvants or immunostimulatory molecules is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminum-phosphylate, MF59, AS03, AS04, AS03-like, AS04-like, AS01B-like, GM-CSF, retinoic acid-inducible gene I (RIG-I), lipid nanoparticles (e.g., LION), and GLA. In some cases, an adjuvant or immunostimulatory molecule included within a vaccine composition provided herein can be a non-naturally occurring (e.g., artificial) adjuvant or immunostimulatory molecule. In some cases, a vaccine composition provided herein can include one or more SARS-CoV-2 polypeptides provided herein (e.g., one or more polypeptides that comprise, consist essentially of, or consist of the amino acid sequence set forth in any of SEQ ID NOs:1-87) and/or nucleic acid encoding one or more of the SARS-CoV-2 polypeptides provided herein (e.g., nucleic acid encoding one or more SARS-CoV-2 polypeptides that comprise, consist essentially of, or consist of the amino acid sequence set forth in any of SEQ ID NOs:1-87), one or more adjuvants and/or one or more immunostimulatory molecules, and one or more pharmaceutically acceptable carriers and/or pharmaceutical excipients.

In some cases, a vaccine composition provided herein can be a multivalent vaccine composition having the ability to induce or increase immune responses against multiple members of the coronavirus family within a mammal (e.g., a human). For example, a vaccine composition provided herein can have the ability to induce or increase immune responses against SARS-CoV-2, 229E, NL63, OC43, HKU1, Middle East Respiratory Syndrome (MERS)-CoV, Severe Acute Respiratory Syndrome (SARS)-CoV, or any combination thereof. In some cases, a vaccine composition provided herein can be used as a multivalent vaccine composition having the ability to induce or increase immune responses against one or more lineages, clades, variants, or strains of SARS-CoV-2. For example, a vaccine composition provided herein can have the ability to induce or increase immune responses against B.1.1.7, B.1.351, P.1, P.2, B.1.427, B.1.429, B.1.617, B.1.525, B.1.526, B.1.617.1, B.1.617.3, B.1.621, B.1.621.1, B.1.1.529, BA.1, BA.1.1, BA.2, BA.2.12, BA.2.12.1, BA.3, BA.4, BA.5, XD, XE, XF, or any combination thereof. In an aspect, a vaccine composition provided by the present disclosure may induce or increase immune responses against future-identified coronavirus variants, or mutants or recombinants of existing variants.

This document also provides methods for increasing an immune response against a coronavirus infection (e.g., a SARS-CoV-2 infection such as COVID-19) within a mammal (e.g., a human). For example, one or more SARS-CoV-2 polypeptides provided herein (e.g., one or more SARS-CoV-2 polypeptides that comprise, consist essentially of, or consist of the amino acid sequence set forth in any of SEQ ID NOs:1-87) and/or nucleic acid encoding one or more of the SARS-CoV-2 polypeptides provided herein (e.g., nucleic acid encoding one or more SARS-CoV-2 polypeptides that comprise, consist essentially of, or consist of the amino acid sequence set forth in any of SEQ ID NOs:1-87) can be administered to a mammal (e.g., human) to induce or increase an immune response against a coronavirus infection (e.g., a SARS-CoV-2 infection such as COVID-19) within the mammal. For example, one or more SARS-CoV-2 polypeptides provided herein (e.g., one or more SARS-CoV-2 polypeptides that comprise, consist essentially of, or consist of the amino acid sequence set forth in any of SEQ ID NOs:1-87) and/or nucleic acid encoding one or more of the SARS-CoV-2 polypeptides provided herein (e.g., nucleic acid encoding one or more SARS-CoV-2 polypeptides that comprise, consist essentially of, or consist of the amino acid sequence set forth in any of SEQ ID NOs:1-87) can be administered to a mammal (e.g., a human) having or at risk of developing a coronavirus infection (e.g., a SARS-CoV-2 infection such as COVID-19) to treat that mammal.

As used herein, the terms "treat" or "treatment" is an approach for obtaining beneficial or desired clinical results. In an aspect, the terms "treat" or "treatment" means to administer a SARS-CoV-2 polypeptide disclosed herein that partially or completely alleviates, ameliorates, relieves, inhibits, delays onset of, reduces severity of, and/or reduces incidence of one or more symptoms, features and causes of a SARS-CoV-2 infection (e.g., a COVID-19 infection). The terms "treat" or "treatment" includes the administration of a SARS-CoV-2 polypeptide disclosed herein to prevent or delay the onset of a symptom, complication, or biochemical indicia of a SARS-CoV-2 infection, alleviating a symptom or arresting or inhibiting further development of a SARS-CoV-2 infection. Treatment may be prophylactic (to prevent or delay the onset of the SARS-CoV-2 infection, or to prevent the manifestation of a clinical or subclinical symptom thereof) or therapeutic suppression or alleviation of a symptom after the manifestation of the SARS-CoV-2 infection.

Any appropriate mammal can be administered one or more SARS-CoV-2 polypeptides provided herein (e.g., one or more SARS-CoV-2 polypeptides that comprise, consist essentially of, or consist of the amino acid sequence set forth in any of SEQ ID NOs:1-87) and/or nucleic acid encoding one or more SARS-CoV-2 polypeptides provided herein (e.g., nucleic acid encoding one or more SARS-CoV-2 polypeptides that comprise, consist essentially of, or consist of the amino acid sequence set forth in any of SEQ ID NOs:1-87) to treat that mammal. Examples of mammals that can be administered one or more SARS-CoV-2 polypeptides provided herein (and/or nucleic acid encoding one or more SARSCoV-2 polypeptides provided herein) include, without limitation, humans, non-human primates (e.g., monkeys or apes), horses, dogs, cats, bovine species, pigs, sheep, mice, rats, hamsters, bats, foxes, goats, mink, and deer. In some cases, a human identified as having or as being at risk of developing a coronavirus infection (e.g., a SARS-CoV-2 infection such as COVID-19) can be administered one or more SARS-CoV-2 polypeptides provided herein (and/or nucleic acid encoding one or more SARS-CoV-2 polypeptides provided herein) to treat that human. In an aspect, a human identified as having or as being at risk of developing a severe illness from a coronavirus infection (e.g., a SARS-CoV-2 infection such as COVID-19) can be administered one or more SARS-CoV-2 polypeptides provided herein (and/or nucleic acid encoding one or more SARS-CoV-2 polypeptides provided herein) to treat that human. In an aspect, a human identified as immunocompromised can be administered one or more SARS-CoV-2 polypeptides provided herein (and/or nucleic acid encoding one or more SARS-CoV-2 polypeptides provided herein) to treat that human. In an aspect, a human identified as an organ transplant recipient can be administered one or more SARS-CoV-2 polypeptides provided herein (and/or nucleic acid encoding one or more SARS-CoV-2 polypeptides provided herein) to treat that human. In an aspect, a human who is diabetic can be administered one or more SARS-CoV-2 polypeptides provided herein (and/or nucleic acid encoding one or more SARS-CoV-2 polypeptides provided herein) to treat that human.

In some cases, the methods described herein can include identifying a mammal (e.g., a human) as needing an induction or an increase in an immune response against a coronavirus infection (e.g., a SARS-CoV-2 infection such as COVID-19). In an aspect, humans identified as having been in recent (e.g., within one to two weeks) contact with one or more humans having or suspected of having a coronavirus infection (e.g., a SARS-CoV-2 infection such as COVID-19) can be identified as needing an induction or an increase in an immune response against a coronavirus such as SARS-CoV-2 and can be administered a vaccine composition provided herein. In an aspect, humans who have tested positive for SARS-CoV-2 infection by a polymerase chain reaction (PCR) or rapid antigen test is identified as needing an induction or an increase in an immune response against a coronavirus such as SARS-CoV-2 and can be administered a vaccine composition provided herein.

In some cases, one or more SARS-CoV-2 polypeptides provided herein (e.g., one or more SARS-CoV-2 polypeptides that comprise, consist essentially of, or consist of the amino acid sequence set forth in any of SEQ ID NOs:1-87) and/or nucleic acid encoding one or more SARS-CoV-2 polypeptides provided herein (e.g., nucleic acid encoding one or more SARS-CoV-2 polypeptides that comprise, consist essentially of, or consist of the amino acid sequence set forth in any of SEQ ID NOs:1-87) can be used to induce or increase an immune response against a coronavirus such as SARS-CoV-2 within a mammal (e.g., a human). For example, a vaccine composition provided herein can be administered to a mammal (e.g., a human) in need thereof (e.g., a mammal needing an induction or an increase in an immune response against a coronavirus infection (e.g., a SARS-CoV-2 infection such as COVID-19) such as a mammal having or at risk of developing COVID-19) to induce or increase an immune response (e.g., an antibody response and/or a T cell response) against a coronavirus such as SARS-CoV-2. In some cases, an immune response against a coronavirus such as SARS-CoV-2 within a mammal (e.g., a human) can be a humoral antibody response. In some cases, an immune response against a coronavirus such as SARS-CoV-2 within a mammal (e.g., a human) can be a cellular immune response. When an immune response against a coronavirus such as SARS-CoV-2 within a mammal (e.g., a human) is cellular immune response, the immune response can be a T helper type 1 (TH1) cell-mediated response, a TH2 cell-mediated response, or a combination thereof. When an immune response against a coronavirus such as SARS-CoV-2 within a mammal (e.g., a human) is cellular immune response, the immune response can involve any appropriate T cells (e.g., CD4$^+$ T cells and CD8$^+$ T cells).

In an aspect, an induction or an increase (or decrease) of immune response against a coronavirus, including but not limited to SARS-CoV-2, is measured by immune assays. In an aspect, an increase of immune response is measured by quantification of IFN-γ by enzyme-linked immunosorbent assays (ELISAs). Exemplary ELISA kits are commercial available at vendors, e.g., Immulon 4 HBX from Thermo Fisher Scientific, and can be performed in accordance with the manufacturer's instructions. In an aspect, an increase of immune response is measured by quantification of cytokine production (e.g., IFN-γ) by ELISPOT assays. Exemplary ELISPOT kits are commercially available at vendors, e.g., BD Biosciences (BD ELISPOT assay), and can be performed in accordance with the manufacturer's instructions. In an aspect, an increase of immune response is measured by quantification of IgG. In an aspect, an increase of immune response is measured by quantification of IgM. In an aspect, an increase of immune response is measured by quantification of total binding antibody or neutralizing antibody (measured by microneutralization assays or plaque-reduction assays). In an aspect, an increase of immune response is measured by a chemiluminescence immunoassay (CLIA). In an aspect, an increase of immune response is measured by an enzyme-linked immunosorbent assays (ELISA). In an aspect, an increase of immune response is measured by an electrochemiluminescence immunoassay (ECLIA). In an aspect, an increase of immune response is measured by a fluorescent microsphere Immunoassay (FMIA). In an aspect, an increase of immune response is measured by a chemiluminescent microparticle immunoassay (CMIA). In an aspect, an increase of immune response is measured by an enzyme-linked fluorescence assay (ELFA). In an aspect, an increase in immune response is quantified relative to known negative and positive controls. Some assays are quantified relative to calibrated standards (e.g., WHO International Standard—a pooled reference serum with a defined quantity of SARS-CoV-2 antibody and a defined neutralizing activity against SARS-CoV-2). Examples of quantification methods can be found in the literature, e.g., M. Wadhwa & Robin Thorpe, "Harmonization and standardization of immunogenicity assessment of biotherapeutic products," Bioanalysis, 11(17): 1593-1604 (2019). In an aspect, an increase in immune response is quantified relative to the patient's immune state before vaccination.

In some cases, one or more SARS-CoV-2 polypeptides provided herein (and/or nucleic acid encoding one or more SARS-CoV-2 polypeptides provided herein) can be used to delay or prevent the development of one or more symptoms of a coronavirus infection (e.g., a SARS-CoV-2 infection such as COVID-19) within a mammal at risk of developing a coronavirus infection (e.g., a SARS-CoV-2 infection such as COVID-19). For example, one or more SARS-CoV-2 polypeptides provided herein (and/or nucleic acid encoding one or more SARS-CoV-2 polypeptides provided herein) can be administered to a mammal (e.g., a human) in need thereof (e.g., a mammal needing an induction or an increase in an immune response against a coronavirus infection (e.g., a SARS-CoV-2 infection such as COVID-19) such as a mammal having or at risk of developing COVID-19) to delay or prevent the development of one or more symptoms of a coronavirus infection (e.g., a SARS-CoV-2 infection such as COVID-19) in the mammal. Symptoms of a coronavirus infection (e.g., a SARS-CoV-2 infection such as COVID-19) include, without limitation, fever, chills, cough, shortness of breath, difficulty breathing, fatigue, muscle aches, body aches, headache, loss of taste, loss of smell, sore throat, congestion, runny nose, nausea, vomiting, diarrhea, persistent pain or pressure in the chest, arterial thromboses, venous thromboses, and ventilatory failure. For example, the materials and methods described herein can be used to delay the onset of one or more symptoms of a coronavirus infection (e.g., a SARS-CoV-2 infection such as COVID-19) within a mammal at risk of developing a coronavirus infection (e.g., a SARS-CoV-2 infection such as COVID-19) by, for example, 10, 20, 30, 40, 50, 60, 70, 80, 90, 95, or more percent.

In some cases, one or more SARS-CoV-2 polypeptides provided herein (and/or nucleic acid encoding one or more SARS-CoV-2 polypeptides provided herein) can be used to reduce the duration and/or the severity of one or more symptoms of a coronavirus infection (e.g., a SARS-CoV-2 infection such as COVID-19) present within a mammal having a coronavirus infection (e.g., a SARS-CoV-2 infection such as COVID-19). For example, one or more SARS-CoV-2 polypeptides provided herein (and/or nucleic acid encoding one or more SARS-CoV-2 polypeptides provided herein) can be administered to a mammal (e.g., a human) in need thereof (e.g., a mammal needing an induction or an increase in an immune response against a coronavirus infection (e.g., a SARS-CoV-2 infection such as COVID-19) such as a mammal having or at risk of developing COVID-19) to reduce the duration and/or the severity of one or more symptoms of a coronavirus infection (e.g., a SARS-CoV-2 infection such as COVID-19) within the mammal. Symptoms of a coronavirus infection (e.g., a SARS-CoV-2 infection such as COVID-19) include, without limitation, fever, chills, cough, shortness of breath, difficulty breathing, fatigue, muscle aches, body aches, headache, loss of taste, loss of smell, sore throat, congestion, runny nose, nausea, vomiting, diarrhea, persistent pain or pressure in the chest, arterial thromboses, venous thromboses, and ventilatory failure. For example, the methods and materials described herein can be used to reduce the duration and/or the severity of one or more symptoms of one or more symptoms of a coronavirus infection (e.g., a SARS-CoV-2 infection such as COVID-19) present within a mammal having a coronavirus infection (e.g., a SARS-CoV-2 infection such as COVID-19) by, for example, 10, 20, 30, 40, 50, 60, 70, 80, 90, 95, or more percent.

When administering a composition (e.g., a vaccine composition) provided herein to a mammal (e.g., a human), any appropriate route of administration can be used. In an aspect, a composition (e.g., a vaccine composition) provided herein can be administered to a mammal (e.g., a human) intramuscularly (e.g., via intramuscular injection), subcutaneously (e.g., via a subcutaneous injection), orally, intranasally, transcutaneously, or via inhalation. In some cases, the route and/or mode of administration of a composition (e.g., a vaccine composition) provided herein can be adjusted for the mammal being treated. In an aspect, different doses of a composition (e.g., a vaccine composition) provided herein are administered to a mammal by the same route of administration. In an aspect, different doses of a composition (e.g., a vaccine composition) provided herein are administered to a mammal by different routes of administration. For example, a first dose of one or more SARS-CoV-2 polypeptides provided herein (e.g., one or more SARS-CoV-2 polypeptides that comprise, consist essentially of, or consist of the amino acid sequence set forth in any of SEQ ID NOs:1-87) may be administered subcutaneously while the second dose is administered intranasally.

In some cases, an effective amount of one or more SARS-CoV-2 polypeptides provided herein (e.g., one or more SARS-CoV-2 polypeptides that comprise, consist essentially of, or consist of the amino acid sequence set forth in any of SEQ ID NOs:1-87) and/or nucleic acid encoding one or more SARS-CoV-2 polypeptides provided herein (e.g., nucleic acid encoding one or more SARS-CoV-2 polypeptides that comprise, consist essentially of, or consist of the amino acid sequence set forth in any of SEQ ID NOs:1-87) can be an amount that induces or increases an immune response against a coronavirus such as SARS-CoV-2 within the mammal (e.g., a human) without producing significant toxicity to the mammal. The effective amount can remain constant or can be adjusted as a sliding scale or variable dose depending on the mammal's response to treatment. Without being bound by theory, various factors can influence the actual effective amount used for a particular application. For example, the severity of a SARS-CoV-2 virus infection (e.g., COVID-19) when treating a mammal having such an infection, the route of administration, the age and general health condition of the mammal, excipient usage, the possibility of co-usage with other therapeutic or prophylactic treatments such as use of other agents (e.g., antiviral agents such as remdesivir (e.g., VEKLURY®), galidesivir, and/or favipiravir (e.g., AVIGAN®), and antibody based treatments such as convalescent human plasma therapy and/or human plasma-derived product therapy), and the judgment of the treating physician may require an increase or decrease in the actual effective amount of one or more SARS-CoV-2 polypeptides provided herein (and/or nucleic acid encoding one or more SARS-CoV-2 polypeptides provided herein) that is administered.

In an aspect, an effective amount of one or more SARS-CoV-2 polypeptides provided herein (e.g., one or more SARS-CoV-2 polypeptides that comprise, consist essentially of, or consist of the amino acid sequence set forth in any of SEQ ID NOs:1-87) is about 0.1 μg, 0.2 μg, 0.3 μg, 0.4 μg, 0.5 μg, 0.6 μg, 0.7 μg, 0.8 μg, 0.9 μg, 0.1 mg, 0.2 mg, 0.3 mg, 0.4 mg, 0.5 mg, 0.6 mg, 0.7 mg, 0.8 mg, 0.9 mg, 1.0 mg, 2 mg, 3 mg, 4 mg, 5 mg, 6 mg, 7 mg, 8 mg, 9 mg, or 10 mg.

In some cases, an effective frequency of administration of one or more SARS-CoV-2 polypeptides provided herein (e.g., one or more SARS-CoV-2 polypeptides that comprise, consist essentially of, or consist of the amino acid sequence set forth in any of SEQ ID NOs:1-87) and/or nucleic acid encoding one or more SARS-CoV-2 polypeptides provided herein (e.g., nucleic acid encoding one or more SARS-CoV-2 polypeptides that comprise, consist essentially of, or consist of the amino acid sequence set forth in any of SEQ ID NOs:1-87) can be a frequency that induces or increases an immune response against a coronavirus such as SARS-CoV-2 within the mammal (e.g., a human) without producing significant toxicity to the mammal. For example, an effective frequency of administration of one or more SARS-CoV-2 polypeptides provided herein (and/or nucleic acid encoding one or more SARS-CoV-2 polypeptides provided herein) can be from about one to about three administrations. The frequency of administration of one or more SARS-CoV-2 polypeptides provided herein (and/or nucleic acid encoding one or more SARS-CoV-2 polypeptides provided herein) can remain constant or can be variable during the duration of treatment. Various factors can influence the actual effective frequency used for a particular application. For example, the severity of a SARS-CoV-2 virus infection (e.g., COVID-19) when treating a mammal having such an infection, the route of administration, the age and general health condition of the mammal, excipient usage, the possibility of co-usage with other therapeutic or prophylactic treatments such as use of other agents (e.g., antiviral agents such as remdesivir (e.g., VEKLURY®), galidesivir, and/or favipiravir (e.g., AVIGAN®), and antibody based treatments such as convalescent human plasma therapy and/or human plasma-derived product therapy), and the judgment of the treating physician may require an increase or decrease in the actual effective frequency of administration of one or more SARS-CoV-2 polypeptides provided herein (and/or nucleic acid encoding one or more SARS-CoV-2 polypeptides provided herein).

In some cases, an effective duration of administration of one or more SARS-CoV-2 polypeptides provided herein (e.g., one or more SARS-CoV-2 polypeptides that comprise, consist essentially of, or consist of the amino acid sequence set forth in any of SEQ ID NOs:1-87) and/or nucleic acid encoding one or more SARS-CoV-2 polypeptides provided herein (e.g., nucleic acid encoding one or more SARS-CoV-2 polypeptides that comprise, consist essentially of, or consist of the amino acid sequence set forth in any of SEQ ID NOs:1-87) can be a duration that induces or increases an immune response against a coronavirus such as SARS-CoV-2 within the mammal (e.g., a human) without producing significant toxicity to the mammal. For example, an effective duration of administration of one or more SARS-CoV-2 polypeptides provided herein (and/or nucleic acid encoding one or more SARS-CoV-2 polypeptides provided herein) can vary from a single time point of administration to several weeks (e.g., 2, 3, or 4 weeks) to several months (e.g., 2 or 3 months). Multiple factors can influence the actual effective duration used for a particular application. For example, the severity of a SARS-CoV-2 virus infection (e.g., COVID-19) when treating a mammal having such an infection, the route of administration, the age and general health condition of the mammal, excipient usage, the possibility of co-usage with other therapeutic or prophylactic treatments such as use of other agents (e.g., antiviral agents such as remdesivir (e.g., VEKLURY®), galidesivir, and/or favipiravir (e.g., AVIGAN®), and antibody based treatments such as convalescent human plasma therapy and/or human plasma-derived product therapy), and the judgment of the treating physician may require an increase or decrease in the actual effective duration of administration of one or more SARS-CoV-2 polypeptides provided herein (and/or nucleic acid encoding one or more SARS-CoV-2 polypeptides provided herein).

In some cases, a mammal (e.g., a human) can be administered a first dose. Then, about 14 days to 1 year later, the mammal can be administered a second dose. In an aspect, the second dose is administered about 14 days, 15 days, 16 days, 17 days, 18 days, 19 days, 20 days, 21 days, 22 days, 23 days, 24 days, 25 days, 26 days, 27 days, 28 days, 29 days, 30 days, 40 days, 50 days, 60 days, 70 days, 80 days, 90 days, 100 days, 110 days, 120 days, 1 month, 2 months, 3 months, 4 months, 5 months, 6 months, 7 months, 8 months, 9 months, 10 months, 11 months, or 12 months after the first dose. In some cases, this can be repeated a third or fourth time. In an aspect, a mammal is administered another dose about 14 days, 15 days, 16 days, 17 days, 18 days, 19 days, 20 days, 21 days, 22 days, 23 days, 24 days, 25 days, 26 days, 27 days, 28 days, 29 days, 30 days, 40 days, 50 days, 60 days, 70 days, 80 days, 90 days, 100 days, 110 days, 120 days, 1 month, 2 months, 3 months, 4 months, 5 months, 6 months, 7 months, 8 months, 9 months, 10 months, 11 months, or 12 months after a previous dose. In an aspect, a mammal is administered a total of two doses, three doses, four doses, five doses, six doses, seven doses, eight doses, nine doses, or ten doses. In some cases, if enough time has passed (e.g., eight months, a year, or more) since this vaccination and the immune response induced in the mammal is determined to be less than effective, then that mammal can be administered another round of vaccinations with the same vaccine composition or with a vaccine composition having a different polypeptide or set of polypeptides (and/or nucleic acid encoding a different polypeptide or set of polypeptides). In an aspect, a mammal is administered with a dose with the same vaccine composition as a previous dose, or with a vaccine composition having a different polypeptide or set of polypeptides (and/or nucleic acid encoding a different polypeptide or set of polypeptides) as a previous dose, after a fixed time interval, e.g., 1 month, 2 months, 3 months, 4 months, 5 months, 6 months, 7 months, 8 months, 9 months, 10 months, 11 months, 12 months, 18 months, or 24 months. In an aspect, a mammal is administered with a dose with the same vaccine composition as a previous dose, or with a vaccine composition having a different polypeptide or set of polypeptides (and/or nucleic acid encoding a different polypeptide or set of polypeptides) as a previous dose, after it has been determined that immune response against SARS-CoV-2 has decreased.

In an aspect, a mammal (e.g., a human) is administered a dose of one or more SARS-CoV-2 polypeptides provided herein (e.g., one or more SARS-CoV-2 polypeptides that comprise, consist essentially of, or consist of the amino acid sequence set forth in any of SEQ ID NOs:1-87), after the mammal has received a different vaccine for SARS-CoV-2. In an aspect, a mammal (e.g., a human) is administered a dose of one or more SARS-CoV-2 polypeptides provided herein (e.g., one or more SARS-CoV-2 polypeptides that comprise, consist essentially of, or consist of the amino acid sequence set forth in any of SEQ ID NOs:1-87), where the mammal has not received a different vaccine for SARS-CoV-2 previously. Examples of other vaccines for SARS-CoV-2 include, but are not limited to the Pfizer-Biontech COMIRNATY, and the Moderna Spikevax. In an aspect, a mammal (e.g., a human) is administered a dose of one or more SARS-CoV-2 polypeptides provided herein (e.g., one or more SARS-CoV-2 polypeptides that comprise, consist essentially of, or consist of the amino acid sequence set forth in any of SEQ ID NOs:1-87), before the mammal has received another vaccine for SARS-CoV-2.

This document also provides kits containing one or more (e.g., one, two, three, four, five, six, seven, eight, nine, ten, 11, 12, 13, 14, 15, 16, 17, 18, 19, 20, or more) SARS-CoV-2 polypeptides provided herein (e.g., one or more substantially pure polypeptides that comprise, consist essentially of, or consist of the amino acid sequence set forth in any of SEQ ID NOs:1-87) and/or nucleic acid encoding one or more SARS-CoV-2 polypeptides provided herein (e.g., nucleic acid encoding one or more SARS-CoV-2 polypeptides that comprise, consist essentially of, or consist of the amino acid sequence set forth in any of SEQ ID NOs:1-87). For example, a kit provided herein can include one or more of the polypeptides set forth in Tables 1, 2, 3, and 4. In an aspect, a kit provided herein can also be used for diagnosis of SARS-CoV-2 infection. In an aspect, a kit provided herein can also be used for monitoring immune response to the COVID-19 vaccines provided herein or by others.

The invention will be further described in the following examples, which do not limit the scope of the invention described in the claims.

EXAMPLES

Example 1: Peptide Based SARS-CoV-2Vaccine

This example describes the identification of immunogenic SARS-CoV-2-derived polypeptides.
Methods
Polypeptide Identification by Mass Spectrometry Human cell lines (such as Caco-2, A549, and THP-1) are infected with live SARS-CoV-2 virus (Wuhan/Washington USA/WA1-F6 strain). Naturally processed and HLA presented SARS-CoV-2-derived polypeptides are identified using strong cation exchange (SCX) chromatography and are analyzed by liquid chromatographic tandem mass spectrometry (LC-MS/MS).

Peptide sequences identified are as shown in Table 1. Identified polypeptides include both SARS-CoV-2 structural (S/RBD, N, and M, n=22 polypeptides) and nonstructural viral proteins (ORF1ab, ORF3a, and ORF9b, n=6 polypeptides).

The identified polypeptides have HLA class I and class II high polypeptides binding properties ($IC_{50}$). Polypeptides having HLA class I binding properties are 8-12 amino acid sequences long. Polypeptides having HLA class II binding properties are 13-25 amino acid sequences long.

An immunoinformatics approach is used for identification of B cell and T cell epitopes in the SARS-CoV-2 proteome as described elsewhere (see, e.g., Crooke et al., *Sci. Rep.,* 10(1):14179 (2020)).
Prediction of SARS-CoV-2 T Cell Epitopes Prediction of HLA class I and class II peptide epitopes is carried out with the 10 protein sequences reported for the Wuhan-Hu-1 isolate: E (GenBank accession: QHD43418), M (QHD43419), N (QHD43423), S (QHD43416), ORF3a (QHD43417), ORF6 (QHD43420), ORF7a (QHD43421), ORF8 (QHD43422), ORF10 (QHI42199), ORF1ab (QHD43415), and applied to the analysis of SARS-CoV-2 protein sequences using methods described elsewhere (see, e.g., Grifoni et al., *Cell Host Microbe,* 8;27(4):671-680.e2 (2020); and Srivastava et al., *bioRxiv,* 2020.04.01.019299).

Prediction and Structural Modeling of SARS-CoV-2 B Cell Epitopes

Linear B cell epitope predictions are performed on the three exposed SARS-CoV-2 structural proteins: S (GenBank accession: QHD43416), M (QHD43419), and E (QHD43418) using the BepiPred 1.0 algorithm. Epitope probability scores are calculated for each amino acid residue using a threshold of 0.35 (corresponding to >0.75 specificity and sensitivity below 0.5), and only epitopes ≥5 amino acid residues in length are further analyzed. The structure of the SARS-CoV-2 S protein is accessed from the Protein Data Bank (PDB ID: 6VSB). Discontinuous (i.e., structural) B cell epitope predictions for the S protein structure are carried out using DiscoTope 1.1 with a score threshold greater than −7.7 (corresponding to >0.75 specificity and sensitivity below 0.5). The main protein structure is modeled in PyMOL (Schrödinger, LLC), with predicted B cell epitopes identified by both BepiPred 1.0 and DiscoTope 1.1 highlighted as spheres.
IFN-γ ELISPOT Assay with Cells from Human Subjects Peripheral blood mononuclear cells (PBMCs) from 28 COVID-19-convalescent human donors with prior documented SARS-CoV-2 infections are used to measure antigen-specific IFN-γ producing cells using the BD (BD Biosciences, San Jose, Calif.) human IFN-γ ELISPOT kit according to the manufacturer's instructions.

For experiments on IFN-γ responses to peptide pool stimulation, the following protocol is used. Frozen PBMCs are thawed according to established laboratory procedure and plated at $2\times10^5$ cells/well in a 96-well BD™ ELISPOT plates coated with anti-human IFN-gamma antibody. Cells are treated with one of the following conditions: RPMI culture media with 5% FBS Penicillin/Streptomycin (CM) for the unstimulated/negative control condition; pooled SARS-CoV-2 peptides (at 10 μg/mL final concentration of each individual peptide) or whole Spike 51, RBD and Nucleocapsid proteins (at 1.25 μg/mL final concentration). Phytohemagglutinin (PHA) at 5 μg/mL is used as a positive control. Samples stimulated with each of the listed conditions are tested in quadruplicate. Cells are incubated at 37° C., 5% $CO_2$ for 18-20 hours. The plates are developed, and immune responses are quantified using the BD' human IFN-γ ELISPOT kit. All plates are scanned and analyzed using the same scanning and counting parameters on ImmunoSpot® S6 Macro Analyzer (Cellular Technology Ltd., Cleveland, Ohio, USA) using the ImmunoSpot® 5.1 Professional software. Peptide pools are considered positive if all of the following criteria are met: (i) the average spot count [stimulated-unstimulated]>4.99, (ii) the fold-change [stimulated compared to unstimulated]>1.99, and (iii) the t-test p-value<0.05.

For experiments on IFN-γ responses to individual peptide stimulation, the following protocol is used. PBMCs are plated at $2\times10^5$ cells/well in a 96-well BD™ ELISPOT plates coated with anti-human IFN-γ antibody. Cells are treated with one of the following conditions in quadruplicate: CM (unstimulated/negative control), or individual SARS-CoV-2 peptides at 10 μg/mL final concentration. PHA (5 μg/mL) is used as a positive control. Cells are incubated at 37° C., 5% $CO_2$ for 18-20 hours. The plates are developed, and immune responses are quantified using the BD' human IFN-g ELISPOT kits. All plates are scanned and analyzed using the same scanning and counting parameters on ImmunoSpot® S6 Macro Analyzer (Cellular Technology Ltd., Cleveland, Ohio, USA) using the ImmunoSpot® 5.1 Professional software. Individual peptides are considered positive if all of the following criteria are met: (i) the average spot count [stimulated-unstimulated]>9.99, (ii) the fold-change [stimulated compared to unstimulated]>1.99, and (iii) the t-test p-value<0.05.

Results

IFN-γ Responses to Peptide Pool Stimulation Using PBMCs from COVID-19 Convalescent Donors Naturally processed and in silico predicted HLA I and II SARS-CoV-2 peptides are identified through mass spectrometry and binding affinity prediction algorithms, as well as by generating overlapping 15-mers peptides from the structural (S, N, M, E) proteins. A total of 397 peptides are initially identified. These 397 peptides are grouped into three sets of 95 peptides (Sets #1, 2, and 4) and one set of 111 peptides (Set #3). Each set of peptides is further analyzed using the same IFN-γ ELISPOT assay protocol as described above.

Figure 1A:
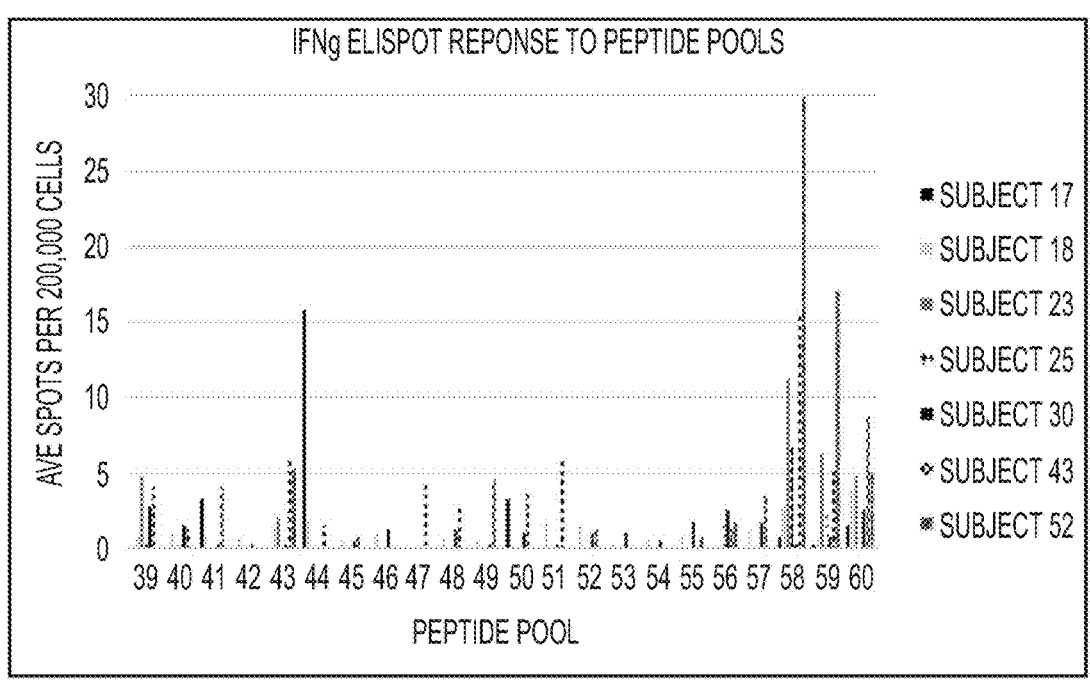
FIG. 1A: IFN-γ ELISPOT responses to SARS-CoV-2 polypeptides pool stimulation.
Figure 1B:
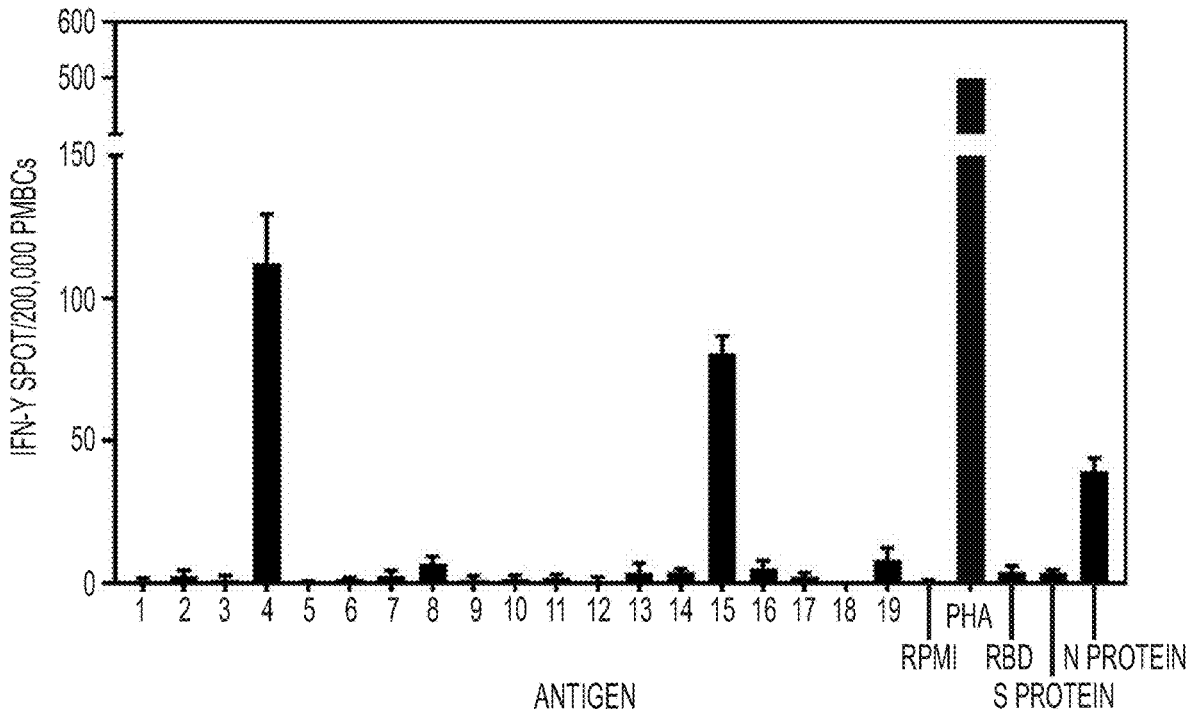
FIG. 1B: IFN-γ ELISPOT responses to SARS-CoV-2 polypeptides stimulation.

For Set #1, the 95 peptides are assigned into 19 pools containing 5 individual peptides each. Representative results are shown in FIGS. 1A-B. FIG. 1A depicts representative ELISPOT response of peptide pools to plasma from convalescent subjects. For example, FIG. 1B depicts IFN-γ ELISPOT response to pools 1-19 of subject 30, showing positive responses from peptide pools 4 and 15. Positive peptide pools are further analyzed at the individual peptide level. Based on the number of responders (3/3 criteria in at least 2 subjects) as well as spot forming units (SFUs) per 200,000 PBMCs (reflective of the magnitude of the T cell response), six pools (#2, 4, 8, 15, 16, 19) from Set #1 are selected for further individual peptide testing. Similarly, sixteen peptide pools from Set #2, sixteen peptide pools from Set #3, and twelve peptide pools from Set #4 are selected.

Human IFN-γ Responses to Individual Peptide Stimulation

Figure 2A:
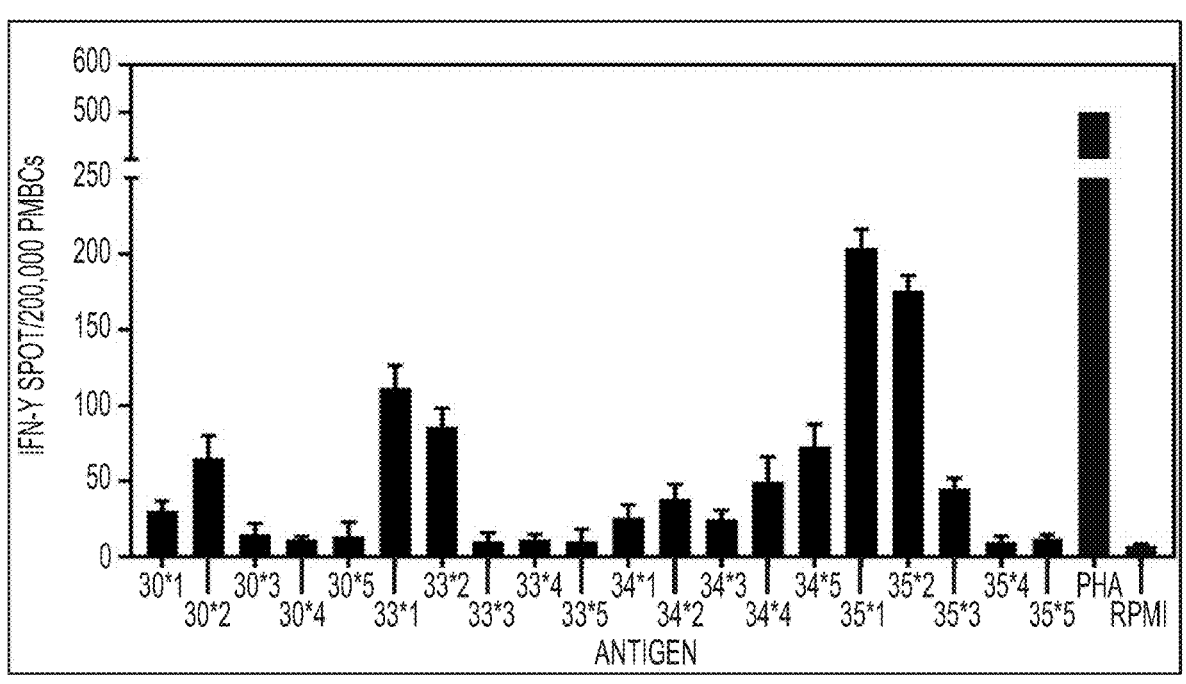
FIG. 2A: IFN-γ ELISPOT responses to individual SARS-CoV-2 polypeptides.
Figure 2B:
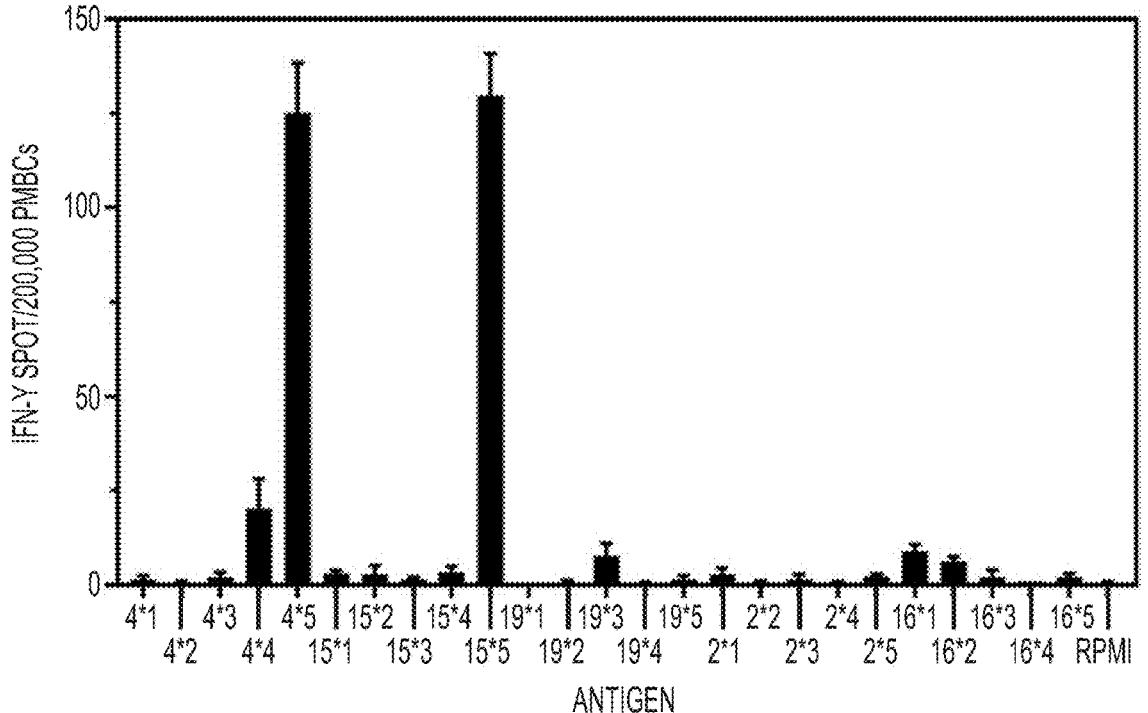
FIG. 2B: IFN-γ ELISPOT responses to individual SARS-CoV-2 polypeptides.
Figure 2C:
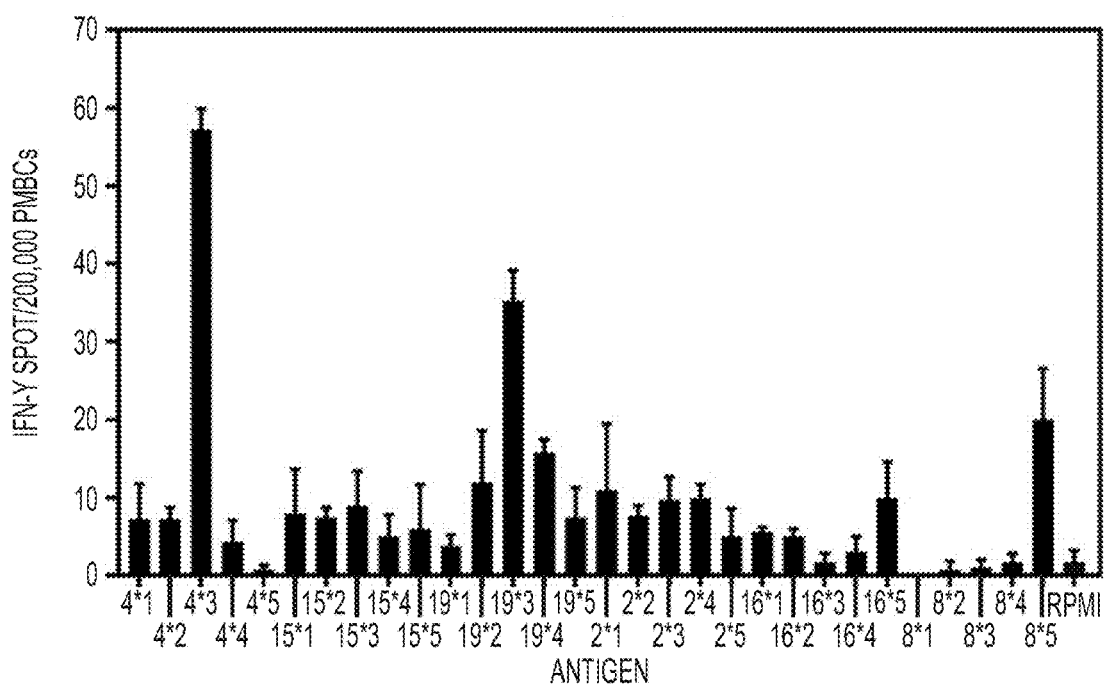
FIG. 2C: IFN-γ ELISPOT responses to individual SARS-CoV-2 polypeptides.

Testing of subjects with individual peptides is performed. Representative results are shown in FIG. 2A-C. FIG. 2A-C depict representative IFN-γ ELISPOT response to individual peptides from convalescent plasma from Subjects 17, 30, and 52 respectively.

A total of eight peptides from Set #1, twelve peptides from Set #2, seven peptides from Set #3, and seven peptides from Set #4 exhibit recall immune responses in PBMCs from convalescent COVID-19 patients and are selected for further testing. The selection is also expanded by adopting a less stringent selection criterion for maximal sensitivity, to include all peptides that meet the three criteria for positive response in at least one convalescent subject. This results in the inclusion of 18 additional peptides, yielding a total of 53 peptides (Table 1, SEQ ID NOs: 1-53) that are selected for large-scale synthesis and further testing in golden Syrian hamsters.

IFN-γ ELISPOT Assay with Cells from Golden Syrian Hamsters

Figure 3:
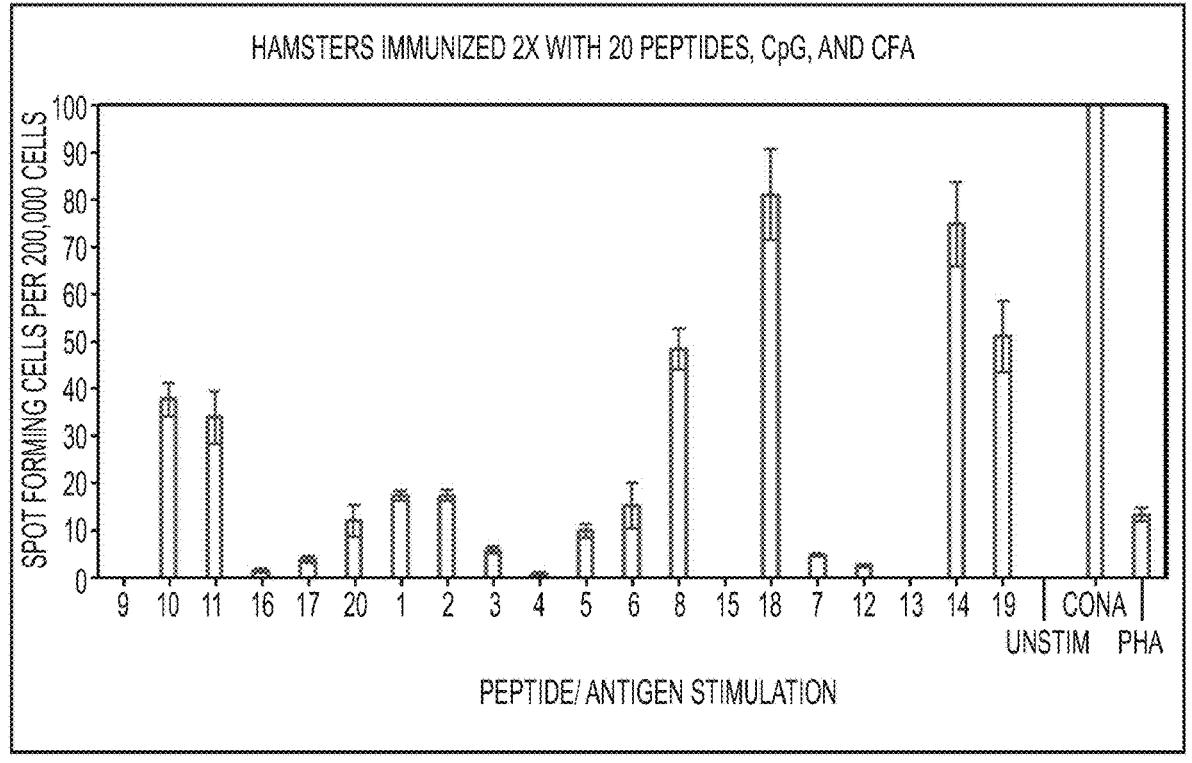
FIG. 3: Peptides induced immune responses in an animal hamster model.

Six hamsters are immunized with 20 μg of each peptide in an emulsion containing complete Freund's adjuvant (CFA) and 100 μg of CpG. 4 weeks later, each animal receives a booster immunization with 20 μg of each peptide in an emulsion containing incomplete Freund's adjuvant (IFA) and 100 μg of CpG. Cells ($2\times10^5$) isolated from harvested spleens and lymph nodes of golden Syrian hamsters 14 days after the second booster immunization (i.e., 28 days after the initial immunization), are plated in a 96-well, polyvinylidene fluoride (PVDF)-backed ELISPOT plates (Millipore) coated with anti-hamster IFN-γ antibody (Monoclonal antibody MTH21 at 0.5 mg/ml concentration; Mabtech, Inc. Cincinnati, Ohio). Cells are treated with one of the following conditions: RPMI culture media with 10% FBS, 0.1 mM non-essential amino acids, 0.5 mM sodium pyruvate, 0.05 mM 2-mercaptoethanol and Penicillin/Streptomycin, (unstimulated/negative control); individual SARS- CoV-2 peptide at 10 μg/mL final concentration, or 1.25 μg/mL Spike 51 and Nucleocapsid proteins. Concanavalin A (Con A) (2 μg/ml) or phytohemaggluttin (PHA) (2 μg/ml) are used as positive control. Samples stimulated with each of the conditions are tested in quadruplicate. Cells are incubated at 37° C., 5% $CO_2$ for 18-20 hours. The plates are developed, and immune responses are quantified using Hamster IFN-γ ELISpotBASIC kits (Mabtech, Inc. Cincinnati, Ohio). All plates are scanned and analyzed using the same counting parameters on ImmunoSpot® S6 Macro Analyzer (Cellular Technology Ltd., Cleveland, Ohio, USA) using the ImmunoSpot® 5.1 Professional software. Peptides are considered positive if the average spot count [stimulated-unstimulated]>9.99, the fold-change [stimulated compared to unstimulated]>1.99, and the t-test p-value<0.05. Results are shown in FIG. 3.

Example 2: Vaccinating Against SARS-CoV-2 in Hamsters

Hamsters have been an animal model of choice to study SARS-CoV-2 infection due to the fact that clinical disease and pathologic features of infection closely resemble those found in human COVID-19 patients. First, hamster ACE2 interacts well with SARS-CoV-2, thus hamster cells are natively susceptible to infection and do not require viral adaptation to the animal or transgenic expression of human ACE2. Second, severe lung injury in hamsters occurs after infection and the degree of lung pathology is associated with infectious dose, much like in human disease. Third, lung abnormalities in hamsters include severe, bilateral, multilobular ground glass opacity and regions of lung consolidation, similar to that found in human disease. Fourth, previously infected hamsters are resistant to re-challenge and protection correlates with antibody titer. A similar protection is believed to exist for human COVID-19 convalescent patients. Fifth, upon infection hamsters display increased secretion of inflammatory cytokines. Lastly, extrapulmonary inflammation is observed in the kidney, liver, and heart.

With regards to SARS-CoV-2, mouse cells are not natively susceptible to infection therefore a variety of models have been developed. The most common models include: genetically modified mice expressing human ACE, the use of mouse-adapted SARS-CoV-2, temporary transduction of hACE into the mouse respiratory tract using adenovirus or adeno-associated viruses. Each of these approaches has limitations, however, and challenge studies typically result in severe illness and death.

Selecting the Adjuvants

Figure 4:
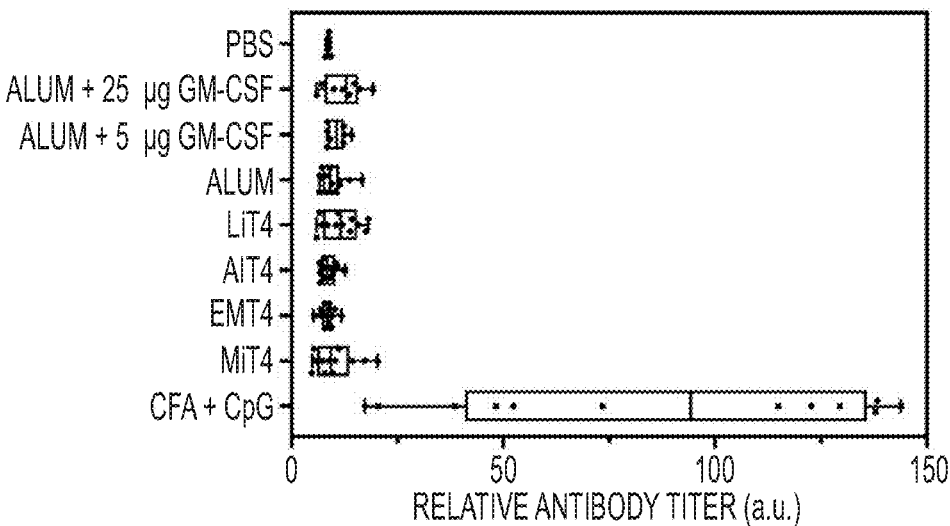
FIG. 4: Immune responses induced by peptides formulated with different adjuvants in hamsters.
Figure 5A:
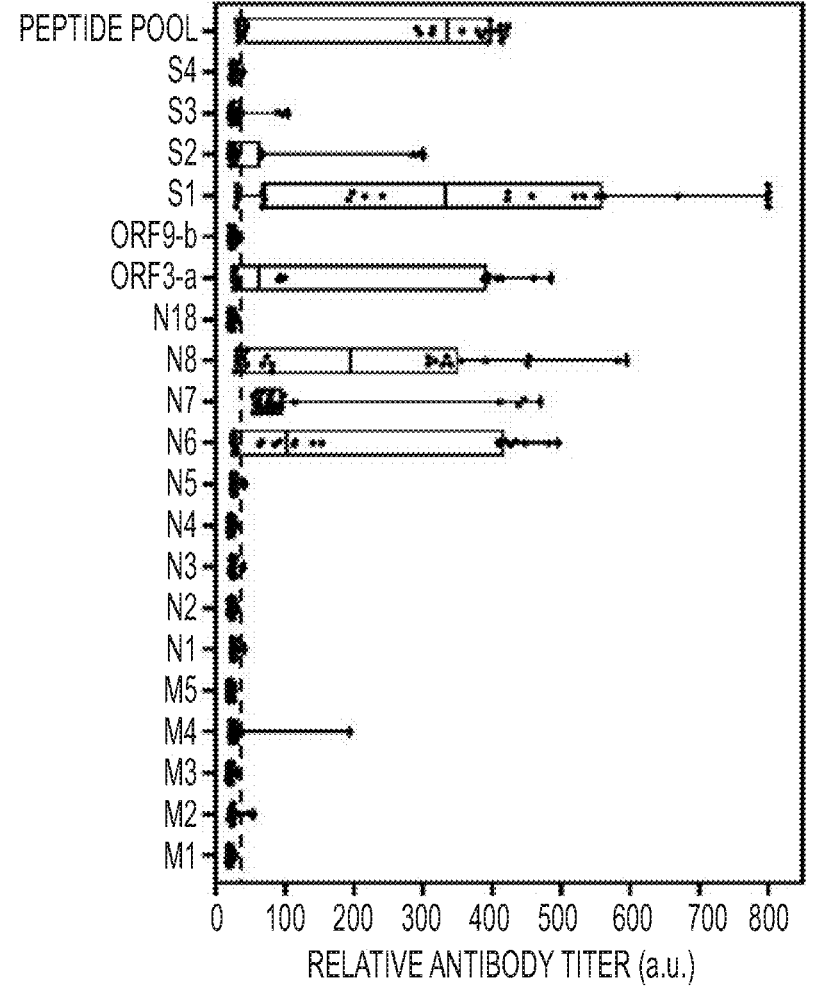
FIG. 5A: Immune responses induced by different peptides in hamsters as measured by IgG ELISA.
Figures 5B, 5C:
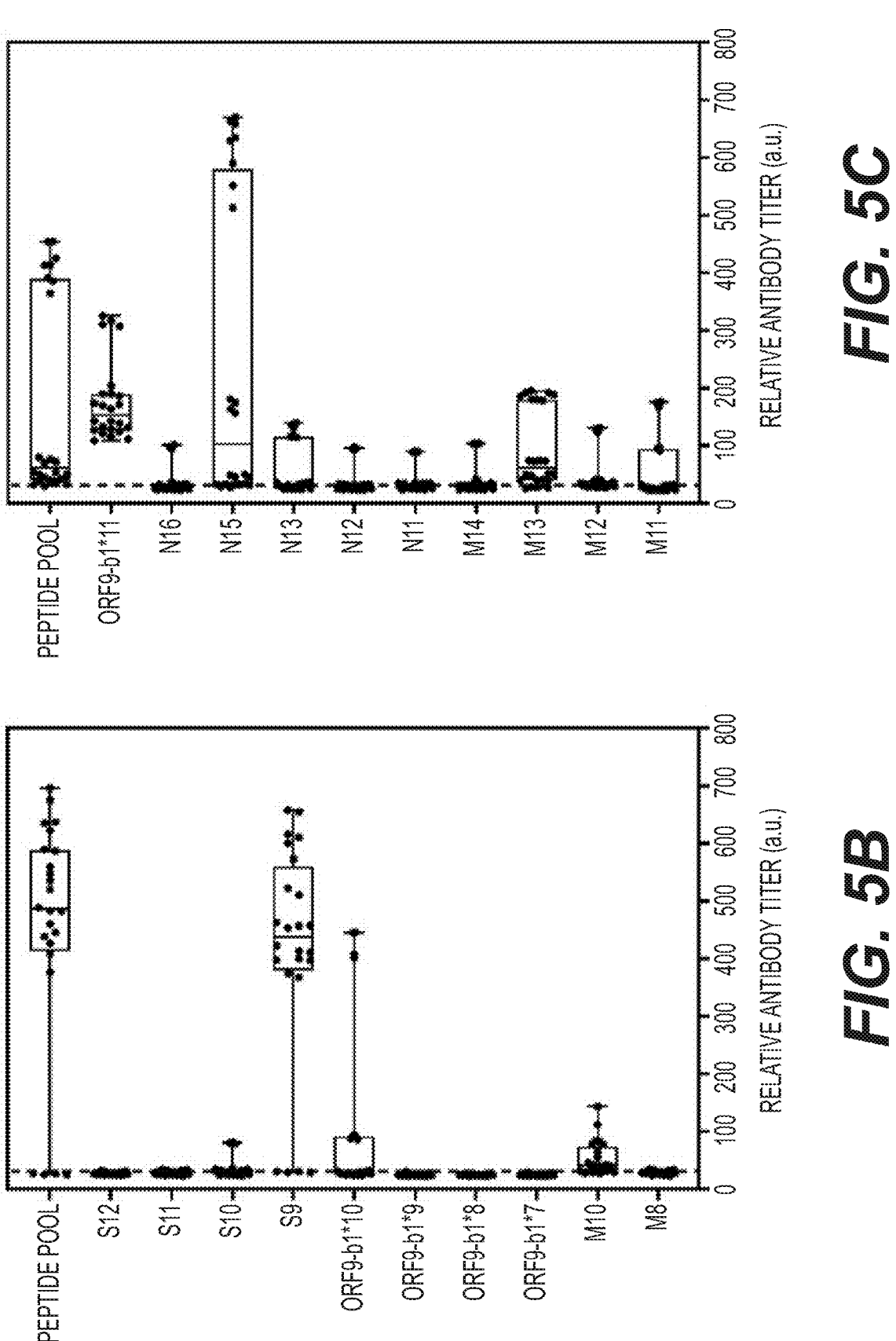
FIG. 5B: Immune responses induced by different peptides in hamsters as measured by IgG ELISA.
FIG. 5C: Immune responses induced by different peptides in hamsters as measured by IgG ELISA.
Figures 5D, 5E:
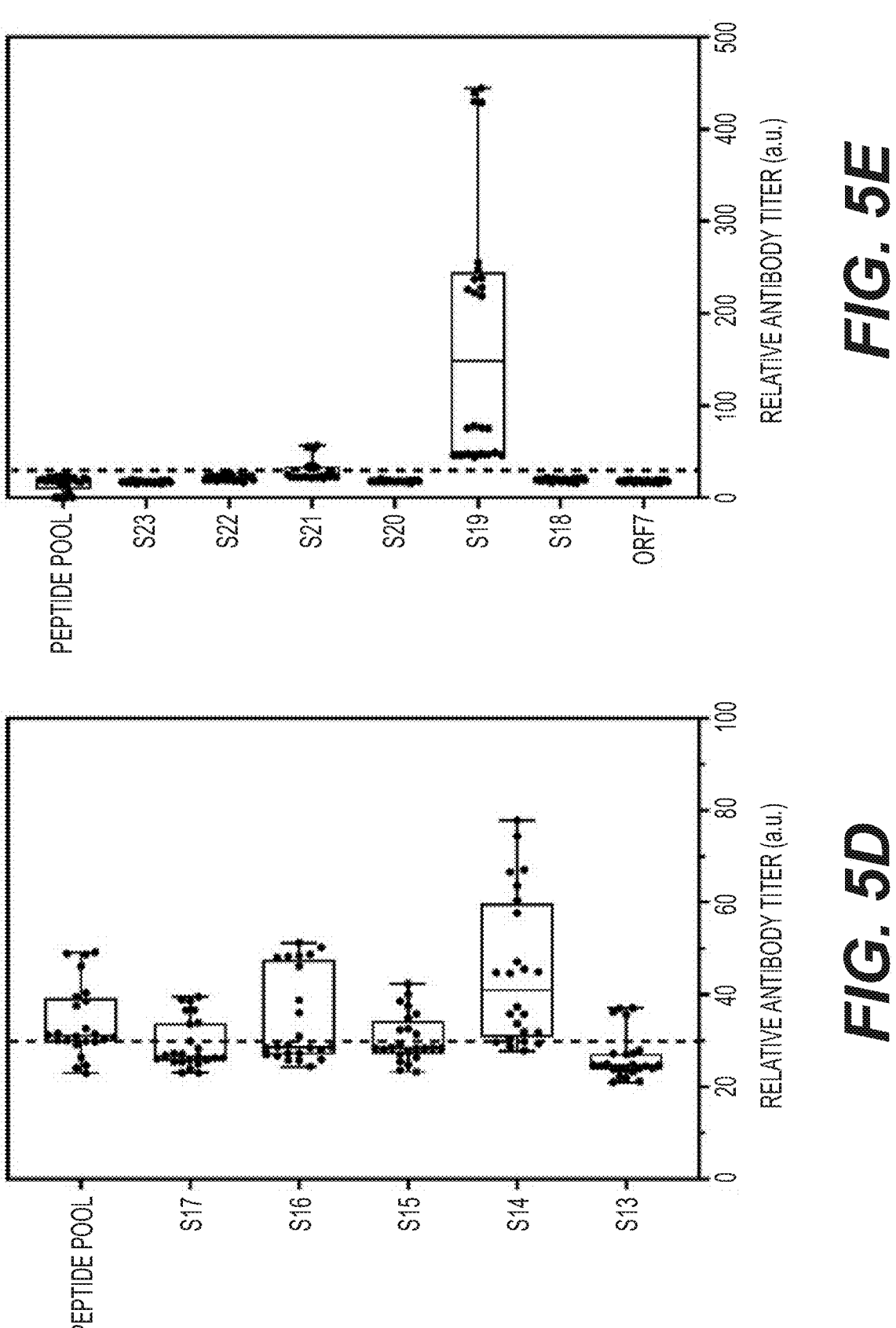
FIG. 5D: Immune responses induced by different peptides in hamsters as measured by IgG ELISA.
FIG. 5E: Immune responses induced by different peptides in hamsters as measured by IgG ELISA.
Figures 6A, 6B:
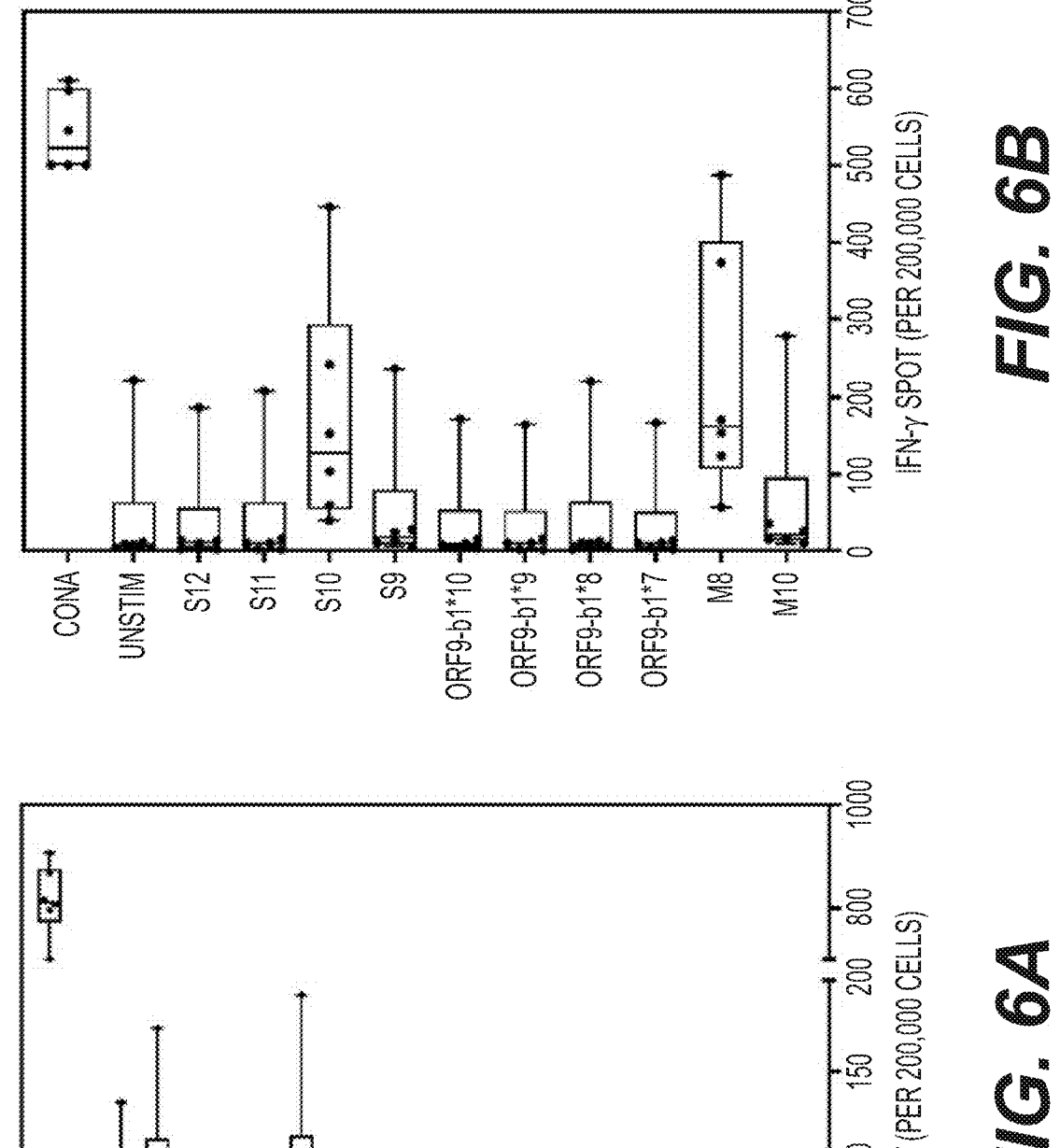
FIG. 6A: Immune responses induced by different peptides in hamsters as measured by IFN-γ ELISPOT.
FIG. 6B: Immune responses induced by different peptides in hamsters as measured by IFN-γ ELISPOT.
Figures 6C, 6D:
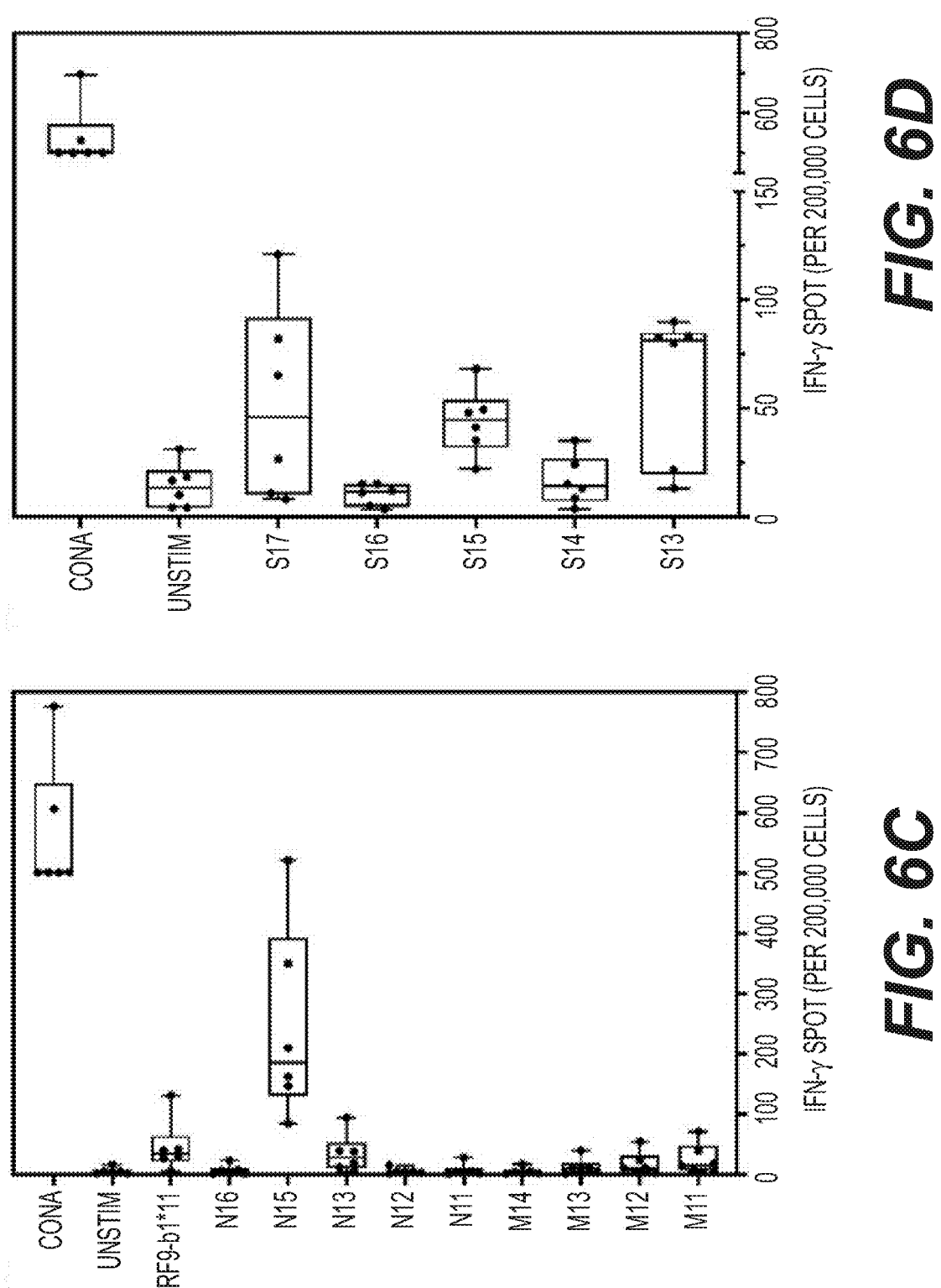
FIG. 6C: Immune responses induced by different peptides in hamsters as measured by IFN-γ ELISPOT.
FIG. 6D: Immune responses induced by different peptides in hamsters as measured by IFN-γ ELISPOT.
Figure 6E:
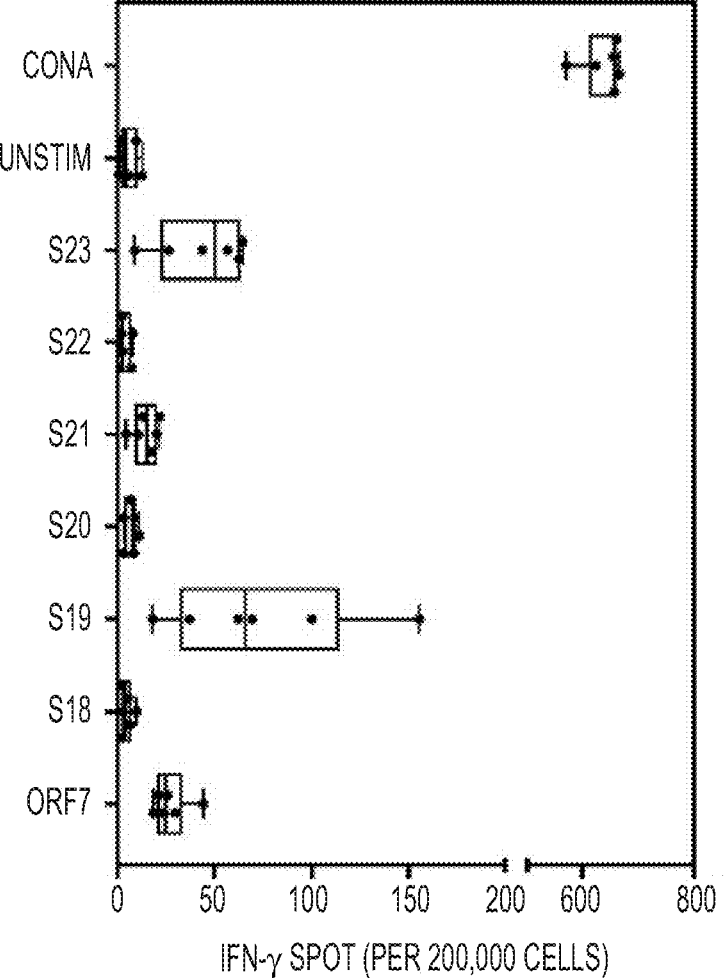
FIG. 6E: Immune responses induced by different peptides in hamsters as measured by IFN-γ ELISPOT.

Initial experiments are performed to screen a variety of adjuvants in Syrian Golden hamsters. First, 20 selected peptides (ORF-9b, ORF-3a, S1-S4, N1-N8, and M1-M5) are formulated with different adjuvants, as shown in Table 5. Of the adjuvants tested, the combination of Complete Freund's Adjuvant (CFA), and CpG clearly induces a robust peptide-specific antibody response (FIG. 4). Other adjuvant combinations induce marginal or no antibody responses. Therefore, this CFA+CpG combination is chosen for further experiments to evaluate immunogenicity of peptides.

TABLE 5

List of adjuvants used in adjuvant screening

| Adjuvant | Properties |
| --- | --- |
| CFA | Complete Freund's Adjuvant<br>Consists of heat-killed Mycobacterium tuberculosis and trehalose 6,6' dimycolate (TDM) in non-metabolizable oils<br>Stimulate Mincle ligands (C-type lectin receptors)<br>for TLR2, TLR4, TLR9 |

TABLE 5-continued

| List of adjuvants used in adjuvant screening | |
| --- | --- |
| Adjuvant | Properties |
| CpG | Class C CpG synthetic oligonucleotides (ODN 2395) |
| | Ligand for human/mouse TLR9 |
| | Induces a Th1 response |
| MiT4 | TLR4 agonist in suspended micelles |
| | Ligand for human/mouse TLR4 |
| EmT4 | TLR4 agonist in an oil-in-water emulsion |
| | Ligand for human/mouse TLR4 |
| AlT4 | TLR4 agonist adsorbed on aluminum hydroxide (alum) particles |
| | Ligand of TLR4 |
| | Induce Th2 response |
| LiT4 | TLR4 agonist in a liposome |
| | Ligand for human/mouse TLR4 |
| Alum | Aluminum hydroxide gel 2% |
| | Induce Th2 response |
| GM-CSF | Granulocyte-Macrophage Colony-Stimulating Factor |
| | Stimulate the development of granulocytes, macrophages |
| | Induce inflammation |

Hamster Immunization:

Female golden Syrian hamsters (Charles River Laboratories, Wilmington, Mass.) are immunized with a 2-dose regimen with a 14-day interval between doses. Two weeks after the second dose, hamsters are euthanized. Hamster blood is collected by cardiac puncture and serum is prepared for the quantification of peptide-specific antibodies by an in-house indirect ELISA method. Spleens and draining lymph nodes serve as a source of cells for the IFN-$\gamma$ ELISPOT and other assays. Unless otherwise noted, water-in-oil emulsions are administered subcutaneously, all other adjuvant formulations are administered intramuscularly. Immunogenicity of Screened Peptides in Hamsters as Determined by ELISA.

A total of 52 peptides are tested for immunogenicity. These peptides are divided into five groups, as shown in FIG. 5A-E, and formulated with CFA and CpG as indicated in FIG. 4. Antibody responses in hamster sera specimens to individual peptides or peptide pools are quantified by ELISA.

Briefly, Immulon 4 HBX 96-well plates for ELISA are obtained from Thermo Fisher Scientific (Waltham, Mass.). The plate is coated with 1 µg/well of either a pool of peptides or individual peptides in coating buffer (50 mM sodium carbonate, pH 9.6) overnight at 4° C. After the coating buffer is removed, the plate is blocked with 2% BSA in PBS for 1 hour at room temperature, followed by washing three times with 0.5% Tween in PBS (PBST). Sera are diluted 1:200 in PBS and added to each well and the plate is incubated for 2 hours at room temperature. After incubation, the plate is washed three times with PBST. The secondary antibody is conjugated with HRP, and iss added at a 1:10,000 dilution in PBS. The plate is incubated for 1 hour at room temperature. After washing three times with PBST, TMBE-100 peroxidase substrate (Rockland Immunochemicals, Inc., Limerick, Pa.) is added, followed by 30 minutes incubation at room temperature. Finally, the enzymatic reaction is stopped by adding 2M $H_2SO_4$. Optical density at 450 nm (OD450) is read within 15 minutes after adding $H_2SO_4$ using a Spectramax® ABS Plus microplate reader (Molecular Devices, San Jose, Calif.) and the SoftMax® 7 Pro Software.

Peptide-specific antibodies in each hamster are quantified in quadruplicate wells with the average response is plotted on FIGS. 5A-E. The dashed line represents the threshold for defining a positive response—a signal-to-noise ratio of 3. As shown in FIGS. 5A-E, many of the screened peptides induces the generation of peptide-specific antibody responses of varying magnitudes in immunized hamsters.

Figure 7:
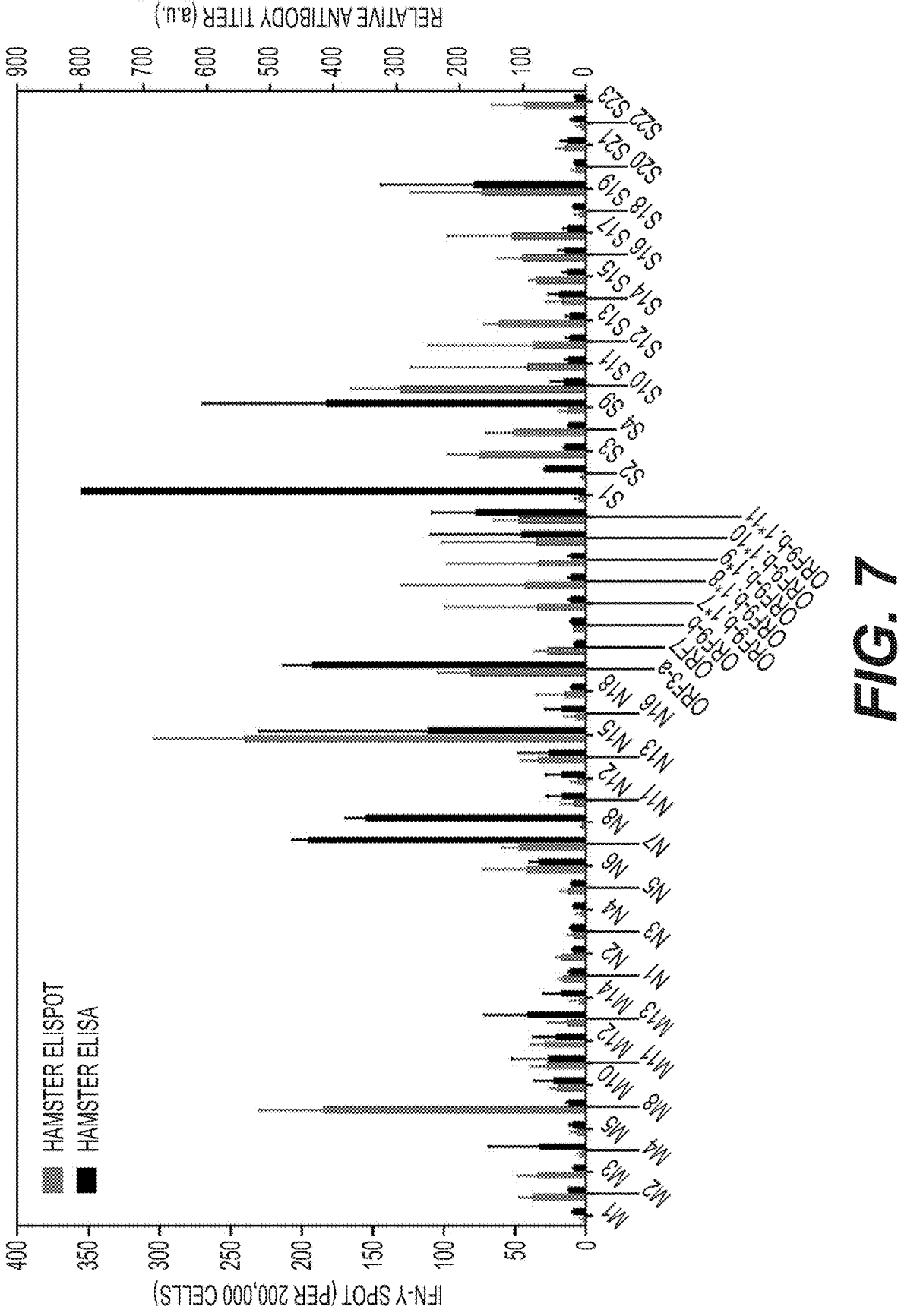
FIG. 7: Summary of immune responses induced by different peptides in hamsters.
Figures 8A, 8B:
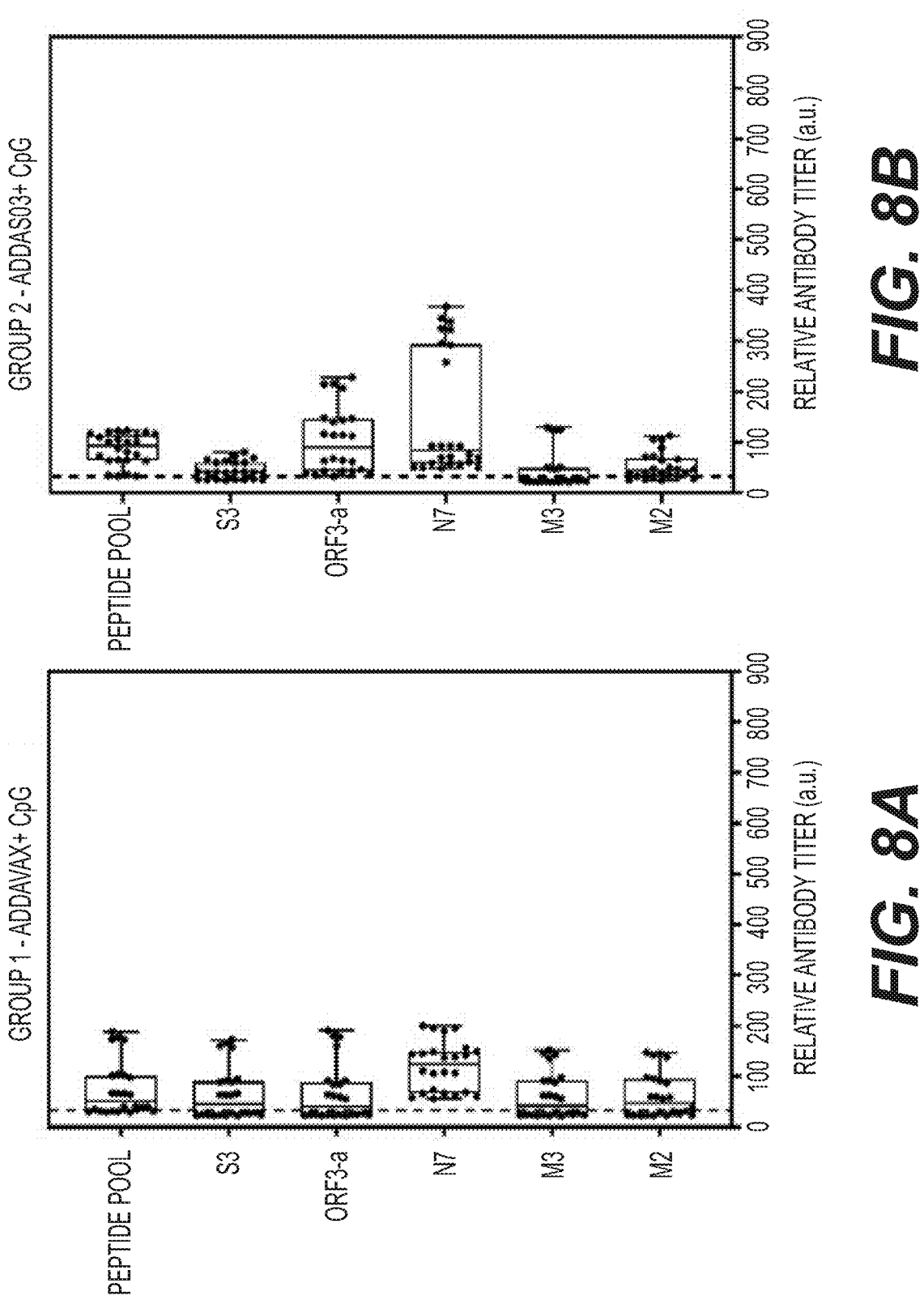
FIG. 8A: Immune responses in hamsters induced by five peptides in combination with Addavax+CpG, as measured by IgG ELISA.
FIG. 8B: Immune responses in hamsters induced by five peptides in combination with AddaSO3+CpG, as measured by IgG ELISA.
Figures 8C, 8D:
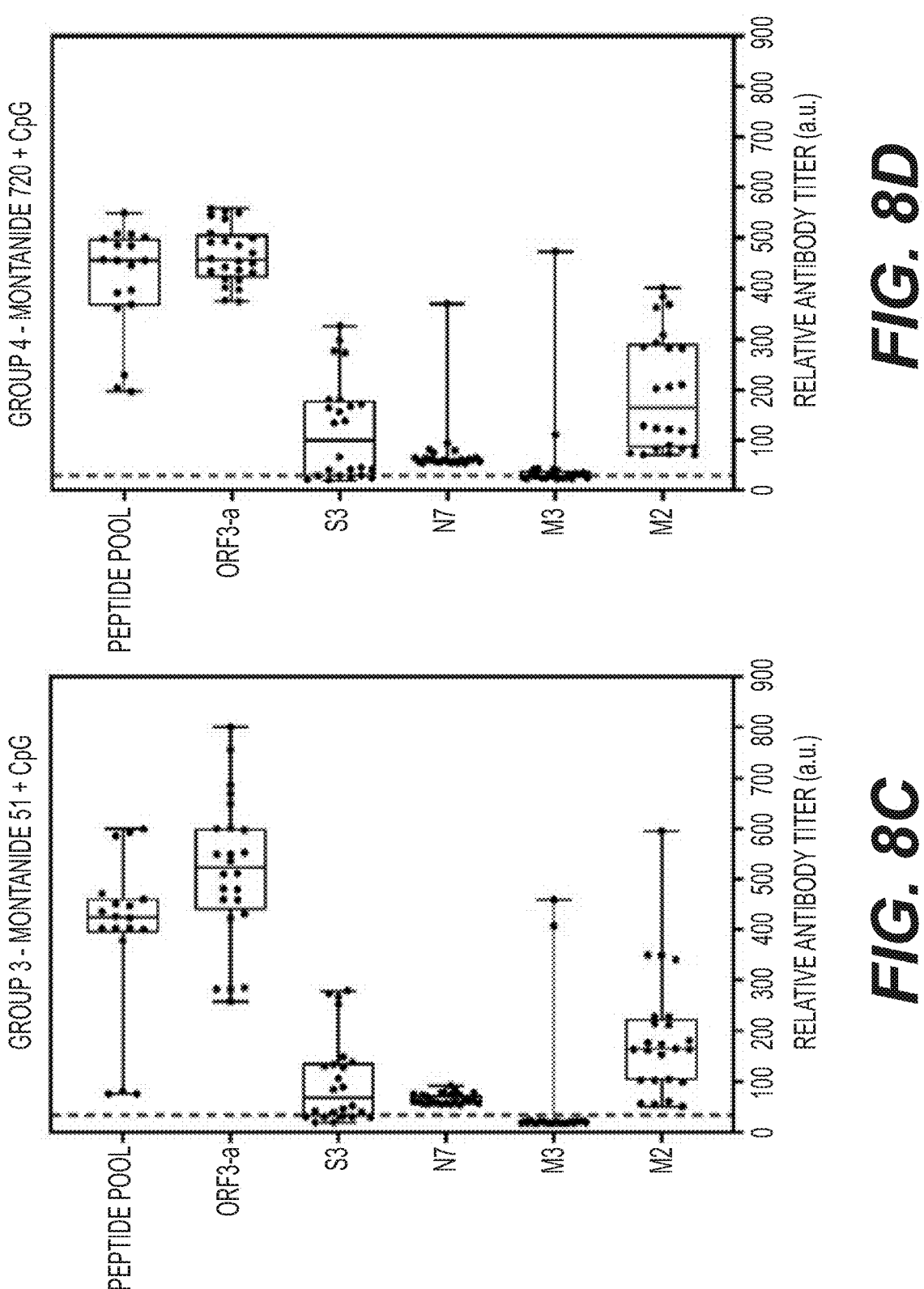
FIG. 8C: Immune responses in hamsters induced by five peptides in combination with Montanide 51+CpG, as measured by IgG ELISA.
FIG. 8D: Immune responses in hamsters induced by five peptides in combination with Montanide 72+CpG, as measured by IgG ELISA.
Figures 8E, 8F:
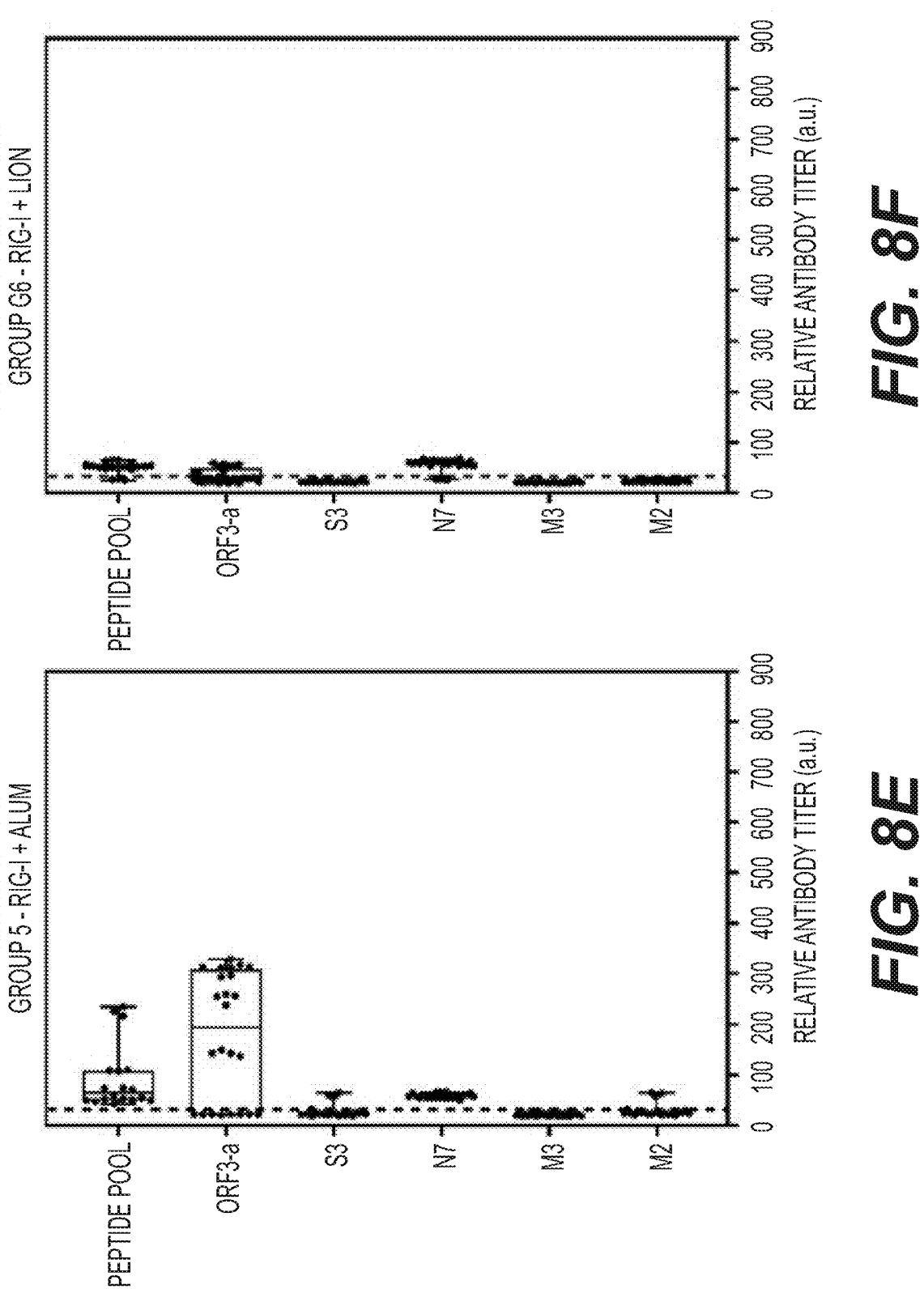
FIG. 8E: Immune responses in hamsters induced by five peptides in combination with RIG-I+Alum, as measured by IgG ELISA.
FIG. 8F: Immune responses in hamsters induced by five peptides in combination with RIG-I+LION, as measured by IgG ELISA.
Figures 8G, 8H:
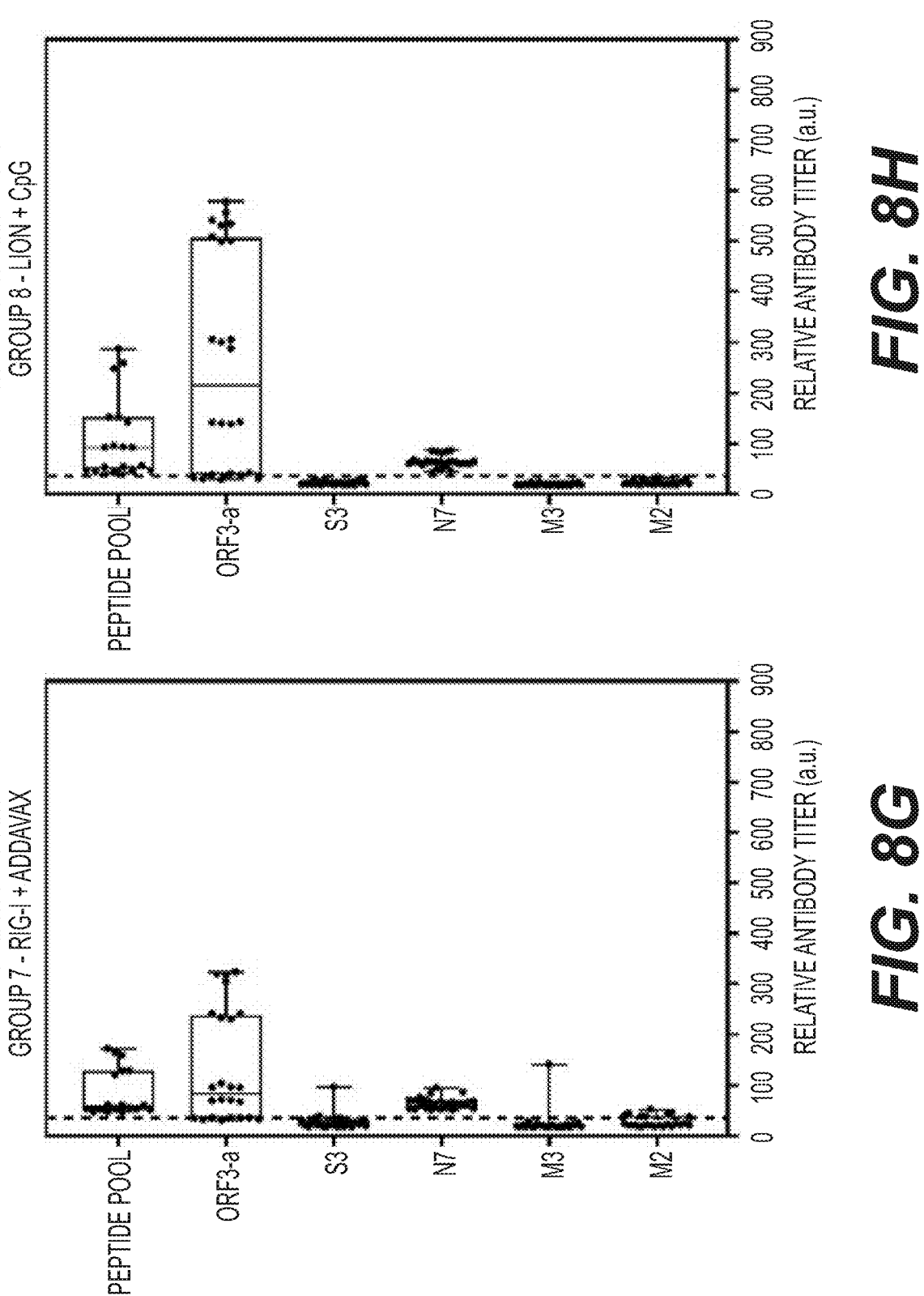
FIG. 8G: Immune responses in hamsters induced by five peptides in combination with RIG-I+Addavax, as measured by IgG ELISA.
FIG. 8H: Immune responses in hamsters induced by five peptides in combination with LION+CpG, as measured by IgG ELISA.
Figures 9A, 9B:
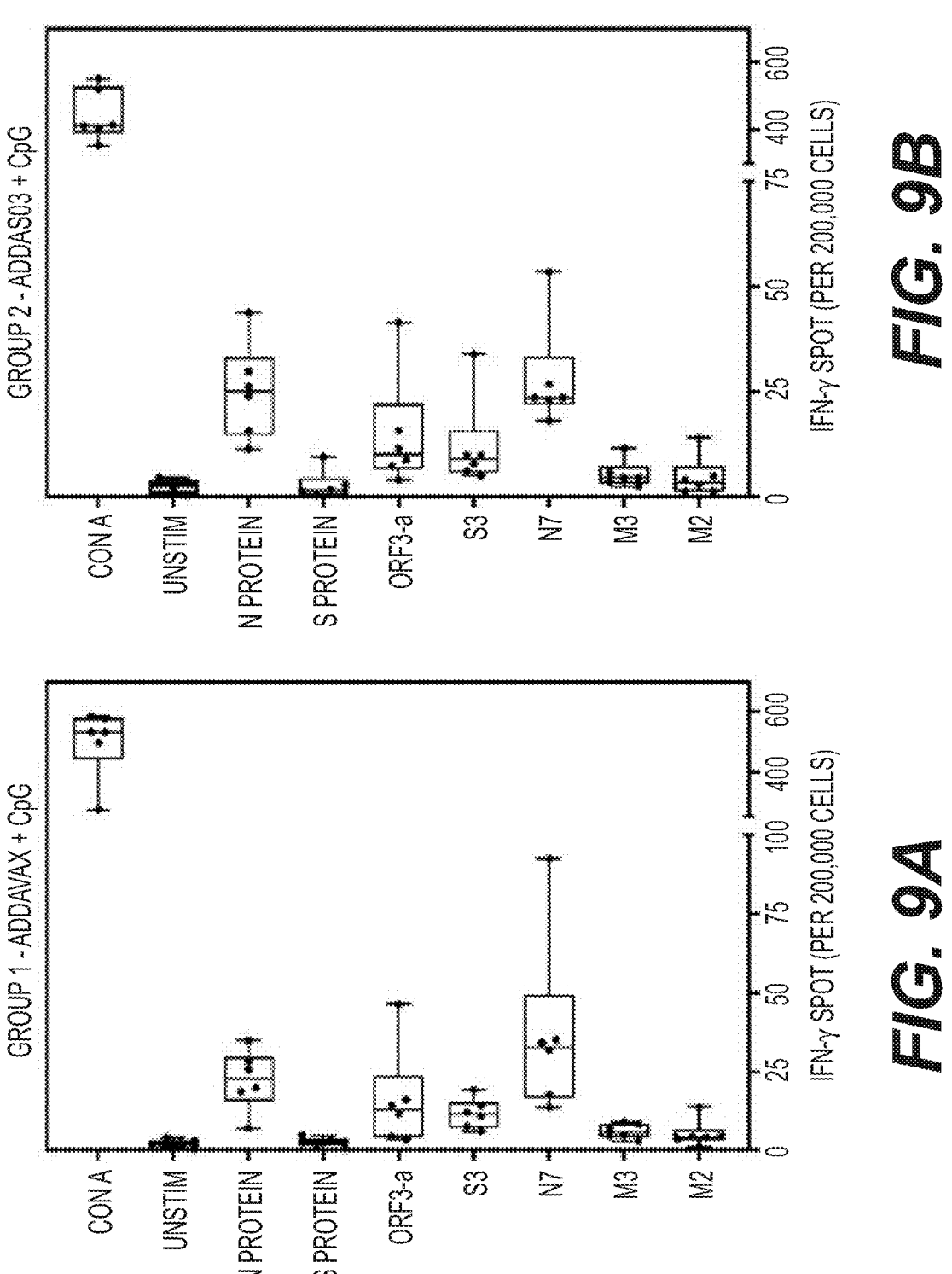
FIG. 9A: Immune responses in hamsters induced by five peptides in combination with Addavax+CpG, as measured by IFN-γ ELISPOT.
FIG. 9B: Immune responses in hamsters induced by five peptides in combination with AddaSO3+CpG, as measured by IFN-γ ELISPOT.
Figures 9C, 9D:
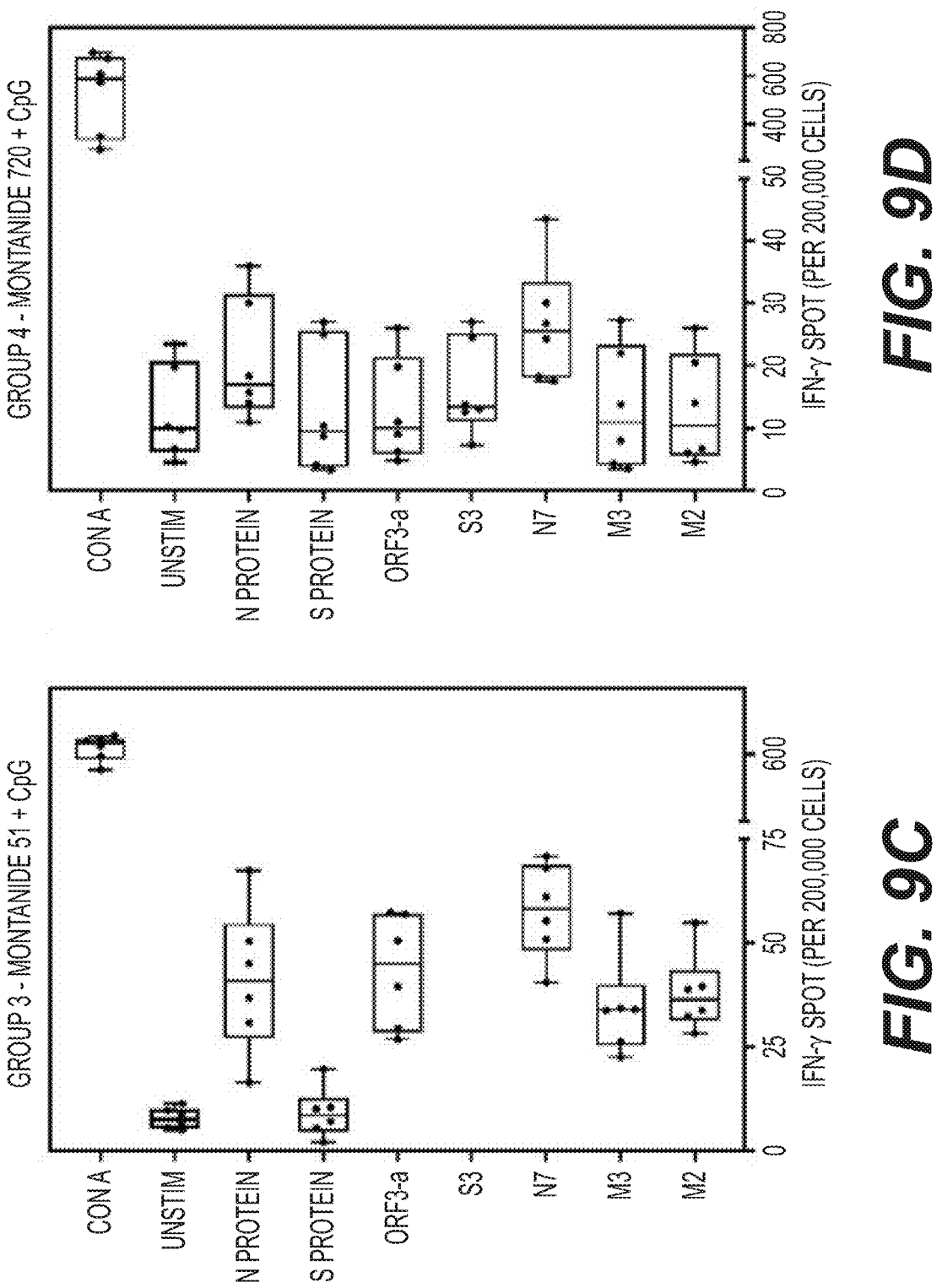
FIG. 9C: Immune responses in hamsters induced by five peptides in combination with Montanide 51+CpG, as measured by IFN-γ ELISPOT.
FIG. 9D: Immune responses in hamsters induced by five peptides in combination with Montanide 72+CpG, as measured by IFN-γ ELISPOT.
Figures 9E, 9F:
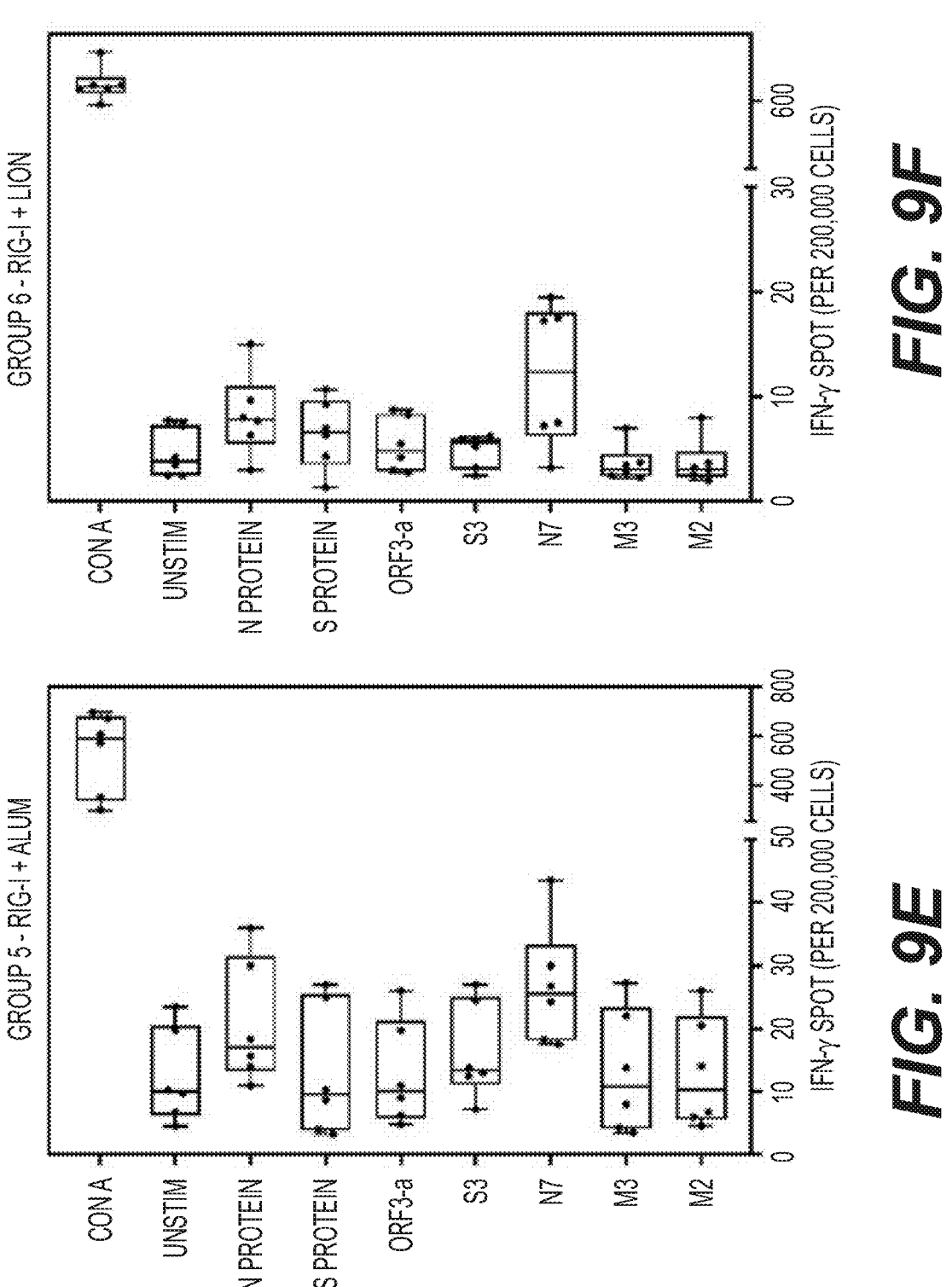
FIG. 9E: Immune responses in hamsters induced by five peptides in combination with RIG-I+Alum, as measured by IFN-γ ELISPOT.
FIG. 9F: Immune responses in hamsters induced by five peptides in combination with RIG-I+LION, as measured by IFN-γ ELISPOT.
Figures 9G, 9H:
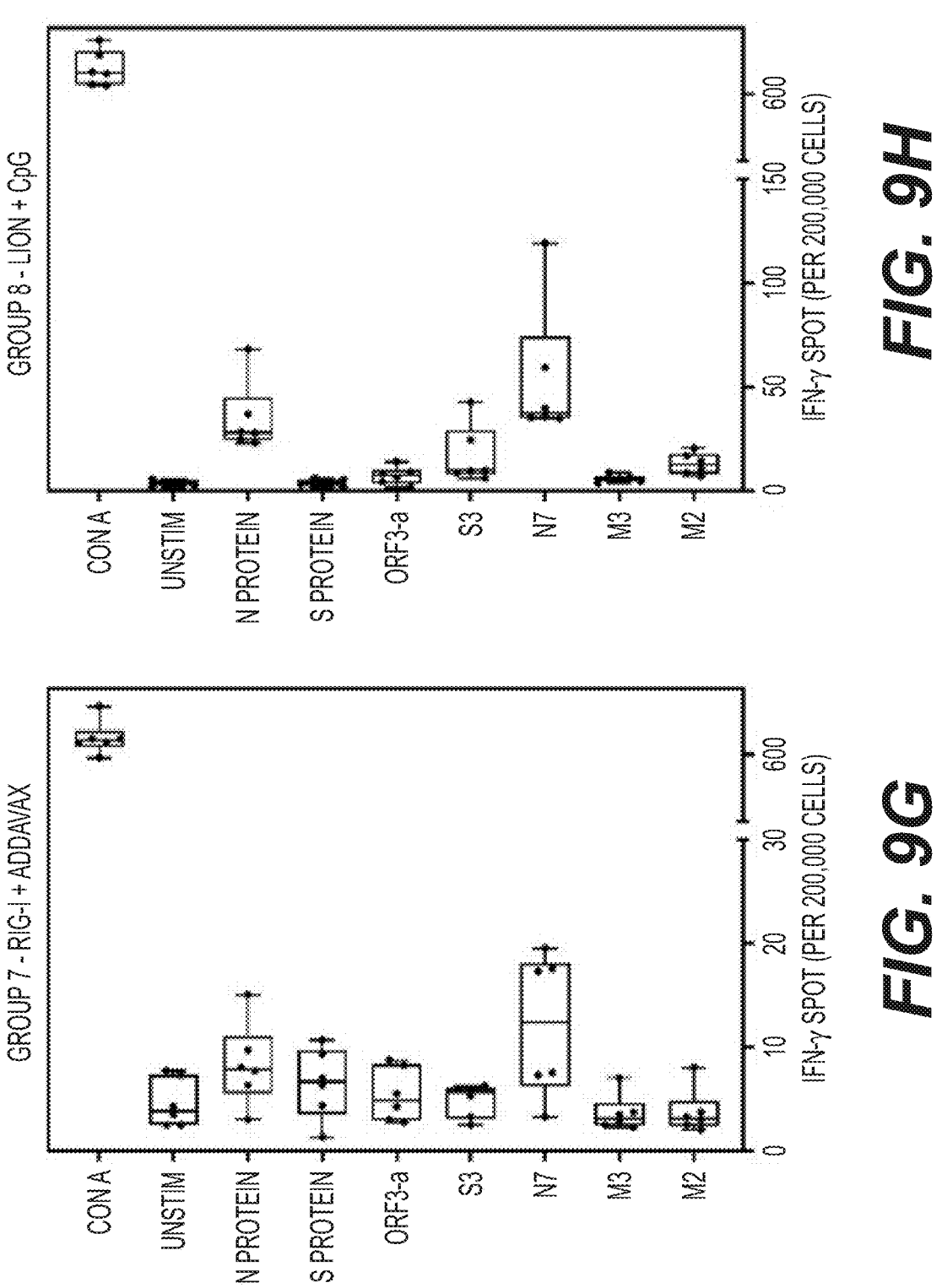
FIG. 9G: Immune responses in hamsters induced by five peptides in combination with RIG-I+Addavax, as measured by IFN-γ ELISPOT.
FIG. 9H: Immune responses in hamsters induced by five peptides in combination with LION+CpG, as measured by IFN-γ ELISPOT.
Figures 10A, 10B:
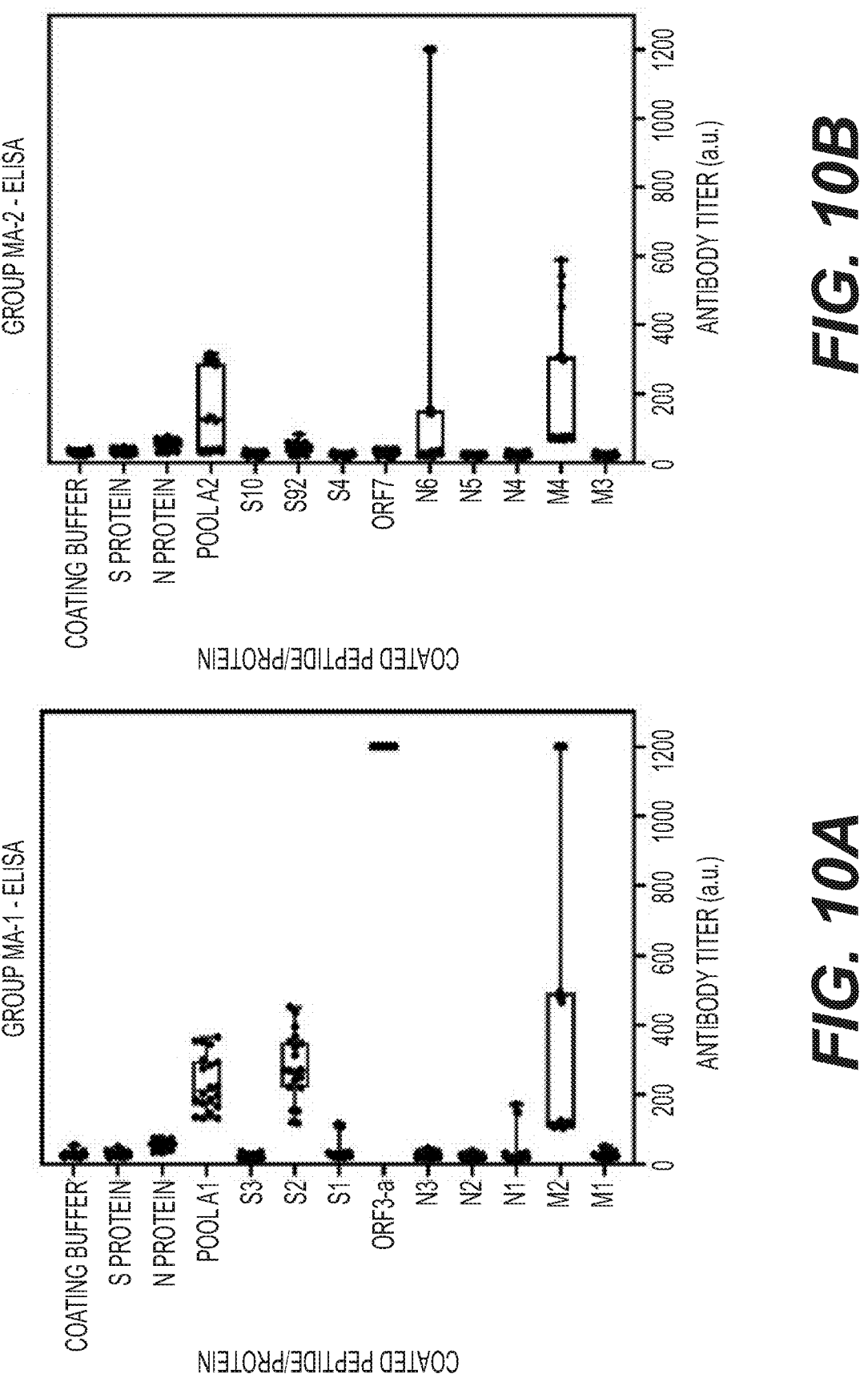
FIG. 10A: Immune responses in mice induced by combinations of peptides, formulated with CFA/IFA+CpG, as measured by IgG ELISA.
FIG. 10B: Immune responses in mice induced by combinations of peptides, formulated with CFA/IFA+CpG, as measured by IgG ELISA.
Figures 10C, 10D:
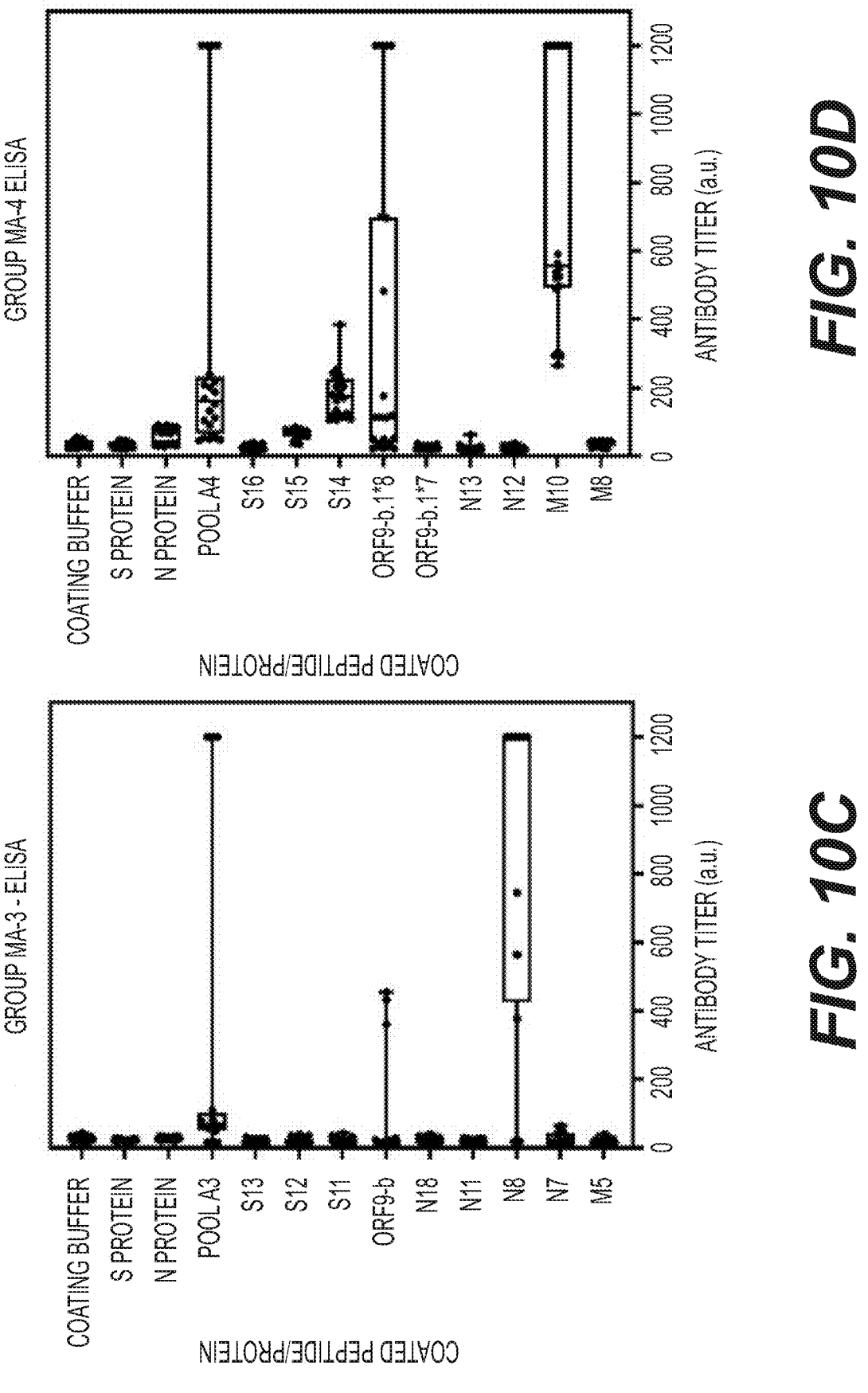
FIG. 10C: Immune responses in mice induced by combinations of peptides, formulated with CFA/IFA+CpG, as measured by IgG ELISA.
FIG. 10D: Immune responses in mice induced by combinations of peptides, formulated with CFA/IFA+CpG, as measured by IgG ELISA.
Figures 10E, 10F:
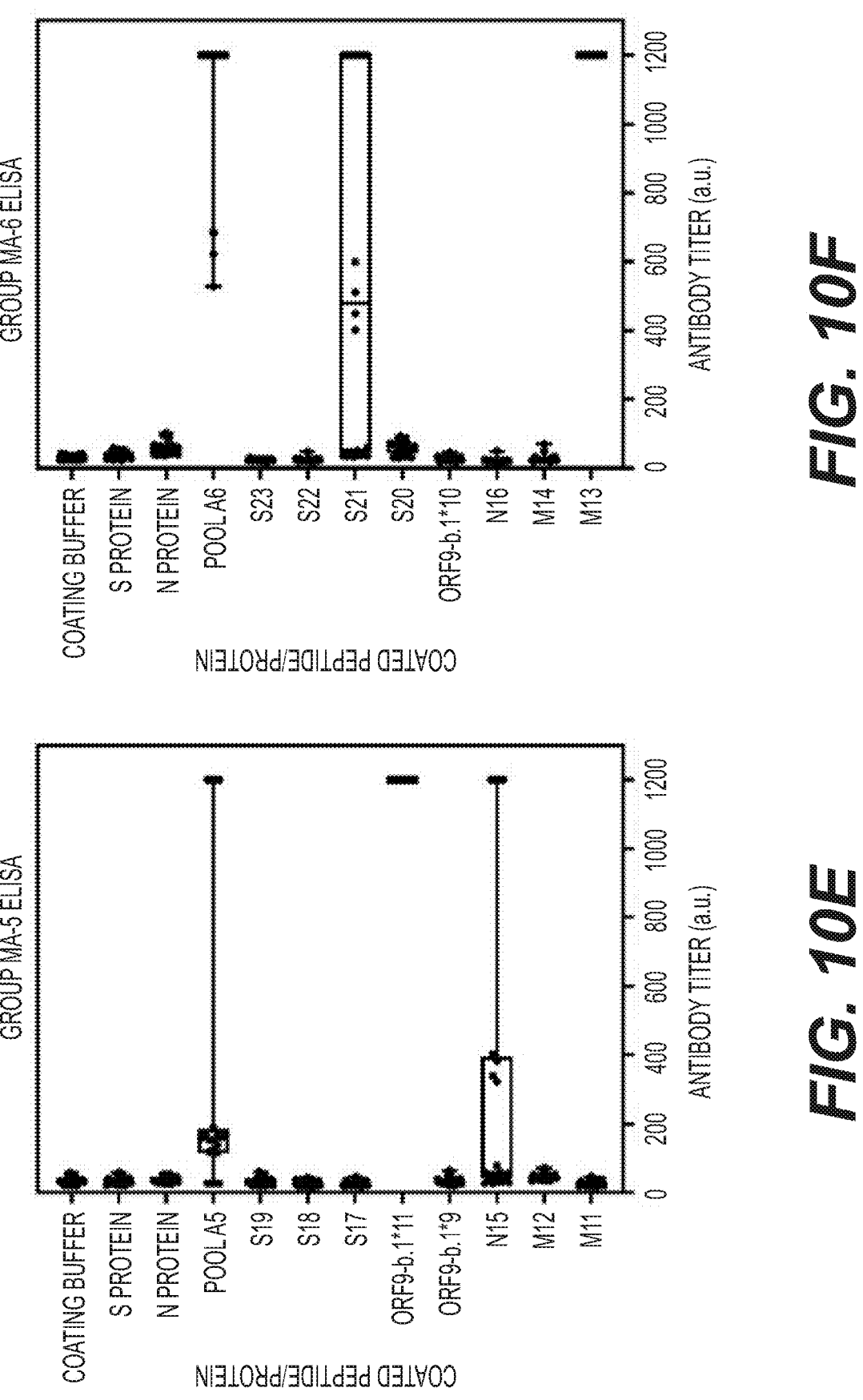
FIG. 10E: Immune responses in mice induced by combinations of peptides, formulated with CFA/IFA+CpG, as measured by IgG ELISA.
FIG. 10F: Immune responses in mice induced by combinations of peptides, formulated with CFA/IFA+CpG, as measured by IgG ELISA.
Figures 10G, 10H:
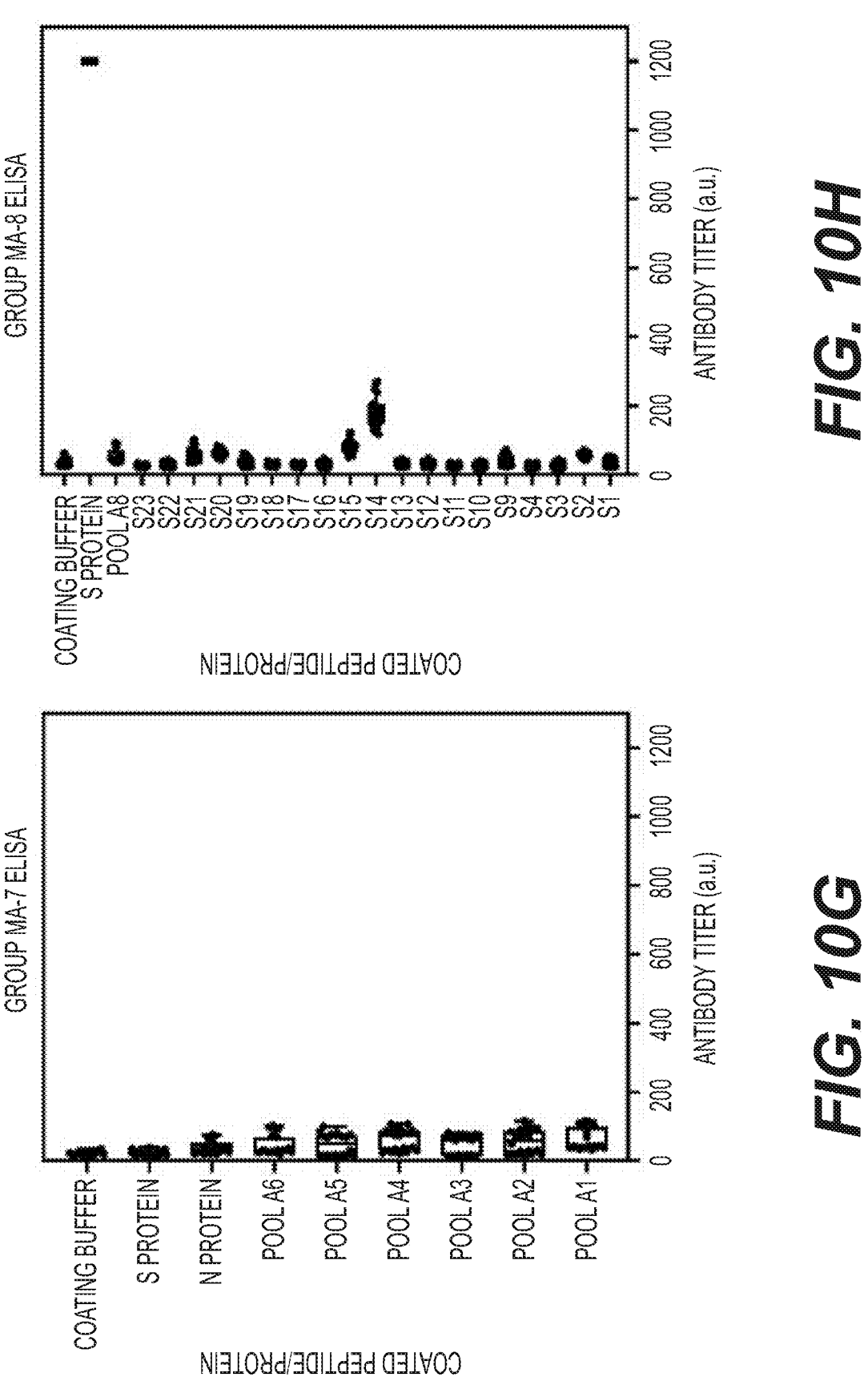
FIG. 10G: Immune responses in mice induced by combinations of peptides, formulated with CFA/IFA+CpG, as measured by IgG ELISA.
FIG. 10H: Immune responses in mice induced by combinations of peptides, formulated with CFA/IFA+CpG, as measured by IgG ELISA.
Figures 10I, 11A:
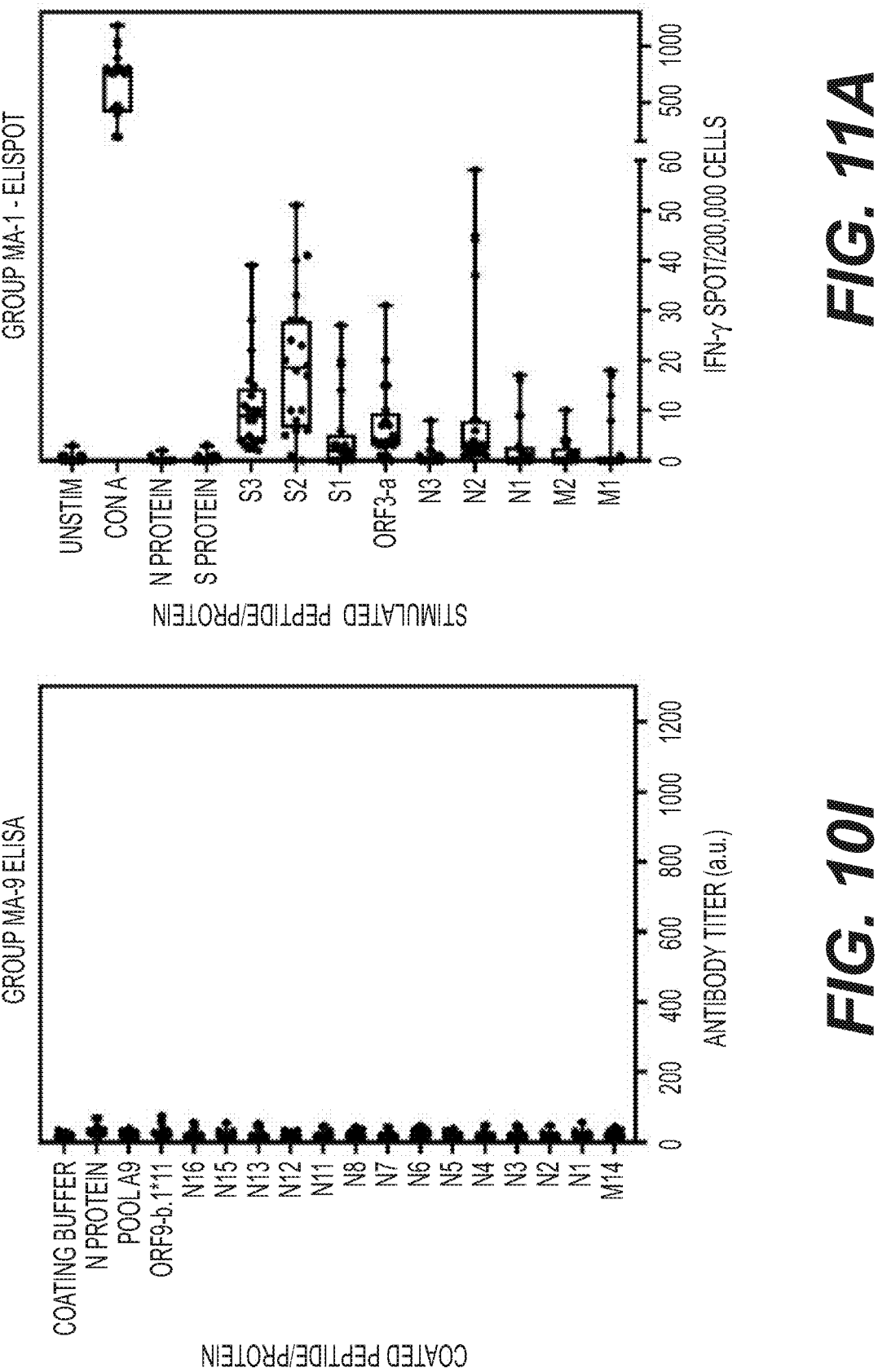
FIG. 10I: Immune responses in mice induced by combinations of peptides, formulated with CFA/IFA+CpG, as measured by IgG ELISA.
FIG. 11A: Immune responses in mice induced by combinations of peptides, formulated with CFA/IFA+CpG, as measured by IFN-γ ELISPOT.
Figure 11C:
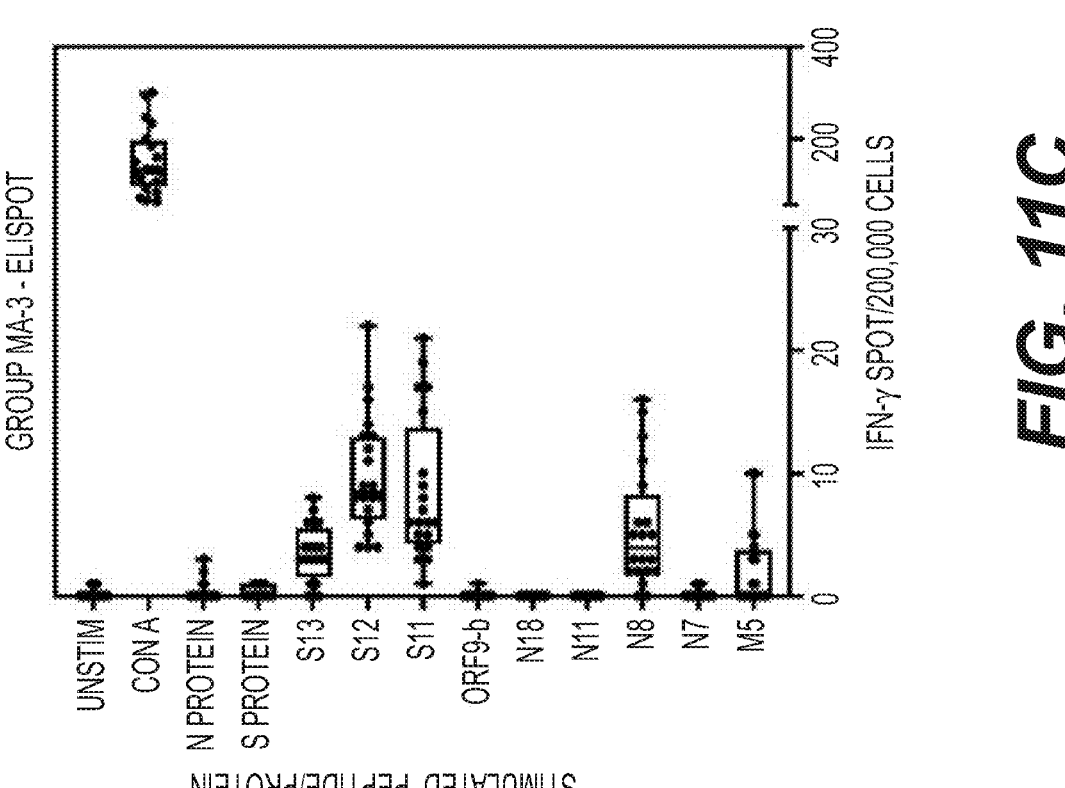
FIG. 11C: Immune responses in mice induced by combinations of peptides, formulated with CFA/IFA+CpG, as measured by IFN-γ ELISPOT.
Figure 11B:
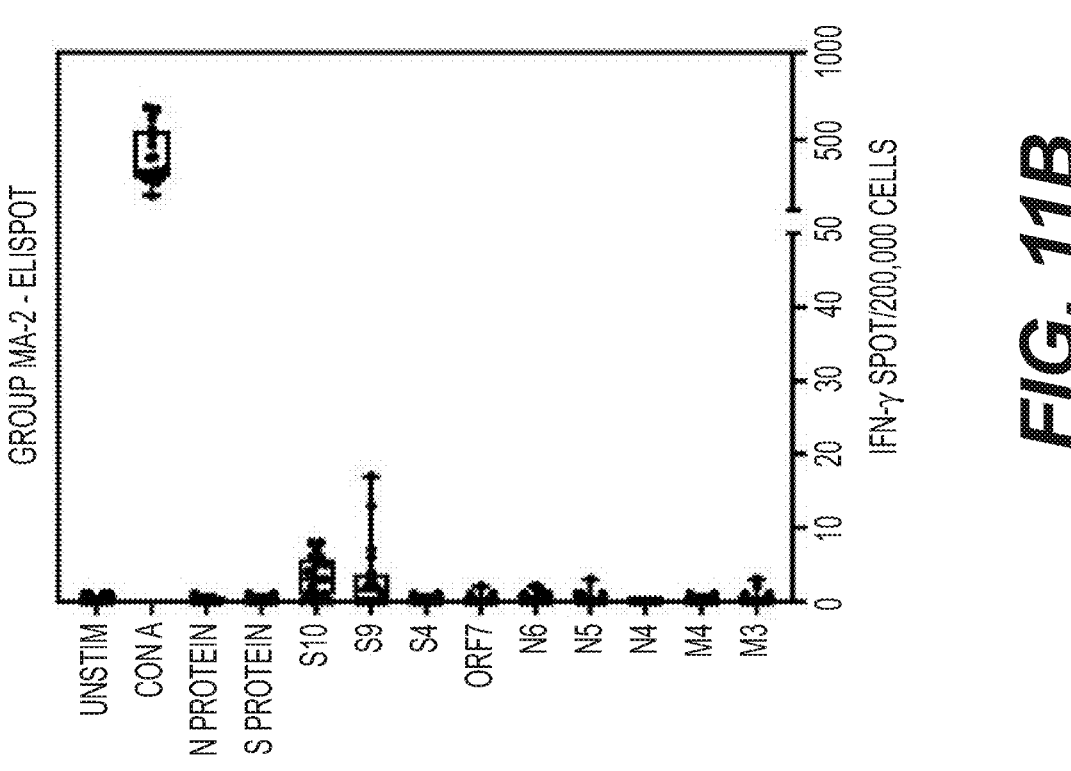
FIG. 11B: Immune responses in mice induced by combinations of peptides, formulated with CFA/IFA+CpG, as measured by IFN-γ ELISPOT.
Figure 11E:
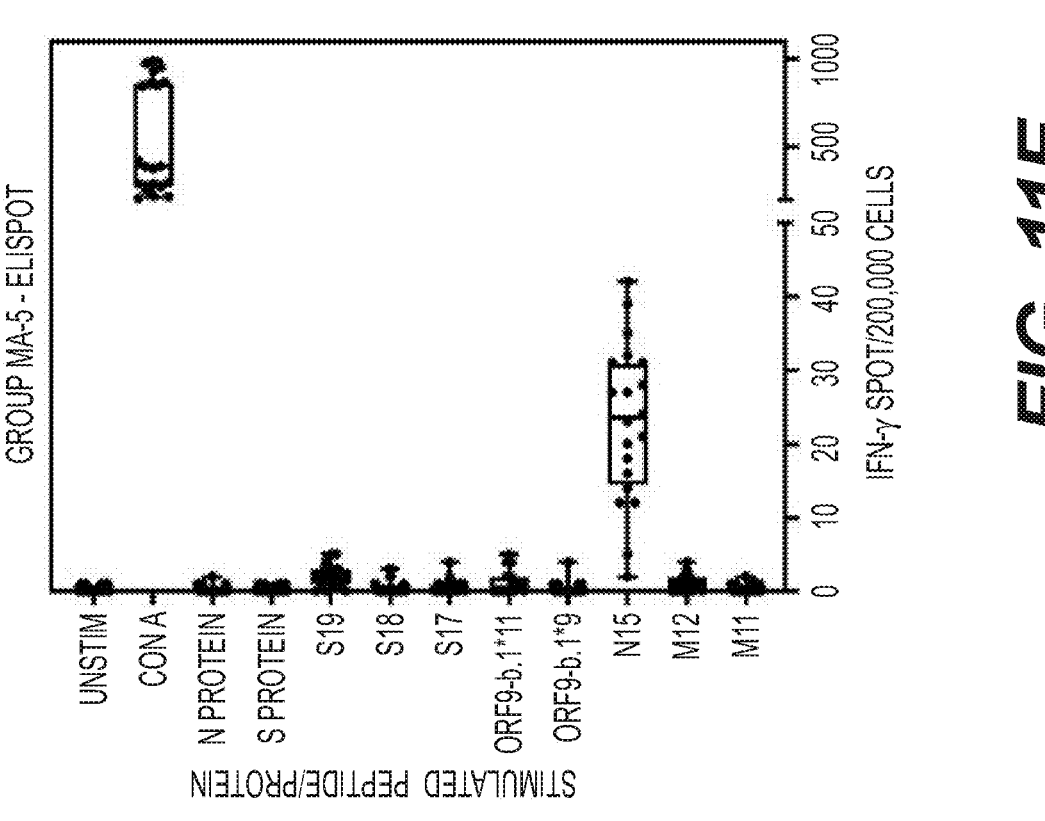
FIG. 11E: Immune responses in mice induced by combinations of peptides, formulated with CFA/IFA+CpG, as measured by IFN-γ ELISPOT.
Figure 11D:
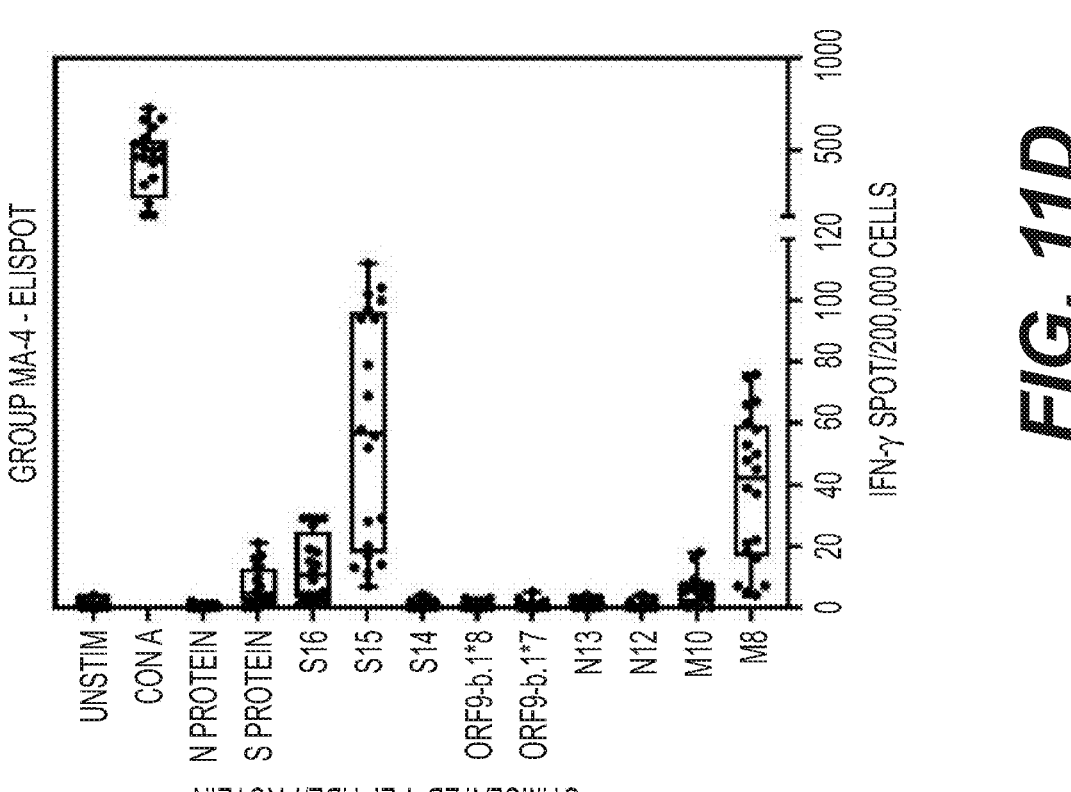
FIG. 11D: Immune responses in mice induced by combinations of peptides, formulated with CFA/IFA+CpG, as measured by IFN-γ ELISPOT.
Figure 11G:
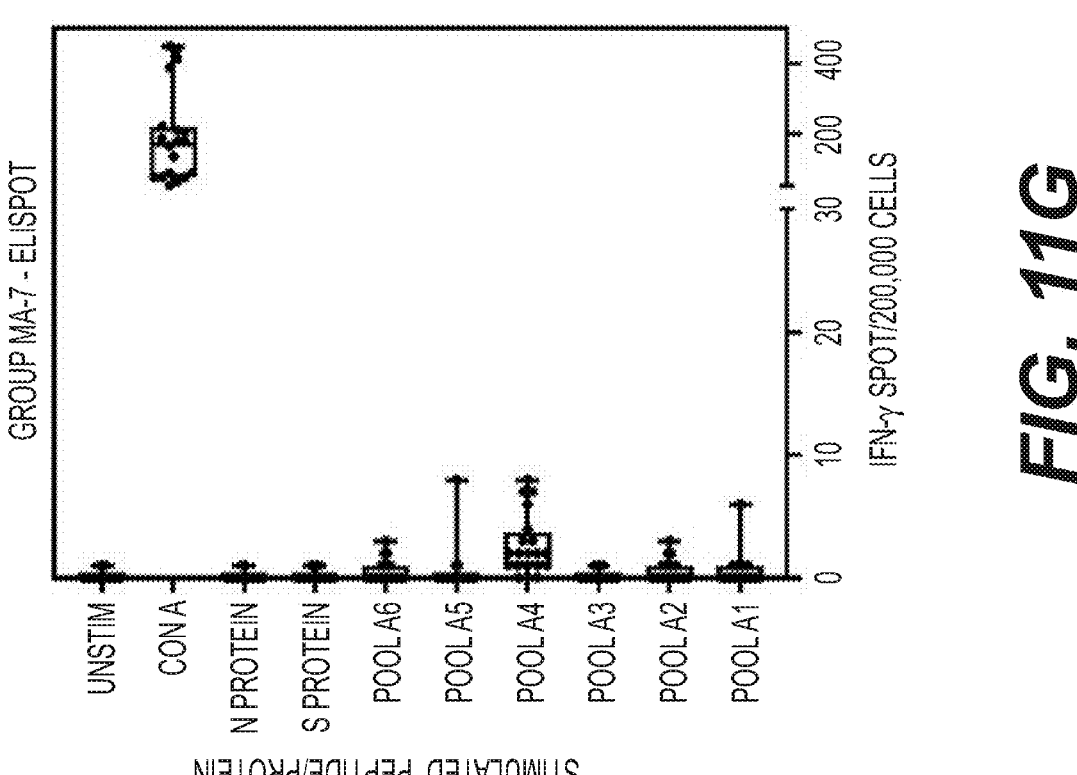
FIG. 11G: Immune responses in mice induced by combinations of peptides, formulated with CFA/IFA+CpG, as measured by IFN-γ ELISPOT.
Figure 11F:
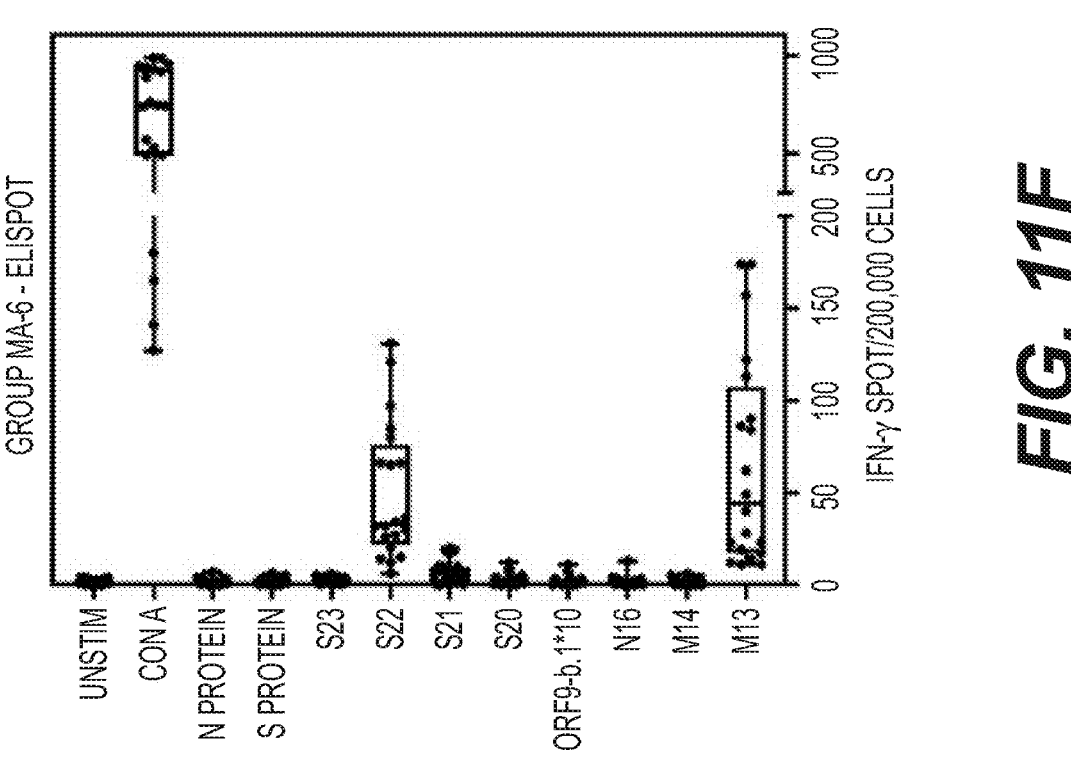
FIG. 11F: Immune responses in mice induced by combinations of peptides, formulated with CFA/IFA+CpG, as measured by IFN-γ ELISPOT.
Figure 11I:
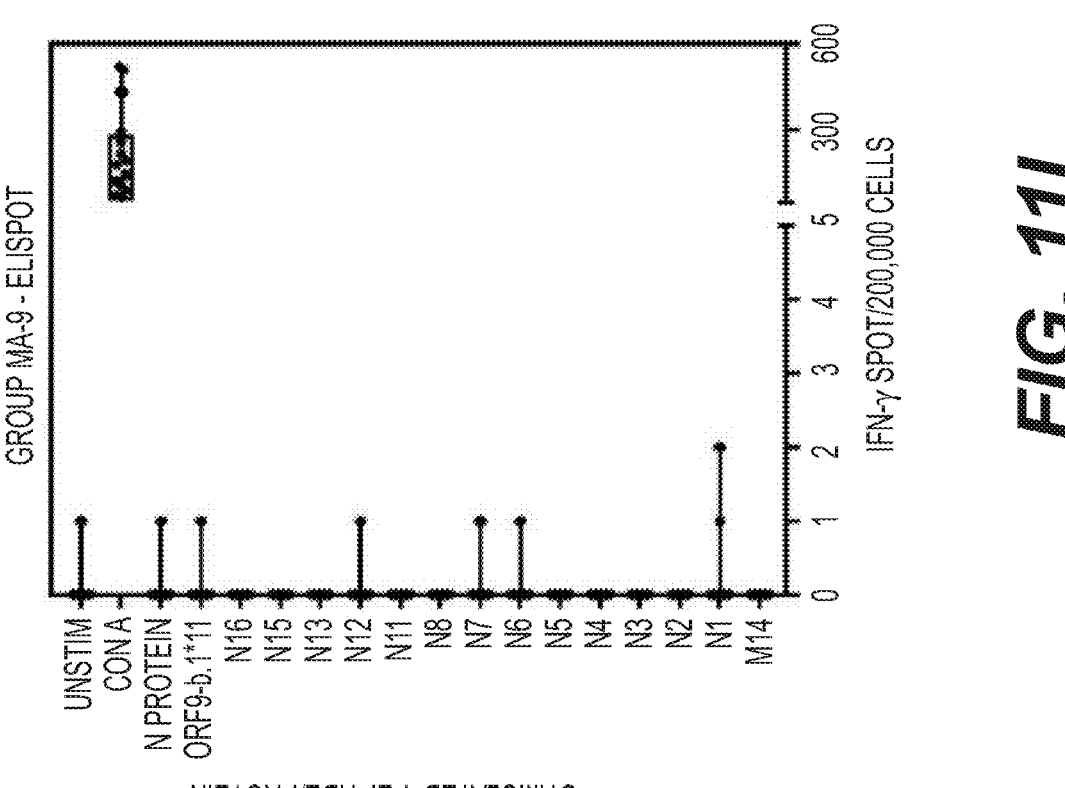
FIG. 11I: Immune responses in mice induced by combinations of peptides, formulated with CFA/IFA+CpG, as measured by IFN-γ ELISPOT.
Figure 11H:
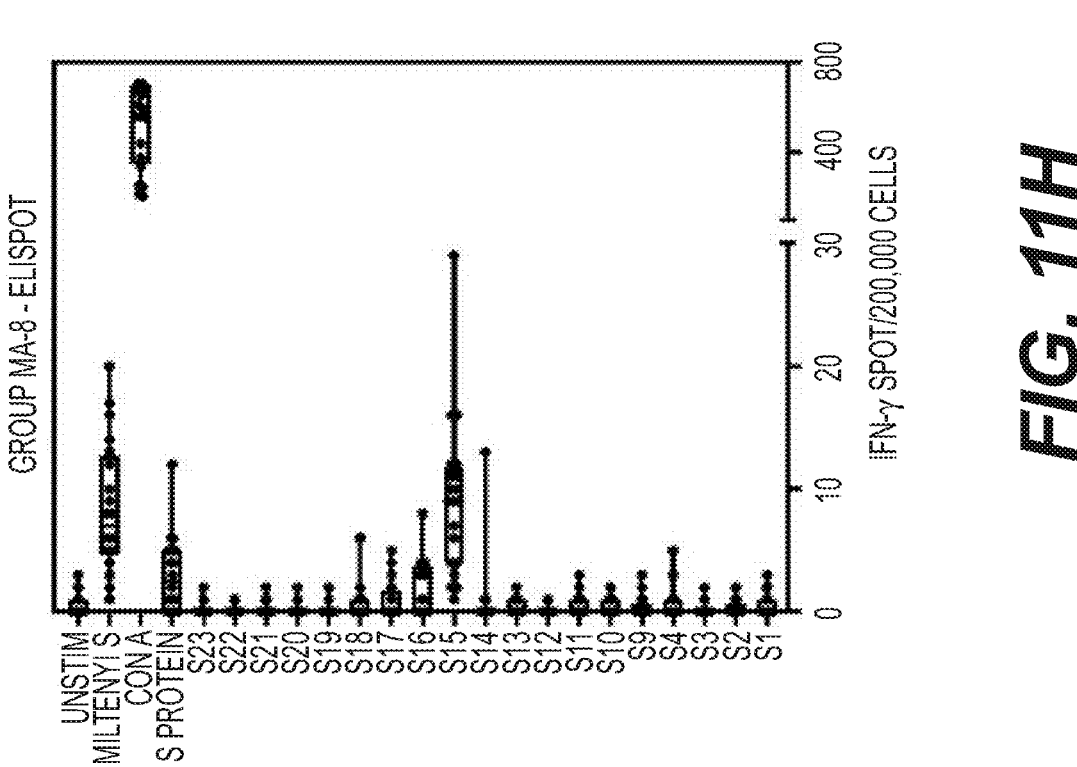
FIG. 11H: Immune responses in mice induced by combinations of peptides, formulated with CFA/IFA+CpG, as measured by IFN-γ ELISPOT.

A summary of peptide-specific antibody titers (as measured by ELISA) and T cell responses (as measured by IFN-$\gamma$ ELISPOT) of selected peptides is shown in FIG. 7. Immunogenicity of Screened Peptides as Determined by IFN-$\gamma$ ELISPOT A total of 52 peptides are tested for immunogenicity. These peptides are divided into five groups, as indicated in FIG. 6A-E, and are formulated with CFA and CpG as indicated in FIG. 4. Antibody responses in hamster sera specimens to individual peptides or peptide pools are quantified by IFN-$\gamma$ ELISPOT assay.

Briefly, a Mabtech™ hamster-specific IFN-$\gamma$ ELISPOT assay is performed similar to that as described above for human PBMC testing (Example 1). In the place of PMBCs, single cell suspensions are created from spleens and draining lymph nodes of immunized or control animals. Concanavalin A (ConA) (10 µg/mL) is used as a positive control (stimulated condition) instead of PHA as it has been shown to perform well as a positive control in hamster cell-based assays. Cell culture media is used as the unstimulated ("unstim") condition. The remaining conditions (cells/well, incubation times, antigen concentrations) are identical to those reported above in Example 1.

The results are shown in FIG. 6A-E, and demonstrate that many of the selected peptides are immunogenic in hamsters, eliciting T cell responses of varying magnitude. Based on these immunogenicity experiments, five exemplary peptides (M2, M3, N7, S3, and ORF-3a) are selected for further testing.

Further Testing of Immunogenicity of Selected Peptides with Different Adjuvants, as Determined by IgG ELISA and IFN-$\gamma$ ELISPOT The five exemplary peptides are tested for their immunogenicity in formulation with different adjuvants (Table 6). The methods are as described in the previous two sections above in this Example.

TABLE 6

| List of adjuvants used to test 5 exemplary peptides | |
| --- | --- |
| Adjuvant | Properties |
| Addavax + CpG | A squalene-based oil-in-water nanoemulsion with a formulation similar to MF59 |
| | Induce both Th1 and Th2 responses |
| | Activate APC, stimulate cytokines, chemokines production by macrophages and granulocytes |
| | TLR9 agonist inducing a Th1 response |
| AddaS03 + CpG | An oil-in-water nanoemulsion with a formulation similar to adjuvant system AS03 |
| | Consists of two biodegradable oils and polysorbate 80 |
| | Trigger NF-kB-dependent innate immune responses |
| | TLR9 agonist inducing a Th1 response |
| Montanide 51 + CpG | A water-in-oil emulsion |
| | Consists of mannide monooleate surfactant and mineral oil |
| | Induce Th1 response |
| | TLR9 agonist inducing a Th1 response |
| Montanide 720 + CpG | A water-in-oil emulsion |
| | Consists of natural metabolize non-mineral oil |
| | Induce Th1 response |
| | TLR9 agonist inducing a Th1 response |
| RIG-I + Alum | Retinoic acid-inducible gene I |
| | Induce type-1 interferon response |
| | Aluminum hydroxide gel 2% inducing a Th2 response |
| RIG-1 + LION | Retinoic acid-inducible gene I |
| | Induce type-1 interferon response |
| | Lipid inorganic nanoparticle |

TABLE 6-continued

List of adjuvants used to test 5 exemplary peptides

| Adjuvant | Properties |
|---|---|
| RIG-1 + Addavax | Retinoic acid-inducible gene I agonist, inducing a type-1 interferon response A squalene-based oil-in-water nanoemulsion with a formulation similar to MF59 Induces both Th1 and Th2 responses Activates APC, stimulate cytokines, chemokines production by macrophages and granulocytes |
| CpG + LION | TLR9 agonist inducing a Th1 response acid-inducible gene I Lipid inorganic nanoparticle |

The results are shown in FIGS. 8A-H (IgG ELISA) and FIGS. 9A-H (IFN-γ ELISPOT). As shown in FIGS. 8A-H and FIGS. 9A-H, the adjuvant combinations tested showed varying levels of immunogenicity, with water-in-oil emulsions (e.g., CFA and the Montanides) exhibiting stronger adjuvant activity, followed by oil-in-water emulsions (e.g., Addavax, AddS03, and EmT4). TLR and RLR agonists (e.g., CpG, Poly I:C, T4, RIG-I agonist) had variable, but generally positive impact on the immune responses observed. Regardless, there is a clear immunodominance pattern that is retained across multiple adjuvants. Some T cell epitopes appear to induce a robust antibody response, while others induce a robust T cell response, and a number of peptides induce both antibody and T cell responses.

Example 3: Vaccinating Against SARS-CoV-2 in Mice

Method:

Male C57BL/6J mice (Jackson Laboratory, Bar Harbor, Me.) in groups of 5 mice are subcutaneously or intramuscularly immunized with a two-dose regimen with a 14-day, 21-day or 28-day interval between vaccine doses. Each mouse receives a single peptide, a pool of selected peptides or a recombinant protein formulated with different adjuvants and/or delivery systems. Mice are euthanized 14 days after the second dose. Mouse blood is collected from euthanized mice by cardiac puncture and serum is prepared by centrifugation at 3000×g for 15 minutes at 4° C. then stored at –80° C. for further analyses. Draining lymph nodes and spleens are harvested and a single cell lymphocyte suspension is prepared for IFN-γ ELISPOT assays.

Pooled Screening of Peptides in Combination with CpG and CFA

Mice are immunized as described in the method section detailed immediately above with 52 peptides (listed in Table 1, with the exception of M9) adjuvanted with CpG and CFA (IFA is used for the boost vaccination as recommended). As summarized in Table 7 below, the 52 peptides are divided into 6 groups (MA1 to MA6) of 5. Groups MA1 to MA6 are subcutaneously immunized with a combination of 9-10 peptides that include peptides from spike (S), nucleocapsid (N), membrane (M) and open reading frame (ORF) proteins from SARS-COV-2. Groups MA7, MA8, and MA9 are designated as control groups and are immunized with CpG+ CFA/IFA only, S protein (20 μg), and N protein (20 μg), respectively.

TABLE 7

Screening 52 exemplary peptides in mice

| Group | Peptide (100 μg each) | Adjuvants | Route |
|---|---|---|---|
| MA1 | M1, M2, N1, N2, N3, ORF3a, S1, S2, S3 | CFA/IFA + CpG | s.c. |
| MA2 | M3, M4, N4, N5, N6, ORF7, S4, S9, S10 | CFA/IFA + CpG | s.c. |
| MA3 | M5, N18, N7, N8, N11, ORF9b, S11, S12, S13 | CFA/IFA + CpG | s.c. |
| MA4 | M8, M10, N12, N13, ORF9b.1*7, ORF9b.1*8, S14, S15, S16 | CFA/IFA + CpG | s.c. |
| MA5 | M11, M12, ORF9b.1*11, N15, ORF9b.1*9, S17, S18, S19 | CFA/IFA + CpG | s.c. |
| MA6 | M13, N16, M14, ORF9b.1*10, S20, S21, S22, S23 | CFA/IFA + CpG | s.c. |
| MA7 | No peptide | CFA/IFA + CpG | s.c. |
| MA8 | Spike (S) protein (20 μg) | CFA/IFA + CpG | s.c. |
| MA9 | Nucleocapsid (N) protein (20 μg) | CFA/IFA + CpG | s.c. |

Figure 12:
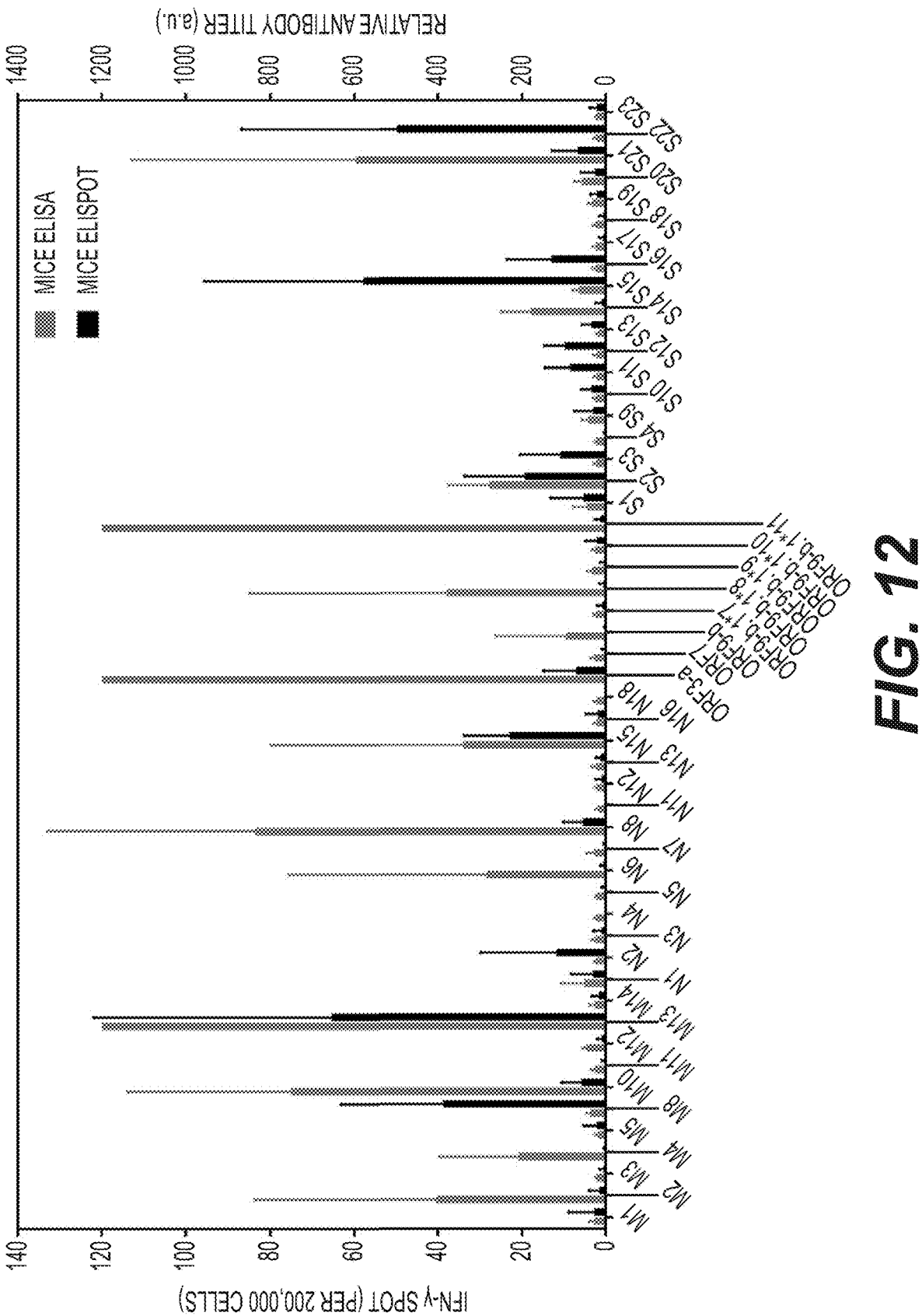
FIG. 12: Summary of immune responses induced by different peptides in mice.
Figures 13A, 13B:
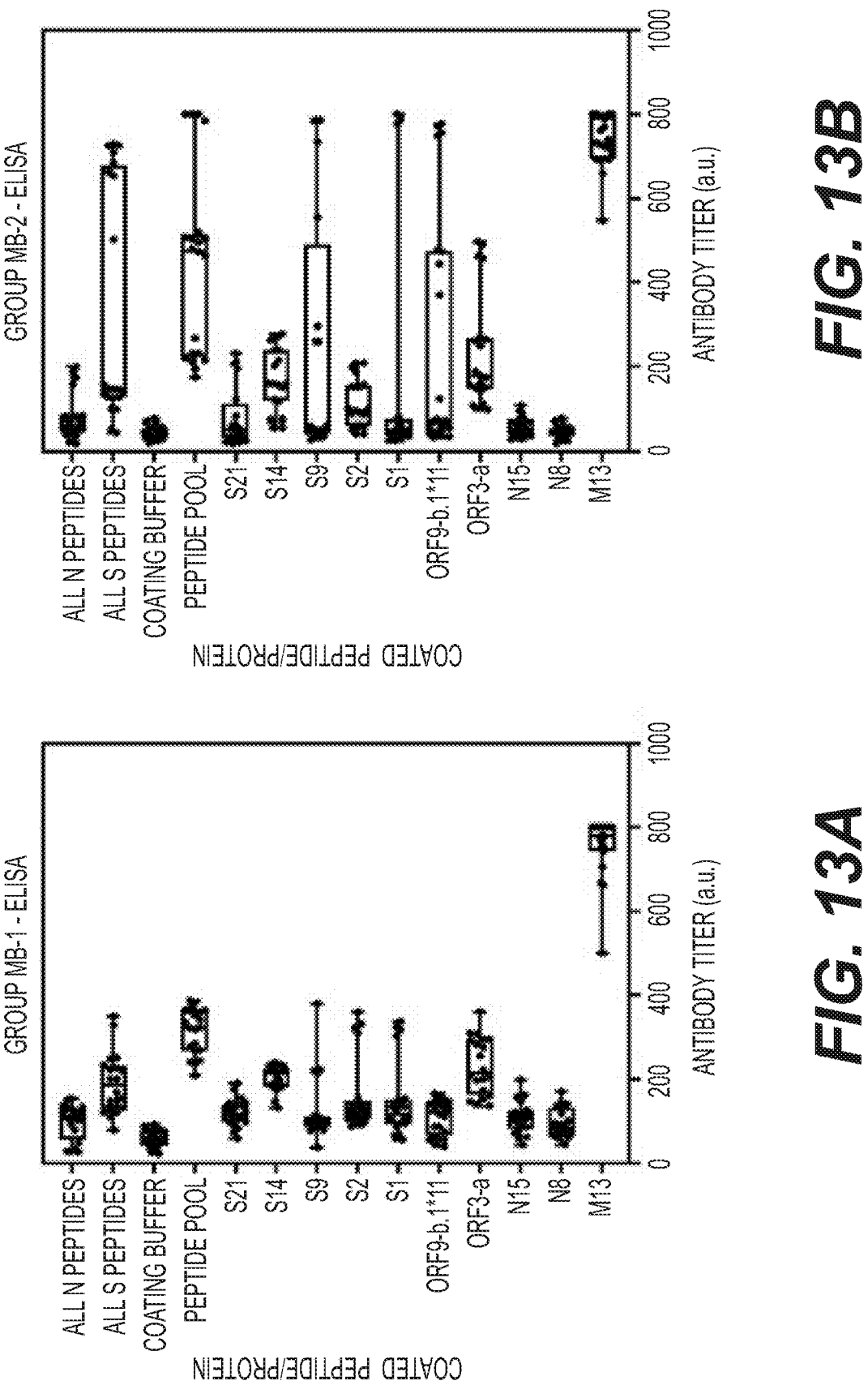
FIG. 13A: Immune responses in mice induced by different peptides, given in two doses at 21-day interval, as measured by ELISA.
FIG. 13B: Immune responses in mice induced by different peptides, given in two doses at 28-day interval, as measured by ELISA.
Figures 13C, 13D:
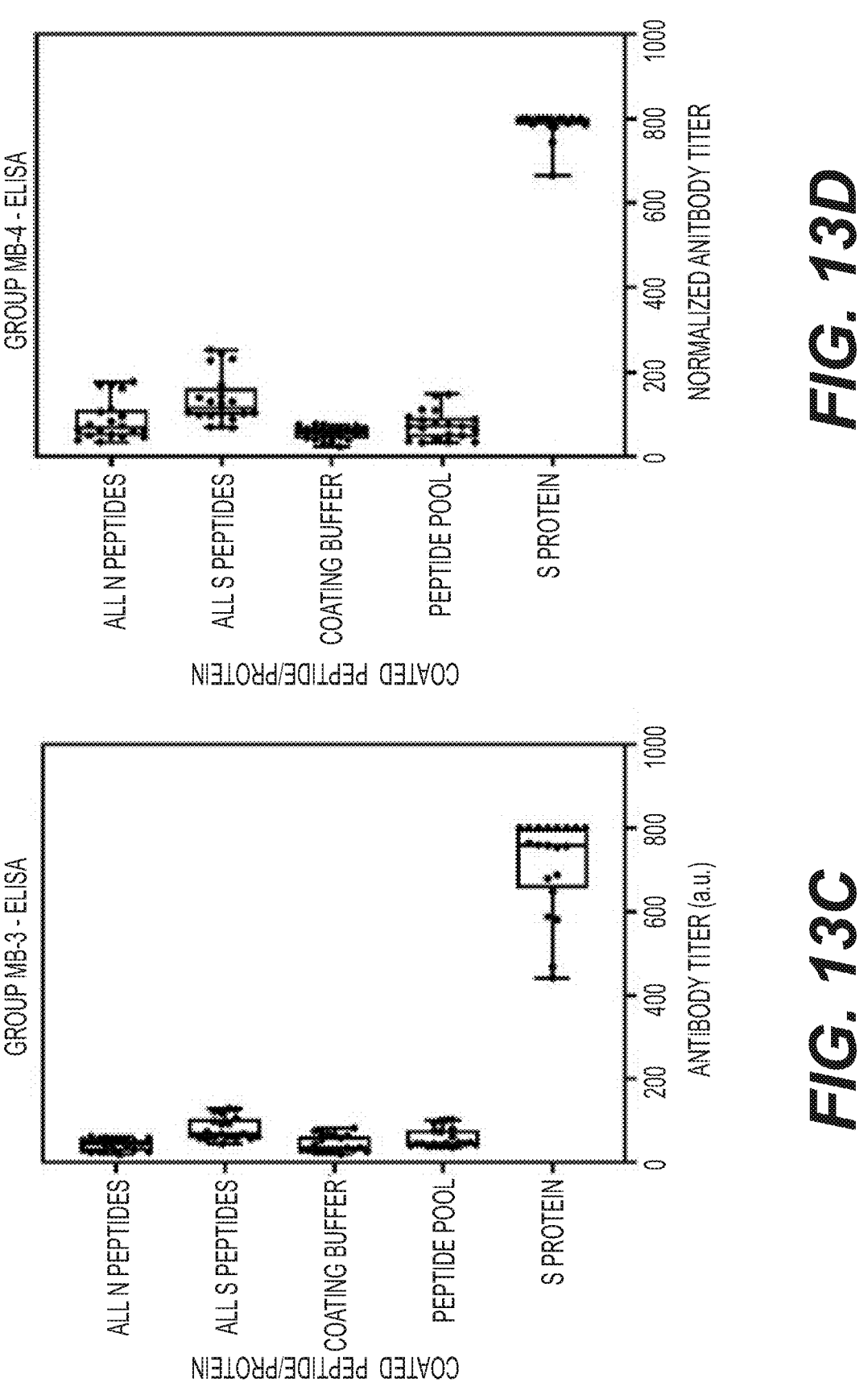
FIG. 13C: Immune responses in mice induced by different peptides, given in two doses at 21-day interval, as measured by ELISA.
FIG. 13D: Immune responses in mice induced by different peptides, given in two doses at 28-day interval, as measured by ELISA.
Figure 13F:
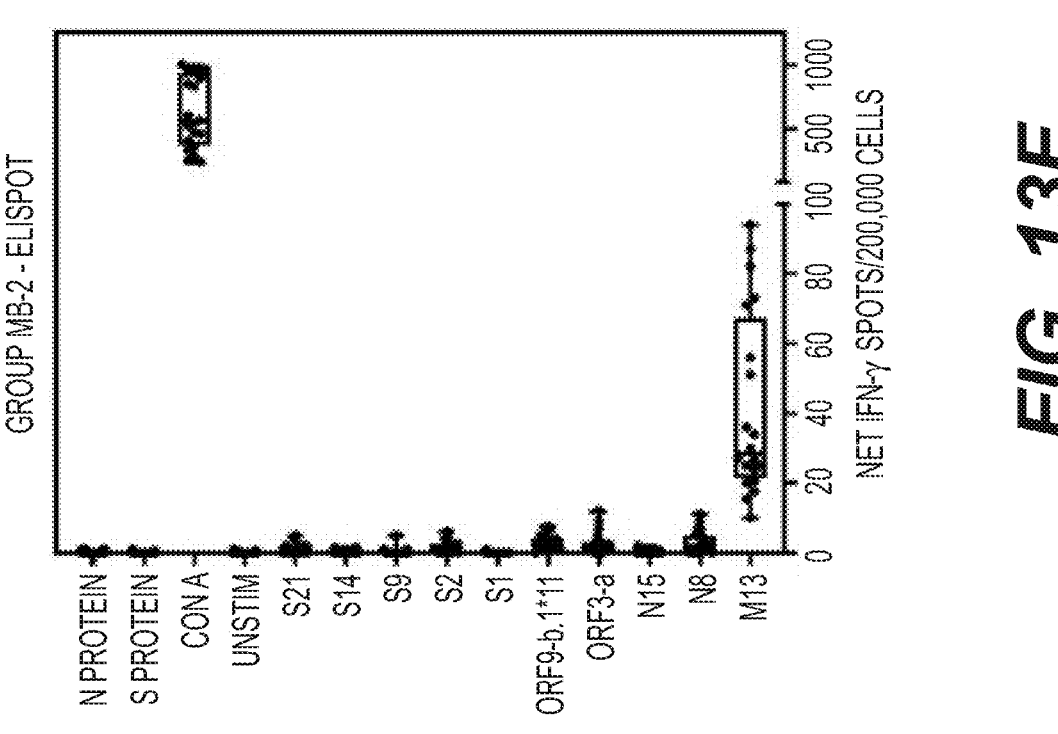
FIG. 13F: Immune responses in mice induced by different peptides, given in two doses at 28-day interval, as measured by IFN-γ ELISPOT.
Figure 13E:
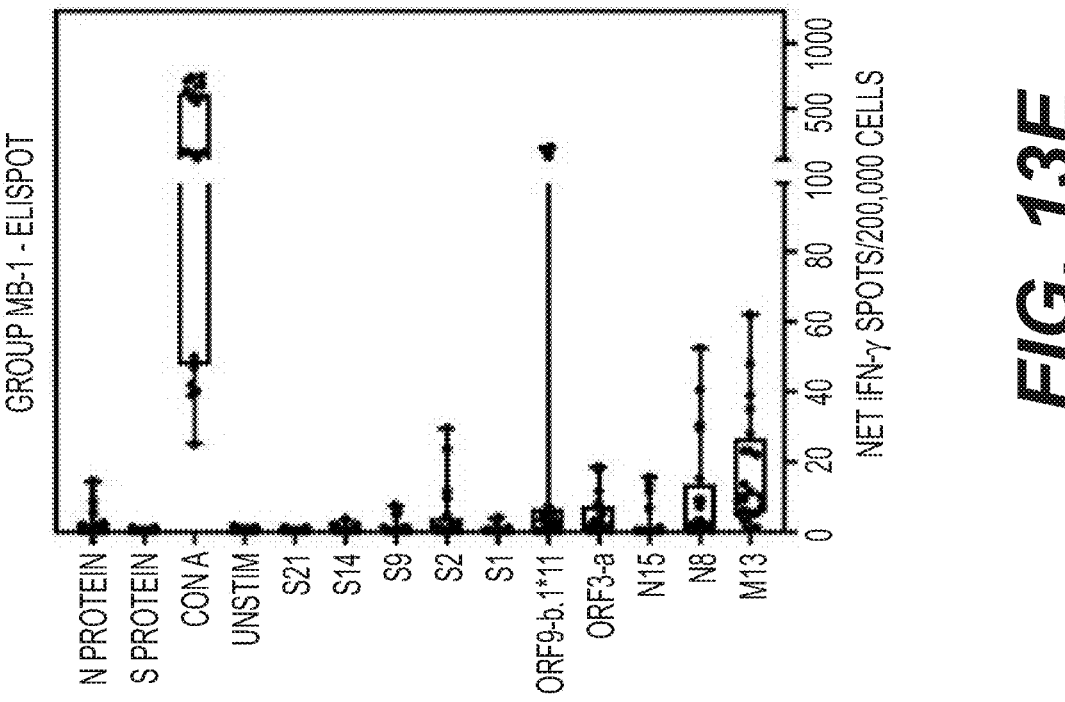
FIG. 13E: Immune responses in mice induced by different peptides, given in two doses at 21-day interval, as measured by IFN-γ ELISPOT.
Figure 13H:
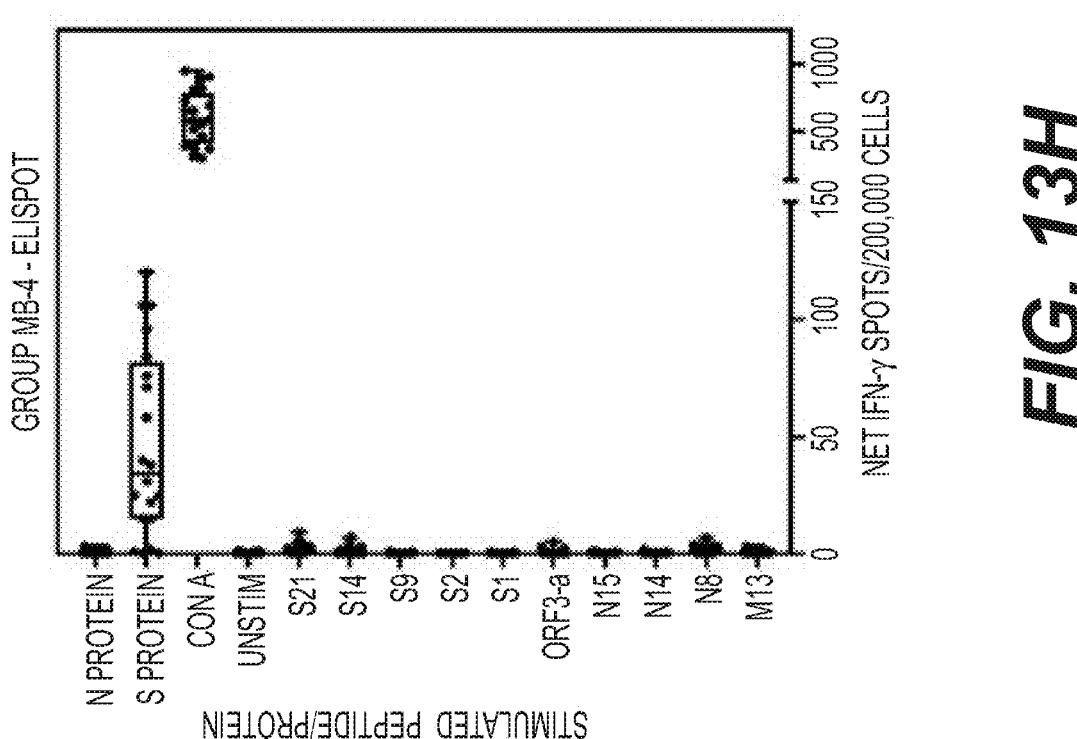
FIG. 13H: Immune responses in mice induced by different peptides, given in two doses at 28-day interval, as measured by IFN-γ ELISPOT.
Figure 13G:
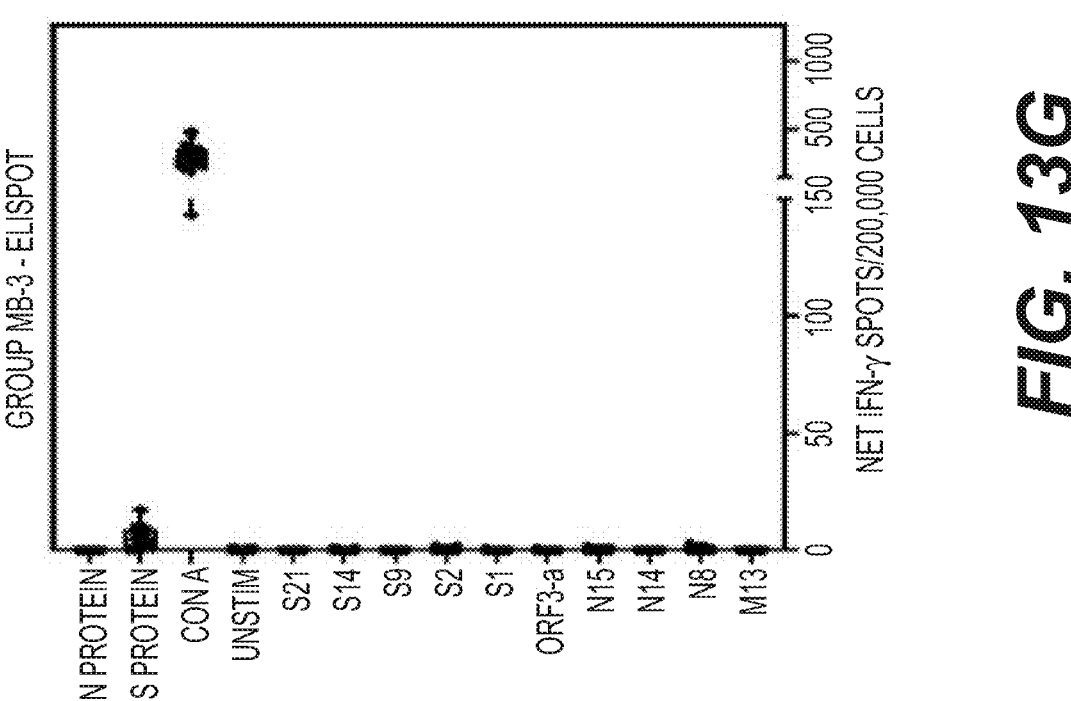
FIG. 13G: Immune responses in mice induced by different peptides, given in two doses at 21-day interval, as measured by IFN-γ ELISPOT.
Figure 14B:
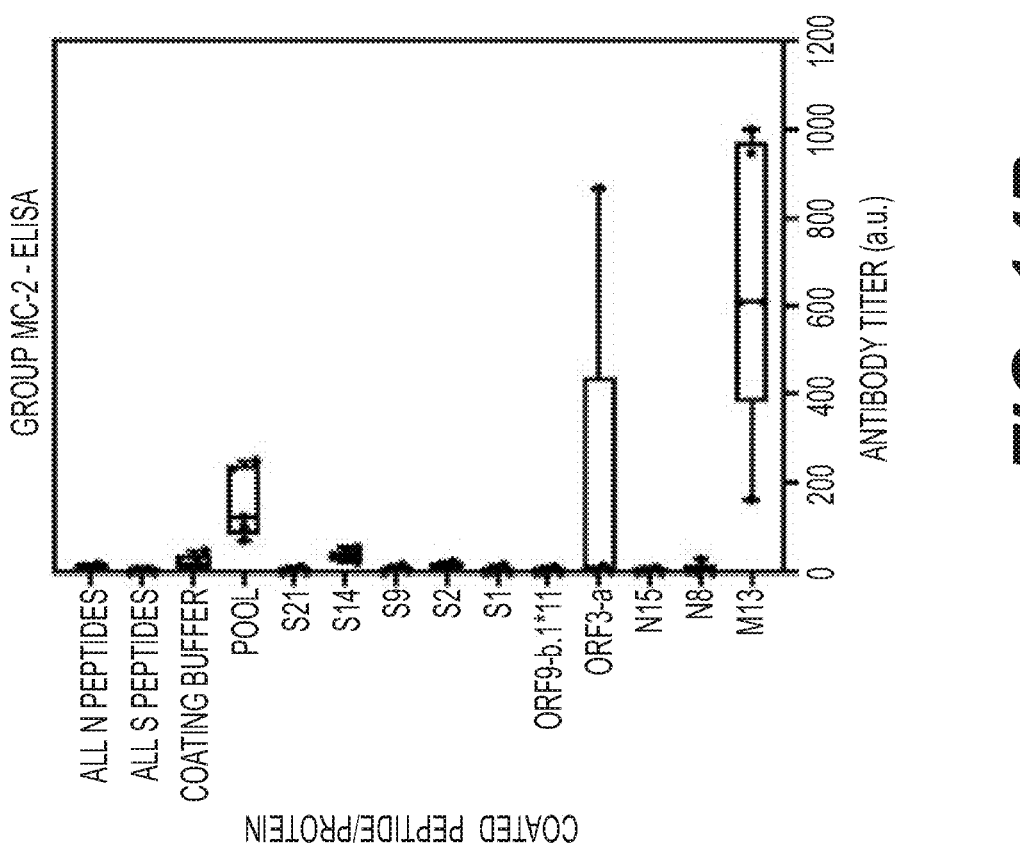
FIG. 14B: Immune responses in mice induced by 10 peptides, formulated with different adjuvants, as measured by IgG ELISA).
Figure 14A:
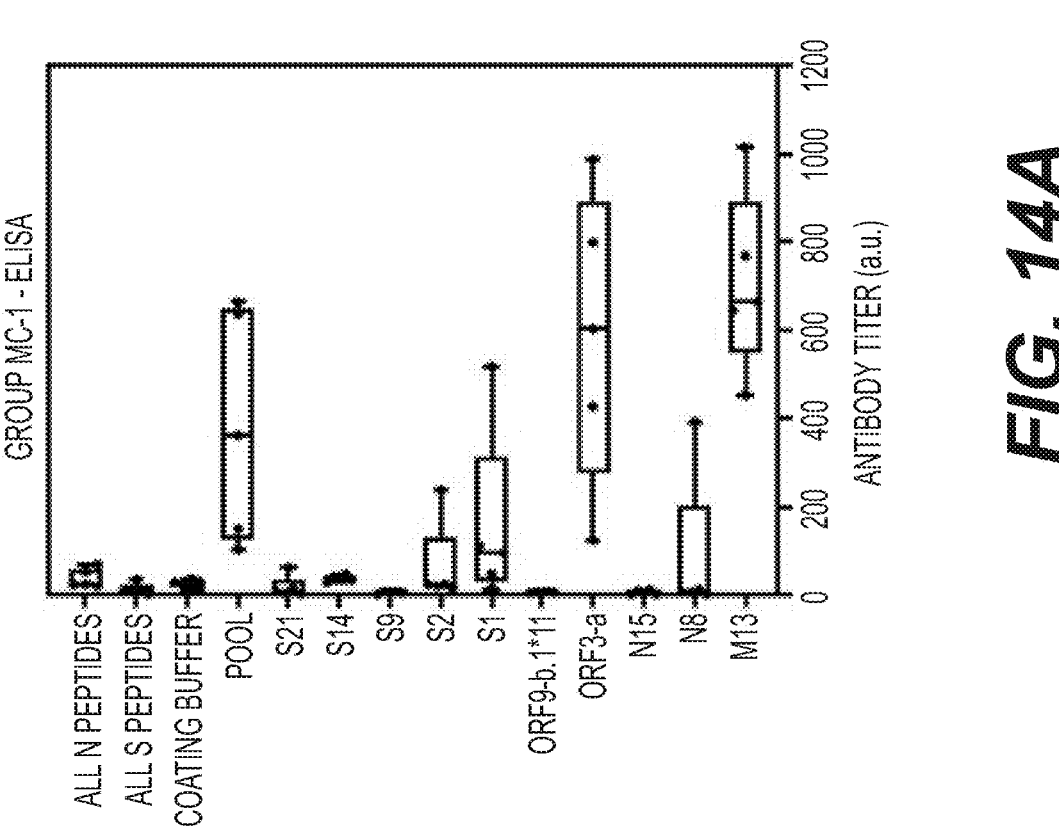
FIG. 14A: Immune responses in mice induced by 10 peptides, formulated with different adjuvants, as measured by IgG ELISA (FIGS. 14A, 14B, 14C, and 14D) and IFN-γ ELISPOT (FIGS. 14E, 14F, 14G, and 14H).
Figures 14C, 14D:
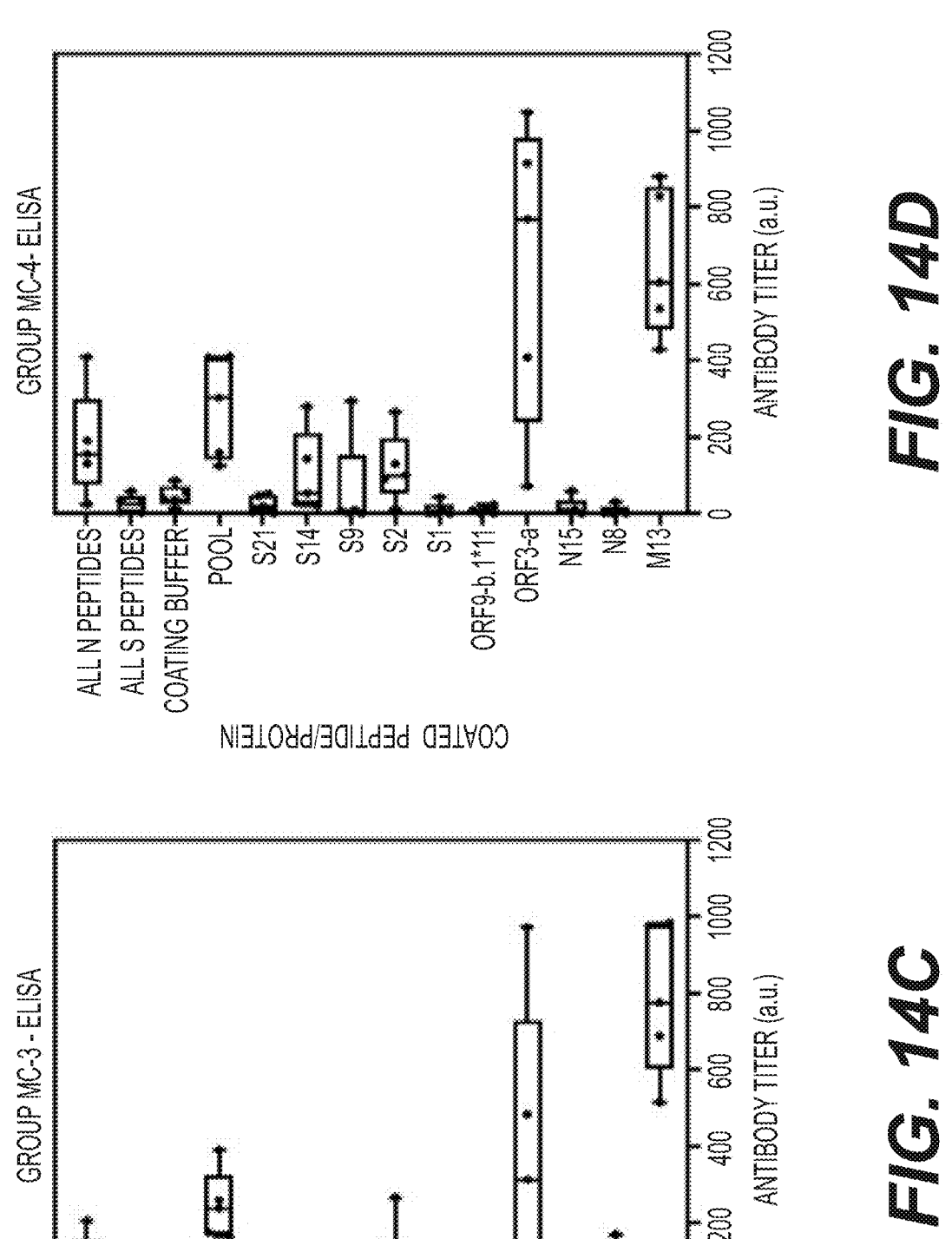
FIG. 14C: Immune responses in mice induced by 10 peptides, formulated with different adjuvants, as measured by IgG ELISA.
FIG. 14D: Immune responses in mice induced by 10 peptides, formulated with different adjuvants, as measured by IgG ELISA.
Figure 14F:
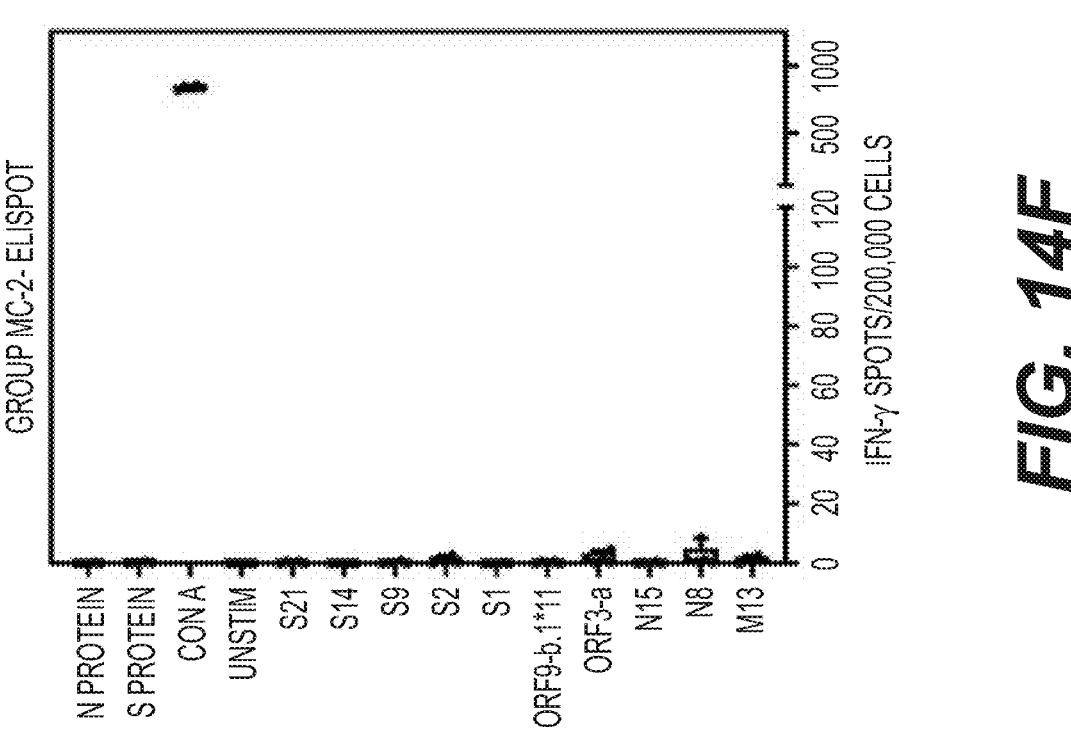
FIG. 14F: Immune responses in mice induced by 10 peptides, formulated with different adjuvants, as measured by IFN-γ ELISPOT.
Figure 14E:
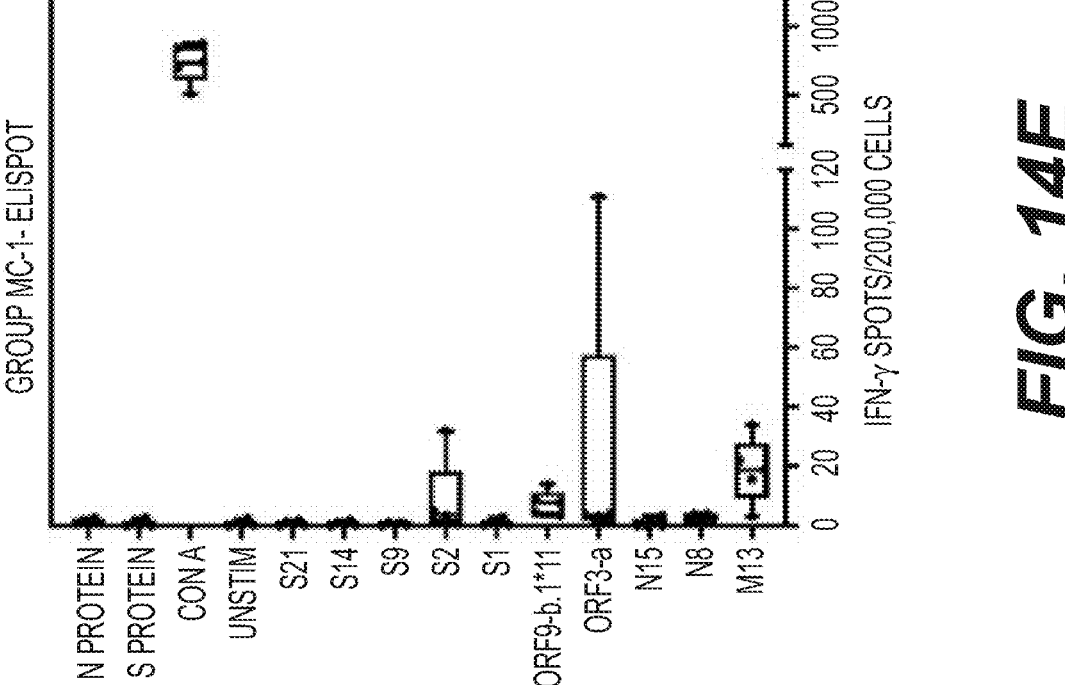
FIG. 14E: Immune responses in mice induced by 10 peptides, formulated with different adjuvants, as measured by IFN-γ ELISPOT.
Figures 14G, 14H:
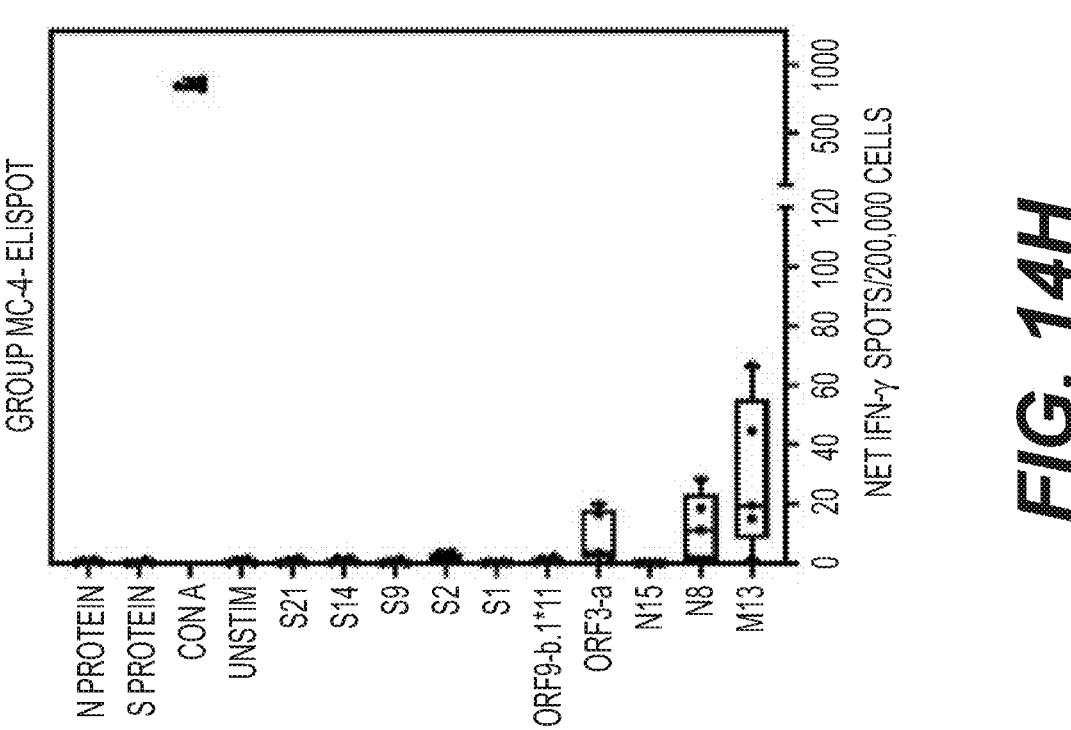
FIG. 14G: Immune responses in mice induced by 10 peptides, formulated with different adjuvants, as measured by IFN-γ ELISPOT.
FIG. 14H: Immune responses in mice induced by 10 peptides, formulated with different adjuvants, as measured by IFN-γ ELISPOT.
Figures 15A, 15B:
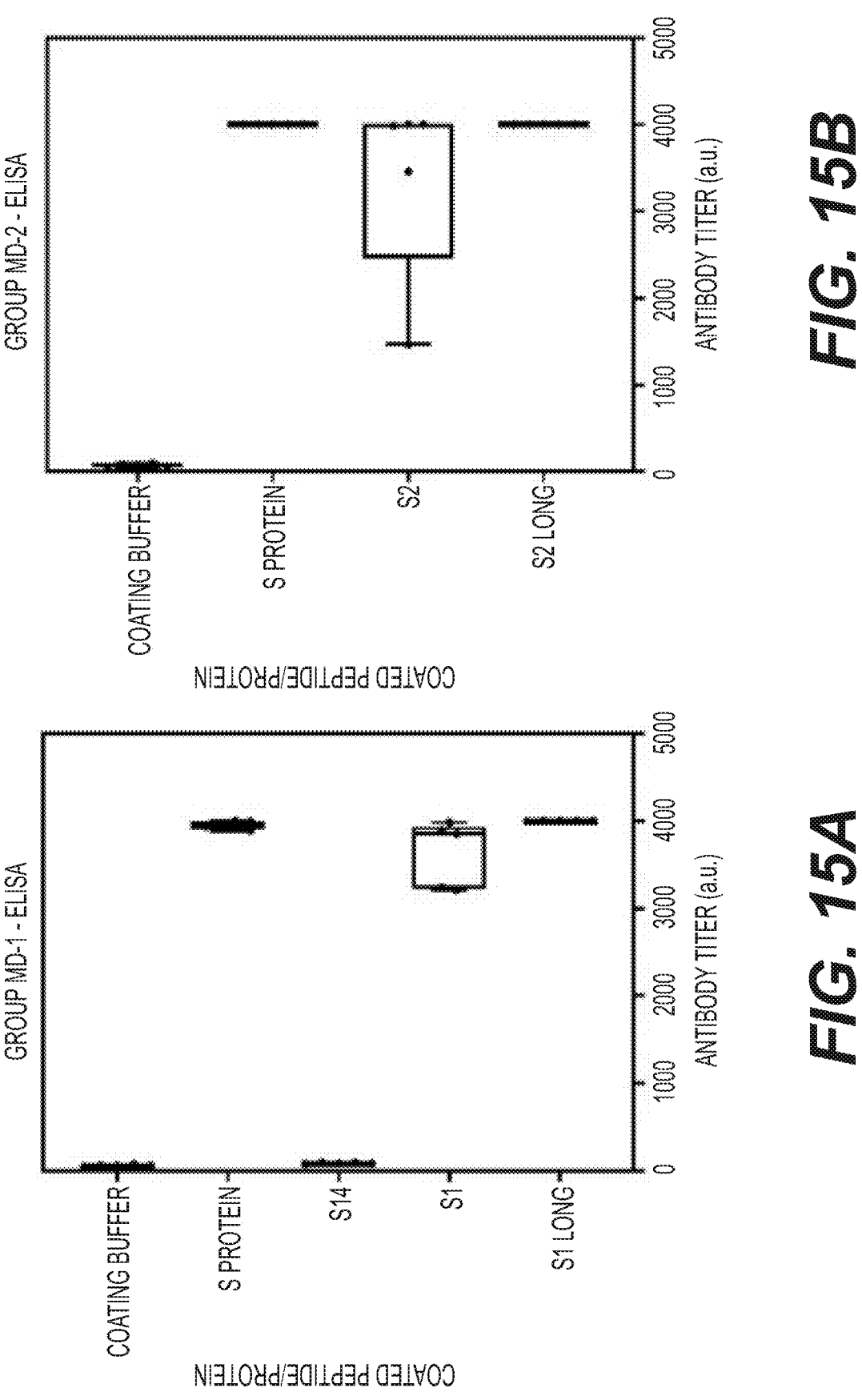
FIG. 15A: Immune responses in mice induced by different long peptides, as measured by IgG ELISA.
FIG. 15B: Immune responses in mice induced by different long peptides, as measured by IgG ELISA.
Figures 15C, 15D:
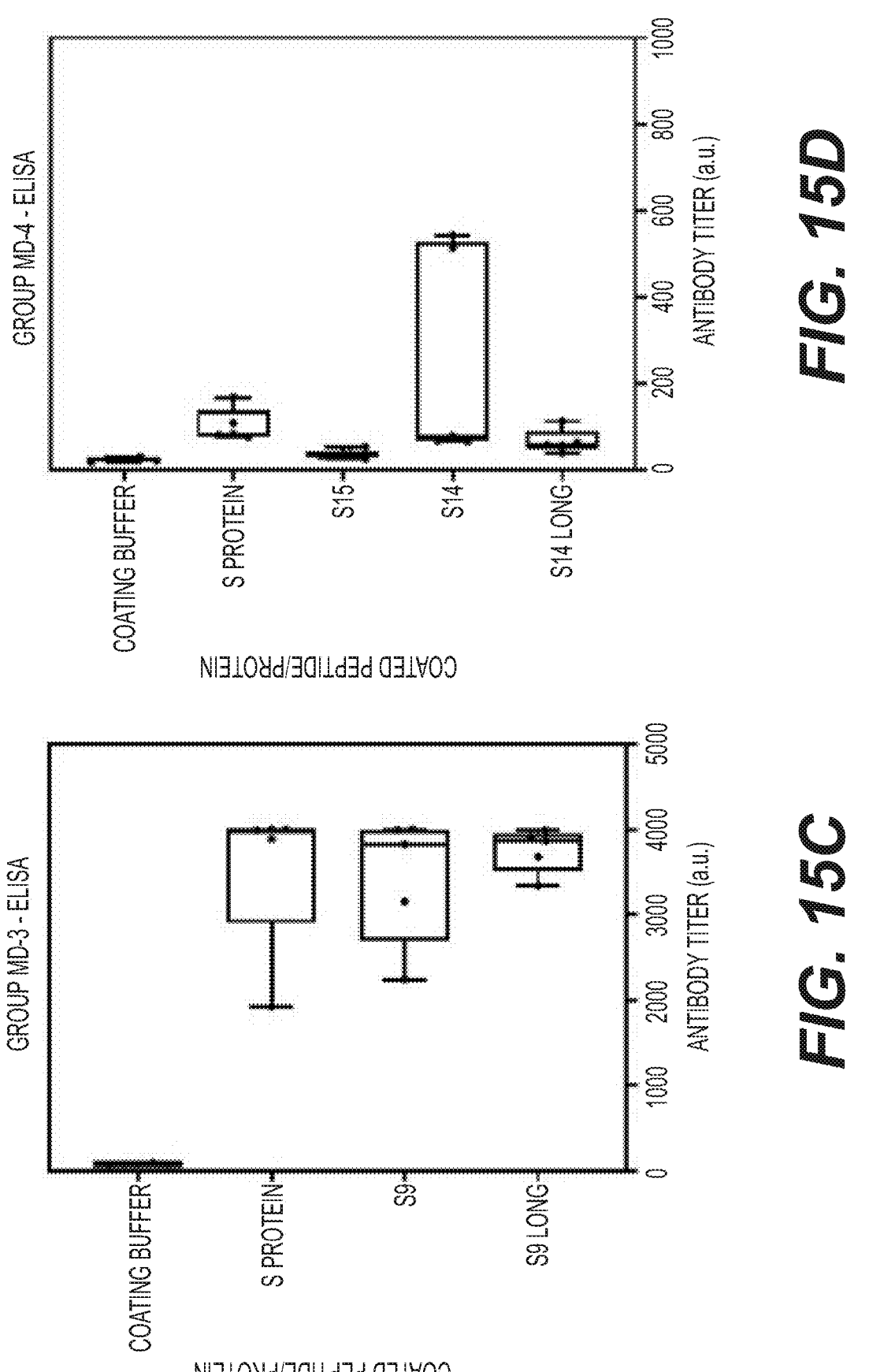
FIG. 15C: Immune responses in mice induced by different long peptides, as measured by IgG ELISA.
FIG. 15D: Immune responses in mice induced by different long peptides, as measured by IgG ELISA.
Figures 15E, 15F:
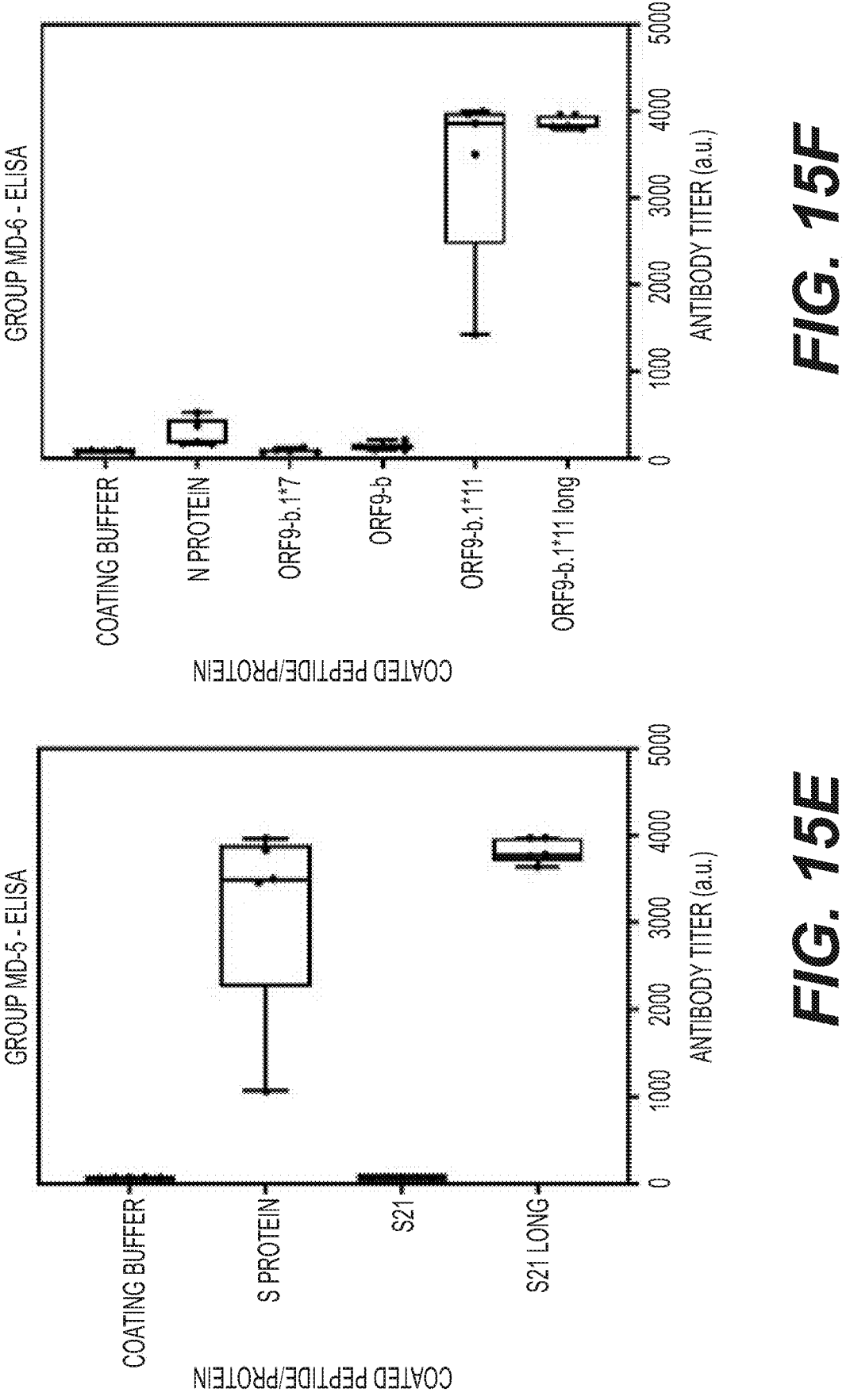
FIG. 15E: Immune responses in mice induced by different long peptides, as measured by IgG ELISA.
FIG. 15F: Immune responses in mice induced by different long peptides, as measured by IgG ELISA.
Figures 15G, 15H:
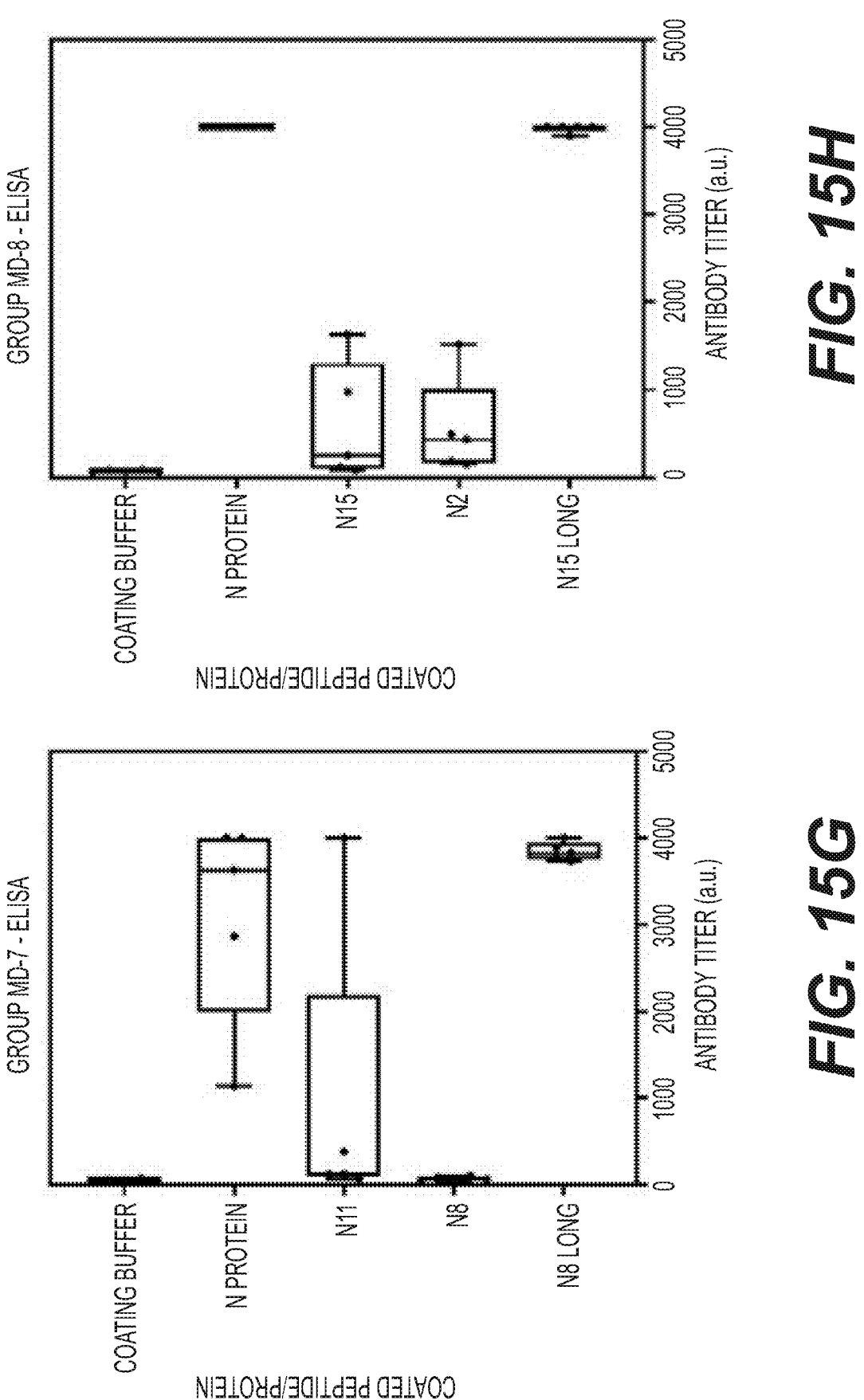
FIG. 15G: Immune responses in mice induced by different long peptides, as measured by IgG ELISA.
FIG. 15H: Immune responses in mice induced by different long peptides, as measured by IgG ELISA.
Figures 15I, 15J:
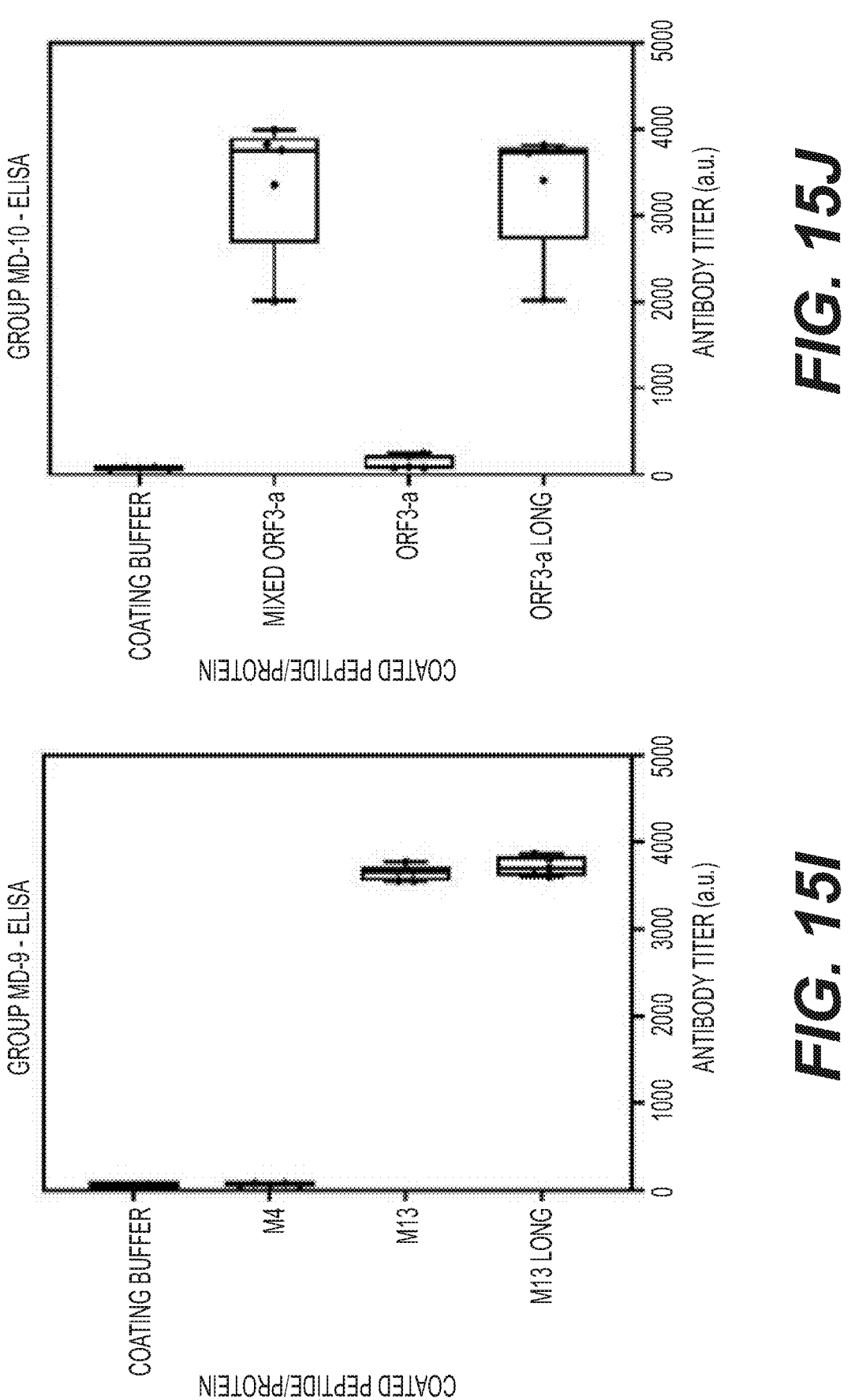
FIG. 15I: Immune responses in mice induced by different long peptides, as measured by IgG ELISA.
FIG. 15J: Immune responses in mice induced by different long peptides, as measured by IgG ELISA.
Figures 15K, 15L:
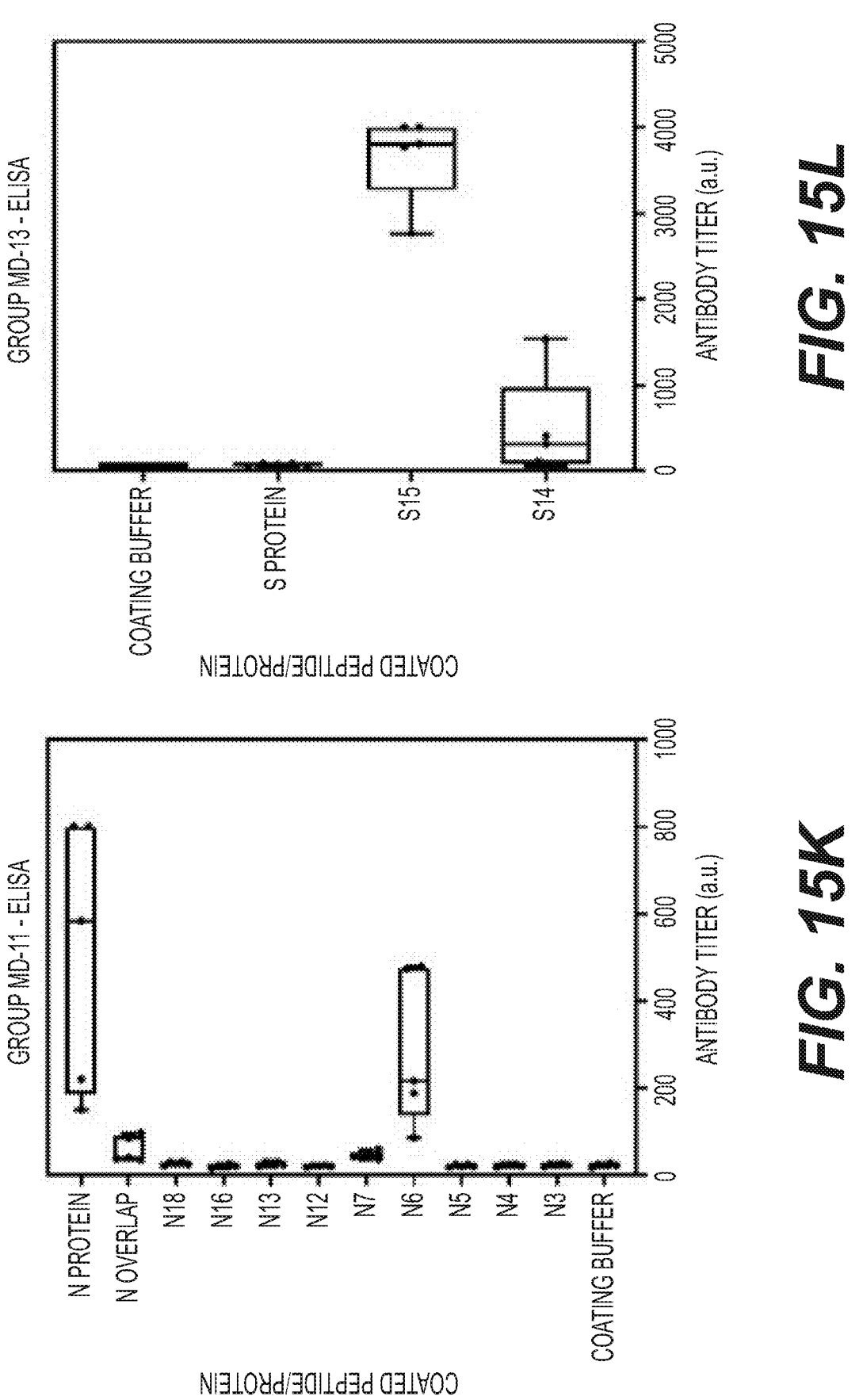
FIG. 15K: Immune responses in mice induced by different long peptides, as measured by IgG ELISA.
FIG. 15L: Immune responses in mice induced by different long peptides, as measured by IgG ELISA.
Figures 16A, 16B:
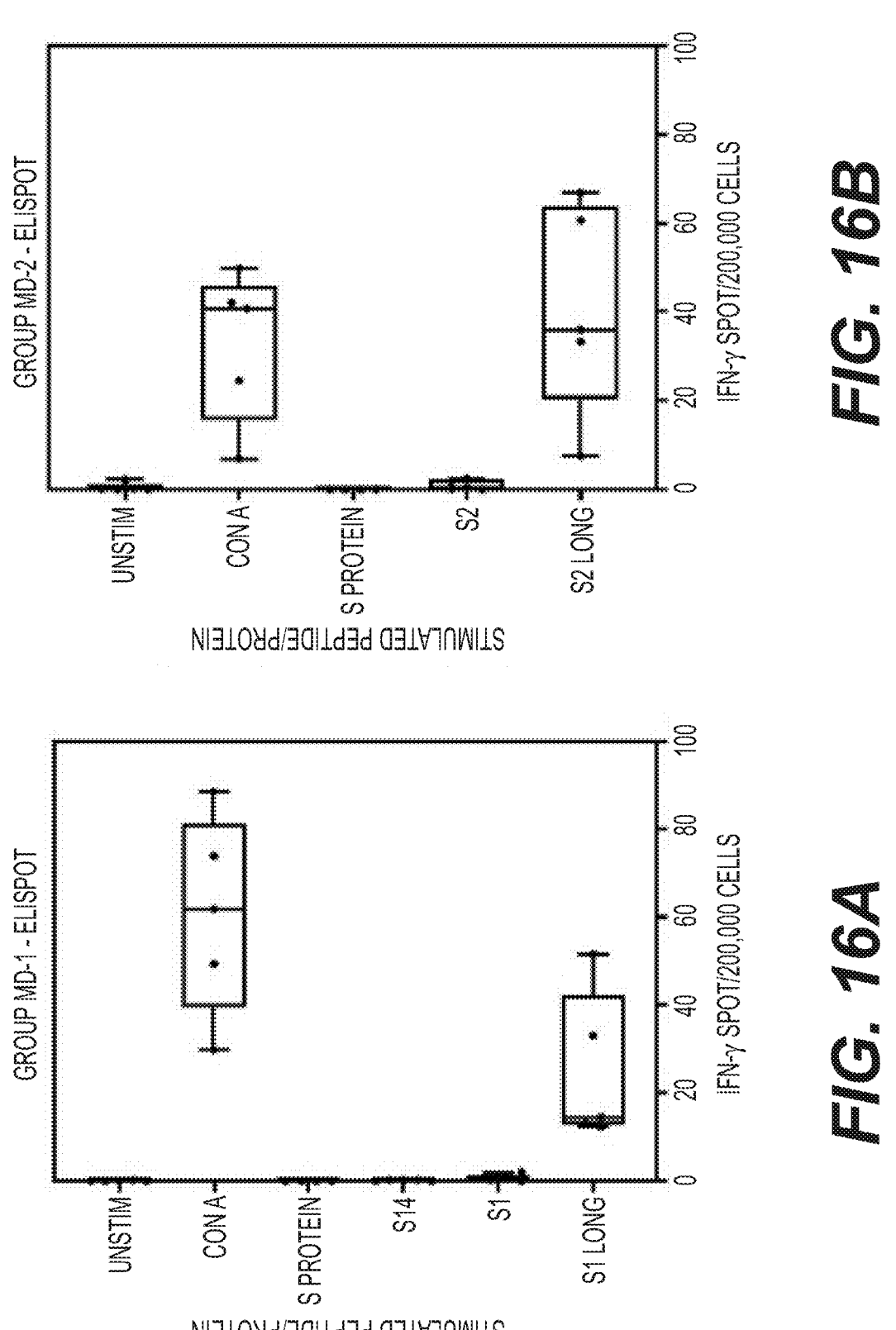
FIG. 16A: Immune responses in mice induced by different long peptides, as measured by IFN-γ ELISPOT.
FIG. 16B: Immune responses in mice induced by different long peptides, as measured by IFN-γ ELISPOT.
Figure 16D:
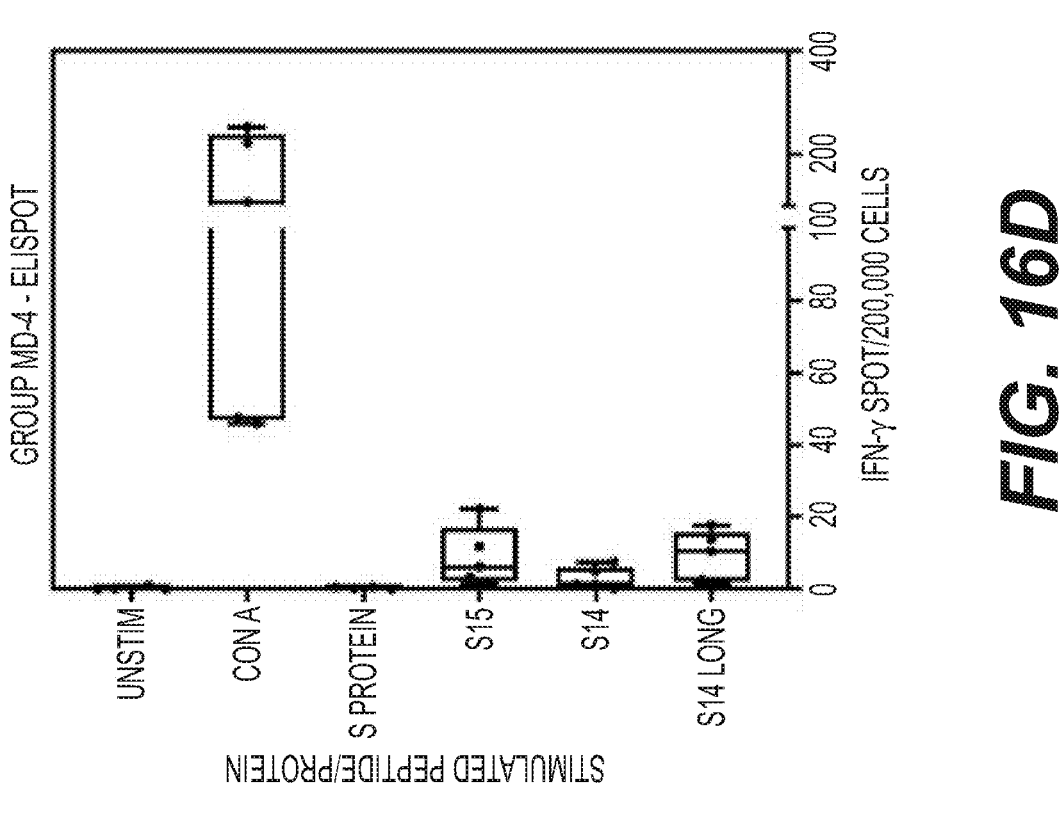
FIG. 16D: Immune responses in mice induced by different long peptides, as measured by IFN-γ ELISPOT.
Figure 16C:
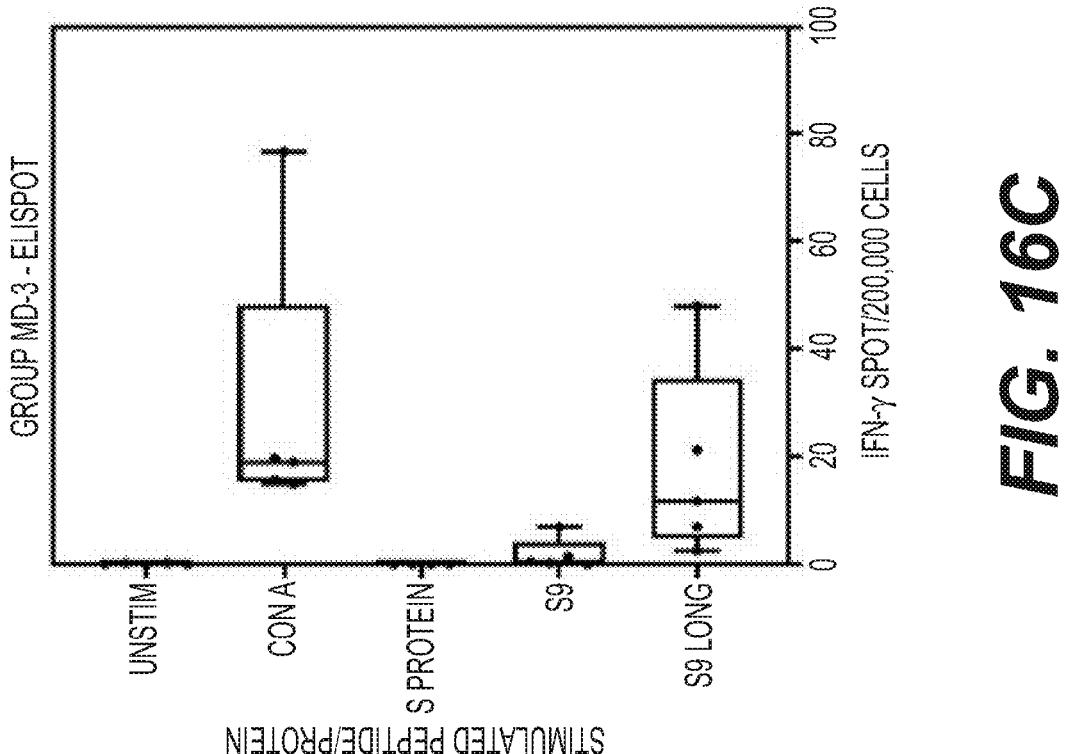
FIG. 16C: Immune responses in mice induced by different long peptides, as measured by IFN-γ ELISPOT.
Figures 16E, 16F:
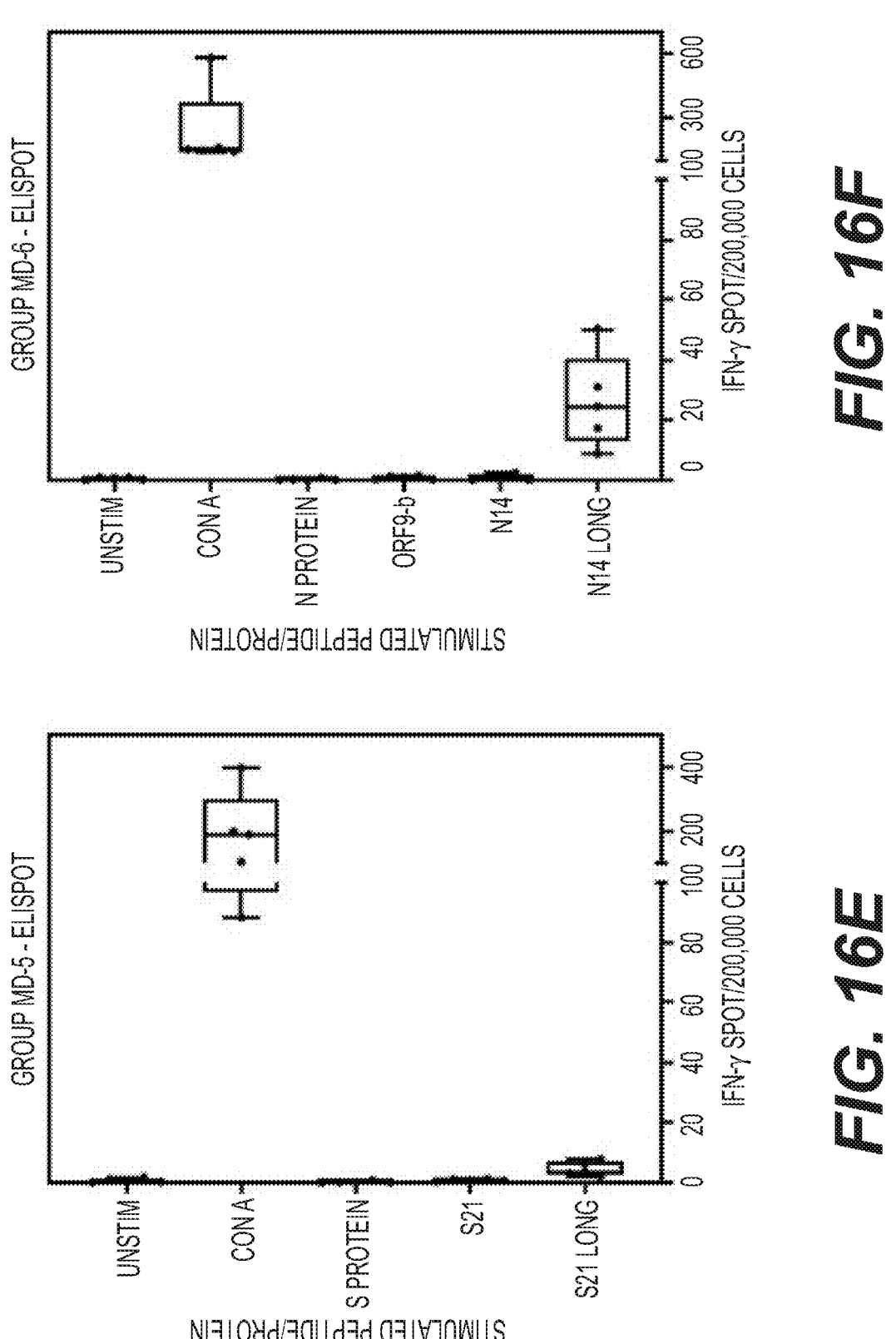
FIG. 16E: Immune responses in mice induced by different long peptides, as measured by IFN-γ ELISPOT.
FIG. 16F: Immune responses in mice induced by different long peptides, as measured by IFN-γ ELISPOT.
Figure 16H:
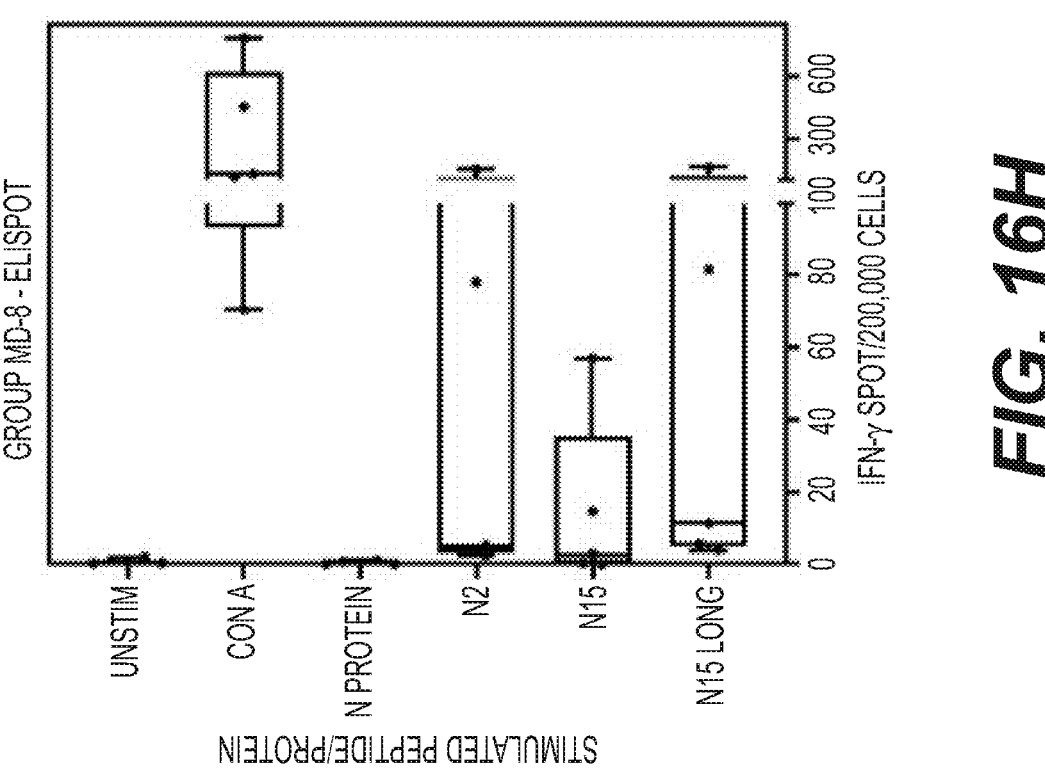
FIG. 16H: Immune responses in mice induced by different long peptides, as measured by IFN-γ ELISPOT.
Figure 16G:
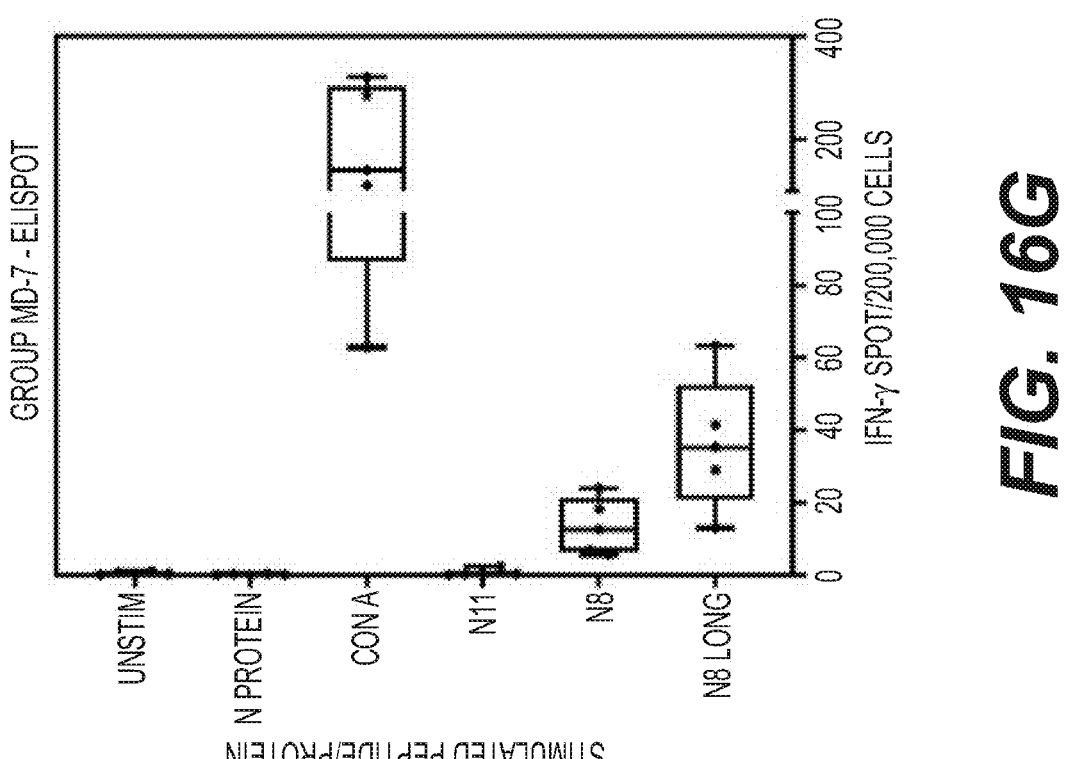
FIG. 16G: Immune responses in mice induced by different long peptides, as measured by IFN-γ ELISPOT.
Figures 16I, 16J:
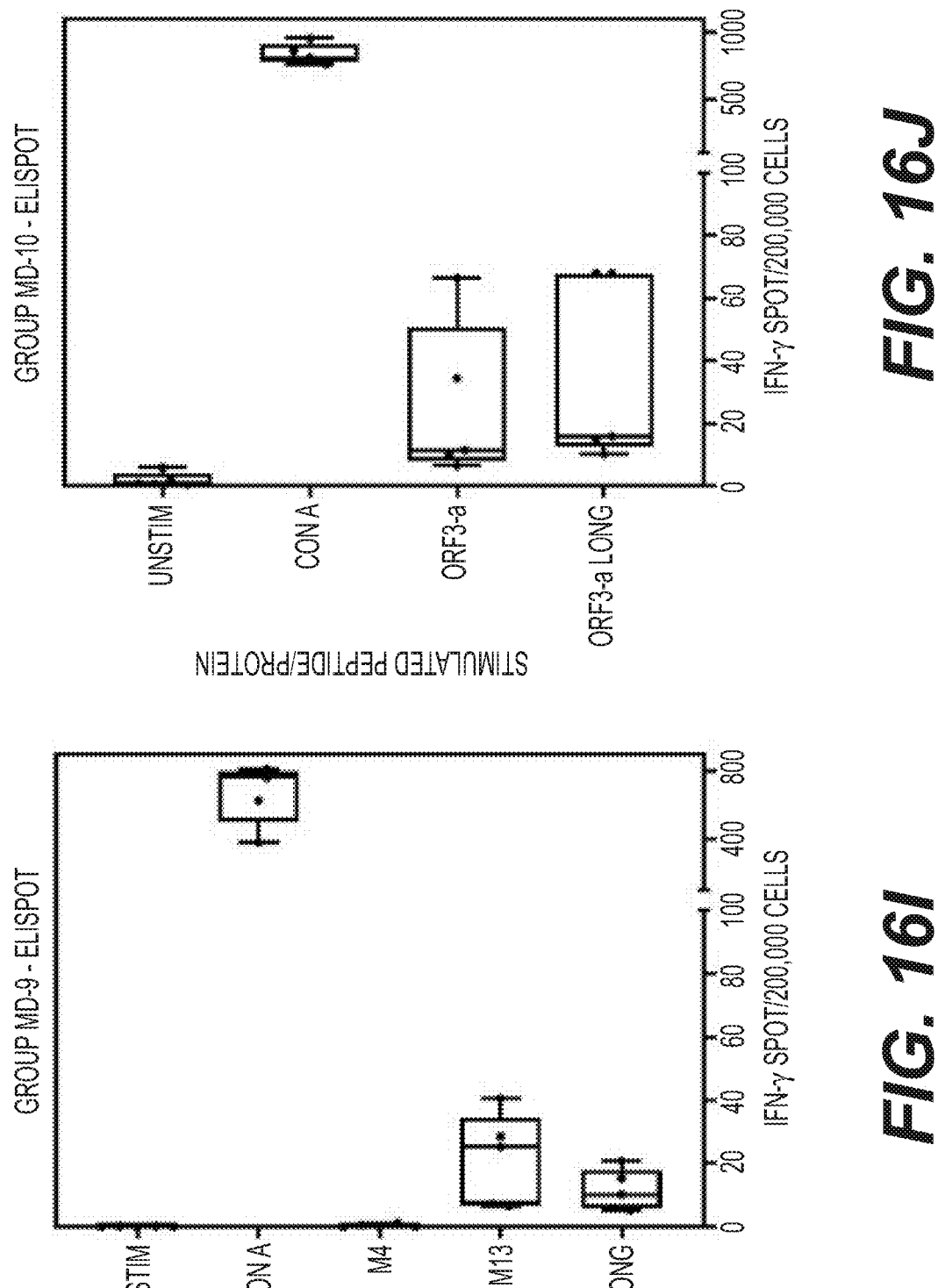
FIG. 16I: Immune responses in mice induced by different long peptides, as measured by IFN-γ ELISPOT.
FIG. 16J: Immune responses in mice induced by different long peptides, as measured by IFN-γ ELISPOT.
Figure 16L:
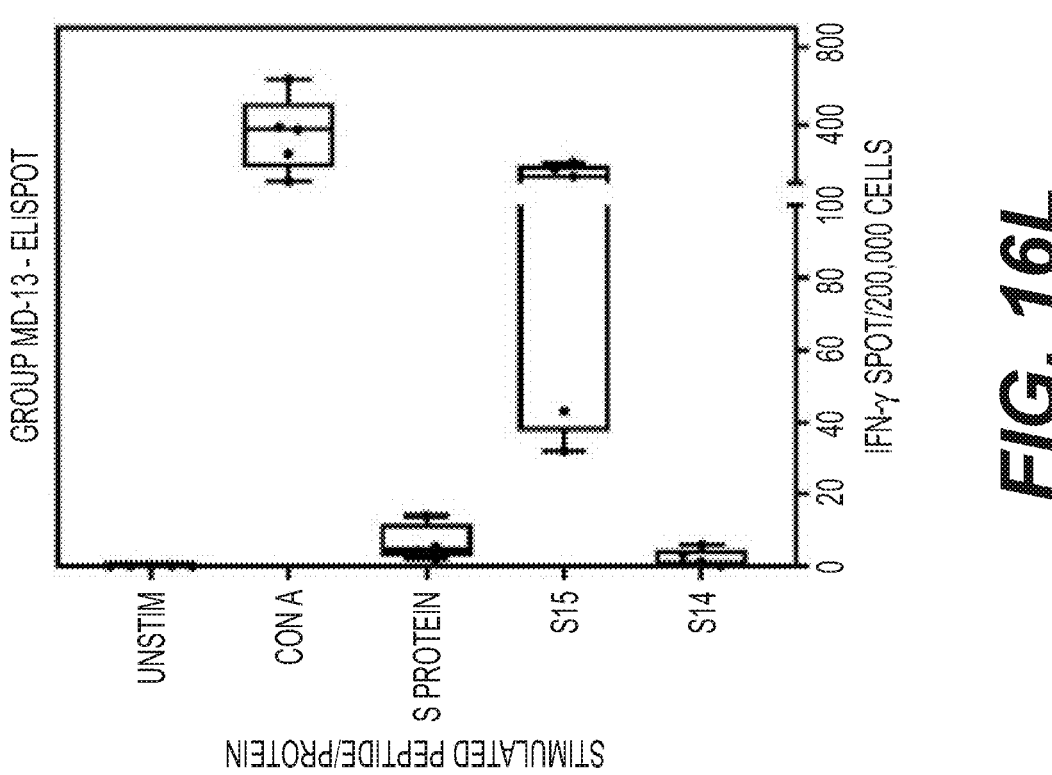
FIG. 16L: Immune responses in mice induced by different long peptides, as measured by IFN-γ ELISPOT.
Figure 16K:
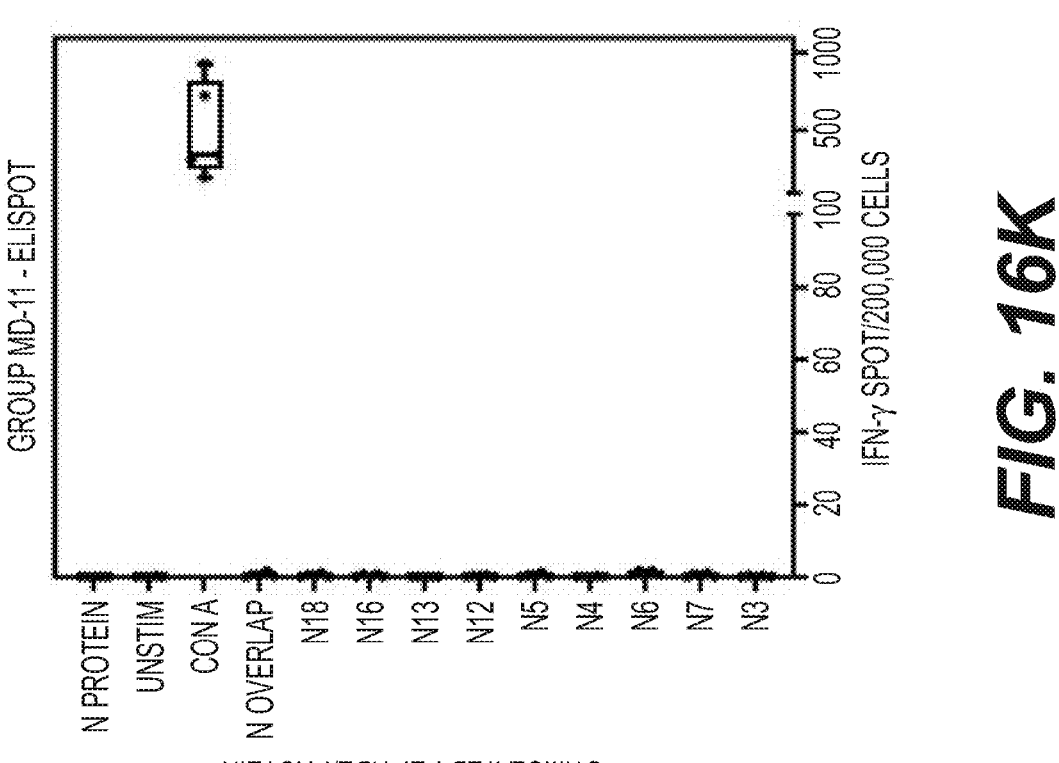
FIG. 16K: Immune responses in mice induced by different long peptides, as measured by IFN-γ ELISPOT.

Results of the peptide screening in mice are shown in FIGS. 10A-I (antibody titers as measured by ELISA), FIGS. 11A-I (T cell responses as measured by IFN-γ ELISPOT). As shown in FIG. 12, twelve peptides elicit detectable antibody responses and seven peptides elicited T cell responses in mice. Three of these peptides elicit both antibody and T cell responses. Twelve of these peptides are also immunogenic in hamsters.

Based on the magnitude of immune responses (combining IFN-γ and antibody ELISA responses) in both hamsters and mice, a set of 10 peptides—S1, S2, S9, S14, S21, ORF9b.1*11, N8, N15, M13, ORF3a—are selected for follow-on experiments with different adjuvants as well as elongated peptide studies.

Table 8 below shows the top 10 immunogenic peptides in mice and hamsters. Peptides are ranked based on magnitude of responses in arbitrary antibody units (a.u.) and counts of Spot Forming Units (SFU/200,000 cells) as measured by IFN-γ ELISPOT and antibody ELISA assays, respectively.

TABLE 8

Peptides with immune responses in mice and hamsters

| Mice | | Hamsters | |
|---|---|---|---|
| ELISA | ELISPOT | ELISA | ELISPOT |
| ORF3a | M13 | S1 | N15 |
| M13 | S15 | N7 | M8 |
| ORF9b.1*11 | S22 | ORF3a | S10 |
| N8 | M8 | S9 | ORF3a |
| S21 | N15 | N8 | S19 |

TABLE 8-continued

| | | | |
|---|---|---|---|
| Peptides with immune responses in mice and hamsters | | | |
| Mice | | Hamsters | |
| ELISA | ELISPOT | ELISA | ELISPOT |
| M10 | S2 | N15 | S3 |
| M2 | S16 | S19 | N7 |
| N15 | N2 | ORF9b.1*11 | S13 |
| S2 | S3 | M13 | ORF9b.1*11 |
| N6 | S12 | N6 | S23 |

Example 4: Comparison of Dose Intervals in Mice

Experiments are performed to test whether varying the intervals between the first and second vaccine doses enhance the immune response to peptides or proteins combined with CFA/IFA+CpG in mice.

Method:

Mice are divided into 4 groups of 5 (MB1 to MB4, as in Table 9 below). Group MB1 is primed with 10 selected peptides (20 µg) combined with CpG+CFA, and is boosted with the same peptide formulation with CpG+IFA after 21 days. Group MB2 is immunized with the identical formulation at an interval of 28 days between the doses. Groups MB3 and MB4 are prime-boosted with SARS-CoV-2 S protein combined with CFA/IFA+CpG at 21-day and 28-day intervals, respectively. Immunogenicity is assessed using IFN-γ ELISPOT and antibody ELISA as described in Examples 2 and 3.

TABLE 9

| | | | | |
|---|---|---|---|---|
| Comparison of peptides at 21-day vs. 28-day dose interval in mice | | | | |
| Group | Peptide (20 µg each) | Adjuvants | Route | Dose interval |
| MB1 | S1, S2, S9, S14, S21, ORF9b.1*11, N8, N15, M13, ORF3a | CFA/IFA + CpG | s.c. | 21 days |
| MB2 | SI, S2, S9, S14, S21, ORF9b.1*11, N8, N15, M13, ORF3a | CFA/IFA + CpG | s.c. | 28 days |
| MB3 | Spike (S) protein | CFA/IFA + CpG | s.c. | 21 days |
| MB4 | Spike (S) protein | CFA/IFA + CpG | s.c. | 28 days |

Results are shown in FIG. 13. The top panels of FIG. 13 depict antibody titers as measured by ELISA while the bottom panels of FIG. 13 depict T cell responses as measured by IFN-γ ELISPOT, induced by either the ten peptides or the spike protein, given twice at dose intervals of 21 or 28 days. The results indicate that a 28-day interval between prime and boost immunization elicits significantly more robust immune responses to peptides in mice.

Example 5: Comparison of Peptides with Different Adjuvants in Mice

Experiments are performed to identify the peptide-adjuvant combinations eliciting the strongest immune responses in mice.

Method:

The mice are divided into 4 groups of 5 (MC1 to MC4) and are immunized via the subcutaneous (s.c) route with two doses of a formulation of 10 peptides (Table 10) combined with different adjuvants and TLR4 agonist GLA, at a 28-day interval. Group MC1 is immunized with peptides combined with water-in-oil emulsion Montanide 51+GLA; Group MC2 is administered 10 peptides+Alum+GLA; Group MC3 receives 10 peptides+EmT4+GLA and group MC4 is immunized with 10 peptides+squalene-based oil-in-water emulsion Addavax+GLA. The mice are euthanized 14 days after the second dose and immune responses are assessed using IFN-γ ELISPOT and antibody ELISA as described in Examples 2 and 3.

TABLE 10

| | | | |
|---|---|---|---|
| Comparison of the effects of different adjuvants in mice | | | |
| Group | Peptide (20 µg each) | Adjuvants | Route |
| MC1 | S1, S2, S9, S14, S21, ORF9b.1*11, N8, N15, M13, ORF3a | Montanide 51 + TLR4 agonist | s.c. |
| MC2 | S1, S2, S9, S14, S21, ORF9b.1*11, N8, N15, M13, ORF3a | Alum + TLR4 agonist | s.c. |
| MC3 | S1, S2, S9, S14, S21, ORF9b.1*11, N8, N15, M13, ORF3a | EmT4 + TLR4 agonist | s.c. |
| MC4 | S1, S2, S9, S14, S21, ORF9b.1*11, N8, N15, M13, ORF3a | Addavax + TLR4 agonist | s.c. |

Results are shown in FIG. 14. The top panels of FIG. 14 depict antibody titers as measured by ELISA while the bottom panels of FIG. 14 depict T cell responses as measured by IFN-γ ELISPOT, induced by a combination of ten peptides formulated with different adjuvants. The results indicate that adjuvants have variable effects on immunogenicity, with water-in-oil emulsion adjuvants inducing superior immune responses, followed by oil-in-water emulsions. TLR4 agonist is shown to boost immunogenicity.

Example 6: Testing the Immunogenicity of Elongated Peptides in Mice

Experiment are performed to assess whether elongation of the selected immunogenic peptides results in enhanced presentation of conformational epitopes and consequently increases in antibody and T cell responses. Using SARS-CoV-2 Wu-1 reference sequence (NCBI Reference Sequence: NC 045512.2) each peptide included in the set of 10 peptides described in Examples 4 and 5 is elongated by extending the amino acid sequence on both the N- and C-termini to make a 40 amino acid long peptide, reflecting the natural SARS-CoV-2 sequence (Table 11). Each of the long peptides includes the full sequence of the respective short peptide in bold.

TABLE 11

Sequences and naming of long peptides (40 aa)

| Peptide Name | Sequence | SEQ ID NO: |
|---|---|---|
| S-1 Long | ESEFRVYSSANNCTFEYVSQPFLMDLEGKQGNFKNLREFV | 68 |
| S-2 Long | TMYICGDSTECSNLLLQYGSFCTQLNRALTGIAVEQDKNT | 69 |
| S-9 Long | QAGSTPCNGVEGFNCYFPLQSYGFQPTNGVGYQPYRVVVL | 70 |
| S-14 Long | SSVLHSTQDLFLPFFSNVTWFHAIHVSGTNGTKRFDNPVL | 71 |
| S-15 Long | VLHSTQDLFLPFFSNVTWFHAIHVSGTNGTKRFDNPVLPF | 72 |
| S-21 Long | SQILPDPSKPSKRSFIEDLLFNKVTLADAGFIKQYGDCLG | 73 |
| ORF9b.1*11 Long | ISEMHPALRLVDPQIQLAVTRMENAVGRDQNNVGPKVYPI | 74 |
| N-8 Long | KMKDLSPRWYFYYLGTGPEAGLPYGANKDGIIWVATEGAL | 75 |
| N-15 Long | NFGDQELIRQGTDYKHWPQIAQFAPSASAFFGMSRIGMEV | 76 |
| M-13 Long | PLHGTILTRPLLESELVIGAVILRGHLRIAGHHLGRCDIK | 77 |
| ORF3a Long | GVKDCVVLHSYFTSDYYQLYSTQLSTDTGVEHVTFFIYNK | 78 |

Method:

The mice are divided into 13 groups of 5 (Table 12). Groups MD1 to MD10 are primed with a single long peptide (100 μg) formulated with CpG+CFA and boosted with the same peptide combined with CpG+IFA after 28 days. Group MD11 is immunized with a single N overlap peptide containing the sequence of nine individual Nucleocapsid protein-derived peptides (N3, N4, N5, N6, N7, N23, N13, N16, N18) within its sequence. Group MD12 is immunized with a pool of all 10 long peptides formulated with CFA/IFA+ CpG. Group MD13 is immunized with an equal molar concentration of short S14 and S15 peptides for comparison with group MD4, which is immunized with S14 long peptide (spanning both S14 and S15 short sequences). This comparison allows us to assess whether or not the differences in flanking amino acid sequences affect immunogenicity. The mice are euthanized 14 days after the second dose and immune responses are assessed using IFN-γ ELISPOT and antibody ELISA, as described in Example 3.

Mouse immune response is also measured with IL-4 ELISPOT and pseudovirus/rVSV microneutralization assay. Briefly, mice T cell production of IL-4 is measured. A BD™ mouse-specific IL-4 ELISPOT assay is performed on single cell suspensions similar to the mouse-specific IFN-γ ELISPOT assay. PMA/Ionomycin (81 nM/1.34 μM) is used as a positive control due to its superior performance to PHA and concanavalin A in IL-4 detection assays. The remaining conditions (cells/well, incubation times, antigen concentrations) are identical to those reported above for IFN-γ ELISPOT assays.

Mouse immune response is also measured with a pseudovirus/rVSV microneutralization assay. Briefly, neutralizing antibody response is assessed using a high-throughput, fluorescence/GFP-based pseudovirus/VSV microneutralization assay, developed in-house to allow for rapid imaging and quantification of cell infection with the ImageXpress® platform/software (Molecular Devices). The assay is based on a replication-competent VSV virus expressing eGFP and the SARS-CoV-2 Spike protein (Wuhan-Hu-1) in place of the native envelope glycoprotein. The correlation between neutralization of SARS-CoV-2 and the pseudovirus/VSV construct has been reported as r=0.9285 (p<0.001). Serial two-fold dilutions are performed from 1:10 up to 1:5,120 (four replicate wells per dilution step) and mixed with an equal volume of tissue culture media/DMEM medium containing 5% FCS and Penicillin/Streptomycin, containing 3,000 PFUs of rVSV-SARS-CoV-2-S virus per well, in a 96-well microplate. The final serum dilutions for neutralization are 1:20 up to 1:10,240. Sera and virus mixtures are incubated for 1 hour at 37° C. at 5% CO2. Virus control wells (n=16 per plate) are incubated with tissue culture medium only. After incubation, serum/virus mixtures are transferred (1:1) to a new 96-well plate containing a monolayer of Vero E6 cells (2×104 cells/well; ATCC® CRL-1586™) and incubated for an additional 22 hours at 37° C./5% CO2. The imaging and quantification of infection/infection reduction in cell monolayers is performed using the ImageXpress™ Nano platform and the MetaXpress™ software (Molecular Devices). Wuhan-Hu-1 Spike-specific 50% end-point titer (Neutralizing Dose, ND50) for each sample is calculated using Karber's formula. For quality control, each testing batch includes a pooled positive control serum, a pooled negative control serum and a human monoclonal neutralizing antibody (IgG1; Active Motif, catalog number 91361). The coefficient of variation/CV of this assay based on repeated control measurements run on different days is 7.38%.

The antibody ELISA is performed using different dilutions of mouse sera. Group MD4 is tested at a 1:250 dilution. All other groups are diluted until antibody responses are no longer saturated. As a results, an extended range of dilutions is tested (FIG. 18).

TABLE 12

Peptides for each group

| Group | Peptide (100 μg each) | Adjuvants | Route |
|---|---|---|---|
| MD-1 | S1 long | CFA/IFA + CpG | s.c. |
| MD-2 | S2 long | CFA/IFA + CpG | s.c. |
| MD-3 | S9 long | CFA/IFA + CpG | s.c. |
| MD-4 | S14 long | CFA/IFA + CpG | s.c. |

TABLE 12-continued

| | Peptides for each group | | |
| --- | --- | --- | --- |
| Group | Peptide (100 μg each) | Adjuvants | Route |
| MD-5 | S21 long | CFA/IFA + CpG | s.c. |
| MD-6 | ORF9b.1*11 long | CFA/IFA + CpG | s.c. |
| MD-7 | N8 long | CFA/IFA + CpG | s.c. |
| MD-8 | N15 long | CFA/IFA + CpG | s.c. |
| MD-9 | M13 long | CFA/IFA + CpG | s.c. |
| MD-10 | ORF3a long | CFA/IFA + CpG | s.c. |
| MD-11 | N overlap peptide | CFA/IFA + CpG | s.c. |
| MD-12 | Combination of 11 long peptides (all of the above except for N overlap) | CFA/IFA + CpG | s.c. |
| MD-13 | S14, S15 | CFA/IFA + CpG | s.c. |

Figures 17A, 17B:
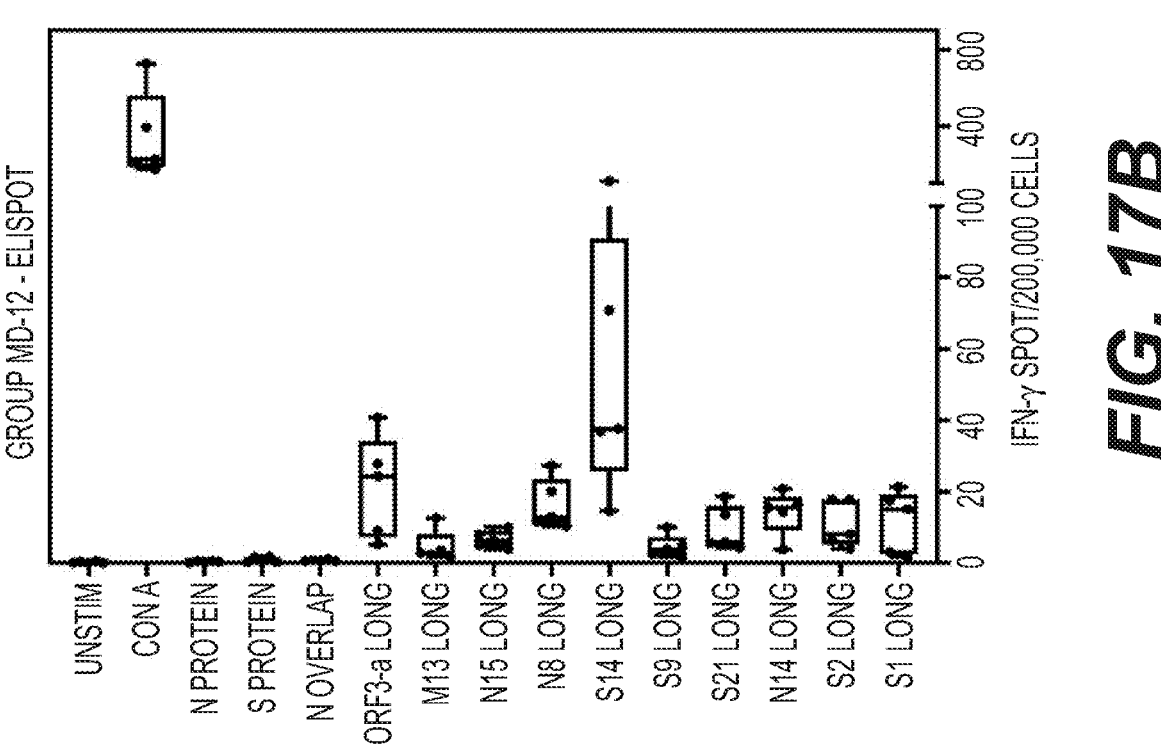
FIG. 17A: Immune responses in mice induced by different long peptides, as measured by IgG ELISA.
FIG. 17B: Immune responses in mice induced by different long peptides, as measured by IFN-γ ELISPOT.
Figure 18B:
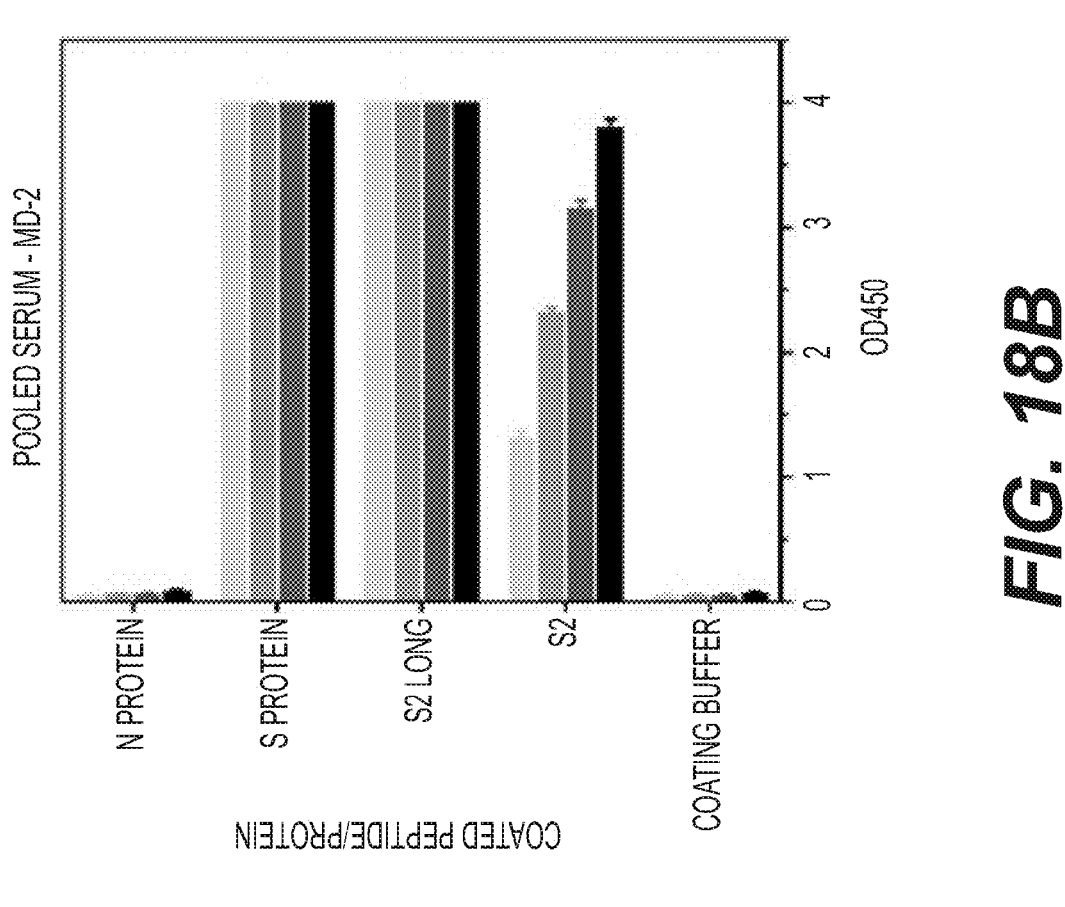
FIG. 18B: Summary of immune responses in mice induced by different long peptides, as measured by IgG ELISA, and performed at different serial dilutions.
Figure 18A:
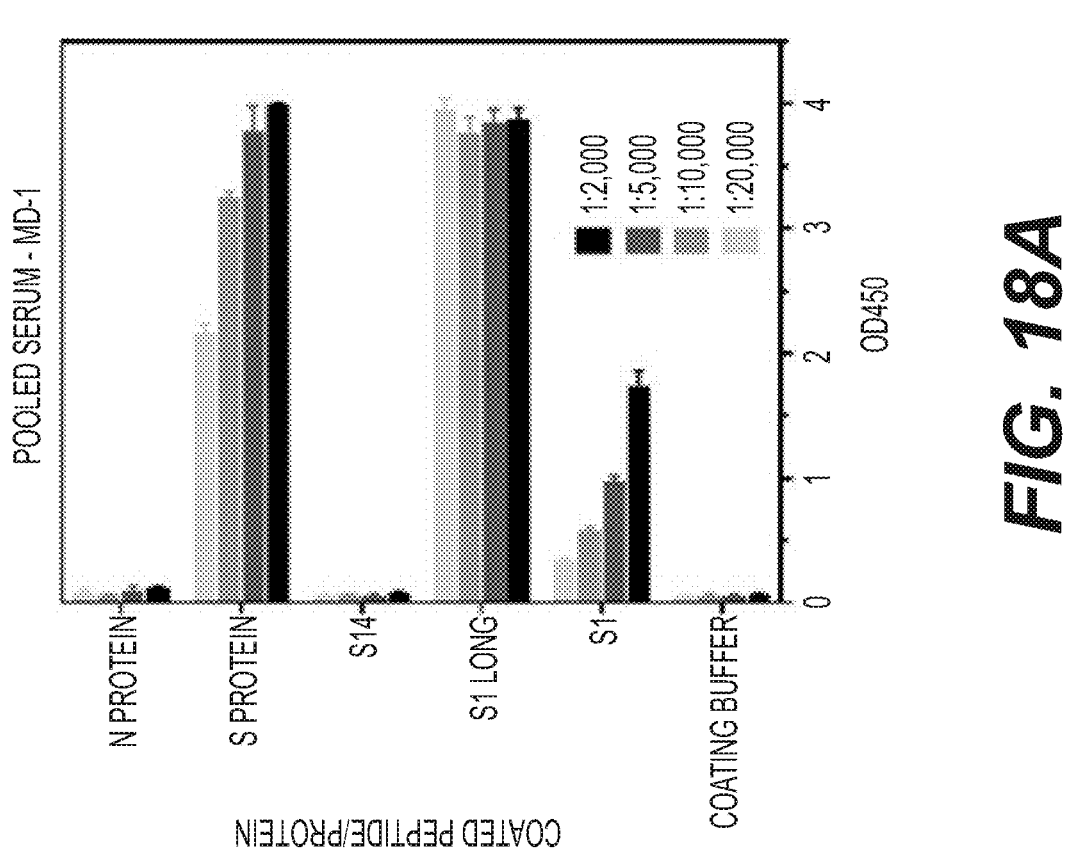
FIG. 18A: Summary of immune responses in mice induced by different long peptides, as measured by IgG ELISA, and performed at different serial dilutions.
Figures 18C, 18D:
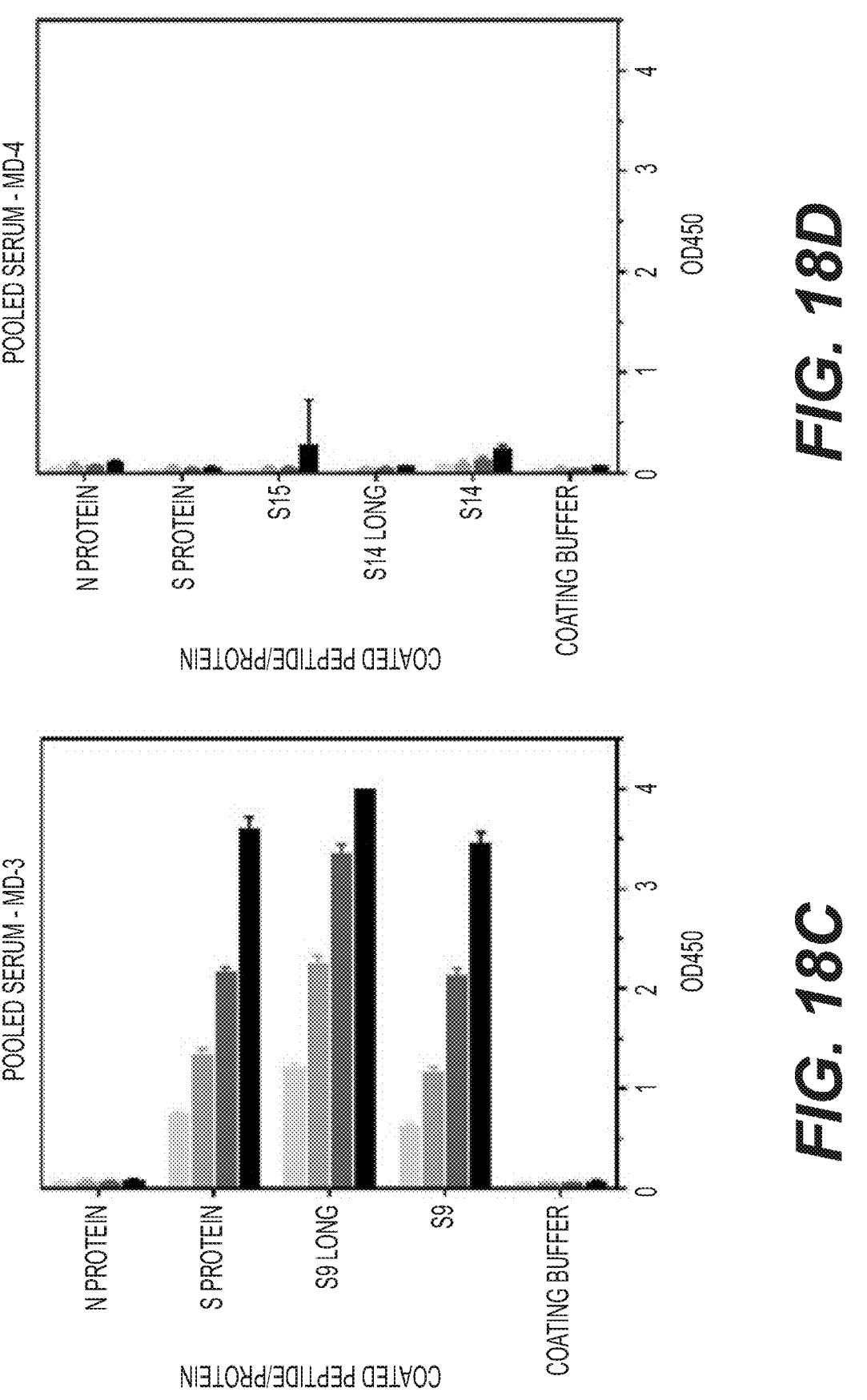
FIG. 18C: Summary of immune responses in mice induced by different long peptides, as measured by IgG ELISA, and performed at different serial dilutions.
FIG. 18D: Summary of immune responses in mice induced by different long peptides, as measured by IgG ELISA, and performed at different serial dilutions.
Figures 18E, 18F:
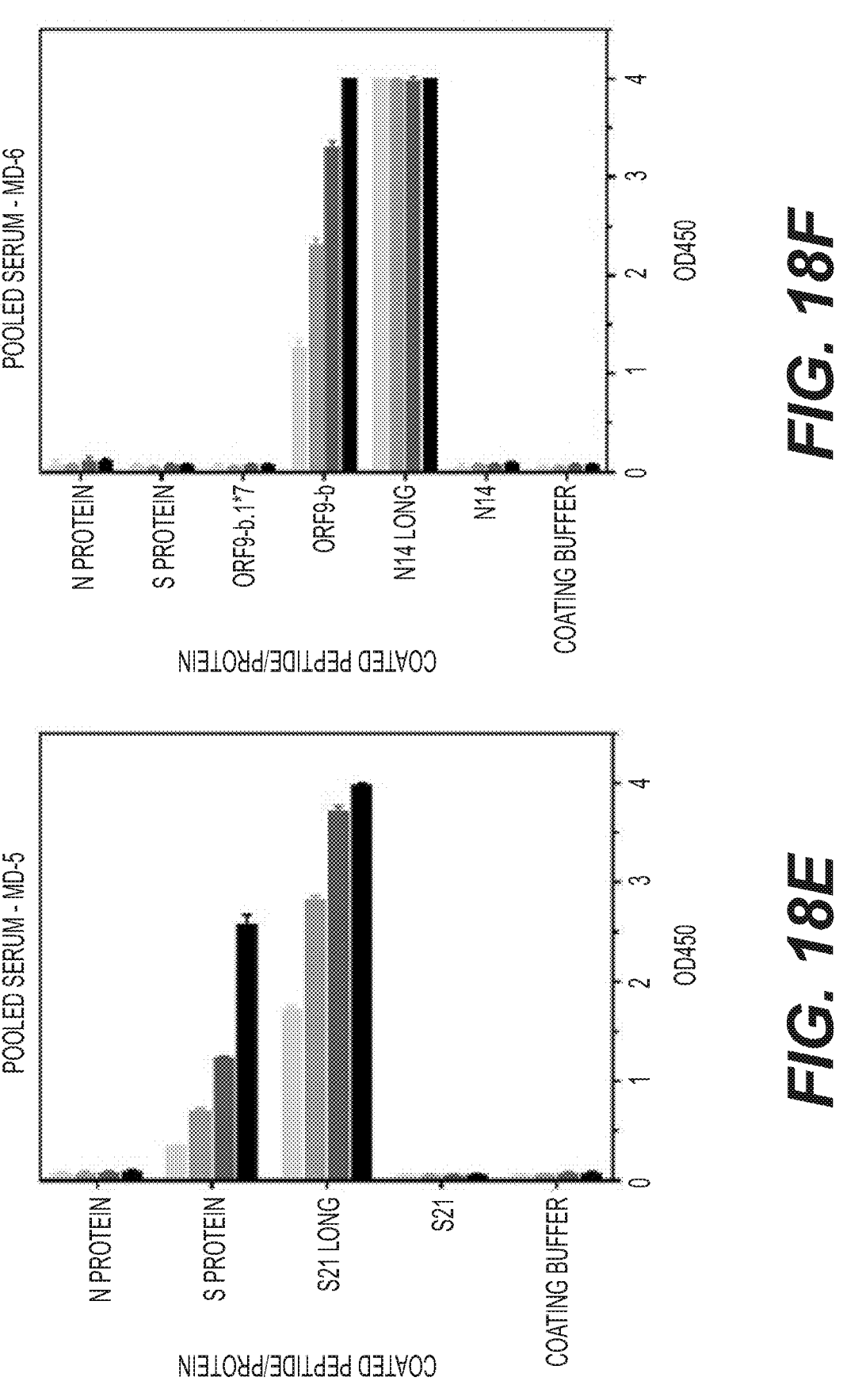
FIG. 18E: Summary of immune responses in mice induced by different long peptides, as measured by IgG ELISA, and performed at different serial dilutions.
FIG. 18F: Summary of immune responses in mice induced by different long peptides, as measured by IgG ELISA, and performed at different serial dilutions.
Figures 18G, 18H:
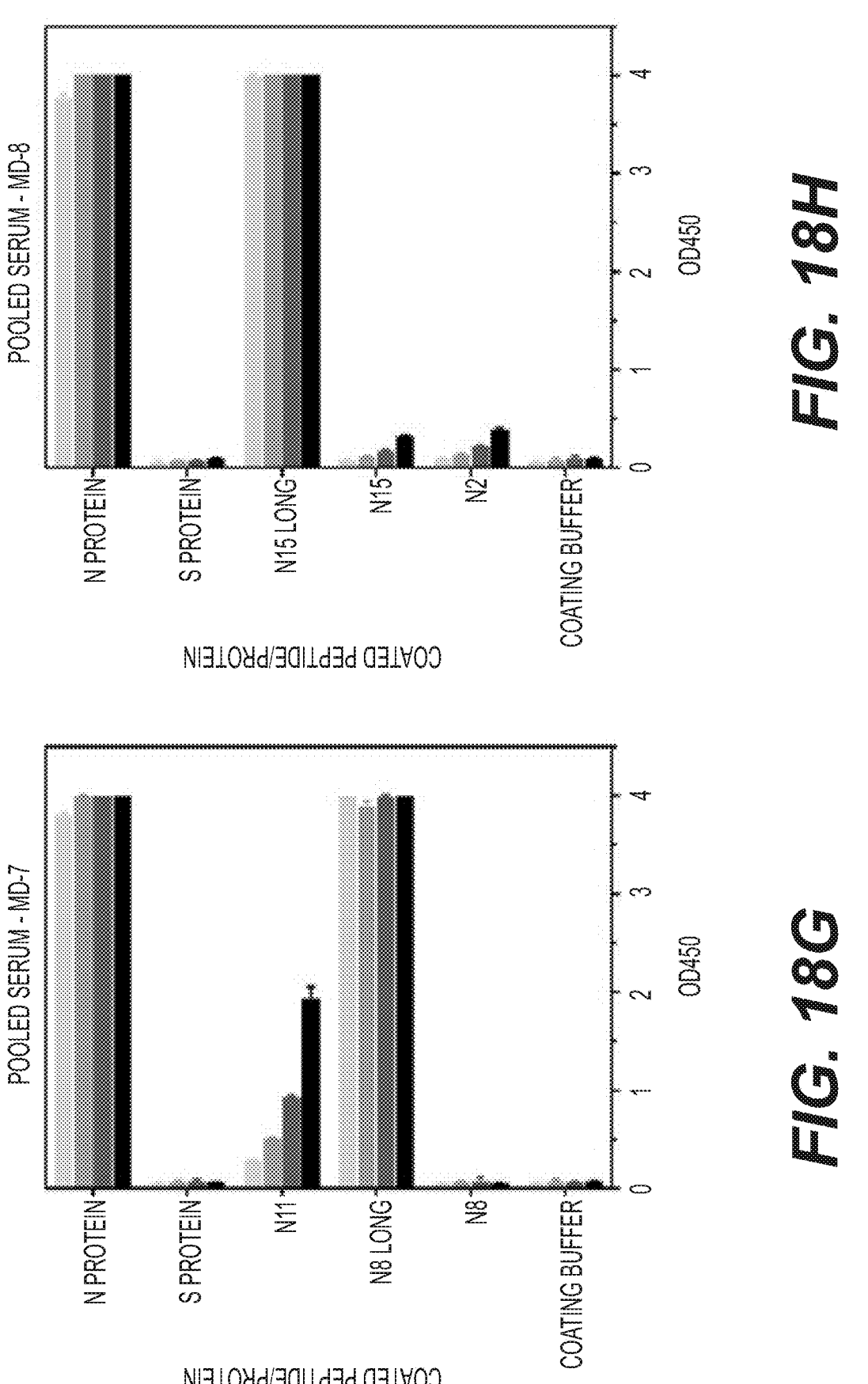
FIG. 18G: Summary of immune responses in mice induced by different long peptides, as measured by IgG ELISA, and performed at different serial dilutions.
FIG. 18H: Summary of immune responses in mice induced by different long peptides, as measured by IgG ELISA, and performed at different serial dilutions.
Figures 18I, 18J:
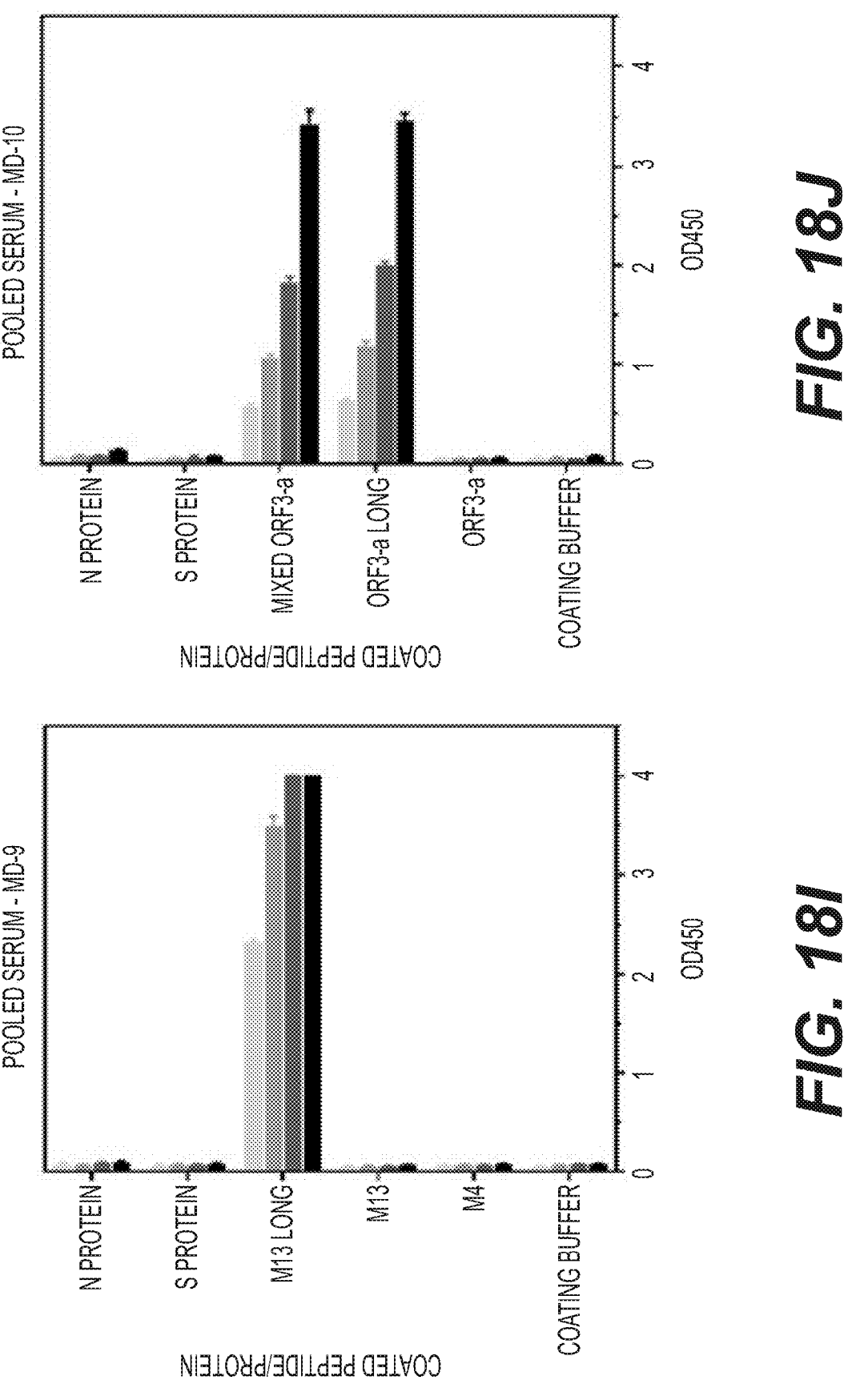
FIG. 18I: Summary of immune responses in mice induced by different long peptides, as measured by IgG ELISA, and performed at different serial dilutions.
FIG. 18J: Summary of immune responses in mice induced by different long peptides, as measured by IgG ELISA, and performed at different serial dilutions.
Figures 18K, 18L:
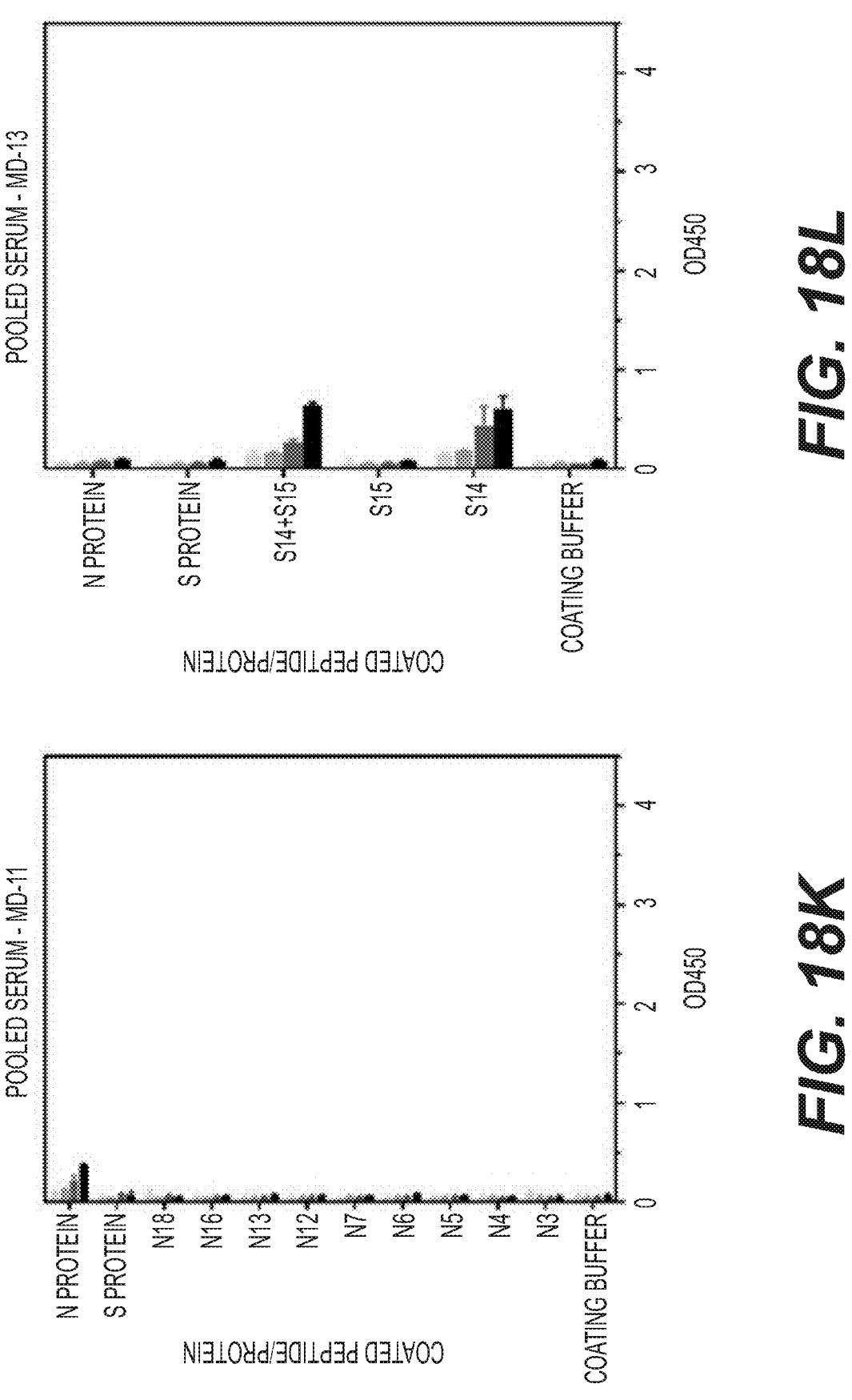
FIG. 18K: Summary of immune responses in mice induced by different long peptides, as measured by IgG ELISA, and performed at different serial dilutions.
FIG. 18L: Summary of immune responses in mice induced by different long peptides, as measured by IgG ELISA, and performed at different serial dilutions.

Results are shown in FIGS. 15-19. FIG. 15 depicts peptide-specific antibody titers induced by individual long peptides, as measured by ELISA. FIG. 16 depicts peptide-specific T cell responses induced by individual long peptides, as measured by IFN-γ ELISPOT. A summary of these responses are shown in FIG. 17. As shown in FIG. 18, huge antibody responses are induced. For example, samples from MD7 and MD8 are still saturated even at dilutions of 1:20,000. Further experiments are needed to at higher dilutions to determine antibody titer levels accurately.

Figure 19:
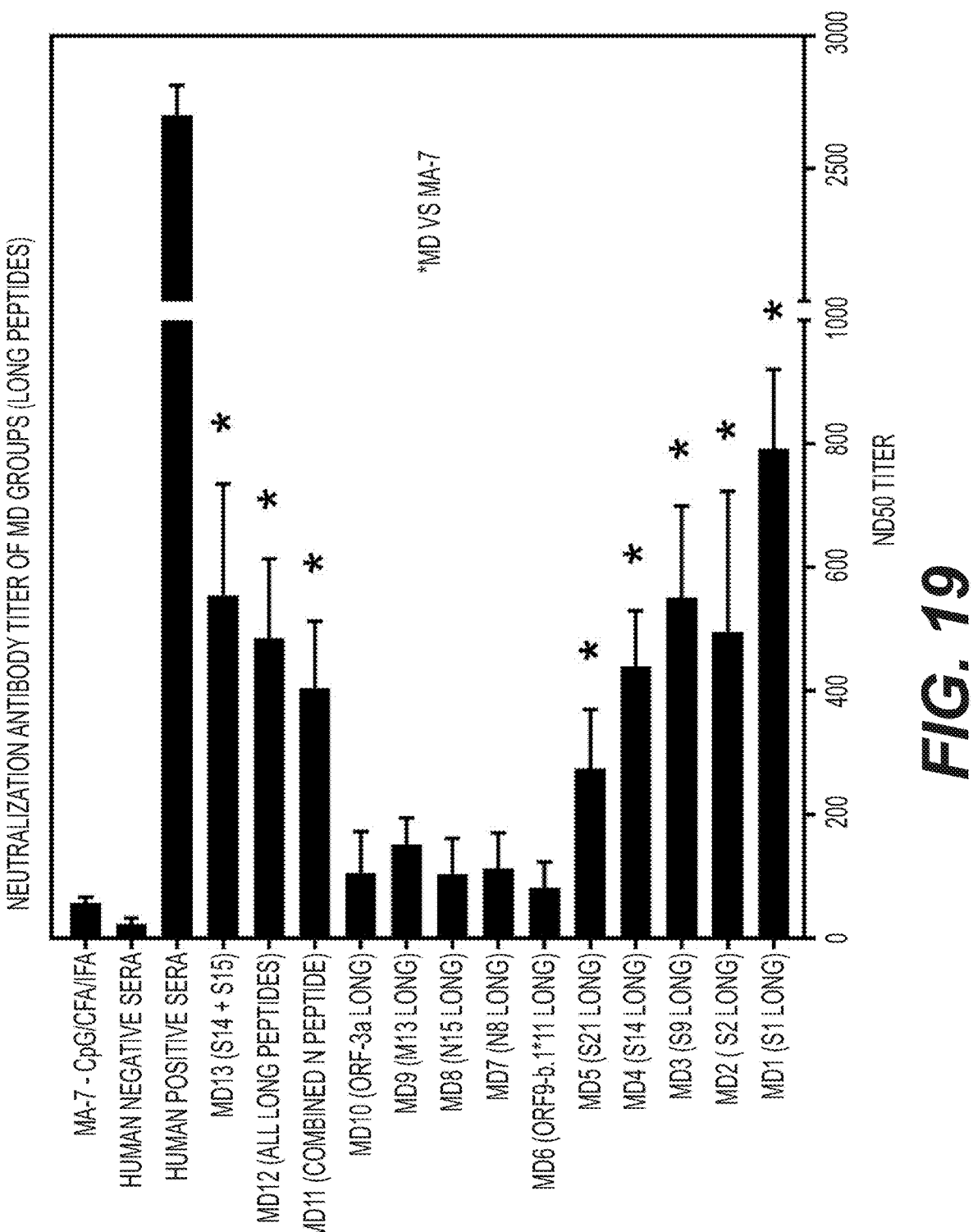
FIG. 19: Immune responses in mice induced by different long peptides, as measured by a neutralizing antibody assay (pseudovirus microneutralization assay).
Figure 20A:
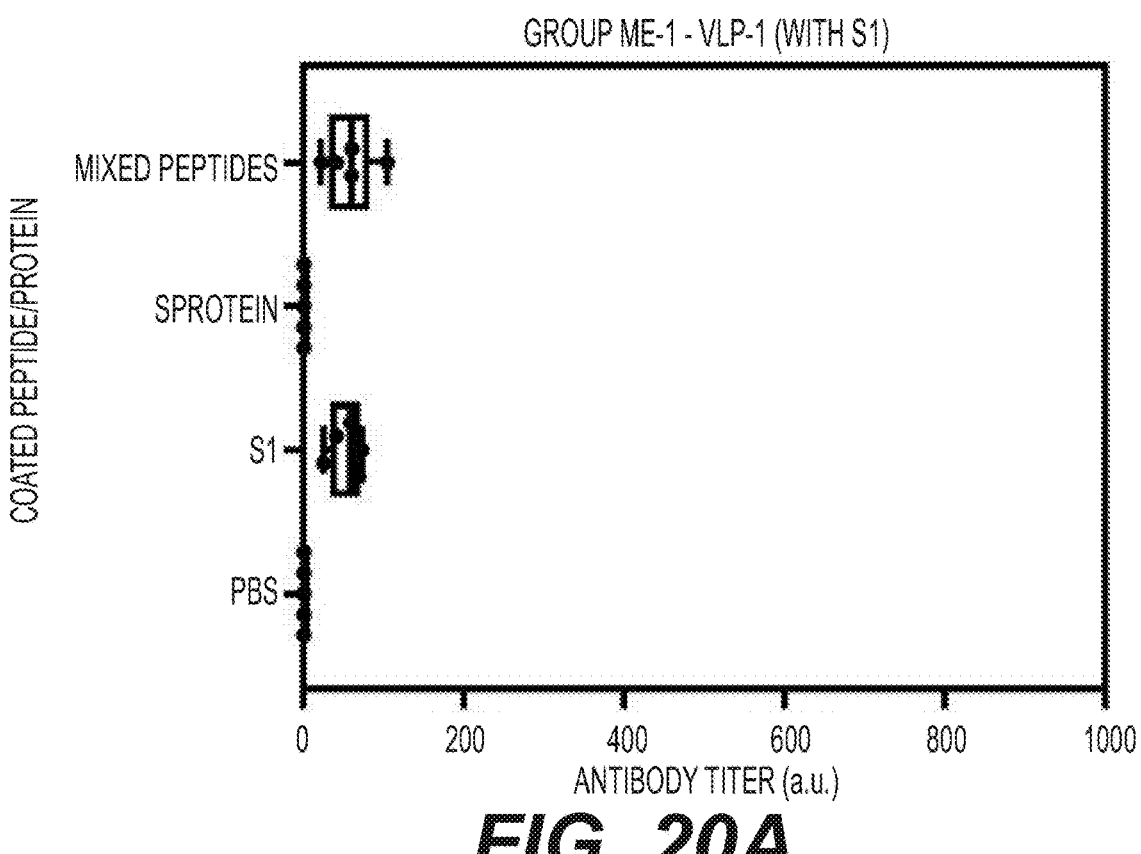
FIG. 20A: Immune responses in mice induced by different long peptides presented on virus-like particles (VLPs), as measured by IgG ELISA.
Figure 20B:
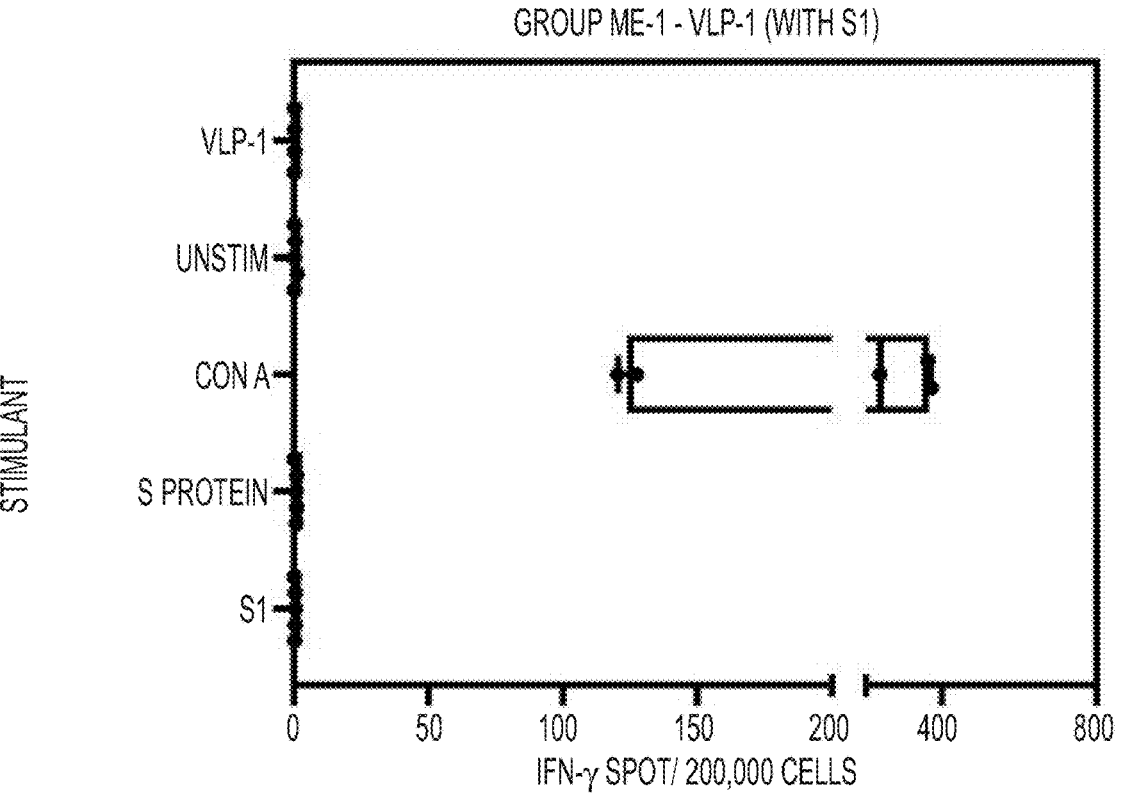
FIG. 20B: Immune responses in mice induced by different long peptides presented on virus-like particles (VLPs), as measured by IFN-γ ELISPOT.
Figure 20C:
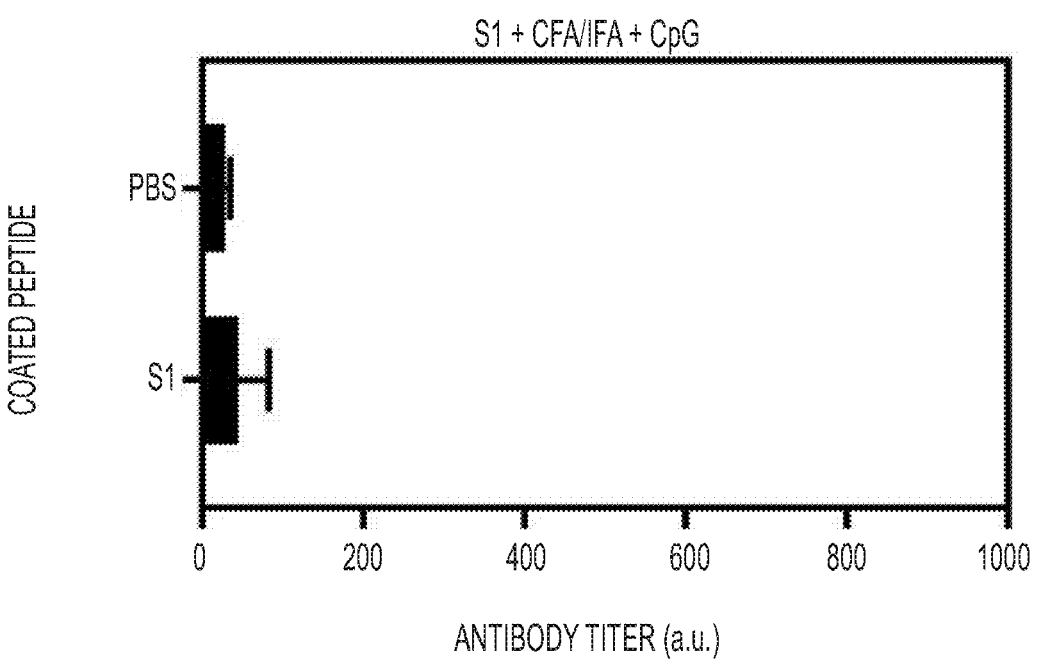
FIG. 20C: Immune responses in mice induced by different long peptides presented on virus-like particles (VLPs), as measured by IgG ELISA.
Figure 20D:
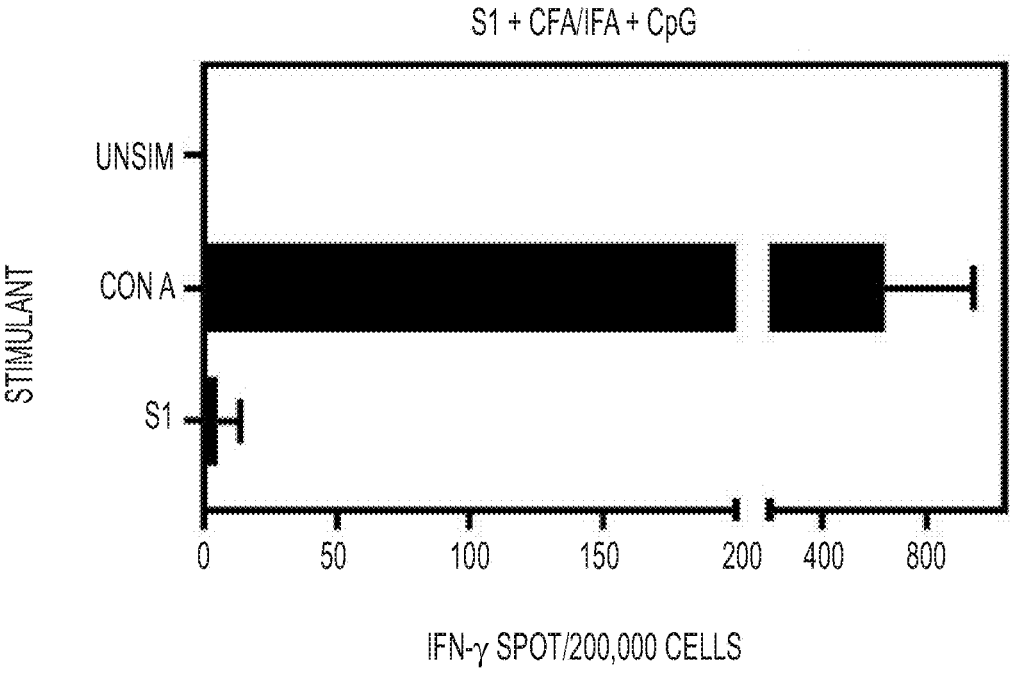
FIG. 20D: Immune responses in mice induced by different long peptides presented on virus-like particles (VLPs), as measured by IFN-γ ELISPOT.
Figure 21A:
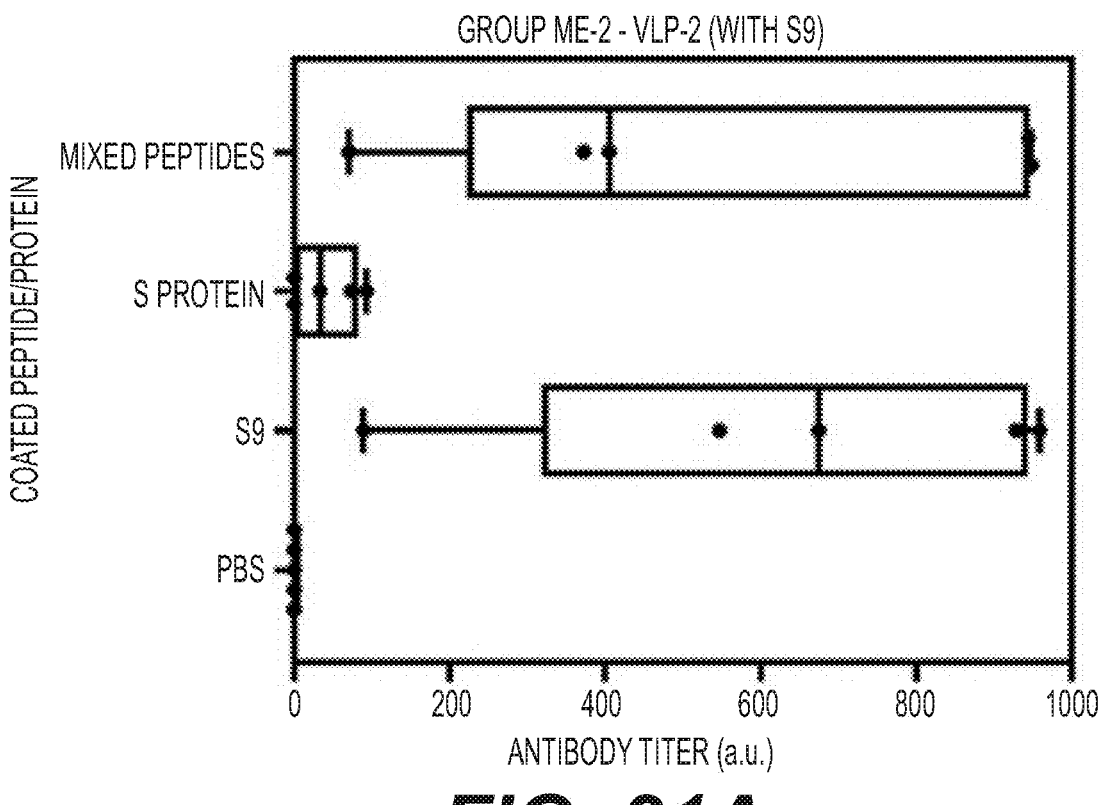
FIG. 21A: Immune responses in mice induced by different long peptides presented on virus-like particles (VLPs), as measured by IgG ELISA.
Figure 21B:
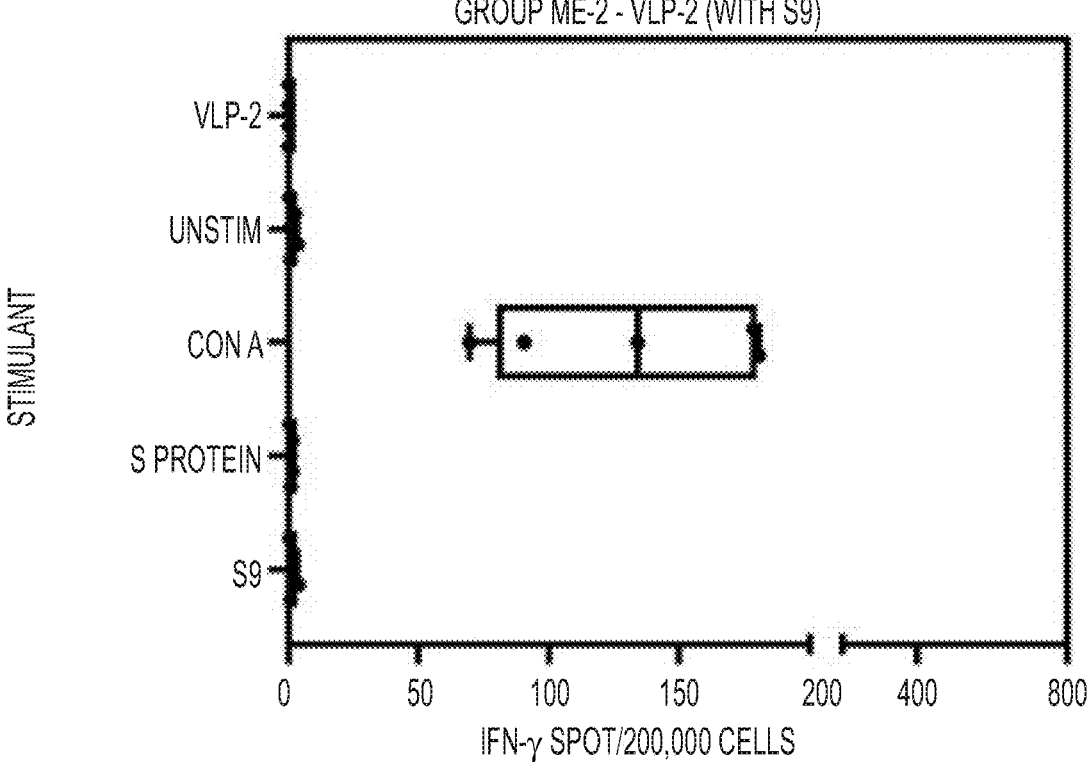
FIG. 21B: Immune responses in mice induced by different long peptides presented on virus-like particles (VLPs), as measured by IFN-γ ELISPOT.
Figure 21C:
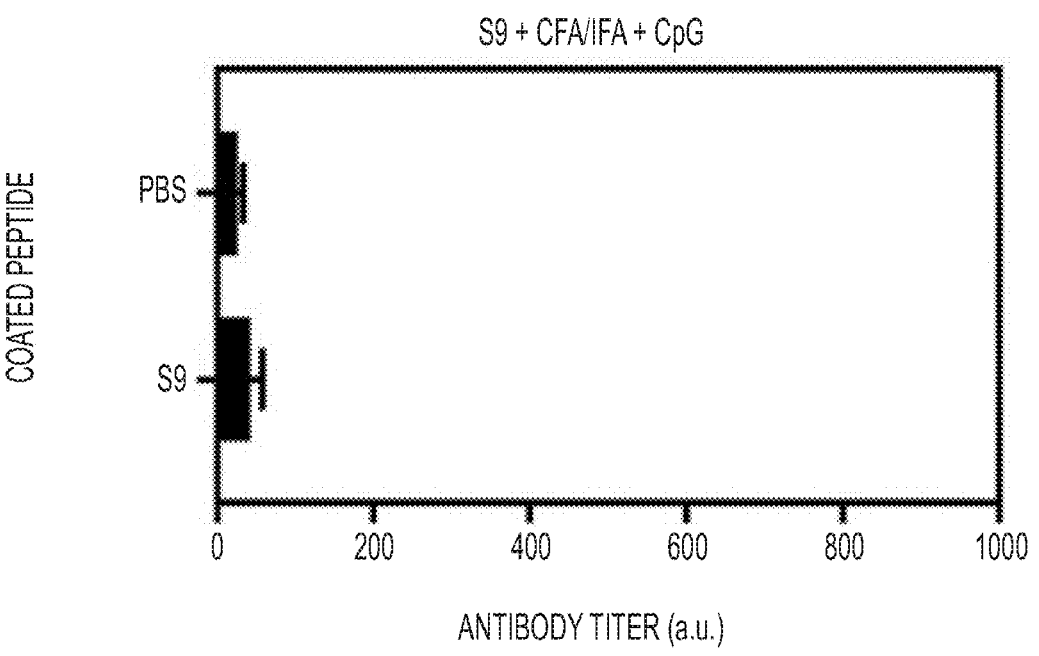
FIG. 21C: Immune responses in mice induced by different long peptides presented on virus-like particles (VLPs), as measured by IgG ELISA.
Figure 21D:
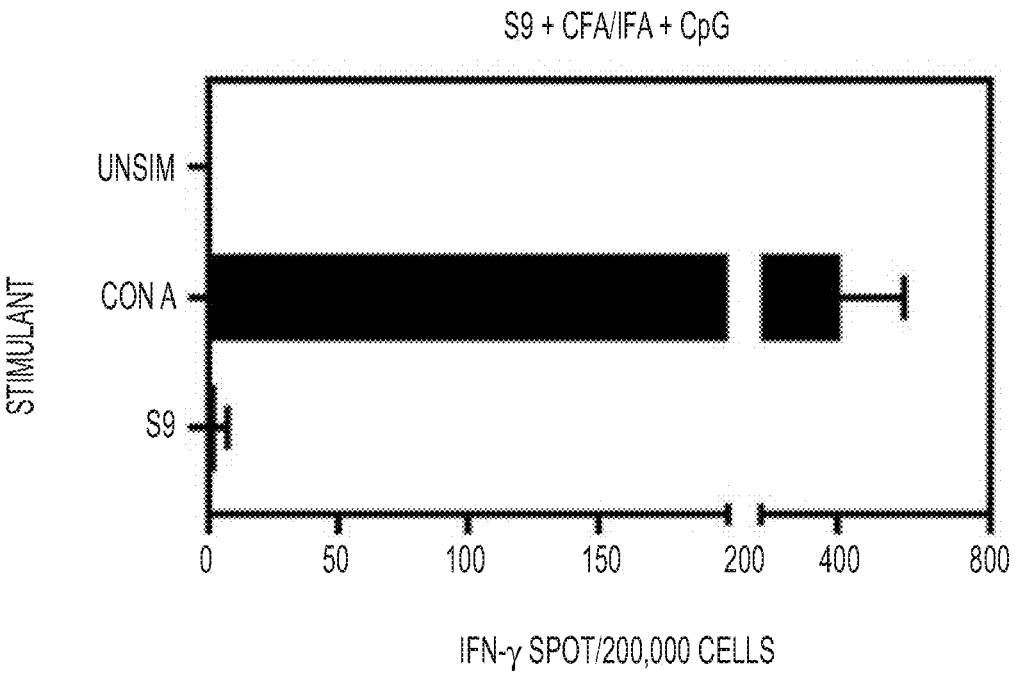
FIG. 21D: Immune responses in mice induced by different long peptides presented on virus-like particles (VLPs), as measured by IFN-γ ELISPOT.

Regardless, it is clear that a strong antibody response is induced by the long peptides. FIG. 19 depicts the neutralization activity of peptide-specific antibody induced by individual long peptides in MD experiment, as measured by the pseudovirus/rVSV microneutralization assay. Sera from mice of MA7 group (mice immunized with CFA/IFA+CpG but no peptides; Example 3, Table 6) are included as a negative control. Asterisks (*) indicate a significant difference in neutralization activity in sera from peptide-vaccinated mice and control mice. Further experiments will be performed to adjust the neutralizing antibody assay protocol to reduce non-specific background like that observed in group MD11.

In conclusion, long peptides generally elicit significantly superior immune responses as compared to short peptides across the immunogenicity assays. Immunization with long peptides is shown to elicit production of binding as well as neutralizing antibodies capable of recognizing full protein sequences. Induction of strong T cell responses is also observed.

Example 7: Testing the Immunogenicity of Peptides Delivered in Virus-Like Particles (VLPs) in Mice Experiments are performed to test virus-like particles (VLPs) as an adjuvant and delivery system for peptides with previously demonstrated high immunogenicity, to evaluate whether this platform of antigen presentation results in increased immunogenicity of the selected peptides. VLPs are nanostructures with diverse applications in immunization, therapeutics, and diagnostics. VLPs possess self-adjuvanting properties and decorating them with individual selected peptides (Table 13) on the surface allows for highly repetitive presentation of over 170 epitopes. In addition to enhanced antigen presentation, using VLPs as the adjuvant/delivery system reduces the amount of peptide needed, requiring only 5%-10% of the dose of peptides used in combination with CpG+CFA (see below). Furthermore, VLPs are easier than emulsions to administer by various routes.

TABLE 13

| | Test groups with VLPs | | |
| --- | --- | --- | --- |
| Group | Loaded peptide | Route | Dose interval |
| ME1 | VLP-1 with S1 | s.c. | 28 days |
| ME2 | VLP-2 with S9 | s.c. | 28 days |
| ME3 | VLP-3 with M8 | s.c. | 28 days |
| ME4 | VLP-4 with N7 | s.c. | 28 days |
| ME5 | VLP-5 with N15 | s.c. | 28 days |
| ME6 | VLP-6 with ORF3a | s.c. | 28 days |
| ME7 | Empty VLPs | s.c. | 28 days |
| ME8 | Pooled 6 VLPs | s.c. | 28 days |

Method:

Peptide-VLP formulations used in our experiments are provided by our research collaborators. Six sets of peptide-VLP combinations labeled VLP1 to VLP6 are created with S1, S9, M8, N7, N15 or ORF3a peptides, respectively. Each VLP is formulated with one type of peptide only.

Two additional groups (ME7 and ME8) are included as control groups, in which mice of ME7 groups are immunized subcutaneously with empty VLPs while mice of ME8 are immunized with a mixture of all 6 peptide-loaded VLPs. Each animal receives a total of 100 μL (containing 20 μg) of the VLP formulation subcutaneously (50 μL in each flank) as a two-dose regimen at a 28-day interval. The mice are euthanized 14 days after the second dose. Immunogenicity is assessed as described in Examples 4-6, using IFN-γ ELISPOT, IL-4 ELISPOT, antibody ELISA and pseudovirus/rVSV microneutralization assay. The immunogenicity results of the selected peptides in VLP (VLP-peptide) and non-VLP formulations (peptide+CFA/IFA+CpG) are compared.

Results are shown in FIGS. 20-26. Results show that VLP+peptide combinations elicit equivalent or stronger T and B cell response than peptides formulated with CFA/IFA+CpG, and require 5%-10% of the antigen dose when compared to CFA/IFA+CpG adjuvanted formulations (Table 14). IL-4 ELISPOT responses are shown to be much lower (and undetectable in some groups) than IFN-γ ELISPOT responses across the experiments, suggesting a Th1-biased immune response.

TABLE 14

| | | | Comparing immunogenicity of VLPs and peptides | | | | | |
| --- | --- | --- | --- | --- | --- | --- | --- | --- |
| VLP | Peptide | Sequence | # peptides per VLP | VLP conc (mg/mL) | MW VLP (kDa) | VLP (μM) | Peptide (MM) | μg peptide/ 20 μg VLP |
| WT-VLP | — | — | 0 | 2.5 | 2542 | 0.98 | 0 | 0.0 |

TABLE 14-continued

Comparing immunogenicity of VLPs and peptides

| VLP | Peptide | Sequence | # peptides per VLP | VLP conc (mg/mL) | MW VLP (kDa) | VLP (µM) | Peptide (MM) | µg peptide/ 20 µg VLP |
|---|---|---|---|---|---|---|---|---|
| VLP-1, batch 1 | S1 | Pra-GSCTFEYVSQPFLMDLE | 50 | 2.5 | 2725 | 0.92 | 46 | 0.7 |
| VLP-2, batch 1 | S9 | Pra-GSFNCYFPLQSYGFQPT | 140 | 2.5 | 2910 | 0.86 | 120 | 1.9 |
| VLP-3, batch 1 | M8 | Pra-GSEITVATSRTLSYYKL | 100 | 1.9 | 2821 | 0.67 | 67 | 1.4 |
| VLP-4, batch 1 | N7 | Pra-GSDQVILLNKHIDAYK | 170 | 2.5 | 2948 | 0.85 | 144 | 2.3 |
| VLP-5, batch 1 | N15 | Pra-GSIRQGTDYKHWPQIAQFA PSASAFFG | 130 | 2.5 | 3021 | 0.83 | 108 | 1.7 |
| VLP-6, batch 1 | Orf3a | Pra-GSYFTSDYYQLYSTQLSTDTGV | 100 | 2.5 | 2882 | 0.87 | 87 | 1.4 |
| VLP-1, batch 2 | S1 | Pra-GSCTFEYVSQPFLMDLE | 95 | 2.5 | 2818 | 0.89 | 84 | 1.4 |
| VLP-3, batch 2 | M8 | Pra-GSEITVATSRTLSYYKL | 128 | 2.5 | 2877 | 0.87 | 111 | 1.8 |

Example 8: Testing the Immunogenicity of Peptides Combined with SARS-CoV-2 RBD Protein Fragments in Mice Experiments are performed to evaluate whether inclusion of SARS-CoV-2 Receptor Binding Domain (RBD) protein fragment would result in an increase in production of neutralizing antibodies and overall superior humoral and/or cellular immune responses.

Method:

Mice are divided into 4 groups (MF1 to MF4) and receive (i) no protein or peptide, (ii) a set of 6 peptides (20 µg each), (iii) recombinant SARS-CoV-2 RBD protein (20 µg) or (iv) 6 peptides combined with SARS-CoV-2 RBD protein (20 µg each) as a two-dose regimen at a 28 day interval (Table 15). Mice are euthanized 14 days after the second dose and immunogenicity assays are performed as described as in Examples 4-7.

TABLE 15

Comparing immunogenicity of RBD and peptides

| Group | Protein/peptide (20 µg each) | Adjuvants | Route | Dose interval |
|---|---|---|---|---|
| MF-1 | No protein/peptide | Montanide 51 + TLR4 agonist | s.c. | 28 days |
| MF-2 | S1, S9, M8, N7, N15, ORF-3a | Montanide 51 + TLR4 agonist | s.c. | 28 days |
| MF-3 | RBD protein | Montanide 51 + TLR4 agonist | s.c. | 28 days |
| MF-4 | RBD, S1, S9, M8, N7, N15, ORF-3a | Montanide 51 + TLR4 agonist | s.c. | 28 days |

As shown in FIG. 27, immunization with SARS-CoV-2 RBD and a combination of peptides elicit robust antibody responses to the RBD protein. T cell responses to SARS-CoV-2 RBD antigen are negligible.

Hamsters are subsequently challenged with live SARS-CoV-2 virus.

Example 9: Comparison of Dose Intervals of Long Peptides in Mice

Experiments are performed to test whether varying the intervals between the first and second vaccine doses enhance the immune response to long peptides when combined with CFA/IFA+CpG in mice.

Mice are divided into groups, primed with selected long peptides (see Example 6) combined with CpG+CFA, and boosted with the same long peptide formulation with CpG+IFA after 21 days. A second group of mice are immunized with the identical formulation at an interval of 28 days between the doses. Two control groups are primed and boosted with SARS-CoV-2 S protein combined with CFA/IFA+CpG at 21-day and 28-day intervals, respectively. Immunogenicity are assessed using IFN-γ ELISPOT and antibody ELISA as described in Examples 2 and 3.

Example 10: Comparison of Long Peptides with Different Adjuvants in Mice

Due to the superior immunogenicity of long peptides+CFA/IFA+CpG as compared to short peptides+CFA/IFA+CpG (as shown above in Example 6), long peptides are tested in combination with different adjuvants previously shown to augment immunogenicity of shorter peptides (see Example 5). Long peptides are tested with Montanide 51+TLR4 agonist, Alum, Alum+TLR4 agonist, EmT4+TLR4 agonist, and Addavax+TLR4 agonist. Additional adjuvants are also tested.

The mice are divided into groups and are immunized with two doses of a formulation of different long peptides combined with different adjuvants and TLR4 agonist GLA, at a 28-day interval. The mice are immunized with peptides combined with water-in-oil emulsion Montanide 51+GLA;

Group MC2 is administered 10 peptides+Alum+GLA; Group MC3 receives 10 peptides +EmT4+GLA and group MC4 is immunized with 10 peptides+squalene-based oil-in-water emulsion Addavax+GLA. The mice are euthanized 14 days after the second dose and immune responses are assessed as described above in Example 7, using IFN-γ ELISPOT, IL-4 ELISPOT, antibody ELISA and pseudovirus/rVSV microneutralization assay.

Example 11: Comparison of Long Peptides with VLPs in Mice

Due to the superior immunogenicity of long peptides+CFA/IFA+CpG as compared to short peptides+CFA/IFA+CpG (as shown above in Example 6), different long peptides are tested in combination with VLPs previously shown to augment immunogenicity of shorter peptides (see Example 5), to evaluate whether this platform of antigen presentation results in increased immunogenicity of the selected long peptides.

Peptide-VLP combinations are created with selected long peptides. Each VLP is formulated with one type of peptide only. Negative controls are also performed with mice immunized with empty VLPs. A group of mice are immunized with a mixture of peptide-loaded VLPs. Each animal is immunized with a two-dose regimen at a 28-day interval. The mice are euthanized 14 days after the second dose. Immunogenicity is assessed as described in Example 7, using IFN-γ ELISPOT, IL-4 ELISPOT, antibody ELISA and pseudovirus/rVSV microneutralization assay. The immunogenicity results of the selected peptides in VLP (VLP-peptide) and non-VLP formulations (peptide+CFA/IFA+CpG).

Example 12: Challenge Experiments in Hamsters and Mice

Syrian Golden Hamsters and hACE2 transgenic mice are challenged with live SARS-CoV-2 virus after a two-dose regimen of the peptides and adjuvants outlined in detail in the previous examples. The study determines whether peptides induce immune responses in hamster and mice models that are effective to prevent the development of a SARS-CoV-2 infection or are effective to reduce the severity and/or duration of symptoms of a SARS-CoV-2 infection.

Genetically outbred hamsters are grouped, and each group receives a two-dose regiment of either short peptides+CFA/IFA+CpG, long peptides+CFA/IFA+CpG, N protein+CFA/IFA+CpG, S protein+CFA/IFA+CpG, or DMSO+CFA/IFA+CpG (negative control). The hamsters are challenged 14 days after the second dose of vaccine, with 50,000 viral particles of SARS-CoV-2 administered intranasally. Viral load in feces is quantified on days 2, 5, and 7. The nasal viral load is quantified daily by a nasal wash. Serum is collected from the hamsters to monitor the immune response before the first dose of vaccine, before the second dose of vaccine, before challenge, and at euthanasia. The immune response is measured by quantifying the neutralizing and IgG antibody levels, S protein binding levels, RBD binding levels, using peptide antibody ELISAs. Pseudo-virus neutralization assays are also performed. The hamsters are euthanized 3 or 7 days after infection and the brain and lung tissues are harvested. The tissues are homogenized and the viral load in each tissue is quantified by qRT-PCR, while the number of infectious virus particles is quantified by a Median Tissue Culture Infectious Dose (TCID50) assay. Blood and lymph nodes are collected at euthanasia to test T-cell response to vaccine peptides using IFN-γ ELISPOT.

Example 13: Comparison with a Vaccine of Proven Efficacy in Hamsters and Mice To compare the immune responses elicited by various combinations of peptides and adjuvants outlined in Examples 1-12 above to immune responses to a vaccine with proven efficacy, hamsters are immunized intramuscularly with 100 μL (6 μg RNA) of Pfizer/BioNTech's SARS-CoV-2 mRNA vaccine (BNT162b2) with a two-dose regimen at a 21-day interval. Immune responses is studied at 14 days and 28 days after the second vaccine dose. A negative control group of hamsters is immunized with saline diluent. Experimental groups are described in Table 16. Results are provided in FIG. 28.

TABLE 16

Evaluating immunogenicity of Pfizer mRNA vaccine in hamsters

| Group | Pfizer mRNA vaccine | Dose interval | Route | Euthanized days after 2nd dose |
|---|---|---|---|---|
| HH-1 | 100 μL each hamster | 21 days | Intramuscular | 14 days |
| HH-2 | 100 μL each hamster | 21 days | Intramuscular | 28 days |
| HH-3 | Control | — | — | — |

To compare the immune responses elicited by various combinations of peptides and adjuvants outlined in Examples 1-12 above to immune responses to a vaccine with proven efficacy, mice are immunized intramuscularly with 100 μL (6 μg RNA) of Pfizer/BioNTech's SARS-CoV-2 mRNA vaccine (BNT162b2) with a two-dose regimen at a 21-day interval. Immune responses is studied at 14 days and 28 days after the second vaccine dose. A negative control group of mice is immunized with saline diluent. Experimental groups are described in Table 17. Results are provided in FIG. 29.

TABLE 17

Evaluating immunogenicity of Pfizer mRNA vaccine in mice

| Group | Pfizer mRNA vaccine | Dose interval | Route | Euthanized days after 2nd dose |
|---|---|---|---|---|
| MG-1 | Control | — | — | — |
| MG-2 | 100 μL each mouse | 21 days | Intramuscular | 14 days |
| MG-3 | 100 μL each mouse | 21 days | Intramuscular | 28 days |

Example 14: Evaluating Immunogenicity of 6 Selected Long Peptides in Hamsters Experiments are performed to assess whether elongation of the selected immunogenic peptides results in enhanced presentation of conformational epitopes and consequently increases in antibody and T cell responses. Using SARS-CoV-2 Wu-1 reference sequence (NCBI Reference Sequence: NC_045512.2) each peptide included in the set of 6 peptides described in Examples 4 and 5 is elongated by extending the amino acid sequence on both the N- and C-termini to make a 40 amino acid long peptide, reflecting the natural SARS-CoV-2 sequence (Table 11). Each of the long peptides includes the full sequence of the respective short peptide in bold. Experimental groups are described in Table 18. Results are provided in FIG. 30.

TABLE 18

One vs. two doses of 6 selected long peptides in hamsters

| Group | Peptide (100 μg each) | Adjuvants | Route |
|-------|------------------------|-----------|-------|
| HH-1 | Control | — | s.c. |
| HH-2 | M13 Long, N15 Long, ORF3-a Long, ORF9-b.1*11 Long, S15 Long, S21 Long | CFA + CpG | s.c. |
| HH-3 | M13 Long, N15 Long, ORF3-a Long, ORF9-b.1*11 Long, S15 Long, S21 Long | CFA/ IFA + CpG | s.c. |

Example 15: Treating SARS-CoV-2

A human identified as needing an induction or an increase in an immune response against a SARS-CoV-2 infection (e.g., COVID-19) such as a human having or at risk of developing COVID-19 is administered one or more SARS-CoV-2 polypeptides provided herein (e.g., one or more SARS-CoV-2 polypeptides that comprise, consist essentially of, or consist of the amino acid sequence set forth in any of SEQ ID NOs:1-87). The administered polypeptide(s) can prevent the development of one or more symptoms of COVID-19.

Example 16: Treating SARS-CoV-2

A human identified as needing an induction or an increase in an immune response against a SARS-CoV-2 infection (e.g., COVID-19) such as a human having or at risk of developing COVID-19 is administered one or more SARS-CoV-2 polypeptides provided herein (e.g., one or more SARS-CoV-2 polypeptides that comprise, consist essentially of, or consist of the amino acid sequence set forth in any of SEQ ID NOs:1-87). The administered polypeptides(s) can reduce the severity of or eliminate one or more symptoms of COVID-19.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. A list of exemplary embodiments is provided:

Embodiment 1. A substantially pure polypeptide consisting essentially of or consisting of the amino acid sequence set forth in any one of SEQ ID NOs:1-87.

Embodiment 2. A composition comprising the substantially pure polypeptide of embodiment 1.

Embodiment 3. A composition comprising at least two polypeptides, wherein each of said at least two polypeptides is a polypeptide consisting essentially of or consisting of the amino acid sequence set forth in any one of SEQ ID NOs:1-87.

Embodiment 4. The composition of any one of embodiments 2-3, wherein said composition comprises a polypeptide consisting of the amino acid sequence set forth in SEQ ID NO:1, a polypeptide consisting of the amino acid sequence set forth in SEQ ID NO:5, a polypeptide consisting of the amino acid sequence set forth in SEQ ID NO:13, a polypeptide consisting of the amino acid sequence set forth in SEQ ID NO:15, a polypeptide consisting of the amino acid sequence set forth in SEQ ID NO:37, and a polypeptide consisting of the amino acid sequence set forth in SEQ ID NO:40.

Embodiment 5. The composition of any one of embodiments 2-3, wherein said composition comprises a polypeptide consisting of the amino acid sequence set forth in SEQ ID NO:1, a polypeptide consisting of the amino acid sequence set forth in SEQ ID NO:9, a polypeptide consisting of the amino acid sequence set forth in SEQ ID NO:12, a polypeptide consisting of the amino acid sequence set forth in SEQ ID NO:18, a polypeptide consisting of the amino acid sequence set forth in SEQ ID NO:21, and a polypeptide consisting of the amino acid sequence set forth in SEQ ID NO:46.

Embodiment 6. The composition of any one of embodiments 2-3, wherein said composition comprises a polypeptide consisting of the amino acid sequence set forth in SEQ ID NO:12, a polypeptide consisting of the amino acid sequence set forth in SEQ ID NO:14, a polypeptide consisting of the amino acid sequence set forth in SEQ ID NO:25, a polypeptide consisting of the amino acid sequence set forth in SEQ ID NO:27, a polypeptide consisting of the amino acid sequence set forth in SEQ ID NO:44, and a polypeptide consisting of the amino acid sequence set forth in SEQ ID NO:45.

Embodiment 7. The composition of any one of embodiments 2-3, wherein said composition comprises a polypeptide consisting of the amino acid sequence set forth in SEQ ID NO:3, a polypeptide consisting of the amino acid sequence set forth in SEQ ID NO:16, a polypeptide consisting of the amino acid sequence set forth in SEQ ID NO:19, a polypeptide consisting of the amino acid sequence set forth in SEQ ID NO:28, a polypeptide consisting of the amino acid sequence set forth in SEQ ID NO:31, and a polypeptide consisting of the amino acid sequence set forth in SEQ ID NO:37.

Embodiment 8. The composition of any one of embodiments 2-3, wherein said composition comprises a polypeptide consisting of the amino acid sequence set forth in SEQ ID NO:2, a polypeptide consisting of the amino acid sequence set forth in SEQ ID NO:9, a polypeptide consisting of the amino acid sequence set forth in SEQ ID NO:17, a polypeptide consisting of the amino acid sequence set forth in SEQ ID NO:24, a polypeptide consisting of the amino acid sequence set forth in SEQ ID NO:27, a polypeptide consisting of the amino acid sequence set forth in SEQ ID NO:39, and a polypeptide consisting of the amino acid sequence set forth in SEQ ID NO:43.

Embodiment 9. The composition of any one of embodiments 2-3, wherein said composition comprises a polypeptide consisting of the amino acid sequence set forth in SEQ ID NO:1, a polypeptide consisting of the amino acid sequence set forth in SEQ ID NO:2, a polypeptide consisting of the amino acid sequence set forth in SEQ ID NO:8, a polypeptide consisting of the amino acid sequence set forth in SEQ ID NO:10, a polypeptide consisting of the amino acid sequence set forth in SEQ ID NO:11, a polypeptide consisting of the amino acid sequence set forth in SEQ ID NO:14, a polypeptide consisting of the amino acid sequence set forth in SEQ ID NO:18, and a polypeptide consisting of the amino acid sequence set forth in SEQ ID NO:19.

Embodiment 10. The composition of any one of embodiments 2-3, wherein said composition comprises a polypeptide consisting of the amino acid sequence set forth in SEQ ID NO:12, a polypeptide consisting of the amino acid sequence set forth in SEQ ID NO:13, a polypeptide consisting of the amino acid sequence set forth in SEQ ID NO:25, a polypeptide consisting of the amino acid sequence set forth in SEQ ID NO:43, a polypeptide consisting of the amino acid sequence set forth in SEQ ID NO:53, a polypeptide consisting of the amino acid sequence set forth in SEQ ID NO:38, a polypeptide consisting of the amino acid sequence set forth in SEQ ID NO:15, a polypeptide consisting of the amino acid sequence set forth in SEQ ID NO:39, a polypeptide consisting of the amino acid sequence set forth in SEQ ID NO:34, and a polypeptide consisting of the amino acid sequence set forth in SEQ ID NO:18.

Embodiment 11. The composition of any one of embodiments 2-3, wherein said composition comprises a polypeptide consisting of the amino acid sequence set forth in SEQ ID NO:68, a polypeptide consisting of the amino acid sequence set forth in SEQ ID NO:69, a polypeptide consisting of the amino acid sequence set forth in SEQ ID NO:70, a polypeptide consisting of the amino acid sequence set forth in SEQ ID NO:71, a polypeptide consisting of the amino acid sequence set forth in SEQ ID NO:72, a polypeptide consisting of the amino acid sequence set forth in SEQ ID NO:73, a polypeptide consisting of the amino acid sequence set forth in SEQ ID NO:74, a polypeptide consisting of the amino acid sequence set forth in SEQ ID NO:75, a polypeptide consisting of the amino acid sequence set forth in SEQ ID NO:76, a polypeptide consisting of the amino acid sequence set forth in SEQ ID NO:77, and a polypeptide consisting of the amino acid sequence set forth in SEQ ID NO:78.

Embodiment 12. The composition of any one of embodiments 2-3, wherein said composition comprises a polypeptide consisting of the amino acid sequence set forth in SEQ ID NO:68, a polypeptide consisting of the amino acid sequence set forth in SEQ ID NO:69, a polypeptide consisting of the amino acid sequence set forth in SEQ ID NO:70, a polypeptide consisting of the amino acid sequence set forth in SEQ ID NO:71, a polypeptide consisting of the amino acid sequence set forth in SEQ ID NO:73, a polypeptide consisting of the amino acid sequence set forth in SEQ ID NO:74, a polypeptide consisting of the amino acid sequence set forth in SEQ ID NO:75, a polypeptide consisting of the amino acid sequence set forth in SEQ ID NO:76, a polypeptide consisting of the amino acid sequence set forth in SEQ ID NO:77, and a polypeptide consisting of the amino acid sequence set forth in SEQ ID NO:78.

Embodiment 13. The composition of any one of embodiments 2-12, wherein said composition comprises an adjuvant or an immunostimulatory molecule.

Embodiment 14. The composition of embodiment 13, wherein said adjuvant or immunostimulatory molecule is selected from the group consisting of a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA.

Embodiment 15. The composition of embodiment 13, wherein said adjuvant or immunostimulatory molecule is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA.

Embodiment 16. The composition of embodiment 13, wherein said adjuvant or immunostimulatory molecule is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, retinoic acid-inducible gene I (RIG-I), lipid nanoparticles (e.g., LION), and GLA.

Embodiment 17. The composition of any one of embodiments 2-12, wherein said polypeptides are attached to one or more virus-like particles (VLP).

Embodiment 18. The composition of embodiment 17, wherein said VLPs are made from viruses selected from the group consisting of Parvoviridae, Retroviridae, Flaviviridae, Paramyxoviridae and bacteriophages.

Embodiment 19. The composition of embodiment 17, wherein said VLPs are made from Q-beta bacteriophage.

Embodiment 20. A composition comprising nucleic acid encoding a polypeptide consisting essentially of or consisting of the amino acid sequence set forth in any one of SEQ ID NOs:1-87.

Embodiment 21. A composition comprising nucleic acid encoding at least two polypeptides, wherein each of said at least two polypeptides is a polypeptide consisting essentially of or consisting of the amino acid sequence set forth in any one of SEQ ID NOs:1-87.

Embodiment 22. The composition of any one of embodiments 20-21, wherein said composition comprises a polypeptide consisting of the amino acid sequence set forth in SEQ ID NO:1, a polypeptide consisting of the amino acid sequence set forth in SEQ ID NO:5, a polypeptide consisting of the amino acid sequence set forth in SEQ ID NO:13, a polypeptide consisting of the amino acid sequence set forth in SEQ ID NO:15, a polypeptide consisting of the amino acid sequence set forth in SEQ ID NO:37, and a polypeptide consisting of the amino acid sequence set forth in SEQ ID NO:40.

Embodiment 23. The composition of any one of embodiments 20-21, wherein said composition comprises a polypeptide consisting of the amino acid sequence set forth in SEQ ID NO:1, a polypeptide consisting of the amino acid sequence set forth in SEQ ID NO:9, a polypeptide consisting of the amino acid sequence set forth in SEQ ID NO:12, a polypeptide consisting of the amino acid sequence set forth in SEQ ID NO:18, a polypeptide consisting of the amino acid sequence set forth in SEQ ID NO:21, and a polypeptide consisting of the amino acid sequence set forth in SEQ ID NO:46.

Embodiment 24. The composition of any one of embodiments 20-21, wherein said composition comprises a polypeptide consisting of the amino acid sequence set forth in SEQ ID NO:12, a polypeptide consisting of the amino acid sequence set forth in SEQ ID NO:14, a polypeptide consisting of the amino acid sequence set forth in SEQ ID NO:25, a polypeptide consisting of the amino acid sequence set forth in SEQ ID NO:27, a polypeptide consisting of the amino acid sequence set forth in SEQ ID NO:44, and a polypeptide consisting of the amino acid sequence set forth in SEQ ID NO:45.

Embodiment 25. The composition of any one of embodiments 20-21, wherein said composition comprises a polypeptide consisting of the amino acid sequence set forth in SEQ ID NO:3, a polypeptide consisting of the amino acid sequence set forth in SEQ ID NO:16, a polypeptide consisting of the amino acid sequence set forth in SEQ ID NO:19, a polypeptide consisting of the amino acid sequence set forth in SEQ ID NO:28, a polypeptide consisting of the amino acid sequence set forth in SEQ ID NO:31, and a polypeptide consisting of the amino acid sequence set forth in SEQ ID NO:37.

Embodiment 26. The composition of any one of embodiments 20-21, wherein said composition comprises a polypeptide consisting of the amino acid sequence set forth in SEQ ID NO:2, a polypeptide consisting of the amino acid sequence set forth in SEQ ID NO:9, a polypeptide consisting of the amino acid sequence set forth in SEQ ID NO:17, a polypeptide consisting of the amino acid sequence set forth in SEQ ID NO:24, a polypeptide consisting of the amino acid sequence set forth in SEQ ID NO:27, a polypeptide consisting of the amino acid sequence set forth in SEQ ID NO:39, and a polypeptide consisting of the amino acid sequence set forth in SEQ ID NO:43.

Embodiment 27. The composition of any one of embodiments 20-21, wherein said composition comprises a polypeptide consisting of the amino acid sequence set forth in SEQ ID NO:1, a polypeptide consisting of the amino acid sequence set forth in SEQ ID NO:2, a polypeptide consisting of the amino acid sequence set forth in SEQ ID NO:8, a polypeptide consisting of the amino acid sequence set forth in SEQ ID NO:10, a polypeptide consisting of the amino acid sequence set forth in SEQ ID NO:11, a polypeptide consisting of the amino acid sequence set forth in SEQ ID NO:14, a polypeptide consisting of the amino acid sequence set forth in SEQ ID NO:18, and a polypeptide consisting of the amino acid sequence set forth in SEQ ID NO:19.

Embodiment 28. The composition of any one of embodiments 20-21, wherein said composition comprises a polypeptide consisting of the amino acid sequence set forth in SEQ ID NO:12, a polypeptide consisting of the amino acid sequence set forth in SEQ ID NO:13, a polypeptide consisting of the amino acid sequence set forth in SEQ ID NO:25, a polypeptide consisting of the amino acid sequence set forth in SEQ ID NO:43, a polypeptide consisting of the amino acid sequence set forth in SEQ ID NO:53, a polypeptide consisting of the amino acid sequence set forth in SEQ ID NO:38, a polypeptide consisting of the amino acid sequence set forth in SEQ ID NO:15, a polypeptide consisting of the amino acid sequence set forth in SEQ ID NO:39, a polypeptide consisting of the amino acid sequence set forth in SEQ ID NO:34, and a polypeptide consisting of the amino acid sequence set forth in SEQ ID NO:18.

Embodiment 29. The composition of any one of embodiments 20-21, wherein said composition comprises a polypeptide consisting of the amino acid sequence set forth in SEQ ID NO:68, a polypeptide consisting of the amino acid sequence set forth in SEQ ID NO:69, a polypeptide consisting of the amino acid sequence set forth in SEQ ID NO:70, a polypeptide consisting of the amino acid sequence set forth in SEQ ID NO:71, a polypeptide consisting of the amino acid sequence set forth in SEQ ID NO:72, a polypeptide consisting of the amino acid sequence set forth in SEQ ID NO:73, a polypeptide consisting of the amino acid sequence set forth in SEQ ID NO:74, a polypeptide consisting of the amino acid sequence set forth in SEQ ID NO:75, a polypeptide consisting of the amino acid sequence set forth in SEQ ID NO:76, a polypeptide consisting of the amino acid sequence set forth in SEQ ID NO:77, and a polypeptide consisting of the amino acid sequence set forth in SEQ ID NO:78.

Embodiment 30. The composition of any one of embodiments 20-21, wherein said composition comprises a polypeptide consisting of the amino acid sequence set forth in SEQ ID NO:68, a polypeptide consisting of the amino acid sequence set forth in SEQ ID NO:69, a polypeptide consisting of the amino acid sequence set forth in SEQ ID NO:70, a polypeptide consisting of the amino acid sequence set forth in SEQ ID NO:71, a polypeptide consisting of the amino acid sequence set forth in SEQ ID NO:73, a polypeptide consisting of the amino acid sequence set forth in SEQ ID NO:74, a polypeptide consisting of the amino acid sequence set forth in SEQ ID NO:75, a polypeptide consisting of the amino acid sequence set forth in SEQ ID NO:76, a polypeptide consisting of the amino acid sequence set forth in SEQ ID NO:77, and a polypeptide consisting of the amino acid sequence set forth in SEQ ID NO:78.

Embodiment 31. The composition of any one of embodiments 20-30, wherein said composition comprises an adjuvant or an immunostimulatory molecule.

Embodiment 32. The composition of embodiment 31, wherein said adjuvant or immunostimulatory molecule is selected from the group consisting of a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA.

Embodiment 33. The composition of embodiment 31, wherein said adjuvant or immunostimulatory molecule is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA.

Embodiment 34. The composition of embodiment 31, wherein said adjuvant or immunostimulatory molecule is selected from the group consisting of a water in oil emulsion (e.g., Montanide 720, Montanide 51), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, retinoic acid-inducible gene I (RIG-I), lipid nanoparticles (e.g., LION), and GLA.

Embodiment 35. The composition of any one of embodiments 20-32, wherein said polypeptides are attached to one or more virus-like particles (VLP).

Embodiment 36. The composition of embodiment 35, wherein said VLPs are made from viruses selected from the group consisting of Parvoviridae, Retroviridae, Flaviviridae, Paramyxoviridae and bacteriophages.

Embodiment 37. The composition of embodiment 35, wherein said VLPs are made from Q-beta bacteriophage.

Embodiment 38. The composition of any one of embodiments 20-32, wherein said nucleic acid is in the form of a non-viral vector.

Embodiment 39. The composition of embodiment 38, wherein said non-viral vector is an expression plasmid.

Embodiment 40. The composition of any one of embodiments 20-32, wherein said nucleic acid is in the form of a viral vector.

Embodiment 41. The composition of embodiment 40, wherein said viral vector is selected from the group consisting of a vector based on an adenoviruses, a vector based on an adeno-associated virus (AAV), a vector based on an retrovirus, a vector based on an lentivirus, a vector based on a measles virus, a vector based on a vesicular stomatitis virus, and a vector based on vaccinia virus.

Embodiment 42. A method for increasing an immune response against a coronavirus in a mammal, wherein said method comprises administering to said mammal a composition comprising a polypeptide consisting essentially of or consisting of the amino acid sequence set forth in any one of SEQ ID NOs:1-87 or nucleic acid encoding said polypeptide.

Embodiment 43. The method of embodiment 42, wherein said mammal is a human.

Embodiment 44. The method of any one of embodiments 42-43, wherein said coronavirus is a severe acute respiratory distress coronavirus 2 (SARS-CoV-2).

Embodiment 45. The method of any one of embodiments 42-44, wherein said composition comprises an adjuvant or an immunostimulatory molecule.

Embodiment 46. The method of embodiment 45, wherein said adjuvant or immunostimulatory molecule is selected from the group consisting of a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA.

Embodiment 47. The method of any one of embodiments 42-46, wherein at least two doses of said composition are administered.

Embodiment 48. The method of any one of embodiments 42-46, wherein two doses of said composition are administered.

Embodiment 49. The method of any one of embodiments 42-48, wherein said polypeptide is presented on one or more virus-like particles (VLP).

Embodiment 50. The method of embodiment 49, wherein said VLPs are made from viruses selected from the group consisting of Parvoviridae, Retroviridae, Flaviviridae, Paramyxoviridae and bacteriophages.

Embodiment 51. The method of embodiment 49, wherein said VLPs are made from Q-beta bacteriophage.

Embodiment 52. A method for treating a mammal at risk of developing a coronavirus infection, wherein said method comprises administering to said mammal a composition comprising a polypeptide consisting essentially of or consisting of the amino acid sequence set forth in any one of SEQ ID NOs:1-87 or nucleic acid encoding said polypeptide.

Embodiment 53. The method of embodiment 52, wherein said mammal is a human.

Embodiment 54. The method of any one of embodiments 52-53, wherein said coronavirus infection is COVID-19.

Embodiment 55. The method of any one of embodiments 52-54, wherein said composition comprises an adjuvant or an immunostimulatory molecule.

Embodiment 56. The method of embodiment 55, wherein said adjuvant or immunostimulatory molecule is selected from the group consisting of a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA.

Embodiment 57. The method of any one of embodiments 52-55, wherein at least two doses of said composition are administered.

Embodiment 58. The method of any one of embodiments 52-55, wherein two doses of said composition are administered.

Embodiment 59. The method of any one of embodiments 52-58, wherein said polypeptide is presented on one or more virus-like particles (VLP).

Embodiment 60. The method of embodiment 59, wherein said VLPs are made from viruses selected from the group consisting of Parvoviridae, Retroviridae, Flaviviridae, Paramyxoviridae and bacteriophages.

Embodiment 61. The method of embodiment 59, wherein said VLPs are made from Q-beta bacteriophage.

Embodiment 62. A method for treating a mammal having a coronavirus infection, wherein said method comprises administering to said mammal a composition comprising a polypeptide consisting essentially of or consisting of the amino acid sequence set forth in any one of SEQ ID NOs:1-87 or nucleic acid encoding said polypeptide.

Embodiment 63. The method of embodiment 62, wherein said mammal is a human.

Embodiment 64. The method of any one of embodiments 62-63, wherein said coronavirus infection is COVID-19.

Embodiment 65. The method of any one of embodiments 62-64, wherein said composition comprises an adjuvant or an immunostimulatory molecule.

Embodiment 66. The method of embodiment 65, wherein said adjuvant or immunostimulatory molecule is selected from the group consisting of a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA.

Embodiment 67. The method of any one of embodiments 62-66, wherein at least two doses of said composition are administered.

Embodiment 68. The method of any one of embodiments 62-66, wherein two doses of said composition are administered.

Embodiment 69. The method of any one of embodiments 62-68, wherein said polypeptide is presented on one or more virus-like particles (VLP).

Embodiment 70. The method of embodiment 69, wherein said VLPs are made from viruses selected from the group consisting of Parvoviridae, Retroviridae, Flaviviridae, Paramyxoviridae and bacteriophages.

Embodiment 71. The method of embodiment 69, wherein said VLPs are made from Q-beta bacteriophage.

---

What is claimed is:

1. A substantially pure polypeptide consisting of the amino acid sequence set forth in SEQ ID NO:75.

2. A composition comprising the substantially pure polypeptide of claim 1.

3. The composition of claim 2, wherein said composition comprises an adjuvant or an immunostimulatory molecule.

4. The composition of claim 3, wherein said adjuvant or immunostimulatory molecule is selected from the group consisting of a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA.

5. The composition of claim 2, wherein said polypeptide is presented on a virus-like particle (VLP).

6. A method for increasing an immune response against a coronavirus in a mammal, wherein said method comprises administering to said mammal a composition comprising a polypeptide consisting of the amino acid sequence set forth in SEQ ID NO: 75 or nucleic acid encoding said polypeptide.

7. The method of claim 6, wherein said coronavirus is a severe acute respiratory distress coronavirus 2 (SARS-COV-2).

8. The method of claim 6, wherein said composition comprises an adjuvant or an immunostimulatory molecule.

9. The method of claim 8, wherein said adjuvant or immunostimulatory molecule is selected from the group consisting of a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA.

10. The method of claim 6, wherein said polypeptide is presented on a virus-like particle (VLP).

11. A method for treating a mammal at risk of developing a coronavirus infection, wherein said method comprises administering to said mammal a composition comprising a polypeptide consisting of the amino acid sequence set forth in SEQ ID NO:75 or nucleic acid encoding said polypeptide.

12. The method of claim 11, wherein said coronavirus infection is COVID-19.

13. The method of claim 11, wherein said composition comprises an adjuvant or an immunostimulatory molecule.

14. The method of claim 13, wherein said adjuvant or immunostimulatory molecule is selected from the group consisting of a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AlT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA.

15. The method of claim 11, wherein said polypeptide is presented on a virus-like particle (VLP).

16. A method for treating a mammal having a coronavirus infection, wherein said method comprises administering to said mammal a composition comprising a polypeptide consisting of the amino acid sequence set forth in SEQ ID NO:75 or nucleic acid encoding said polypeptide.

17. The method of claim 16, wherein said coronavirus infection is COVID-19.

18. The method of claim 16, wherein said composition comprises an adjuvant or an immunostimulatory molecule.

19. The method of claim 18, wherein said adjuvant or immunostimulatory molecule is selected from the group consisting of a water in oil emulsion (e.g., Montanide 720, Montanide 51), Complete Freund's Adjuvant (CFA), Incomplete Freund's Adjuvant (IFA), a CpG oligonucleotide motif, toll-like receptor 4 (TLR4) agonists (e.g., MiT4, EmT4, AIT4, LiT4), aluminum sulfate, aluminum hydroxide, aluminum phosphate, aluminum potassium sulfate, monophosphoryl lipid A, aluminumphosphylate, MF59, AS03, AS04, AS03-like, AS04-like, AS01B-like, GM-CSF, Addavax, AddaS03, retinoic acid-inducible gene I (RIG-I), lipid nanoparticles (e.g., LION), and GLA.

20. The method of claim 16, wherein said polypeptide is presented on a virus-like particle (VLP).

* * * * *